(12) United States Patent
Prasad et al.

(10) Patent No.: US 11,548,937 B2
(45) Date of Patent: *Jan. 10, 2023

(54) DNA-BINDING DOMAIN OF CRISPR SYSTEM, NON-FUCOSYLATED AND PARTIALLY FUCOSYLATED PROTEINS, AND METHODS THEREOF

(71) Applicant: Zumutor Biologies Inc., San Francisco, CA (US)

(72) Inventors: Bhargav Prasad, Chennai (IN); Divya Unnikrishnan, Bangalore (IN); Jahnabi Hazarika, Bangalore (IN); Kavitha Iyer Rodrigues, Bangalore (IN); Maloy Ghosh, Bangalore (IN); Pavithra M, Kundapur (IN); Pravin Kumar D, Chennai (IN); Sanghamitra Bhattacharjee, Bangalore (IN); Sathyabalan M, Bangalore (IN); Sankaranarayanan Srinivasan, Bangalore (IN); Sohang Chatterjee, Bangalore (IN); Sunit Maity, Bangalore (IN); Veeresha K, Bangalore (IN); Vivek Halan, Aravenu (IN); Yogendra Manjunath B. M., Bangalore (IN); Anuradha Hora, Sitapur (IN); Bairavabalakumar N, Chennai (IN); Karthika Nair, Bangalore (IN); Aswini Thanigaivel, Chennai (IN); Amol Maliwalave, Bangalore (IN); Bharath R Shenoy, Bangalore (IN); Rajeshwari Pendse, Bangalore (IN); Prabhat Kumar Pathak, Varanas (IN); Anisha Kurup, Delhi (IN); Sahana Bhima Rao, Bangalore (IN)

(73) Assignee: Zumutor Biologics Inc., San Francisco, CA (US)

( * ) Notice: Subject to any disclaimer, the term of this patent is extended or adjusted under 35 U.S.C. 154(b) by 269 days.

This patent is subject to a terminal disclaimer.

(21) Appl. No.: 16/921,491

(22) Filed: Jul. 6, 2020

(65) Prior Publication Data
US 2020/0339666 A1 Oct. 29, 2020

Related U.S. Application Data

(62) Division of application No. 15/526,971, filed as application No. PCT/IB2015/058777 on Nov. 13, 2015, now Pat. No. 10,752,674.

(30) Foreign Application Priority Data

Nov. 15, 2014 (IN) .............................. 5767CHE2014

(51) Int. Cl.
*C12N 15/63* (2006.01)
*C07K 16/06* (2006.01)
*C12N 15/113* (2010.01)
*C07K 16/00* (2006.01)
*A61K 48/00* (2006.01)
*C12N 5/07* (2010.01)
*C12N 5/16* (2006.01)
*C12N 15/10* (2006.01)

(52) U.S. Cl.
CPC ........ *C07K 16/065* (2013.01); *A61K 48/0016* (2013.01); *C07K 16/00* (2013.01); *C12N 5/0601* (2013.01); *C12N 5/163* (2013.01); *C12N 15/102* (2013.01); *C12N 15/1137* (2013.01); *C12Y 204/01068* (2013.01); *C12Y 402/01047* (2013.01); *C07K 2317/41* (2013.01); *C12N 2310/20* (2017.05)

(58) Field of Classification Search
CPC .. C07K 16/065; C07K 16/00; C07K 2317/41; C12N 5/0601; C12N 5/163; C12N 15/102; C12N 15/1137; C12N 2310/20; C12Y 204/01068; C12Y 402/01047
See application file for complete search history.

(56) References Cited

U.S. PATENT DOCUMENTS

| 10,752,674 B2 | 8/2020 | Prasad et al. |
| 2019/0112358 A1 | 4/2019 | Prasad et al. |

FOREIGN PATENT DOCUMENTS

| EP | 1 676 860 | 7/2006 |
| EP | 1 792 987 | 6/2007 |
| WO | WO 2003/035835 | 5/2003 |
| WO | WO 2012/120500 A2 | 9/2012 |
| WO | WO 2013/013013 | 1/2013 |
| WO | WO 2015/010114 | 1/2015 |
| WO | WO 2015/052231 | 4/2015 |

(Continued)

OTHER PUBLICATIONS

Campbell and Yarema, "Large-scale approaches for glycobiology," Genome Biol 6(11):236, Nov. 3, 2005.

(Continued)

*Primary Examiner* — Catherine S Hibbert
(74) *Attorney, Agent, or Firm* — Fish & Richardson P.C.

(57) ABSTRACT

The present disclosure relates to a method of obtaining a cell where fucosylation pathways are modified, leading to production of partially fucosylated and non-fucosylated protein products, specifically antibodies from the cell. The present disclosure employs the Clustered Regularly Interspaced Short Palindromic Repeats (CRISPR) technology. The method of the present disclosure targets the Fut8 gene and GMD gene in a cell. Such products are used in developing therapeutics and biomarkers, and in diagnosis and prognosis of diseases.

18 Claims, 55 Drawing Sheets

Specification includes a Sequence Listing.

(56) References Cited

FOREIGN PATENT DOCUMENTS

WO    WO 2016/075662      5/2016

OTHER PUBLICATIONS

GenBank Accession No. NM_001246696.1, "Cricetulus griseus GDP-mannose 4,6-dehydratase (Gmds), mRNA," dated May 9, 2014, 2 pages.

GenBank Accession No. NW_003613635.1, "Cricetulus griseus unplaced genomic scaffold, CriGri_1.0 scaffold833, whole genome shotgun sequence," dated Aug. 14, 2014, 2 pages.

GenBank Accession No. NW_003613860, "Cricetulus griseus unplaced genomic scaffold, CriGri_1.0 scaffold1390, whole genome shotgun sequence," dated Aug. 14, 2014, 2 pages.

GenBank Accession No. XM_003501735.1, "PREDICTED: Cricetulus griseus fucosyltransferase 8 (alpha (1,6) fucosyltransferase) (Fut8), transcript variant XI, mRNA," dated Apr. 30, 2014, 2 pages.

Harris et al., "Crystallographic Structure of an Intact IgGl Monoclonal Antibody," J Mol Biol 275(5):861-872, Feb. 6, 1998.

Helenius and Aebi, "Roles of N-Linked Glycans in the Endoplasmic Reticulum," Ann Rev Biochem 73(1):1019-1049, Jul. 2004.

International Preliminary Report on Patentability in Application No. PCT/IB2015/058777, dated Feb. 14, 2017, 12 pages.

International Search Report in Application No. PCT/IB2015/058777, dated May 23, 2016, 23 pages.

Kanada et al., "Establishment of a GDP-mannose 4,6-dehydratase (GMD) knockout host cell line: A new strategy for generating completely non-fucosylated recombinant therapeutics", J Biotech 130(3):300-310, Jun. 19, 2007.

Malphettes "Highly efficient deletion of FUT8 in CHO cell lines using zinc-finger nucleases yields cells that produce completely nonfucosylated antibodies," Biotechnology and Bioengineering 106(5):774-783, Aug. 1, 2010.

Miyoshi, "The α1-6-fucosyltransferase gene and its biological significance," Biochimica et Biophysica Acta (BBA)-General Subjects 1473(1):9-20, Dec. 17, 1999.

Niwa et al., "Defucosylated Chimeric Anti-CC Chemokine Receptor 4 IgGl with Enhanced Antibody-Dependent Cellular Cytotoxicity Shows Potent Therapeutic Activity to T-Cell Leukemia and Lymphoma," Cancer Res64(6):2127-33, Mar. 15, 2004.

Niwa et al., "Enhancement of the Antibody-Dependent Cellular Cytotoxicity of Low-Fucose IgGl is Independent of FcγRIIIa Functional Polymorphism," Clin Cancer Res 10(18):6248-6255, Sep. 15, 2004.

Radaev et al., "The Stucture of a Human Type III Fcγ Receptor in Complex with Fc*," J Biol Chem 276(19): 16469-16477, Jan. 31, 2001.

Ronda et al., "Accelerating genome editing in CHO cells using CRISPR Cas9 and CRISPy, a web-based target finding tool," Biotechnology and Bioengineering 111(8):1604-1616, Aug. 22, 2014.

Score report result for SEQ ID No. 41 to Heiman et al. of W02012120500-A2. Sep. 13, 2012 (Year: 2012).

Shields et al., "Lack of Fucose on Human IgGl N-Linked Oligosaccharide Improves Binding to Human FcγRIII and Antibody-dependent Cellular Toxicity," J Biol Chem 277(30):26733-26740, Jul. 26, 2002.

Shinkawa et al., "The Absence of Fucose but Not the Presence of Galactose or Bisecting N-Acetylglucosamine of Human IgGl Complex-type Oligosaccharides Shows the Critical Role of Enhancing Antibody-dependent Cellular Cytotoxicity," J Biological Chem 278(5):3466-3473, Jan. 31, 2003.

Webb et al., "Crystal structure of a tetrameric GDP-D-mannose 4,6-dehydratase from a bacterial GDP-D-rhamnose biosynthetic pathway," Protein Sci 13(2):529-539, Feb. 1, 2004.

Written Opinion in Application No. PCT/IB2015/058777, dated Dec. 13, 2016, 11 pages.

Yamane-Ohnuki et al., "Establishment of FUT8 knockout Chinese hamster ovary cells: An ideal host cell line for producing completely defucosylated antibodies with enhanced antibody-dependent cellular cytotoxicity," Biotechnol and Bioengin 87(5):614-622, Aug. 17, 2004.

MRAWTGSMRWIMLILFAWGTLLFYIGGHLVRDNDHPDHSSRELSKILAKLERLKQQNEDLRRMAESLRIPEGPID

QGTATGRVRVLEEQLVKAKEQIENYKQARNDLGKDHEILRRRIENGAKELWFFLOSELKLKKLEGNELQRHAD

EILLDLGHHERSIMTDLYYLSQTDGAGEWREKEAKDLTELVQRRITYLQNPKDCSKARKLVCNINKGCYGCQLH

HVVYCFMIAYGTQRTLILESQNWRYATGGWETVFRPVSETCTDRSGLSTGHWSGEVKDKNVQVELPIVDSLHPR

PPYLPLAVPEDLADRLLRVHGDPAVWMVSQFVKYLIRPQPWLEREIEETTKKLGFKHPVIGVHVRRTDKVGTEAA

FHPIEEYMVHVEEHFQLLERRMKVDKKRVYLATDDPSLLKEAKTKYSNYEFISDNSISWSAGLHNRYTENSLRGV

ILDIHFLSQADFLVCTFSSQVCRVAYEIMQTLHPDASANFHSLDDIYFGGQNAHNQIAVYPHQPRTKEEIPMEP

GDIIGVAGNHWNGYSKQVNRKLGKTGLYPSYKVREKIETVKYPTYPEAEK

FIG. 2A

CACCCAGCGAACACTCATCTTGGAATCTCAGAATTGGCGCTATGCTACTGGAGGATG
GTGGGTCGCTTGTGAGTAGAACCTTAGAGTCTTAACCGCGATACGATGACCTCCTAC

FIG. 3B

GACCTCACCGACAGCACCTGCCTAGTAAAATCATCAATGAAGTCAAACCTACAGAGA
CTGGAGTGGCTGTCGTGGACGGATCATTTTAGTAGTTACTTCAGTTTGGATGTCTCT

FIG. 4C

TGGAGTTGGCACCTTGCGGCTTCTGGATG
ACCTCAACCGTGGAACGCCGAAGACCTAC

FIG. 4D

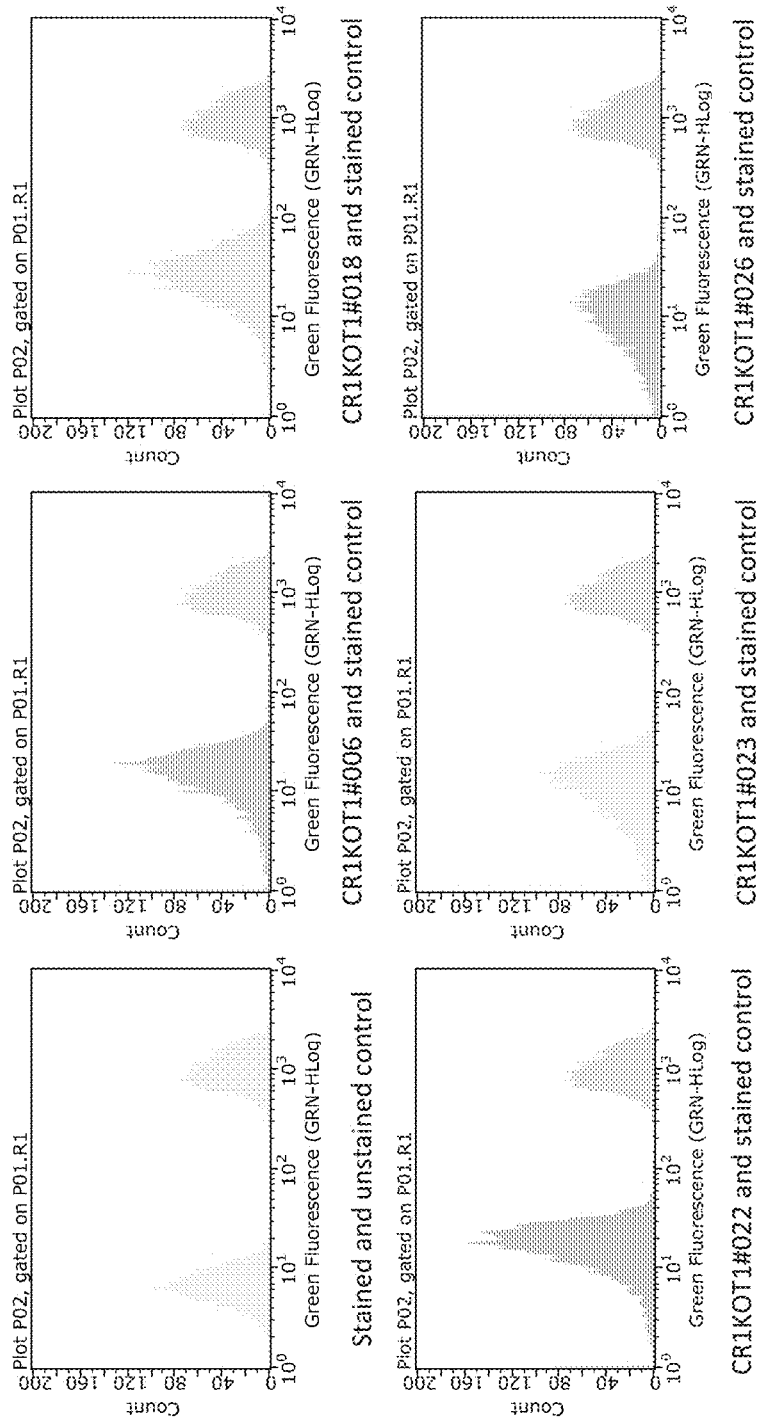
FIG. 8A – page 1

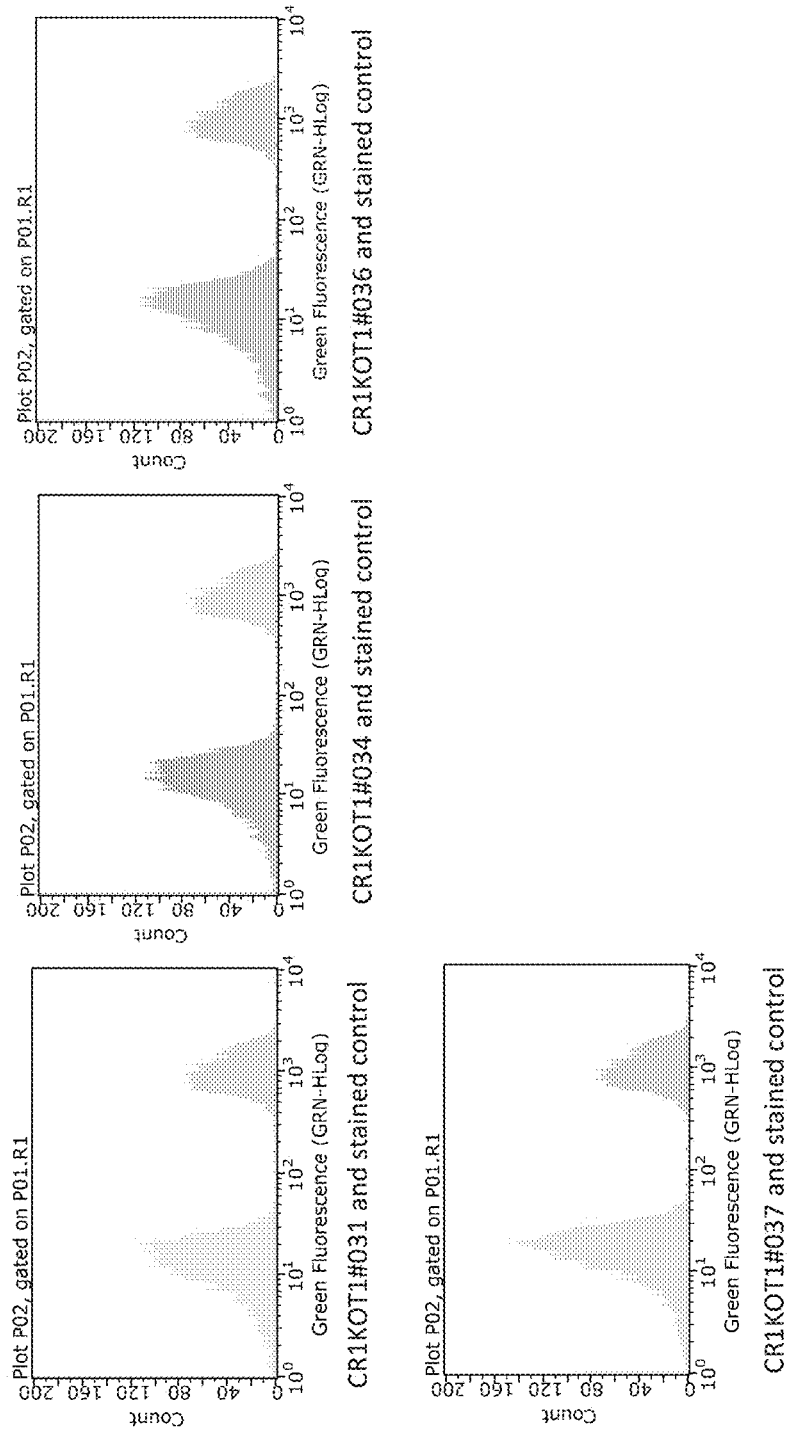
FIG. 8A – page 2

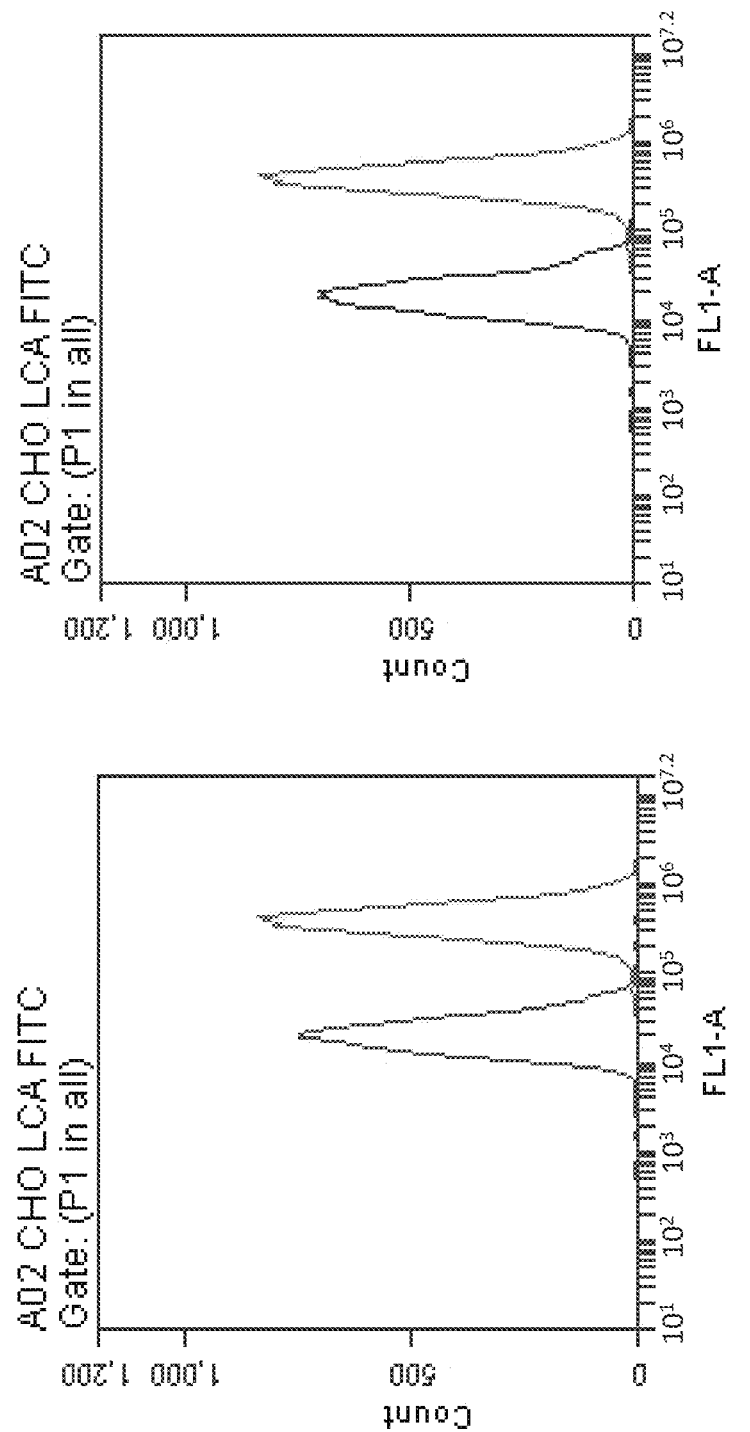
FIG. 8B – page 1

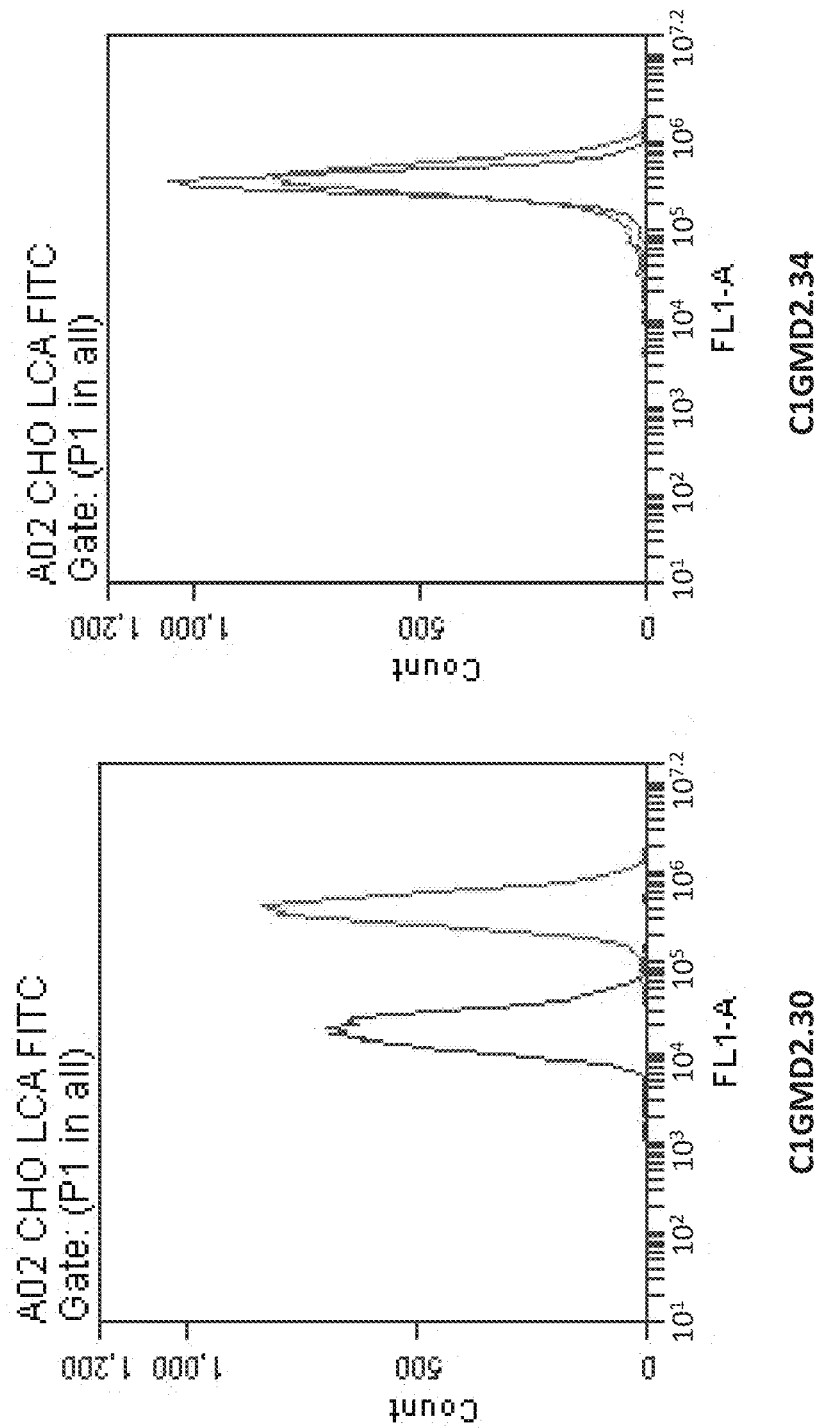
FIG. 8B – page 2

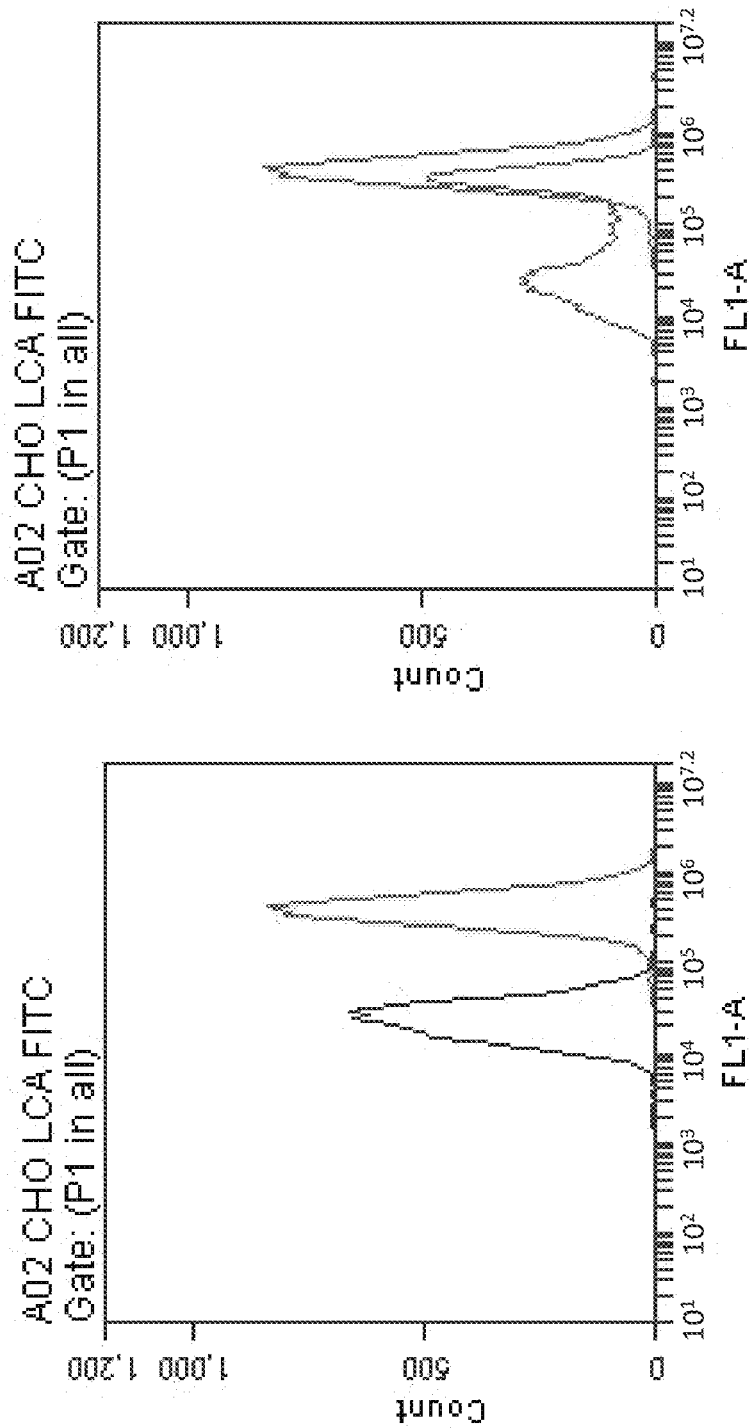
FIG. 8B – page 3

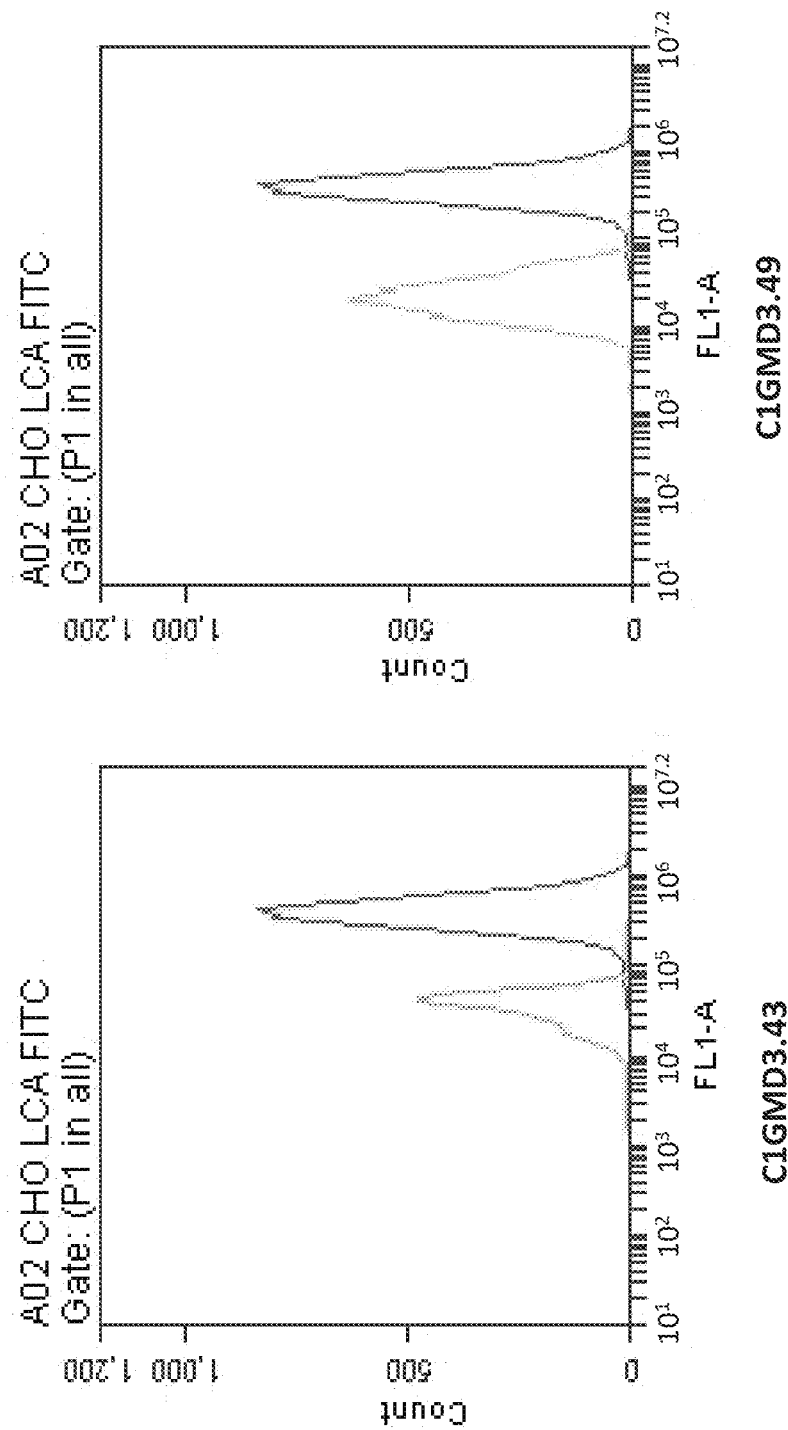
FIG. 8B – page 4

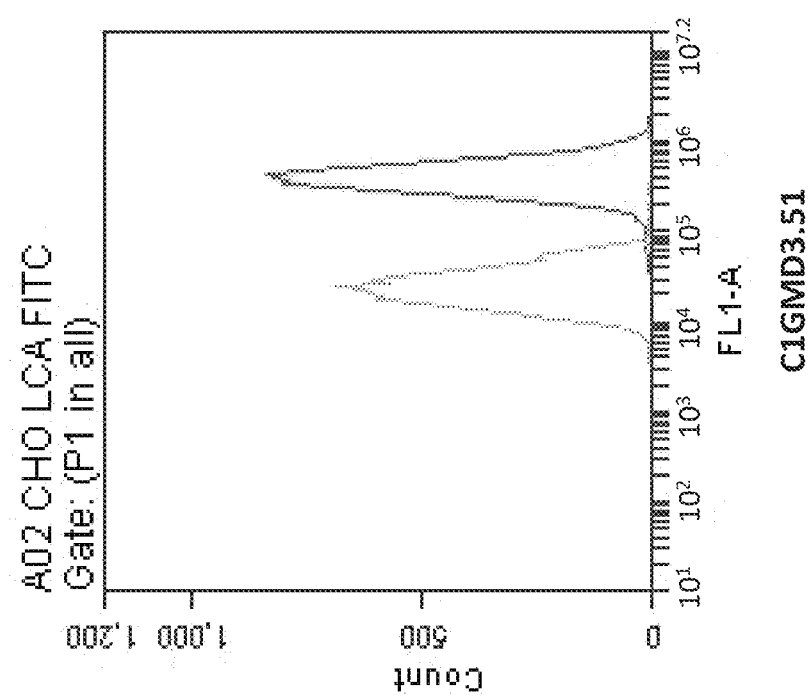
FIG. 8B – page 5

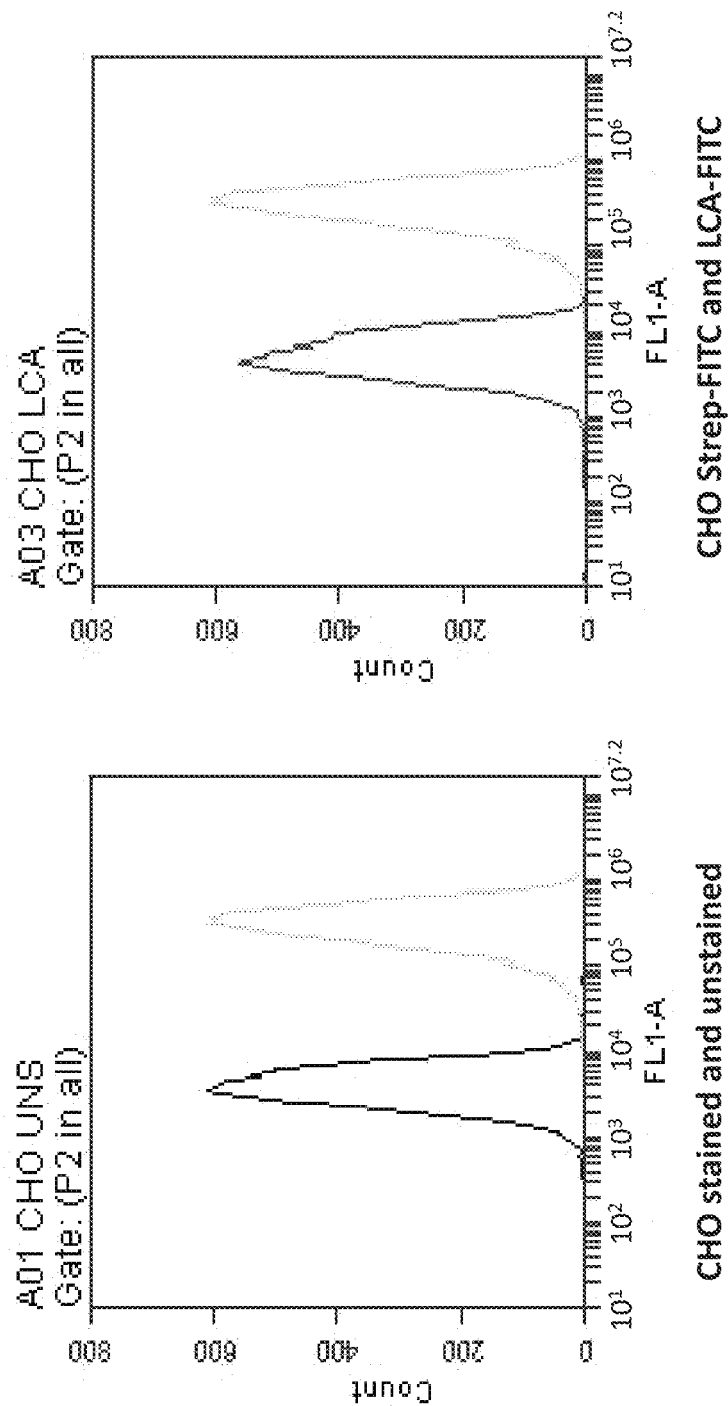
FIG. 8C – page 1

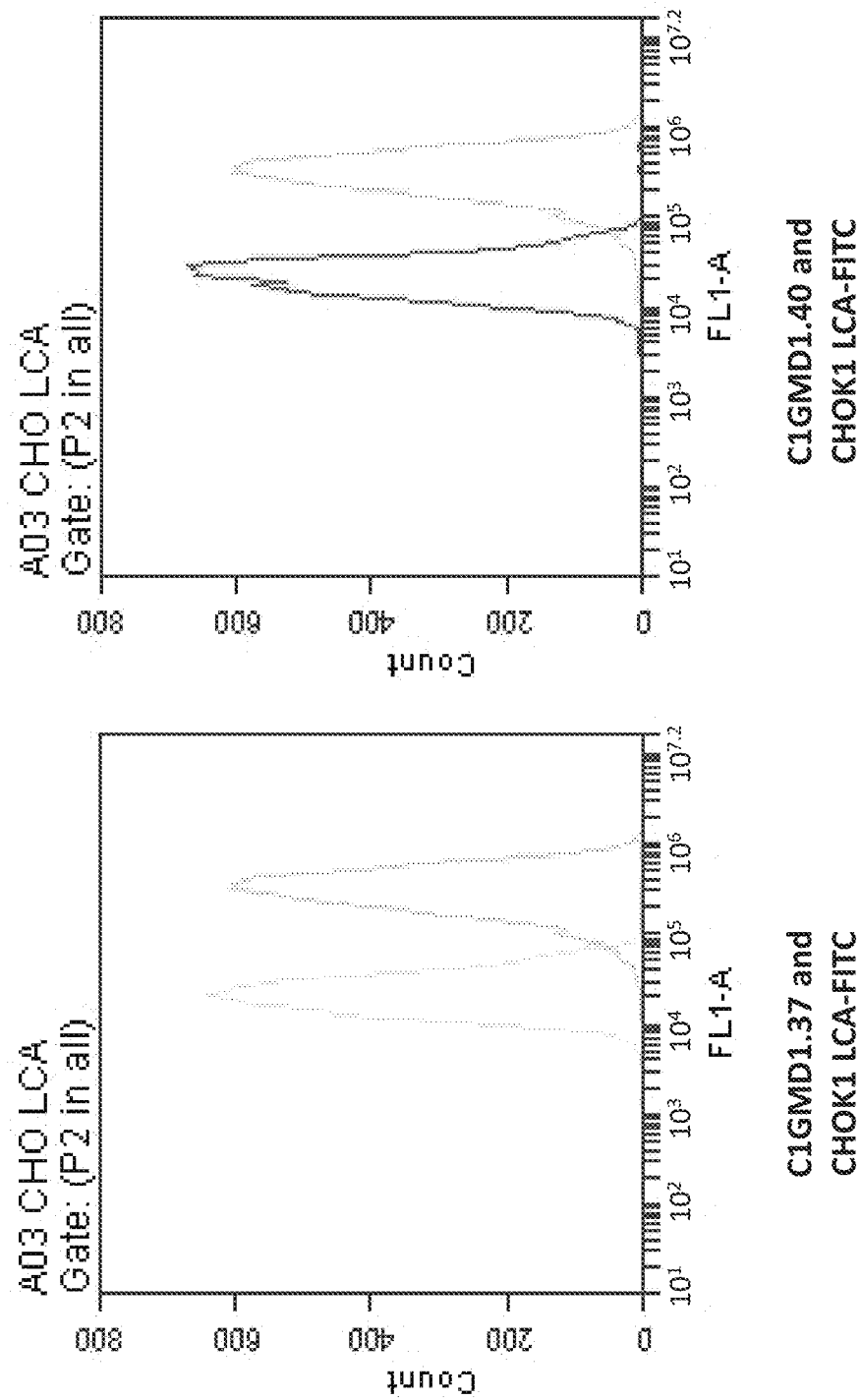
FIG. 8C – page 2

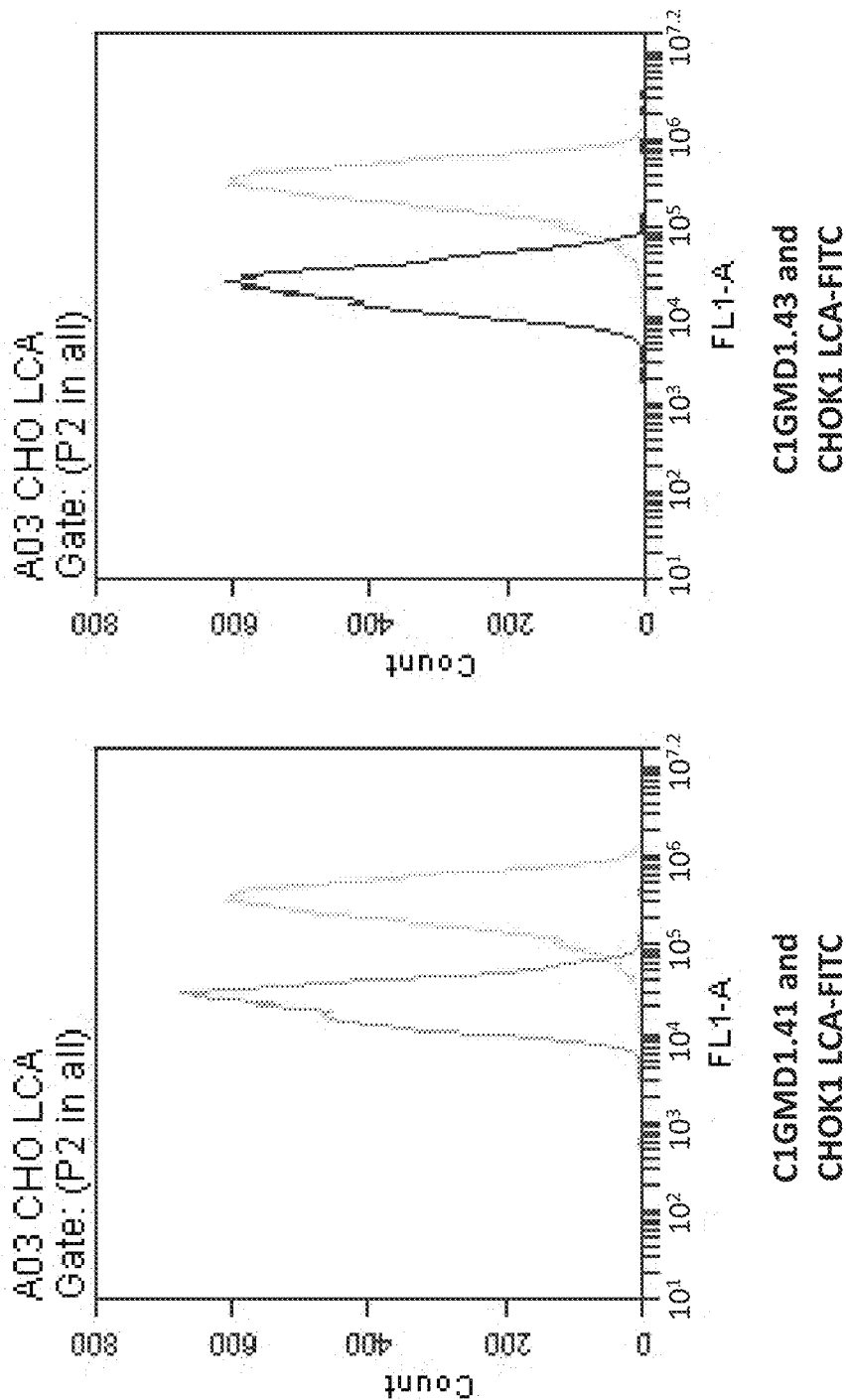
FIG. 8C – page 3

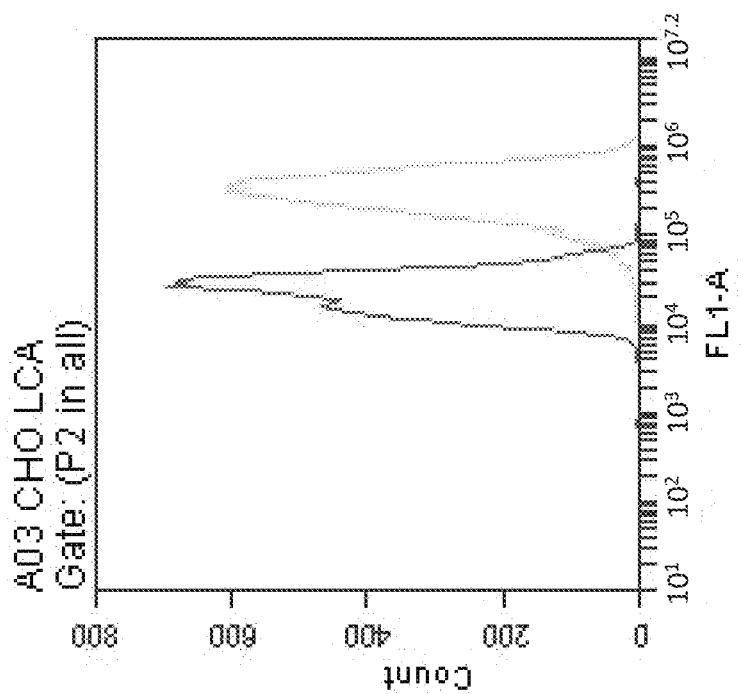
FIG. 8C – page 4

```
GMD Exon 3 control  ACATGAAGTT  GCACTATGGT  GACCTCACCG  ACAGCACCTG  CCTAGTAAAA   59
GMD 1.27            ACATGAAGTT  GCACTATGGT  GACCTCACCG  ACAGCACCTG  CCTAGT       46
GMD 1.43            ACATGAAGTT  TGGT        GACCTCACCG  ACAGCACCTG  CCTAGTAAAA  AATCATCAAT 44
GMD 1.44            ACATGAAGTT  GCACTATGGT  GACCTCACCG  A                                    32
GMD 1.41            TAGATCT     CTGTAGGTTT  GACTTCATTG                                       28

GMD Exon 3 control  GAAGTCAAAC  CTACAGAGAT  CTACAATCTT  GGTGCCCAGA  GCCATGTCAA  G 110
GMD 1.27            GAAGTCAAAC  CTACAGAGAT  CTACAATCTT  GGTGCCCAGA  GCCATGTCAA  G 97
GMD 1.43            GAAGTCAAAC  CTACAGAGAT  CTACAATCTT  GGTGCCCAGA  GCCATGTCAA  G 95
GMD 1.44            GAAGTCAAAC  CTACAGAGAT  CTACAATCTT  GGTGCCCAGA  GCCATGTCAA  G 83
GMD 1.41            TGAAGAT     CTACAATCTT  GGTGCCCAGA  GCCATGTCAA  G 66
```

FIG. 17I

```
GMD Exon 3 control  ACATGAAGTT  GCACTATGGT  GACCTCACCG  ACAGCACCTG  CAAAATGTCG   60
GMD 1.12            ACATGAAGTT  GCACTATGGT  GACCTCACCG  ACAGCACCTG  TGTTTTGGCA  CCAAAATCAA  CGGGACTTTC  CAAAATGTCG GMD Exon 3 control                                                                                    60
GMD 1.12            CGCAAATGGA  GAATGCCCA   GGGGATCGGC  CTGCCCCACT  TCTGGCGGG   CAGAAACAGC  GAGTGGCGCT  CGCAAGAGCG GMD Exon 3 control                                                                                    20
GMD 1.12            ATTGTTTGGT  GATGAACCGC  TGGGGCGGGT  TGGAAGGCTTA  AGGGACTGG  AGATGCAGGA  TTTGATTGTG  TCTAGTAAAA GMD Exon 3 control  TACAGAGATC  TACAATCTTG  GTGCCCAGAG  CCATGTCAAG  110
GMD 1.12            TACAGAGATC  TACAATCTTG  GTGCCCAGAG  CCATGTCAAG  340
```

```
GMD Exon 3 control  ACATGAAGTT  GCAACTATGGT  GACCCTCACCG  ACAGCACCTG  CCTAGTAAAA  ATCATC
        GMD 1.37  ACATGAAGTT  GCAACTATGGT  GACCCTCACCG  ACAGCACCTG  CCTAGTAAAA  ATCATCTGAC  ATCATC GMD Exon 3 control  GATCTACAAT  CTTGGTGCCC  AGAGGCATGT            CAAG 110
        GMD 1.37  GATCTACAAT  CTTGGTGCCC  AGAGGCATGT            CAAG 134
```

FIG. 17J

```
GMD Exon 4 Control  ATTTCCTTTG  ACTTAGCAGA  GTACACTGCA  GATGTTGATG                              
        GMD 2.30  ATTTCCTTTG  ACTTAGCAGA  GTACACTGCA  GATGTTGATG  AGTTGGCAC  CTTGCGGGTT  CTGGATGCAA  TTAAGACTTG
                                                                  AGTTGGCAC                  CTGGATGCAA  TTAAGACTTG GMD Exon 4 Control  AGTTCTACCA  GGGCTCAACT  AGTGAACTGT  ATGGAAAAGT  GCAAGAAATA  CCCCAGAAAG  AGACCACCCC  TTTCTATCCA
        GMD 2.30  AGTTCTACCA  GGGCTCAACT  AGTGAACTGT  ATGGAAAAGT  GCAAGAAATA  CCCCAGAAAG  AGACCACCCC  TTTCTATCCA
```

FIG. 17K

```
GMD Exon 4 Control  ATTTCCTTTG  ACTTAGCAGA  GTACACTGCA  GATGTTGATG                 GAGTTGGCAC  CTTGGGGGTT  CTGGATGCAA  TTAAGACTTG
    GMD 3.51 Exon4  ATTTCCTTTG  ACTTAGCAGA  GTACACTGCA  GATGTTGA                                              GACTTG GMD Exon 4 Control  AGTTCTACCA  GGGCTCAACT  AGTGAACTGT  ATGGAAAAGT  GCAAGAAATA  CCCCAGAAAG  AGACCACCCC  TTTCTATCCA
    GMD 3.51 Exon4  AGTTCTACCA  GGGCTCAACT  AGTGAACTGT  ATGGAAAAGT  GCAAGAAATA  CCCCAGAAAG  AGACCACCCC  TTTCTATCCA
```

```
CHOK1 control  NPKDCSKARK LVCNINKGCG YGCQLHHVVY CFMIAYGTQR TLILESQMWR YATGGMETVF RPVSETTCT DRSGLSTGHW S 79
CRIKOT1#018    NPKDCSKARK LVCNINKGCG YGCQLHHVVY CFMIAYGTQR TLILESQMWR YATGGMETVF RPVSETTCT DRSGLSTGHW S 71
CRIKOT1#044    NPKDCSKARK LVCNINKGCG YGCQLHHVVY CFMIAYGTQR TLIL      SGGMETVF  RPVSETTCT DRSGLSTGHW S 70
CRIKOT1#051    NPKDCSKARK LVCNINKGCG YGCQLHHVVY CFMIAYGTQR TLIL      ESVF     RPVSETTCT DRSGLSTGHW S 67
CRIKOT1#055    NPKDCSKARK LVCNINKGCG YGCQLHHVVY CFMIAYGTQR THL       RGISELALCY WRMGDCV* 80
CRIKOT1#057    NPKDCSKARK LVCNINKGCG YGCQLHHVVY CFMIA     HL         RGISELALCY WRMGDCV*  54
CRIKOT1#051    NPKDCSKARK LVCNINKGCG YGCQLHHVVY CFMIAYGTQI GAML      LEDGRLGL DL*  55
```

```
CHOK1 control  NPKDCSKARK LVCNINKGCG YGCQLHHVVY CFMIAYGTQR TLIL      ESQMW     RYATGGMETV FRPVSETLTD RGGLSTGHWS 79
CRIKOT1#02     NPKDCSKARK LVCNINKGCG YGCQLHHVVY CFMIAYGTQR TLILR     ESQMW     CTGGMETV  RPVSETCTD RGGLSTGHWS 81
CRIKOT1#22     NPKDCSKARK LVCNINKGCG YGCQLHHVVY CFMIAYGTQR TLIL      ESQMW     NLR       TD         PGLPDEH*  60
CRIKOT1#28     NPKDCSKARK LVCNINKGCG YGCQLHHVVY CFMIAYGTQR TLILESQMW NLR       IGAMLL    EGGRLCLOL*  70
CRIKOT1#29     NPKDCSKARK LVCNINKGCG YGCQLHHVVY CFMIAYGTQR TLILESQMW RFG       ISELALL   EGGRLCLOL*  69
CRIKOT1#23     NPKDCSKARK LVCNINKGCG YGCQLHHVVY CFMIAYGTQR TLDI      GKN*                           48
CRIKOT1#37     NPKDCSKARK LVCNINKGCG YGCQLHHVVY CFMIAYGT   LILGA     ATQIALCYW RMGD                 V* 62
```

```
GMD Exon 3 control  MKLHYGDLTD STCLVKIINE VKPTEIYNLG AQSHVK 36
GMD 1.44            MKLHYGDLTD           E  KIINE VKPTEIYNLG AQSHVK 27
GMD 1.43            VTSPTAPA*              KIINE VKPTEIYNLG AQSHVK 31
GMD 1.27            MKLHYGDLTD STCLVK  SN LQRSTILVPR AMS     31
GMD 1.41            *IS                 VGL TSLMKIYNLG AQSHVK 22
```

FIG. 18C

```
GMD Exon 3 control  MKLHYGDLTD STCLV------ ------KIINEVK PTEIYN---- ---------- ----------    28
GMD 1.12            MKLHYGDLTD STCVLAPKST GLSKMS**PR PVDANGESRR GMACRTFWRA ETASGAGKSV    60

GMD Exon 3 control  ---------- ---------- ---------- -L GAQSHVK                            36
GMD 1.12            DSSTGIIVA* *TARGAGRLN ATRDAGFDCV **KSSMKSNL QRSTILVPRA MS           112
```

FIG. 18D

```
GMD Exon 3 control  MKLHYGDLTD STCLVKII-- ---------- NEVK PTEIYNLGAQ SHVK              36
GMD 1.37            MKLHYGDLTD STCLVKII*P FGRKTINEVK PTEIYNLGAQ SHVK                   44
```

FIG. 18E

```
GMA Exon4 Control   ISFDLAEYTA DVDGVGTLRL ------LDAIKTC GLINSVKFYQ ASTSELYGKV QEIPQKETTP    57
GMD 2.30            ISFDLAEYTA DVDGVGTSSG NDLWPYKFC EVLPGL   NTVWKSA RNTPKRDH**P     54
```

FIG. 18F

```
GMA Exon4 Control   ISFDLAEYTA DVDGVGTLRL LDAIKTCGLI NSVKFYQAST SELYGKVQEI PQKETTPFYP    60
GMD 3.51 Exon 4     IS------DAYTA DVE---------- ---TCGLI NSVKFYQAST SELYGKVQEI PQKETTPFYP    45

GMA Exon4 Control   RSPY                                                                  64
GMD 3.51 Exon 4     RSPY                                                                  49
```

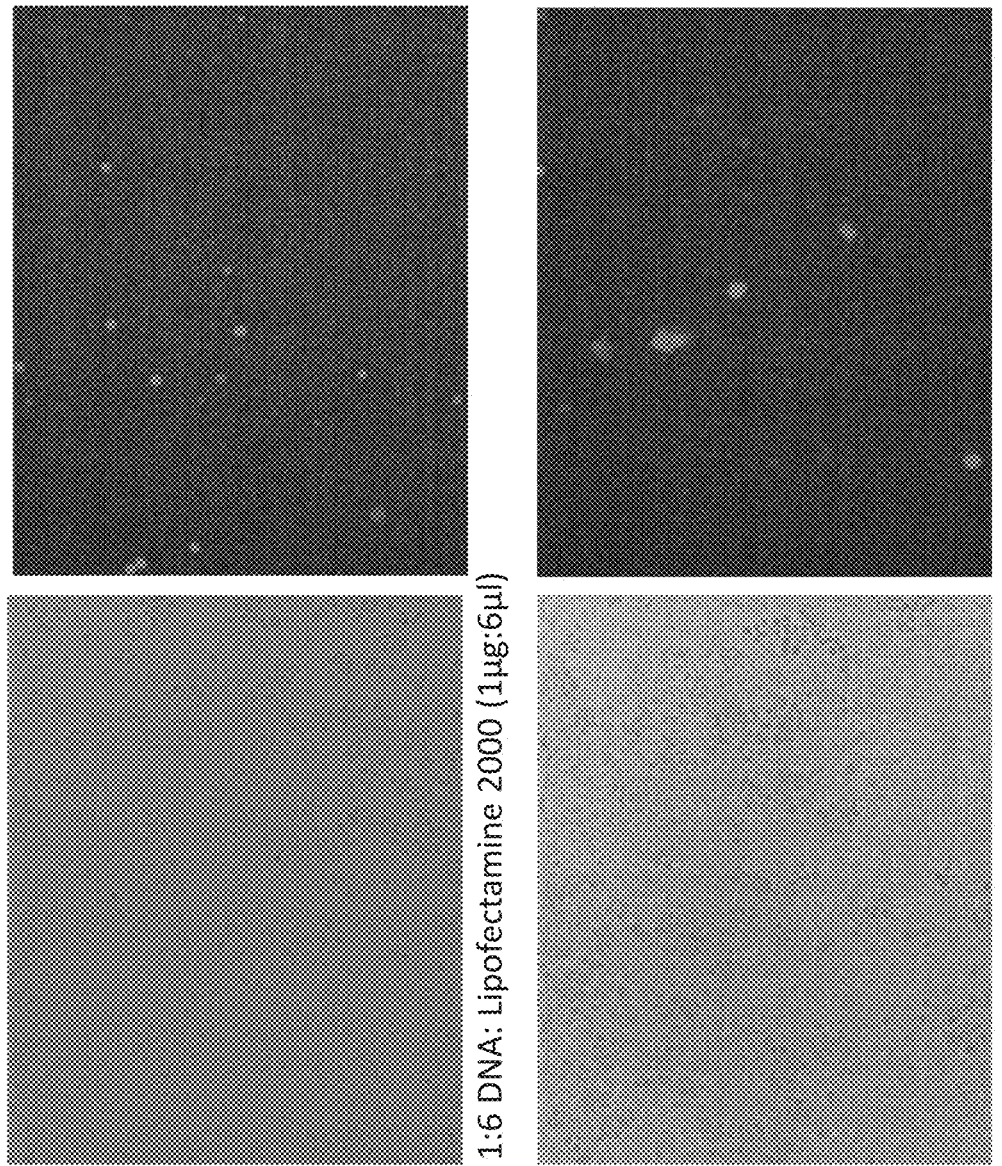
FIG. 20 – page 1

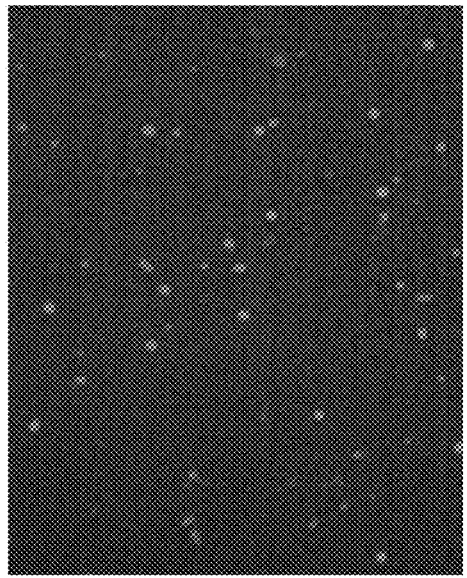
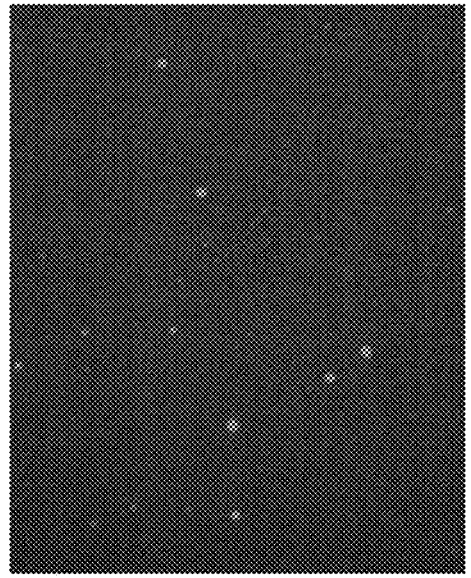
1:3 DNA: Lipofectamine 2000 (2µg:6µl)
1:2.4 DNA: Lipofectamine 2000 (2.5µg:6µl)
FIG. 20 – page 2

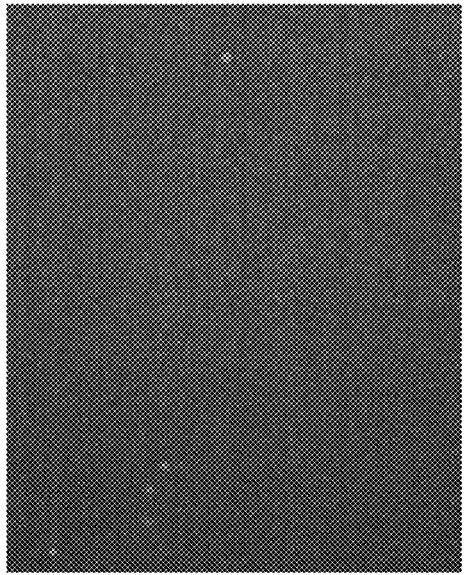
FIG. 20 – page 3

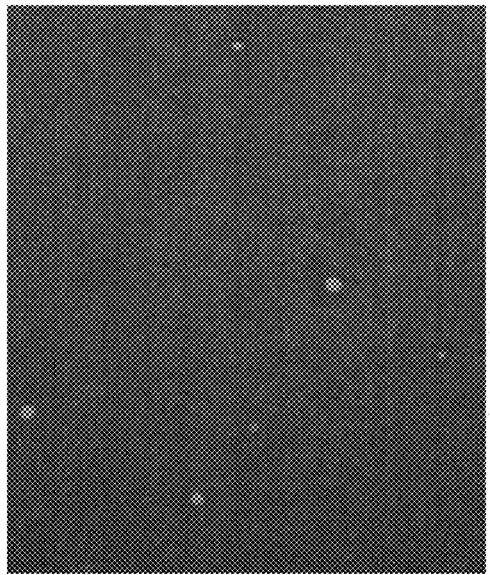
1:3 DNA: Mirus Trans IT CHO transfection kit (2.5µg:7.5µl) with 1.25µl CHO Mojo reagent)
1:3 DNA: Mirus Trans IT X2 (2.5µg:7.5µl)
FIG. 20 – page 4

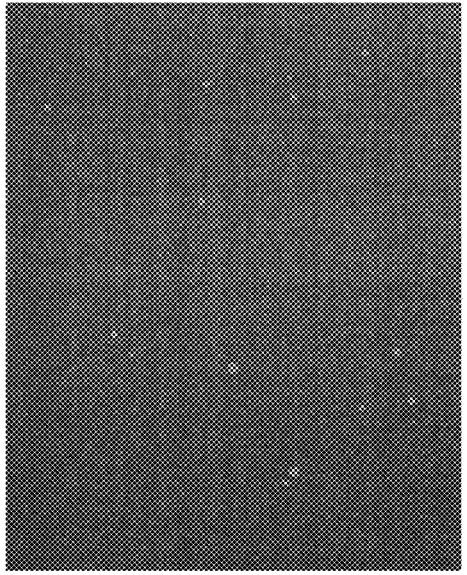
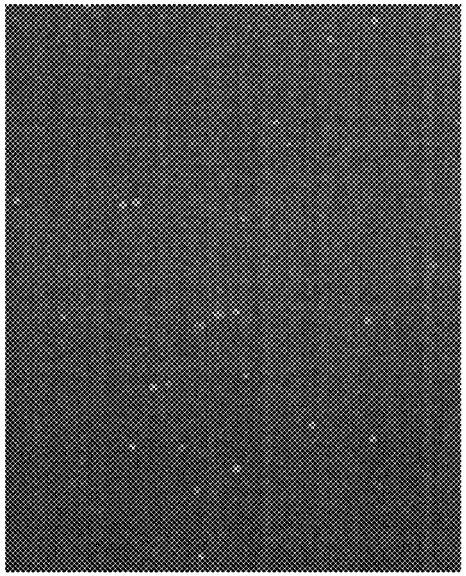
1:3 DNA: Lipofectamine 3000 (2.5µg:7.5µl)
1:3 DNA: Lipofectamine LTX (2.5µg:7.5µl)
FIG. 20 – page 5

SEQUENCE LISTING

```
<160> NUMBER OF SEQ ID NOS: 151

<210> SEQ ID NO 1
<211> LENGTH: 3126
<212> TYPE: DNA
<213> ORGANISM: Cricetulus griseus
<220> FEATURE:
<221> NAME/KEY: mRNA
<222> LOCATION: (1)..(3126)
<223> OTHER INFORMATION: Cricetulus griseus Fut8 mRNA

<400> SEQUENCE: 1
caggttgctg ctctggctta ggccatctat gaccctggtg gtgttttcat tcactataag      60
tccttcccat ctttattaac tgagcaagtt cagctagtaa ttttagagac cgaggttcaa     120
gcaataacac ctatctctgc aataccgtgt ggctttcttc aatgtcttac atcctaagga     180
aaggaagcat gtagagccca ggaagcacag gacaagaaag ctgcctcctt gtatcaccag     240
gaagatcttt ttgtaagagt catcacagta taccagagag actaattttg tctgaagcat     300
catgtgttga aacaacagaa acttattttc ctgtgtggct aactagaacc agagtacaat     360
gtttccaatt ctttgagctc cgagaagaca gaagggagtt gaaactctga aaatgcgggc     420
atggactggt tcctggcgtt ggattatgct cattcttttt gcctggggga ccttattgtt     480
ttatataggt ggtcatttgg ttcgagataa tgaccaccct gaccattcta gcagagaact     540
ctccaagatt cttgcaaagc tggagcgctt aaaacaacaa aatgaagact tgaggagaat     600
ggctgagtct ctccgaatac cagaaggccc tattgatcag gggacagcta caggaagagt     660
ccgtgtttta gaagaacagc ttgttaaggc caaagaacag attgaaaatt acaagaaaca     720
agctaggaat gatctgggaa aggatcatga aatcttaagg aggaggattg aaaatggagc     780
taaagagctc tggttttttc tacaaagtga attgaagaaa ttaaagaaat tagaaggaaa     840
cgaactccaa agacatgcag atgaaattct tttggattta ggacatcatg aaaggtctat     900
catgacagat ctatactacc tcagtcaaac agatggagca ggtgagtggc gggaaaaaga     960
agccaaagat ctgacagagc tggtccagcg gagaataaca tatctgcaga atcccaagga    1020
ctgcagcaaa gccagaaagc tggtatgtaa tatcaacaaa ggctgtggct atggatgtca    1080
actccatcat gtggtttact gcttcatgat tgcttatggc acccagcgaa cactcatctt    1140
```

```
ggaatctcag aattggcgct atgctactgg aggatgggag actgtgttta gacctgtaag    1200
tgagacatgc acagacaggt ctggcctctc cactggacac tggtcaggtg aagtgaagga    1260
caaaaatgtt caagtggtcg agctccccat tgtagacagc ctccatcctc gtcctcctta    1320 cttaccttg gctgtaccag aagaccttgc agatcgactc ctgagagtcc atggtgatcc     1380
tgcagtgtgg tgggtatccc agtttgtcaa atacttgatc cgtccacaac cttggctgga    1440
aagggaaata aagaaaccca ccaagaagct tggcttcaaa catccagtta ttggagtcca    1500
tgtcagacgc actgacaaag tgggaacaga agcagccttc catcccattg aggaatacat    1560
ggtacacgtt gaagaacatt ttcagcttct cgaacgcaga atgaaagtgg ataaaaaaag    1620
agtgtatctg gccactgatg acccttcttt gttaaaggag gcaaagacaa agtactccaa    1680
ttatgaattt attagtgata actctatttc ttggtcagct ggactacaca accgatacac    1740
agaaaattca cttcggggcg tgatcctgga tatacacttt ctctcccagg ctgacttcct    1800
tgtgtgtact ttttcatccc aggtctgtag ggttgcttat gaaatcatgc aaacactgca    1860
tcctgatgcc tctgcaaact tccattcttt agatgacatc tactattttg gaggccaaaa    1920
tgcccacaac cagattgcag tttatcctca ccaacctcga actaaagagg aaatccccat    1980
ggaacctgga gatatcattg tgtggctgga aaaccattgg aatggttact ctaaaggtgt    2040
caacagaaaa ctaggaaaaa caggcctgta cccttcctac aaagtccgag agaagataga    2100
aacagtcaaa taccctacat atcctgaagc tgaaaaatag agatggagtg taagagatta    2160
acaacagaat ttagttcaga ccatctcagc caagcagaag acccagacta acatatggtt    2220
cattgacaga catgctccgc accaagagca agtgggaacc ctcagatgct gcactggtgg    2280
aacgcctctt tgtgaagggc tgctgtgccc tcaagcccat gcacagtaaa ataatgtact    2340
cacacataac atacaaatgg attatttttct actttgccct ttaaatattc tgtccccatg    2400
aaacaaacac tgccacatta tgtaatttaa gtgacacaga cgttttgtgt gagacttcaa    2460
acatggtgcc tatatctgag agacctctgt gattactga gaagatgaga acagctccct     2520
tctgtgggga agttggttct tagtcagtgg tggactggcc actgaattca ctgcaatcaa    2580
cagattcaga atgagaatgg atgttttccc tttatatggt tgtctggatt tttttttaaag   2640 taatttcatc agttcagttc atccacctca ttaataaatg aaggaatata ccaataaaat    2700
caaatgaaat attcactgtc cattaggaag ttttataaaa caatgccatg aacaaaaaat    2760
tctttagtac tcaatgtttc tggacattct ctttgataac aaaaataaat tttaaaaagg    2820
aattttgtaa agtttctggg attctgtatc actggatgat gtagttataa gctttgtagt    2880
agaaatatgg gaagtgggtt tatagctttt aagattttt tctacttttg tcctacttt      2940 tctatttctg atagaataat catatttcaa gagaagcatt ggtcccctct aatactagta    3000
actgccttta gtcatgcata ttatatgaag ttgctaagaa cacgctttgg gggaggtgtt    3060
cactctctta gtttgatatt gttgacttga tataattgaa tgaaatagtc attctcttgc    3120
ttccag                                                               3126
```

<210> SEQ ID NO 2
<211> LENGTH: 1360
<212> TYPE: DNA
<213> ORGANISM: Cricetulus griseus
<220> FEATURE:
<221> NAME/KEY: mRNA
<222> LOCATION: (1)..(1360)
<223> OTHER INFORMATION: Cricetulus griseus GMD mRNA

<400> SEQUENCE: 2

```
ccaggatggc tcatacttgg cagaattcct gctggagaaa ggatacgagg ttcatggaat      60
tgtacggcga tccagttcat ttaatacagg tcgaattgaa catttatata agaatccaca     120
ggctcatatt gaaggaaaca tgaagttgca ctatggtgac ctcaccgaca gcacctgcct     180
agtaaaaatc atcaatgaag tcaaacctac agagatctac aatcttggtg cccagagcca     240
tgtcaagatt cctttgact tagcagagta cactgcagat gttgatggag ttggcacctt      300
gcggcttctg gatgcaatta agacttgtgg cctt ataaat tctgtgaagt tctaccaggc    360
ctcaactagt gaactgtatg gaaaagtgca agaaataccc cagaaagaga ccaccccttt     420
ctatccaagg tcgccctatg gagcagccaa acttttatgcc tattggattg tagtgaactt    480
tcgagaggct tataatctct ttgcggtgaa cggcattctc ttcaatcatg agagtcctag     540
aagaggagct aattttgtta ctcgaaaaat tagccggtca gtagctaaga tttaccttgg     600
acaactggaa tgtttcagtt tgggaaatct ggacgccaaa cgagactggg gccatgccaa     660
ggactatgtc gaggctatgt ggctgatgtt acaaaatgat gaaccagagg actttgtcat     720
agctactggg gaagttcata gtgtccgtga atttgttgag aaatcattca tgcacattgg     780
aaagaccatt gtgtgggaag aaagaatga aaatgaagtg ggcagatgta agagaccgg      840 caaaattcat gtgactgtgg atctgaaata ctaccgacca actgaagtgg acttcctgca    900
gggagactgc tccaaggcgc agcagaaact gaactggaag ccccgcgttg cctttgacga    960
gctggtgagg gagatggtgc aagccgatgt ggagctcatg agaaccaacc ccaacgcctg   1020
agcacctcta caaaaaattc gcgagacatg gactatggtg cagagccagc caaccagagt   1080
ccagccactc ctgagaccat cgaccataaa ccctcgactg cctgtgtcgt ccccacagct   1140
aagagctggg ccacaggttt gtgggcacca ggacggggac actccagagc taaggccact   1200
tcgcttttgt caaaggctcc tctgaatgat tttgggaaat caagaagttt aaaatcacat   1260
actcatttta cttgaaatta tgtcactaga caacttaaat ttttgagtct tgagattgtt   1320 tttctcttt cttattaaat gatctttcta tgaaccagca                           1360

<210> SEQ ID NO 3
<211> LENGTH: 4101
<212> TYPE: DNA
<213> ORGANISM: Streptococcus pyogenes
<220> FEATURE:
<221> NAME/KEY: gene
<222> LOCATION: (1)..(4101)
<223> OTHER INFORMATION: Cas9 nucleotide sequence

<400> SEQUENCE: 3
gacaagaagt acagcatcgg cctggacatc ggcaccaact ctgtgggctg ggccgtgatc      60
accgacgagt acaaggtgcc cagcaagaaa ttcaaggtgc tgggcaacac cgaccggcac     120
agcatcaaga agaacctgat cggagccctg ctgttcgaca cggcgaaac agccgaggcc      180 acccggctga agagaaccgc cagaagaaga taccaccgac ggaagaaccg gatctgctat    240
ctgcaagaga tcttcagcaa cgagatggcc aaggtggacg acagcttctt ccacagactg     300
gaagagtcct tcctggtgga agaggataag aagcacgagc ggcaccccat cttcggcaac     360
atcgtggaca aggtggccta ccacgagaag taccccacca tctaccacct gagaaagaaa     420
ctggtggaca gcaccgacaa ggccgacctg cggctgatct atctggccct ggcccacatg     480
atcaagttcc ggggccactt cctgatcgag ggcgacctga accccgacaa cagcgacgtg     540
gacaagctgt tcatccagct ggtgcagacc tacaaccagc tgttcgagga aaaccccatc     600
```

```
aacgccagcg gcgtggacgc caaggccatc ctgtctgcca gactgagcaa gagcagacgg    660
ctggaaaatc tgatcgccca gctgcccggc gagaagaaga atggcctgtt cggaaacctg    720
attgccctga gcctgggcct gacccccaac ttcaagagca acttcgacct ggccgaggat    780
gccaaactgc agctgagcaa ggacacctac gacgacgacc tggacaacct gctggcccag    840
atcggcgacc agtacgccga cctgtttctg gccgccaaga acctgtccga cgccatcctg    900
ctgagcgaca tcctgagagt gaacaccgag atcaccaagg cccccctgag cgcctctatg    960
atcaagagat acgacgagca ccaccaggac ctgaccctgc tgaaagctct cgtgcggcag   1020
cagctgcctg agaagtacaa agagatttt ttcgaccaga gcaagaacgg ctacgccggc   1080
tacattgacg gcggagccag ccaggaagag ttctacaagt catcaagcc catcctggaa   1140 aagatggacg gcaccgagga actgctcgtg aagctgaaca gagaggacct gctgcggaag   1200
cagcggacct tcgacaacgg cagcatcccc caccagatcc acctgggaga gctgcacgcc   1260
attctgcggc ggcaggaaga ttttacccca ttcctgaagg acaaccggga aaagatcgag   1320
aagatcctga ccttccgcat ccctactac gtgggccctc tggccagggg aaacagcaga   1380
ttcgcctgga tgaccagaaa gagcgaggaa accatcaccc cctggaactt cgaggaagtg   1440
gtggacaagg gcgcttccgc ccagagcttc atcgagcgga tgaccaactt cgataagaac   1500
ctgcccaacg agaaggtgct gcccaagcac agcctgctgt acgagtactt caccgtgtat   1560
aacgagctga ccaaagtgaa atacgtgacc gagggaatga gaaagcccgc cttcctgagc   1620
ggcgagcaga aaaaggccat cgtggacctg ctgttcaaga ccaaccggaa agtgaccgtg   1680
aagcagctga aagaggacta cttcaagaaa atcgagtgct tcgactccgt ggaaatctcc   1740
ggcgtggaag atcggttcaa cgcctccctg ggcacatacc acgatctgct gaaaattatc   1800
aaggacaagg acttcctgga caatgaggaa acgaggaca ttctggaaga tatcgtgctg   1860
accctgacac tgtttgagga cagagagatg atcgaggaac ggctgaaaac ctatgcccac   1920
ctgttcgacg acaaagtgat gaagcagctg aagcggcgga gatacaccgg ctggggcagg   1980
ctgagccgga agctgatcaa cggcatccgg gacaagcagt ccggcaagac aatcctggat   2040
ttcctgaagt ccgacggctt cgccaacaga aacttcatgc agctgatcca cgacgacagc   2100 ctgacctta aagaggacat ccagaaagcc caggtgtccg gccagggcga tagcctgcac   2160
gagcacattg ccaatctggc cggcagcccc gccattaaga agggcatcct gcagacagtg   2220
aaggtggtgg acgagctcgt gaaagtgatg ggccggcaca gcccgagaa catcgtgatc   2280 gaaatggcca gagagaacca gaccacccag aagggacaga gaacagccg cgagagaatg   2340 aagcggatcg aagagggcat caaagagctg ggcagccaga tcctgaaaga acaccccgtg   2400
gaaaacaccc agctgcagaa cgagaagctg tacctgtact acctgcagaa tgggcgggat   2460
atgtacgtgg accaggaact ggacatcaac cggctgtccg actacgatgt ggaccatatc   2520
gtgcctcaga gctttctgaa ggacgactcc atcgacaaca aggtgctgac cagaagcgac   2580
aagaaccggg gcaagagcga caacgtgccc tccaagagg tcgtgaagaa gatgaagaac   2640
tactggcggc agctgctgaa cgccaagctg attacccaga gaaagttcga caatctgacc   2700
aaggccgaga gaggcggcct gagcgaactg gataaggccg gcttcatcaa gagacagctg   2760
gtggaaaccc ggcagatcac aaagcacgtg gcacagatcc tggactcccg gatgaacact   2820
aagtacgacg agaatgacaa gctgatccgg gaagtgaaag tgatcaccct gaagtccaag   2880
ctggtgtccg attccggaa ggatttccag ttttacaaag tgcgcgagat caacaactac   2940
caccacgccc acgacgccta cctgaacgcc gtcgtgggaa ccgccctgat caaaaagtac   3000
```

-continued

```
cctaagctgg aaagcgagtt cgtgtacggc gactacaagg tgtacgacgt gcggaagatg    3060
atcgccaaga gcgagcagga aatcggcaag gctaccgcca agtacttctt ctacagcaac    3120
atcatgaact ttttcaagac cgagattacc ctggccaacg gcgagatccg aagcggcct    3180
ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga cagcgataa gctgatcgcc    3360
agaaagaagg actgggaccc taagaagtac ggcggcttcg acagccccac cgtggcctat    3420
tctgtgctgg tggtggccaa gtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780
cacaagcact acctggacga gatcatcgag cagatcagcg agttctccaa gagagtgatc    3840
ctggccgacg ctaatctgga caaagtgctg tccgcctaca caagcaccg ggataagccc    3900
atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga c                                              4101
```

<210> SEQ ID NO 4
<211> LENGTH: 1367
<212> TYPE: PRT
<213> ORGANISM: Streptococcus pyogenes
<220> FEATURE:
<221> NAME/KEY: PEPTIDE
<222> LOCATION: (1)..(1367)
<223> OTHER INFORMATION: Cas9 amino acid sequence

<400> SEQUENCE: 4

```
Asp Lys Lys Tyr Ser Ile Gly Leu Asp Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
```

```
            145                 150                 155                 160
        Ile Lys Phe Arg Gly His Phe Leu Ile Glu Gly Asp Leu Asn Pro Asp
                        165                 170                 175
        Asn Ser Asp Val Asp Lys Leu Phe Ile Gln Leu Val Gln Thr Tyr Asn
                        180                 185                 190
        Gln Leu Phe Glu Glu Asn Pro Ile Asn Ala Ser Gly Val Asp Ala Lys
                        195                 200                 205
        Ala Ile Leu Ser Ala Arg Leu Ser Lys Ser Arg Arg Leu Glu Asn Leu
        210                 215                 220
        Ile Ala Gln Leu Pro Gly Glu Lys Lys Asn Gly Leu Phe Gly Asn Leu
        225                 230                 235                 240
        Ile Ala Leu Ser Leu Gly Leu Thr Pro Asn Phe Lys Ser Asn Phe Asp
                        245                 250                 255
        Leu Ala Glu Asp Ala Lys Leu Gln Leu Ser Lys Asp Thr Tyr Asp Asp
                        260                 265                 270
        Asp Leu Asp Asn Leu Leu Ala Gln Ile Gly Asp Gln Tyr Ala Asp Leu
                        275                 280                 285
        Phe Leu Ala Ala Lys Asn Leu Ser Asp Ala Ile Leu Leu Ser Asp Ile
        290                 295                 300
        Leu Arg Val Asn Thr Glu Ile Thr Lys Ala Pro Leu Ser Ala Ser Met
        305                 310                 315                 320
        Ile Lys Arg Tyr Asp Glu His His Gln Asp Leu Thr Leu Leu Lys Ala
                        325                 330                 335
        Leu Val Arg Gln Gln Leu Pro Glu Lys Tyr Lys Glu Ile Phe Phe Asp
                        340                 345                 350
        Gln Ser Lys Asn Gly Tyr Ala Gly Tyr Ile Asp Gly Gly Ala Ser Gln
                        355                 360                 365
        Glu Glu Phe Tyr Lys Phe Ile Lys Pro Ile Leu Glu Lys Met Asp Gly
                        370                 375                 380
        Thr Glu Glu Leu Leu Val Lys Leu Asn Arg Glu Asp Leu Leu Arg Lys
        385                 390                 395                 400
        Gln Arg Thr Phe Asp Asn Gly Ser Ile Pro His Gln Ile His Leu Gly
                        405                 410                 415
        Glu Leu His Ala Ile Leu Arg Arg Gln Glu Asp Phe Tyr Pro Phe Leu
                        420                 425                 430
        Lys Asp Asn Arg Glu Lys Ile Glu Lys Ile Leu Thr Phe Arg Ile Pro
                        435                 440                 445
        Tyr Tyr Val Gly Pro Leu Ala Arg Gly Asn Ser Arg Phe Ala Trp Met
                        450                 455                 460
        Thr Arg Lys Ser Glu Glu Thr Ile Thr Pro Trp Asn Phe Glu Glu Val
        465                 470                 475                 480
        Val Asp Lys Gly Ala Ser Ala Gln Ser Phe Ile Glu Arg Met Thr Asn
                        485                 490                 495
        Phe Asp Lys Asn Leu Pro Asn Glu Lys Val Leu Pro Lys His Ser Leu
                        500                 505                 510
        Leu Tyr Glu Tyr Phe Thr Val Tyr Asn Glu Leu Thr Lys Val Lys Tyr
                        515                 520                 525
        Val Thr Glu Gly Met Arg Lys Pro Ala Phe Leu Ser Gly Glu Gln Lys
                        530                 535                 540
        Lys Ala Ile Val Asp Leu Leu Phe Lys Thr Asn Arg Lys Val Thr Val
        545                 550                 555                 560
        Lys Gln Leu Lys Glu Asp Tyr Phe Lys Lys Ile Glu Cys Phe Asp Ser
                        565                 570                 575
```

```
Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
            900                 905                 910

Ala Gly Phe Ile Lys Arg Gln Leu Val Glu Thr Arg Gln Ile Thr Lys
        915                 920                 925

His Val Ala Gln Ile Leu Asp Ser Arg Met Asn Thr Lys Tyr Asp Glu
    930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
            980                 985                 990
```

```
Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 5
<211> LENGTH: 4101
<212> TYPE: DNA
```

<213> ORGANISM: Streptococcus pyogenes
<220> FEATURE:
<221> NAME/KEY: gene
<222> LOCATION: (1)..(4101)
<223> OTHER INFORMATION: Cas9n nucleotide sequence

<400> SEQUENCE: 5

| | | | | | |
|---|---|---|---|---|---|
| gacaagaagt | acagcatcgg | cctggccatc | ggcaccaact | ctgtgggctg | ggccgtgatc | 60 |
| accgacgagt | acaaggtgcc | cagcaagaaa | ttcaaggtgc | tgggcaacac | cgaccggcac | 120 |
| agcatcaaga | agaacctgat | cggagccctg | ctgttcgaca | gcggcgaaac | agccgaggcc | 180 |
| acccggctga | agagaaccgc | cagaagaaga | tacaccagac | ggaagaaccg | gatctgctat | 240 |
| ctgcaagaga | tcttcagcaa | cgagatggcc | aaggtggacg | acagcttctt | ccacagactg | 300 |
| gaagagtcct | tcctggtgga | agaggataag | aagcacgagc | ggcacccat | cttcggcaac | 360 |
| atcgtggacg | aggtggccta | ccacgagaag | taccccacca | tctaccacct | gagaaagaaa | 420 |
| ctggtggaca | gcaccgacaa | ggccgacctg | cggctgatct | atctggccct | ggcccacatg | 480 |
| atcaagttcc | ggggccactt | cctgatcgag | ggcgacctga | accccgacaa | cagcgacgtg | 540 |
| gacaagctgt | tcatccagct | ggtgcagacc | tacaaccagc | tgttcgagga | aaaccccatc | 600 |
| aacgccagcg | gcgtggacgc | caaggccatc | ctgtctgcca | gactgagcaa | gagcagacgg | 660 |
| ctggaaaatc | tgatcgccca | gctgcccggc | gagaagaaga | atggcctgtt | cggaaacctg | 720 |
| attgccctga | gcctgggcct | gacccccaac | ttcaagagca | acttcgacct | ggccgaggat | 780 |
| gccaaactgc | agctgagcaa | ggacacctac | gacgacgacc | tggacaacct | gctggcccag | 840 |
| atcggcgacc | agtacgccga | cctgtttctg | gccgccaaga | acctgtccga | cgccatcctg | 900 |
| ctgagcgaca | tcctgagagt | gaacaccgag | atcaccaagg | cccccctgag | cgcctctatg | 960 |
| atcaagagat | acgacgagca | ccaccaggac | ctgaccctgc | tgaaagctct | cgtgcggcag | 1020 |
| cagctgcctg | agaagtacaa | agagattttc | ttcgaccaga | gcaagaacgg | ctacgccggc | 1080 |
| tacattgacg | gcggagccag | ccaggaagag | ttctacaagt | tcatcaagcc | catcctggaa | 1140 |
| aagatggacg | gcaccgagga | actgctcgtg | aagctgaaca | gagaggacct | gctgcggaag | 1200 |
| cagcggacct | tcgacaacgg | cagcatcccc | caccagatcc | acctgggaga | gctgcacgcc | 1260 |
| attctgcggc | ggcaggaaga | tttttaccca | ttcctgaagg | acaaccggga | aaagatcgag | 1320 |
| aagatcctga | ccttccgcat | cccctactac | gtgggccctc | tggccagggg | aaacagcaga | 1380 |
| ttcgcctgga | tgaccagaaa | gagcgaggaa | accatcaccc | cctggaactt | cgaggaagtg | 1440 |
| gtggacaagg | gcgcttccgc | ccagagcttc | atcgagcgga | tgaccaactt | cgataagaac | 1500 |
| ctgcccaacg | agaaggtgct | gcccaagcac | agcctgctgt | acgagtactt | caccgtgtat | 1560 |
| aacgagctga | ccaaagtgaa | atacgtgacc | gagggaatga | gaaagcccgc | cttcctgagc | 1620 |
| ggcgagcaga | aaaaggccat | cgtggacctg | ctgttcaaga | ccaaccggaa | agtgaccgtg | 1680 |
| aagcagctga | agaggactac | cttcaagaaa | atcgagtgct | tcgactccgt | ggaaatctcc | 1740 |
| ggcgtggaag | atcggttcaa | cgcctccctg | ggcacatacc | acgatctgct | gaaaattatc | 1800 |
| aaggacaagg | acttcctgga | caatgaggaa | aacgaggaca | ttctggaaga | tatcgtgctg | 1860 |
| accctgacac | tgtttgagga | cagagagatg | atcgaggaac | ggctgaaaac | ctatgcccac | 1920 |
| ctgttcgacg | acaaagtgat | gaagcagctg | aagcggcgga | gatacaccgg | ctggggcagg | 1980 |
| ctgagccgga | agctgatcaa | cggcatccgg | gacaagcagt | ccggcaagac | aatcctggat | 2040 |
| ttcctgaagt | ccgacggctt | cgccaacaga | aacttcatgc | agctgatcca | cgacgacagc | 2100 |
| ctgaccttta | agaggacat | ccagaaagcc | caggtgtccg | gccagggcga | tagcctgcac | 2160 |

-continued

```
gagcacattg ccaatctggc cggcagcccc gccattaaga agggcatcct gcagacagtg    2220
aaggtggtgg acgagctcgt gaaagtgatg ggccggcaca agcccgagaa catcgtgatc    2280
gaaatggcca gagagaacca gaccacccag aagggacaga agaacagccg cgagagaatg    2340
aagcggatcg aagagggcat caaagagctg gcagccagat cctgaaaga caccccgtg     2400 gaaaacaccc agctgcagaa cgagaagctg tacctgtact acctgcagaa tgggcgggat    2460
atgtacgtgg accaggaact ggacatcaac cggctgtccg actacgatgt ggaccatatc    2520
gtgcctcaga gctttctgaa ggacgactcc atcgacaaca aggtgctgac cagaagcgac    2580
aagaaccggg gcaagagcga caacgtgccc tccgaagagg tcgtgaagaa gatgaagaac    2640
tactggcggc agctgctgaa cgccaagctg attacccaga aaagttcga caatctgacc    2700 aaggccgaga gaggcggcct gagcgaactg gataaggccg gcttcatcaa gagacagctg    2760
gtggaaaccc ggcagatcac aaagcacgtg gcacagatcc tggactcccg gatgaacact    2820
aagtacgacg agaatgacaa gctgatccgg gaagtgaaag tgatcaccct gaagtccaag    2880
ctggtgtccg atttccggaa ggatttccag ttttacaaag tgcgcgagat caacaactac    2940
caccacgccc acgacgccta cctgaacgcc gtcgtgggaa ccgccctgat caaaaagtac    3000
cctaagctgg aaagcgagtt cgtgtacggc gactacaagg tgtacgacgt gcggaagatg    3060
atcgccaaga gcgagcagga aatcggcaag gctaccgcca gtacttctt ctacagcaac    3120 atcatgaact tttcaagac cgagattacc ctggccaacg gcgagatccg gaagcggcct    3180
ctgatcgaga caaacggcga aaccggggag atcgtgtggg ataagggccg ggattttgcc    3240
accgtgcgga aagtgctgag catgccccaa gtgaatatcg tgaaaaagac cgaggtgcag    3300
acaggcggct tcagcaaaga gtctatcctg cccaagagga cagcgataa gctgatcgcc    3360 agaaagaagg actgggaccc taagaagtac ggcggcttcg acagccccac cgtggcctat    3420
tctgtgctgg tggtggccaa agtggaaaag ggcaagtcca agaaactgaa gagtgtgaaa    3480
gagctgctgg ggatcaccat catggaaaga agcagcttcg agaagaatcc catcgacttt    3540
ctggaagcca agggctacaa agaagtgaaa aaggacctga tcatcaagct gcctaagtac    3600
tccctgttcg agctggaaaa cggccggaag agaatgctgg cctctgccgg cgaactgcag    3660
aagggaaacg aactggccct gccctccaaa tatgtgaact tcctgtacct ggccagccac    3720
tatgagaagc tgaagggctc ccccgaggat aatgagcaga acagctgtt tgtggaacag    3780 cacaagcact acctggacga gatcatcgag cagatcagcg agttctccaa gagagtgatc    3840
ctggccgacg ctaatctgga caaagtgctg tccgcctaca acaagcaccg ggataagccc    3900
atcagagagc aggccgagaa tatcatccac ctgtttaccc tgaccaatct gggagcccct    3960
gccgccttca gtactttga caccaccatc gaccggaaga ggtacaccag caccaaagag    4020
gtgctggacg ccaccctgat ccaccagagc atcaccggcc tgtacgagac acggatcgac    4080
ctgtctcagc tgggaggcga c                                              4101
```

<210> SEQ ID NO 6
<211> LENGTH: 1367
<212> TYPE: PRT
<213> ORGANISM: Streptococcus pyogenes
<220> FEATURE:
<221> NAME/KEY: PEPTIDE
<222> LOCATION: (1)..(1367)
<223> OTHER INFORMATION: Cas9n amino acid sequence

<400> SEQUENCE: 6

-continued

```
Asp Lys Lys Tyr Ser Ile Gly Leu Ala Ile Gly Thr Asn Ser Val Gly
1               5                  10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

Ala Leu Leu Phe Asp Ser Gly Glu Thr Ala Glu Ala Thr Arg Leu Lys
    50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

Phe Leu Ala Ala Lys Asn Leu Ser Asp Ala Ile Leu Leu Ser Asp Ile
    290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
            340                 345                 350

Gln Ser Lys Asn Gly Tyr Ala Gly Tyr Ile Asp Gly Gly Ala Ser Gln
        355                 360                 365

Glu Glu Phe Tyr Lys Phe Ile Lys Pro Ile Leu Glu Lys Met Asp Gly
    370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
```

```
                420             425             430
Lys Asp Asn Arg Glu Lys Ile Glu Lys Ile Leu Thr Phe Arg Ile Pro
            435             440             445

Tyr Tyr Val Gly Pro Leu Ala Arg Gly Asn Ser Arg Phe Ala Trp Met
            450             455             460

Thr Arg Lys Ser Glu Glu Thr Ile Thr Pro Trp Asn Phe Glu Glu Val
465             470             475             480

Val Asp Lys Gly Ala Ser Ala Gln Ser Phe Ile Glu Arg Met Thr Asn
            485             490             495

Phe Asp Lys Asn Leu Pro Asn Glu Lys Val Leu Pro Lys His Ser Leu
            500             505             510

Leu Tyr Glu Tyr Phe Thr Val Tyr Asn Glu Leu Thr Lys Val Lys Tyr
            515             520             525

Val Thr Glu Gly Met Arg Lys Pro Ala Phe Leu Ser Gly Glu Gln Lys
            530             535             540

Lys Ala Ile Val Asp Leu Leu Phe Lys Thr Asn Arg Lys Val Thr Val
545             550             555             560

Lys Gln Leu Lys Glu Asp Tyr Phe Lys Lys Ile Glu Cys Phe Asp Ser
            565             570             575

Val Glu Ile Ser Gly Val Glu Asp Arg Phe Asn Ala Ser Leu Gly Thr
            580             585             590

Tyr His Asp Leu Leu Lys Ile Ile Lys Asp Lys Asp Phe Leu Asp Asn
            595             600             605

Glu Glu Asn Glu Asp Ile Leu Glu Asp Ile Val Leu Thr Leu Thr Leu
            610             615             620

Phe Glu Asp Arg Glu Met Ile Glu Glu Arg Leu Lys Thr Tyr Ala His
625             630             635             640

Leu Phe Asp Asp Lys Val Met Lys Gln Leu Lys Arg Arg Arg Tyr Thr
            645             650             655

Gly Trp Gly Arg Leu Ser Arg Lys Leu Ile Asn Gly Ile Arg Asp Lys
            660             665             670

Gln Ser Gly Lys Thr Ile Leu Asp Phe Leu Lys Ser Asp Gly Phe Ala
            675             680             685

Asn Arg Asn Phe Met Gln Leu Ile His Asp Asp Ser Leu Thr Phe Lys
            690             695             700

Glu Asp Ile Gln Lys Ala Gln Val Ser Gly Gln Gly Asp Ser Leu His
705             710             715             720

Glu His Ile Ala Asn Leu Ala Gly Ser Pro Ala Ile Lys Lys Gly Ile
            725             730             735

Leu Gln Thr Val Lys Val Val Asp Glu Leu Val Lys Val Met Gly Arg
            740             745             750

His Lys Pro Glu Asn Ile Val Ile Glu Met Ala Arg Glu Asn Gln Thr
            755             760             765

Thr Gln Lys Gly Gln Lys Asn Ser Arg Glu Arg Met Lys Arg Ile Glu
            770             775             780

Glu Gly Ile Lys Glu Leu Gly Ser Gln Ile Leu Lys Glu His Pro Val
785             790             795             800

Glu Asn Thr Gln Leu Gln Asn Glu Lys Leu Tyr Leu Tyr Tyr Leu Gln
            805             810             815

Asn Gly Arg Asp Met Tyr Val Asp Gln Glu Leu Asp Ile Asn Arg Leu
            820             825             830

Ser Asp Tyr Asp Val Asp His Ile Val Pro Gln Ser Phe Leu Lys Asp
            835             840             845
```

```
Asp Ser Ile Asp Asn Lys Val Leu Thr Arg Ser Asp Lys Asn Arg Gly
850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
                885                 890                 895

Asp Asn Leu Thr Lys Ala Glu Arg Gly Gly Leu Ser Glu Leu Asp Lys
                900                 905                 910

Ala Gly Phe Ile Lys Arg Gln Leu Val Glu Thr Arg Gln Ile Thr Lys
            915                 920                 925

His Val Ala Gln Ile Leu Asp Ser Arg Met Asn Thr Lys Tyr Asp Glu
        930                 935                 940

Asn Asp Lys Leu Ile Arg Glu Val Lys Val Ile Thr Leu Lys Ser Lys
945                 950                 955                 960

Leu Val Ser Asp Phe Arg Lys Asp Phe Gln Phe Tyr Lys Val Arg Glu
                965                 970                 975

Ile Asn Asn Tyr His His Ala His Asp Ala Tyr Leu Asn Ala Val Val
                980                 985                 990

Gly Thr Ala Leu Ile Lys Lys Tyr Pro Lys Leu Glu Ser Glu Phe Val
            995                 1000                1005

Tyr Gly Asp Tyr Lys Val Tyr Asp Val Arg Lys Met Ile Ala Lys
    1010                1015                1020

Ser Glu Gln Glu Ile Gly Lys Ala Thr Ala Lys Tyr Phe Phe Tyr
    1025                1030                1035

Ser Asn Ile Met Asn Phe Phe Lys Thr Glu Ile Thr Leu Ala Asn
    1040                1045                1050

Gly Glu Ile Arg Lys Arg Pro Leu Ile Glu Thr Asn Gly Glu Thr
    1055                1060                1065

Gly Glu Ile Val Trp Asp Lys Gly Arg Asp Phe Ala Thr Val Arg
    1070                1075                1080

Lys Val Leu Ser Met Pro Gln Val Asn Ile Val Lys Lys Thr Glu
    1085                1090                1095

Val Gln Thr Gly Gly Phe Ser Lys Glu Ser Ile Leu Pro Lys Arg
    1100                1105                1110

Asn Ser Asp Lys Leu Ile Ala Arg Lys Lys Asp Trp Asp Pro Lys
    1115                1120                1125

Lys Tyr Gly Gly Phe Asp Ser Pro Thr Val Ala Tyr Ser Val Leu
    1130                1135                1140

Val Val Ala Lys Val Glu Lys Gly Lys Ser Lys Lys Leu Lys Ser
    1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
    1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245
```

```
Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 7
<211> LENGTH: 238
<212> TYPE: DNA
<213> ORGANISM: Cricetulus griseus
<220> FEATURE:
<221> NAME/KEY: gene
<222> LOCATION: (1)..(238)
<223> OTHER INFORMATION: Fut8 Exon 7 nucleotide sequence

<400> SEQUENCE: 7
aatcccaagg actgcagcaa agccagaaag ctggtatgta atatcaacaa aggctgtggc      60
tatggatgtc aactccatca tgtggtttac tgcttcatga ttgcttatgg cacccagcga     120
acactcatct ggaatctca gaattggcgc tatgctactg gaggatggga gactgtgttt      180
agacctgtaa gtgagacatg cacagacagg tctggcctct ccactggaca ctggtcag      238

<210> SEQ ID NO 8
<211> LENGTH: 79
<212> TYPE: PRT
<213> ORGANISM: Cricetulus griseus
<220> FEATURE:
<221> NAME/KEY: PEPTIDE
<222> LOCATION: (1)..(79)
<223> OTHER INFORMATION: Fut8 Exon 7 aminoa cid sequence

<400> SEQUENCE: 8

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Arg Thr Leu Ile Leu Glu Ser Gln Asn
        35                  40                  45

Trp Arg Tyr Ala Thr Gly Gly Trp Glu Thr Val Phe Arg Pro Val Ser
    50                  55                  60

Glu Thr Cys Thr Asp Arg Ser Gly Leu Ser Thr Gly His Trp Ser
65                  70                  75

<210> SEQ ID NO 9
<211> LENGTH: 110
<212> TYPE: DNA
<213> ORGANISM: Cricetulus griseus
<220> FEATURE:
<221> NAME/KEY: gene
<222> LOCATION: (1)..(110)
```

<223> OTHER INFORMATION: GMD Exon 3 nucleotide sequence

<400> SEQUENCE: 9
acatgaagtt gcactatggt gacctcaccg acagcacctg cctagtaaaa atcatcaatg    60
aagtcaaacc tacagagatc tacaatcttg gtgcccagag ccatgtcaag              110

<210> SEQ ID NO 10
<211> LENGTH: 193
<212> TYPE: DNA
<213> ORGANISM: Cricetulus griseus
<220> FEATURE:
<221> NAME/KEY: gene
<222> LOCATION: (1)..(193)
<223> OTHER INFORMATION: GMD Exon 4 nucleotide sequence

<400> SEQUENCE: 10
atttcctttg acttagcaga gtacactgca gatgttgatg gagttggcac cttgcggctt    60
ctggatgcaa ttaagacttg tggccttata aattctgtga agttctacca ggcctcaact   120
agtgaactgt atggaaaagt gcaagaaata ccccagaaag agaccacccc tttctatcca   180
aggtcgccct atg                                                      193

<210> SEQ ID NO 11
<211> LENGTH: 36
<212> TYPE: PRT
<213> ORGANISM: Cricetulus griseus
<220> FEATURE:
<221> NAME/KEY: PEPTIDE
<222> LOCATION: (1)..(36)
<223> OTHER INFORMATION: GMD Exon-3 amino acid sequence

<400> SEQUENCE: 11

Met Lys Leu His Tyr Gly Asp Leu Thr Asp Ser Thr Cys Leu Val Lys
1               5                   10                  15

Ile Ile Asn Glu Val Lys Pro Thr Glu Ile Tyr Asn Leu Gly Ala Gln
            20                  25                  30

Ser His Val Lys
        35

<210> SEQ ID NO 12
<211> LENGTH: 64
<212> TYPE: PRT
<213> ORGANISM: Cricetulus griseus
<220> FEATURE:
<221> NAME/KEY: PEPTIDE
<222> LOCATION: (1)..(64)
<223> OTHER INFORMATION: GMD Exon-4 amino acid sequence

<400> SEQUENCE: 12

Ile Ser Phe Asp Leu Ala Glu Tyr Thr Ala Asp Val Asp Gly Val Gly
1               5                   10                  15

Thr Leu Arg Leu Leu Asp Ala Ile Lys Thr Cys Gly Leu Ile Asn Ser
            20                  25                  30

Val Lys Phe Tyr Gln Ala Ser Thr Ser Glu Leu Tyr Gly Lys Val Gln
            35                  40                  45

Glu Ile Pro Gln Lys Glu Thr Thr Pro Phe Tyr Pro Arg Ser Pro Tyr
        50                  55                  60

<210> SEQ ID NO 13
<211> LENGTH: 23
<212> TYPE: DNA
<213> ORGANISM: Artificial Sequence
<220> FEATURE:

<223> OTHER INFORMATION: CRISPR recognition sequence 1
<220> FEATURE:
<221> NAME/KEY: misc_feature
<222> LOCATION: (1)..(23)

<400> SEQUENCE: 13
aattggcgct atgctactgg agg                                              23

<210> SEQ ID NO 14
<211> LENGTH: 23
<212> TYPE: RNA
<213> ORGANISM: Artificial Sequence
<220> FEATURE:
<223> OTHER INFORMATION: CRISPR Recognition mRNA sequence 1
<220> FEATURE:
<221> NAME/KEY: misc_feature
<222> LOCATION: (1)..(23)

<400> SEQUENCE: 14
aauuggcgcu augcuacugg agg                                              23

<210> SEQ ID NO 15
<211> LENGTH: 23
<212> TYPE: DNA
<213> ORGANISM: Artificial Sequence
<220> FEATURE:
<223> OTHER INFORMATION: CRISPR Recognition sequence 2
<220> FEATURE:
<221> NAME/KEY: misc_feature
<222> LOCATION: (1)..(23)

<400> SEQUENCE: 15
ccagcgaaca ctcatcttgg aat                                              23

<210> SEQ ID NO 16
<211> LENGTH: 23
<212> TYPE: RNA
<213> ORGANISM: Artificial Sequence
<220> FEATURE:
<223> OTHER INFORMATION: CRISPR Recognition mRNA sequence 2
<220> FEATURE:
<221> NAME/KEY: misc_feature
<222> LOCATION: (1)..(23)

<400> SEQUENCE: 16
ccagcgaaca cucaucuugg aau                                              23

<210> SEQ ID NO 17
<211> LENGTH: 56
<212> TYPE: DNA
<213> ORGANISM: Artificial Sequence
<220> FEATURE:
<223> OTHER INFORMATION: CRISPR Recognition sequence 3
<220> FEATURE:
<221> NAME/KEY: misc_feature
<222> LOCATION: (1)..(56)

<400> SEQUENCE: 17
tgaccaccct gaccattcta gcagagaact ctccaagatt cttgcaaagc tggagc          56

<210> SEQ ID NO 18
<211> LENGTH: 59
<212> TYPE: DNA
<213> ORGANISM: Artificial Sequence
<220> FEATURE:
<223> OTHER INFORMATION: CRISPR Recognition sequence 4
<220> FEATURE:
<221> NAME/KEY: misc_feature
<222> LOCATION: (1)..(59)

<400> SEQUENCE: 18
tctccaagat tcttgcaaag ctggagcgct taaaacaaca aaatgaagac ttgaggaga    59

<210> SEQ ID NO 19
<211> LENGTH: 45
<212> TYPE: DNA
<213> ORGANISM: Artificial Sequence
<220> FEATURE:
<223> OTHER INFORMATION: CRISPR Recognition sequence 5
<220> FEATURE:
<221> NAME/KEY: misc_feature
<222> LOCATION: (1)..(45)

<400> SEQUENCE: 19
aggccaaaga acagattgaa aattacaaga aacaagctag gaatg    45

<210> SEQ ID NO 20
<211> LENGTH: 56
<212> TYPE: DNA
<213> ORGANISM: Artificial Sequence
<220> FEATURE:
<223> OTHER INFORMATION: CRISPR Recognition sequence 6
<220> FEATURE:
<221> NAME/KEY: misc_feature
<222> LOCATION: (1)..(56)

<400> SEQUENCE: 20
aatcccaagg actgcagcaa agccagaaag ctggtatgta atatcaacaa aggctg    56

<210> SEQ ID NO 21
<211> LENGTH: 58
<212> TYPE: DNA
<213> ORGANISM: Artificial Sequence
<220> FEATURE:
<223> OTHER INFORMATION: CRISPR Recognition sequence 7
<220> FEATURE:
<221> NAME/KEY: misc_feature
<222> LOCATION: (1)..(58)

<400> SEQUENCE: 21
gcacccagcg aacactcatc ttggaatctc agaattggcg ctatgctact ggaggatg    58

<210> SEQ ID NO 22
<211> LENGTH: 57
<212> TYPE: DNA
<213> ORGANISM: Artificial Sequence
<220> FEATURE:
<223> OTHER INFORMATION: CRISPR Recognition sequence 8
<220> FEATURE:
<221> NAME/KEY: misc_feature
<222> LOCATION: (1)..(57)

<400> SEQUENCE: 22
agacctgtaa gtgagacatg cacagacagg tctggcctct ccactggaca ctggtca    57

<210> SEQ ID NO 23
<211> LENGTH: 57
<212> TYPE: DNA
<213> ORGANISM: Artificial Sequence
<220> FEATURE:
<223> OTHER INFORMATION: CRISPR Recognition sequence 9
<220> FEATURE:
<221> NAME/KEY: misc_feature
<222> LOCATION: (1)..(57)

<400> SEQUENCE: 23
cacccagcga acactcatct tggaatctca gaattggcgc tatgctactg gaggatg    57

<210> SEQ ID NO 24
<211> LENGTH: 56
<212> TYPE: DNA
<213> ORGANISM: Artificial Sequence
<220> FEATURE:
<223> OTHER INFORMATION: CRISPR Recognition sequence 10
<220> FEATURE:
<221> NAME/KEY: misc_feature
<222> LOCATION: (1)..(56)

<400> SEQUENCE: 24
ttacccttgg ctgtaccaga agaccttgca gatcgactcc tgagagtcca tggtga     56

<210> SEQ ID NO 25
<211> LENGTH: 57
<212> TYPE: DNA
<213> ORGANISM: Artificial Sequence
<220> FEATURE:
<223> OTHER INFORMATION: CRISPR Recognition sequence 11
<220> FEATURE:
<221> NAME/KEY: misc_feature
<222> LOCATION: (1)..(57)

<400> SEQUENCE: 25
gtaccagaag accttgcaga tcgactcctg agagtccatg gtgatcctgc agtgtgg    57

<210> SEQ ID NO 26
<211> LENGTH: 56
<212> TYPE: DNA
<213> ORGANISM: Artificial Sequence
<220> FEATURE:
<223> OTHER INFORMATION: CRISPR Recognition sequence 12
<220> FEATURE:
<221> NAME/KEY: misc_feature
<222> LOCATION: (1)..(56)

<400> SEQUENCE: 26
agaccttgca gatcgactcc tgagagtcca tggtgatcct gcagtgtggt gggtat     56

<210> SEQ ID NO 27
<211> LENGTH: 60
<212> TYPE: DNA
<213> ORGANISM: Artificial Sequence
<220> FEATURE:
<223> OTHER INFORMATION: CRISPR Recognition sequence 13
<220> FEATURE:
<221> NAME/KEY: misc_feature
<222> LOCATION: (1)..(60)

<400> SEQUENCE: 27
gatccgtcca caaccttggc tggaaaggga aatagaagaa accaccaaga agcttggctt  60

<210> SEQ ID NO 28
<211> LENGTH: 56
<212> TYPE: DNA
<213> ORGANISM: Artificial Sequence
<220> FEATURE:
<223> OTHER INFORMATION: CRISPR Recognition sequence 14
<220> FEATURE:
<221> NAME/KEY: misc_feature
<222> LOCATION: (1)..(56)

<400> SEQUENCE: 28
cgtccacaac cttggctgga aagggaaata gaagaaacca ccaagaagct tggctt     56

<210> SEQ ID NO 29
<211> LENGTH: 59

```
<212> TYPE: DNA
<213> ORGANISM: Artificial Sequence
<220> FEATURE:
<223> OTHER INFORMATION: CRISPR Recognition sequence 15
<220> FEATURE:
<221> NAME/KEY: misc_feature
<222> LOCATION: (1)..(59)

<400> SEQUENCE: 29
catcctgatg cctctgcaaa cttccattct ttagatgaca tctactattt tggaggcca       59

<210> SEQ ID NO 30
<211> LENGTH: 56
<212> TYPE: DNA
<213> ORGANISM: Artificial Sequence
<220> FEATURE:
<223> OTHER INFORMATION: CRISPR Recognition sequence 16
<220> FEATURE:
<221> NAME/KEY: misc_feature
<222> LOCATION: (1)..(56)

<400> SEQUENCE: 30
catcctgatg cctctgcaaa cttccattct ttagatgaca tctactattt tggagg          56

<210> SEQ ID NO 31
<211> LENGTH: 59
<212> TYPE: DNA
<213> ORGANISM: Artificial Sequence
<220> FEATURE:
<223> OTHER INFORMATION: CRISPR Recognition sequence 17
<220> FEATURE:
<221> NAME/KEY: misc_feature
<222> LOCATION: (1)..(59)

<400> SEQUENCE: 31
caaccagatt gcagtttatc ctcaccaacc tcgaactaaa gaggaaatcc ccatggaac       59

<210> SEQ ID NO 32
<211> LENGTH: 59
<212> TYPE: DNA
<213> ORGANISM: Artificial Sequence
<220> FEATURE:
<223> OTHER INFORMATION: CRISPR Recognition sequence 18
<220> FEATURE:
<221> NAME/KEY: misc_feature
<222> LOCATION: (1)..(59)

<400> SEQUENCE: 32
gaacctggag atatcattgg tgtggctgga aaccattgga atggttactc taaaggtgt       59

<210> SEQ ID NO 33
<211> LENGTH: 57
<212> TYPE: DNA
<213> ORGANISM: Artificial Sequence
<220> FEATURE:
<223> OTHER INFORMATION: CRISPR Recognition sequence 19
<220> FEATURE:
<221> NAME/KEY: misc_feature
<222> LOCATION: (1)..(57)

<400> SEQUENCE: 33
aaaccattgg aatggttact ctaaaggtgt caacagaaaa ctaggaaaaa caggcct         57

<210> SEQ ID NO 34
<211> LENGTH: 58
<212> TYPE: DNA
<213> ORGANISM: Artificial Sequence
<220> FEATURE:
<223> OTHER INFORMATION: CRISPR Recognition sequence 20
```

<220> FEATURE:
<221> NAME/KEY: misc_feature
<222> LOCATION: (1)..(58)

<400> SEQUENCE: 34
caacctcgaa ctaaagagga aatccccatg gaacctggag atatcattgg tgtggctg    58

<210> SEQ ID NO 35
<211> LENGTH: 57
<212> TYPE: DNA
<213> ORGANISM: Artificial Sequence
<220> FEATURE:
<223> OTHER INFORMATION: CRISPR Recognition sequence 21
<220> FEATURE:
<221> NAME/KEY: misc_feature
<222> LOCATION: (1)..(57)

<400> SEQUENCE: 35
tcaccaacct cgaactaaag aggaaatccc catggaacct ggagatatca ttggtgt    57

<210> SEQ ID NO 36
<211> LENGTH: 56
<212> TYPE: DNA
<213> ORGANISM: Artificial Sequence
<220> FEATURE:
<223> OTHER INFORMATION: CRISPR Recognition sequence
<220> FEATURE:
<221> NAME/KEY: misc_feature
<222> LOCATION: (1)..(56)

<400> SEQUENCE: 36
atccccatgg aacctggaga tatcattggt gtggctggaa accattggaa tggtta    56

<210> SEQ ID NO 37
<211> LENGTH: 20
<212> TYPE: DNA
<213> ORGANISM: Artificial Sequence
<220> FEATURE:
<223> OTHER INFORMATION: CRISPR recognition sequence 22
<220> FEATURE:
<221> NAME/KEY: misc_feature
<222> LOCATION: (1)..(20)

<400> SEQUENCE: 37
attccaagat gagtgttcgc    20

<210> SEQ ID NO 38
<211> LENGTH: 20
<212> TYPE: RNA
<213> ORGANISM: Artificial Sequence
<220> FEATURE:
<223> OTHER INFORMATION: CRISPR Recognition mRNA sequence 3
<220> FEATURE:
<221> NAME/KEY: misc_feature
<222> LOCATION: (1)..(20)

<400> SEQUENCE: 38
auuccaagau gaguguucgc    20

<210> SEQ ID NO 39
<211> LENGTH: 20
<212> TYPE: DNA
<213> ORGANISM: Artificial Sequence
<220> FEATURE:
<223> OTHER INFORMATION: CRISPR Recognition sequence 23
<220> FEATURE:
<221> NAME/KEY: misc_feature
<222> LOCATION: (1)..(20)

```
<400> SEQUENCE: 39
aattggcgct atgctactgg                                                    20

<210> SEQ ID NO 40
<211> LENGTH: 20
<212> TYPE: RNA
<213> ORGANISM: Artificial Sequence
<220> FEATURE:
<223> OTHER INFORMATION: CRISPR Recognition mRNA sequence 4
<220> FEATURE:
<221> NAME/KEY: misc_feature
<222> LOCATION: (1)..(20)

<400> SEQUENCE: 40
aauuggcgcu augcuacugg                                                    20

<210> SEQ ID NO 41
<211> LENGTH: 20
<212> TYPE: DNA
<213> ORGANISM: Artificial Sequence
<220> FEATURE:
<223> OTHER INFORMATION: CRISPR Recognition sequence 24
<220> FEATURE:
<221> NAME/KEY: misc_feature
<222> LOCATION: (1)..(20)

<400> SEQUENCE: 41
actaggcagg tgctgtcggt                                                    20

<210> SEQ ID NO 42
<211> LENGTH: 20
<212> TYPE: RNA
<213> ORGANISM: Artificial Sequence
<220> FEATURE:
<223> OTHER INFORMATION: CRISPR Recognition mRNA sequence 5
<220> FEATURE:
<221> NAME/KEY: misc_feature
<222> LOCATION: (1)..(20)

<400> SEQUENCE: 42
acuaggcagg ugcugucggu                                                    20

<210> SEQ ID NO 43
<211> LENGTH: 20
<212> TYPE: DNA
<213> ORGANISM: Artificial Sequence
<220> FEATURE:
<223> OTHER INFORMATION: CRISPR Recognition sequence 25
<220> FEATURE:
<221> NAME/KEY: misc_feature
<222> LOCATION: (1)..(20)

<400> SEQUENCE: 43
catcaatgaa gtcaaaccta                                                    20

<210> SEQ ID NO 44
<211> LENGTH: 20
<212> TYPE: RNA
<213> ORGANISM: Artificial Sequence
<220> FEATURE:
<223> OTHER INFORMATION: CRISPR Recognition mRNA sequence 6
<220> FEATURE:
<221> NAME/KEY: misc_feature
<222> LOCATION: (1)..(20)

<400> SEQUENCE: 44
caucaaugaa gucaaaccua                                                    20
```

```
<210> SEQ ID NO 45
<211> LENGTH: 20
<212> TYPE: DNA
<213> ORGANISM: Artificial Sequence
<220> FEATURE:
<223> OTHER INFORMATION: CRISPR Recogntion sequence 26
<220> FEATURE:
<221> NAME/KEY: misc_feature
<222> LOCATION: (1)..(20)

<400> SEQUENCE: 45
agttggcacc ttgcggcttc                                           20

<210> SEQ ID NO 46
<211> LENGTH: 20
<212> TYPE: RNA
<213> ORGANISM: Artificial Sequence
<220> FEATURE:
<223> OTHER INFORMATION: CRISPR Recognition mRNA sequence 7
<220> FEATURE:
<221> NAME/KEY: misc_feature
<222> LOCATION: (1)..(20)

<400> SEQUENCE: 46
aguuggcacc uugcggcuuc                                           20

<210> SEQ ID NO 47
<211> LENGTH: 58
<212> TYPE: DNA
<213> ORGANISM: Artificial Sequence
<220> FEATURE:
<223> OTHER INFORMATION: CRISPR Recognition sequence 27
<220> FEATURE:
<221> NAME/KEY: misc_feature
<222> LOCATION: (1)..(58)

<400> SEQUENCE: 47
gacctcaccg acagcacctg cctagtaaaa atcatcaatg aagtcaaacc tacagaga       58

<210> SEQ ID NO 48
<211> LENGTH: 60
<212> TYPE: DNA
<213> ORGANISM: Artificial Sequence
<220> FEATURE:
<223> OTHER INFORMATION: CRISPR Recognition sequence 28
<220> FEATURE:
<221> NAME/KEY: misc_feature
<222> LOCATION: (1)..(60)

<400> SEQUENCE: 48
gacctcaccg acagcacctg cctagtaaaa atcatcaatg aagtcaaacc tacagagatc     60

<210> SEQ ID NO 49
<211> LENGTH: 56
<212> TYPE: DNA
<213> ORGANISM: Artificial Sequence
<220> FEATURE:
<223> OTHER INFORMATION: CRISPR Recognition sequence 29
<220> FEATURE:
<221> NAME/KEY: misc_feature
<222> LOCATION: (1)..(56)

<400> SEQUENCE: 49
gcactatggt gacctcaccg acagcacctg cctagtaaaa atcatcaatg aagtca         56

<210> SEQ ID NO 50
<211> LENGTH: 57
<212> TYPE: DNA
```

-continued

```
<213> ORGANISM: Artificial Sequence
<220> FEATURE:
<223> OTHER INFORMATION: CRISPR Recognition sequence 31
<220> FEATURE:
<221> NAME/KEY: misc_feature
<222> LOCATION: (1)..(57)

<400> SEQUENCE: 50
cttctggatg caattaagac ttgtggcctt ataaattctg tgaagttcta ccaggcc        57

<210> SEQ ID NO 51
<211> LENGTH: 58
<212> TYPE: DNA
<213> ORGANISM: Artificial Sequence
<220> FEATURE:
<223> OTHER INFORMATION: CRISPR Recognition sequence 32
<220> FEATURE:
<221> NAME/KEY: misc_feature
<222> LOCATION: (1)..(58)

<400> SEQUENCE: 51
cttctggatg caattaagac ttgtggcctt ataaattctg tgaagttcta ccaggcct       58

<210> SEQ ID NO 52
<211> LENGTH: 58
<212> TYPE: DNA
<213> ORGANISM: Artificial Sequence
<220> FEATURE:
<223> OTHER INFORMATION: CRISPR Recognition sequence 33
<220> FEATURE:
<221> NAME/KEY: misc_feature
<222> LOCATION: (1)..(58)

<400> SEQUENCE: 52
caccttgcgg cttctggatg caattaagac ttgtggcctt ataaattctg tgaagttc       58

<210> SEQ ID NO 53
<211> LENGTH: 56
<212> TYPE: DNA
<213> ORGANISM: Artificial Sequence
<220> FEATURE:
<223> OTHER INFORMATION: CRISPR Recognition sequence 34
<220> FEATURE:
<221> NAME/KEY: misc_feature
<222> LOCATION: (1)..(56)

<400> SEQUENCE: 53
ggccttataa attctgtgaa gttctaccag gcctcaacta gtgaactgta tggaaa         56

<210> SEQ ID NO 54
<211> LENGTH: 60
<212> TYPE: DNA
<213> ORGANISM: Artificial Sequence
<220> FEATURE:
<223> OTHER INFORMATION: CRISPR Recognition sequence 36
<220> FEATURE:
<221> NAME/KEY: misc_feature
<222> LOCATION: (1)..(60)

<400> SEQUENCE: 54
tgcctattgg attgtagtga actttcgaga ggcttataat ctctttgcgg tgaacggcat     60

<210> SEQ ID NO 55
<211> LENGTH: 56
<212> TYPE: DNA
<213> ORGANISM: Artificial Sequence
<220> FEATURE:
<223> OTHER INFORMATION: CRISPR Recognition sequence 37
<220> FEATURE:
```

```
<221> NAME/KEY: misc_feature
<222> LOCATION: (1)..(56)

<400> SEQUENCE: 55
ttaccttgga caactggaat gtttcagttt gggaaatctg gacgccaaac gagact        56

<210> SEQ ID NO 56
<211> LENGTH: 60
<212> TYPE: DNA
<213> ORGANISM: Artificial Sequence
<220> FEATURE:
<223> OTHER INFORMATION: CRISPR Recognition sequence 38
<220> FEATURE:
<221> NAME/KEY: misc_feature
<222> LOCATION: (1)..(60)

<400> SEQUENCE: 56
taccttggac aactggaatg tttcagtttg gaaatctgg acgccaaacg agactggggc     60

<210> SEQ ID NO 57
<211> LENGTH: 58
<212> TYPE: DNA
<213> ORGANISM: Artificial Sequence
<220> FEATURE:
<223> OTHER INFORMATION: CRISPR Recognition sequence 38
<220> FEATURE:
<221> NAME/KEY: misc_feature
<222> LOCATION: (1)..(58)

<400> SEQUENCE: 57
tggctgatgt tacaaaatga tgaaccagag gactttgtca tagctactgg ggaagttc     58

<210> SEQ ID NO 58
<211> LENGTH: 46
<212> TYPE: DNA
<213> ORGANISM: Artificial Sequence
<220> FEATURE:
<223> OTHER INFORMATION: CRISPR Recognition sequence 39
<220> FEATURE:
<221> NAME/KEY: misc_feature
<222> LOCATION: (1)..(46)

<400> SEQUENCE: 58
aaccctcgac tgcctgtgtc gtccccacag ctaagagctg ggccac                   46

<210> SEQ ID NO 59
<211> LENGTH: 45
<212> TYPE: DNA
<213> ORGANISM: Artificial Sequence
<220> FEATURE:
<223> OTHER INFORMATION: CRISPR Recogntiion sequence 40
<220> FEATURE:
<221> NAME/KEY: misc_feature
<222> LOCATION: (1)..(45)

<400> SEQUENCE: 59
aaccctcgac tgcctgtgtc gtccccacag ctaagagctg ggcca                    45

<210> SEQ ID NO 60
<211> LENGTH: 56
<212> TYPE: DNA
<213> ORGANISM: Artificial Sequence
<220> FEATURE:
<223> OTHER INFORMATION: CRISPR Recognition sequence 41
<220> FEATURE:
<221> NAME/KEY: misc_feature
<222> LOCATION: (1)..(56)

<400> SEQUENCE: 60
```
tgcctgtgtc gtccccacag ctaagagctg ggccacaggt ttgtgggcac caggac        56

<210> SEQ ID NO 61
<211> LENGTH: 60
<212> TYPE: DNA
<213> ORGANISM: Artificial Sequence
<220> FEATURE:
<223> OTHER INFORMATION: CRISPR Recognition sequence 42
<220> FEATURE:
<221> NAME/KEY: misc_feature
<222> LOCATION: (1)..(60)

<400> SEQUENCE: 61
aaccccaacg cctgagcacc tctacaaaaa attcgcgaga catggactat ggtgcagagc        60

<210> SEQ ID NO 62
<211> LENGTH: 59
<212> TYPE: DNA
<213> ORGANISM: Artificial Sequence
<220> FEATURE:
<223> OTHER INFORMATION: CRISPR Recognition sequence 42
<220> FEATURE:
<221> NAME/KEY: misc_feature
<222> LOCATION: (1)..(59)

<400> SEQUENCE: 62
accccaacgc tgagcacct ctacaaaaaa ttcgcgagac atggactatg gtgcagagc        59

<210> SEQ ID NO 63
<211> LENGTH: 57
<212> TYPE: DNA
<213> ORGANISM: Artificial Sequence
<220> FEATURE:
<223> OTHER INFORMATION: CRISPR Recognition sequence 43
<220> FEATURE:
<221> NAME/KEY: misc_feature
<222> LOCATION: (1)..(57)

<400> SEQUENCE: 63
gagctcatga gaaccaaccc caacgcctga gcacctctac aaaaaattcg cgagaca        57

<210> SEQ ID NO 64
<211> LENGTH: 56
<212> TYPE: DNA
<213> ORGANISM: Artificial Sequence
<220> FEATURE:
<223> OTHER INFORMATION: CRISPR Recognition sequence 44
<220> FEATURE:
<221> NAME/KEY: misc_feature
<222> LOCATION: (1)..(56)

<400> SEQUENCE: 64 caacccaac gcctgagcac ctctacaaaa aattcgcgag acatggacta tggtgc        56

<210> SEQ ID NO 65
<211> LENGTH: 59
<212> TYPE: DNA
<213> ORGANISM: Artificial Sequence
<220> FEATURE:
<223> OTHER INFORMATION: CRISPR Recognition sequence 45
<220> FEATURE:
<221> NAME/KEY: misc_feature
<222> LOCATION: (1)..(59)

<400> SEQUENCE: 65
agaccatcga ccataaaccc tcgactgcct gtgtcgtccc cacagctaag agctgggcc        59

```
<210> SEQ ID NO 66
<211> LENGTH: 60
<212> TYPE: DNA
<213> ORGANISM: Artificial Sequence
<220> FEATURE:
<223> OTHER INFORMATION: CRISPR Recognition sequence 46
<220> FEATURE:
<221> NAME/KEY: misc_feature
<222> LOCATION: (1)..(60)

<400> SEQUENCE: 66
gaaccaaccc caacgcctga gcacctctac aaaaaattcg cgagacatgg actatggtgc      60

<210> SEQ ID NO 67
<211> LENGTH: 60
<212> TYPE: DNA
<213> ORGANISM: Artificial Sequence
<220> FEATURE:
<223> OTHER INFORMATION: CRISPR Recognition sequence 47
<220> FEATURE:
<221> NAME/KEY: misc_feature
<222> LOCATION: (1)..(60)

<400> SEQUENCE: 67
agaccatcga ccataaaccc tcgactgcct gtgtcgtccc cacagctaag agctgggcca      60

<210> SEQ ID NO 68
<211> LENGTH: 48
<212> TYPE: DNA
<213> ORGANISM: Artificial Sequence
<220> FEATURE:
<223> OTHER INFORMATION: CRISPR Recognition sequence 48
<220> FEATURE:
<221> NAME/KEY: misc_feature
<222> LOCATION: (1)..(48)

<400> SEQUENCE: 68
acactccaga gctaaggcca cttcgctttt gtcaaaggct cctctgaa                   48

<210> SEQ ID NO 69
<211> LENGTH: 54
<212> TYPE: DNA
<213> ORGANISM: Artificial Sequence
<220> FEATURE:
<223> OTHER INFORMATION: CRISPR Recognition sequence 49
<220> FEATURE:
<221> NAME/KEY: misc_feature
<222> LOCATION: (1)..(54)

<400> SEQUENCE: 69
agtcttgaga ttgtttttct cttttcttat taaatgatct ttctatgaac cagc            54

<210> SEQ ID NO 70
<211> LENGTH: 57
<212> TYPE: DNA
<213> ORGANISM: Artificial Sequence
<220> FEATURE:
<223> OTHER INFORMATION: CRISPR Recognition sequence 50
<220> FEATURE:
<221> NAME/KEY: misc_feature
<222> LOCATION: (1)..(57)

<400> SEQUENCE: 70
ccactcctga gaccatcgac cataaaccct cgactgcctg tgtcgtcccc acagcta         57

<210> SEQ ID NO 71
<211> LENGTH: 29
<212> TYPE: DNA
<213> ORGANISM: Artificial Sequence
```

```
<220> FEATURE:
<223> OTHER INFORMATION: CRISPR Recognition sequence 51
<220> FEATURE:
<221> NAME/KEY: misc_feature
<222> LOCATION: (1)..(29)

<400> SEQUENCE: 71
tgacctcacc gacagcacct gcctagtaa                                            29

<210> SEQ ID NO 72
<211> LENGTH: 29
<212> TYPE: DNA
<213> ORGANISM: Artificial Sequence
<220> FEATURE:
<223> OTHER INFORMATION: CRISPR Recognition sequence 52
<220> FEATURE:
<221> NAME/KEY: misc_feature
<222> LOCATION: (1)..(29)

<400> SEQUENCE: 72
atgttgatgg agttggcacc ttgcggctt                                            29

<210> SEQ ID NO 73
<211> LENGTH: 29
<212> TYPE: DNA
<213> ORGANISM: Artificial Sequence
<220> FEATURE:
<223> OTHER INFORMATION: CRISPR Recognition sequence 53
<220> FEATURE:
<221> NAME/KEY: misc_feature
<222> LOCATION: (1)..(29)

<400> SEQUENCE: 73
accccagaaa gagaccaccc ctttctatc                                            29

<210> SEQ ID NO 74
<211> LENGTH: 29
<212> TYPE: DNA
<213> ORGANISM: Artificial Sequence
<220> FEATURE:
<223> OTHER INFORMATION: CRISPR Recognition sequence 54
<220> FEATURE:
<221> NAME/KEY: misc_feature
<222> LOCATION: (1)..(29)

<400> SEQUENCE: 74
aggcctcaac tagtgaactg tatggaaaa                                            29

<210> SEQ ID NO 75
<211> LENGTH: 29
<212> TYPE: DNA
<213> ORGANISM: Artificial Sequence
<220> FEATURE:
<223> OTHER INFORMATION: CRISPR recognition sequence 55
<220> FEATURE:
<221> NAME/KEY: misc_feature
<222> LOCATION: (1)..(29)

<400> SEQUENCE: 75
tggagttggc accttgcggc ttctggatg                                            29

<210> SEQ ID NO 76
<211> LENGTH: 29
<212> TYPE: DNA
<213> ORGANISM: Artificial Sequence
<220> FEATURE:
<223> OTHER INFORMATION: CRISPR Recognition sequence 56
<220> FEATURE:
<221> NAME/KEY: misc_feature
```

```
<222> LOCATION: (1)..(29)

<400> SEQUENCE: 76
ttggattgta gtgaactttc gagaggctt                                    29

<210> SEQ ID NO 77
<211> LENGTH: 29
<212> TYPE: DNA
<213> ORGANISM: Artificial Sequence
<220> FEATURE:
<223> OTHER INFORMATION: CRISPR Recognition sequence 57
<220> FEATURE:
<221> NAME/KEY: misc_feature
<222> LOCATION: (1)..(29)

<400> SEQUENCE: 77
gcttataatc tctttgcggt gaacggcat                                    29

<210> SEQ ID NO 78
<211> LENGTH: 29
<212> TYPE: DNA
<213> ORGANISM: Artificial Sequence
<220> FEATURE:
<223> OTHER INFORMATION: CRISPR Recognition sequence 58
<220> FEATURE:
<221> NAME/KEY: misc_feature
<222> LOCATION: (1)..(29)

<400> SEQUENCE: 78
acgccaaacg agactggggc catgccaag                                    29

<210> SEQ ID NO 79
<211> LENGTH: 29
<212> TYPE: DNA
<213> ORGANISM: Artificial Sequence
<220> FEATURE:
<223> OTHER INFORMATION: CRISPR Recognition sequence 59
<220> FEATURE:
<221> NAME/KEY: misc_feature
<222> LOCATION: (1)..(29)

<400> SEQUENCE: 79
gctccaaggc gcagcagaaa ctgaactgg                                    29

<210> SEQ ID NO 80
<211> LENGTH: 29
<212> TYPE: DNA
<213> ORGANISM: Artificial Sequence
<220> FEATURE:
<223> OTHER INFORMATION: CRISPR Recognition sequence 60
<220> FEATURE:
<221> NAME/KEY: misc_feature
<222> LOCATION: (1)..(29)

<400> SEQUENCE: 80
aaccccaacg cctgagcacc tctacaaaa                                    29

<210> SEQ ID NO 81
<211> LENGTH: 29
<212> TYPE: DNA
<213> ORGANISM: Artificial Sequence
<220> FEATURE:
<223> OTHER INFORMATION: CRISPR Recognition sequence 61
<220> FEATURE:
<221> NAME/KEY: misc_feature
<222> LOCATION: (1)..(29)

<400> SEQUENCE: 81
```
actcctgaga ccatcgacca taaaccctc                                29

<210> SEQ ID NO 82
<211> LENGTH: 29
<212> TYPE: DNA
<213> ORGANISM: Artificial Sequence
<220> FEATURE:
<223> OTHER INFORMATION: CRISPR Recognition sequence 62
<220> FEATURE:
<221> NAME/KEY: misc_feature
<222> LOCATION: (1)..(29)

<400> SEQUENCE: 82
accccaacgc ctgagcacct ctacaaaaa                                29

<210> SEQ ID NO 83
<211> LENGTH: 29
<212> TYPE: DNA
<213> ORGANISM: Artificial Sequence
<220> FEATURE:
<223> OTHER INFORMATION: CRISPR Recognition sequence 63
<220> FEATURE:
<221> NAME/KEY: misc_feature
<222> LOCATION: (1)..(29)

<400> SEQUENCE: 83
caaccccaac gcctgagcac ctctacaaa                                29

<210> SEQ ID NO 84
<211> LENGTH: 29
<212> TYPE: DNA
<213> ORGANISM: Artificial Sequence
<220> FEATURE:
<223> OTHER INFORMATION: CRISPR Recognition sequence 64
<220> FEATURE:
<221> NAME/KEY: misc_feature
<222> LOCATION: (1)..(29)

<400> SEQUENCE: 84
agaccatcga ccataaaccc tcgactgcc                                29

<210> SEQ ID NO 85
<211> LENGTH: 29
<212> TYPE: DNA
<213> ORGANISM: Artificial Sequence
<220> FEATURE:
<223> OTHER INFORMATION: CRISPR Recognition sequence 65

<400> SEQUENCE: 85
ctctacaaaa aattcgcgag acatggact                                29

<210> SEQ ID NO 86
<211> LENGTH: 29
<212> TYPE: DNA
<213> ORGANISM: Artificial Sequence
<220> FEATURE:
<223> OTHER INFORMATION: CRISPR Recognition sequence 66
<220> FEATURE:
<221> NAME/KEY: misc_feature
<222> LOCATION: (1)..(29)

<400> SEQUENCE: 86
gcaccaggac ggggacactc cagagctaa                                29

<210> SEQ ID NO 87
<211> LENGTH: 29
<212> TYPE: DNA
<213> ORGANISM: Artificial Sequence

```
<220> FEATURE:
<223> OTHER INFORMATION: CRISPR Recognition sequence 67
<220> FEATURE:
<221> NAME/KEY: misc_feature
<222> LOCATION: (1)..(29)

<400> SEQUENCE: 87
taaggccact tcgcttttgt caaaggctc                              29

<210> SEQ ID NO 88
<211> LENGTH: 29
<212> TYPE: DNA
<213> ORGANISM: Artificial Sequence
<220> FEATURE:
<223> OTHER INFORMATION: CRISPR Recognition sequence 68
<220> FEATURE:
<221> NAME/KEY: misc_feature
<222> LOCATION: (1)..(29)

<400> SEQUENCE: 88
cgaccataaa ccctcgactg cctgtgtcg                              29

<210> SEQ ID NO 89
<211> LENGTH: 29
<212> TYPE: DNA
<213> ORGANISM: Artificial Sequence
<220> FEATURE:
<223> OTHER INFORMATION: CRISPR Recognition sequence 69
<220> FEATURE:
<221> NAME/KEY: misc_feature
<222> LOCATION: (1)..(29)

<400> SEQUENCE: 89
gaaccaaccc caacgcctga gcacctcta                              29

<210> SEQ ID NO 90
<211> LENGTH: 29
<212> TYPE: DNA
<213> ORGANISM: Artificial Sequence
<220> FEATURE:
<223> OTHER INFORMATION: CRISPR Recognition sequence 70
<220> FEATURE:
<221> NAME/KEY: misc_feature
<222> LOCATION: (1)..(29)

<400> SEQUENCE: 90
aaccctcgac tgcctgtgtc gtccccaca                              29

<210> SEQ ID NO 91
<211> LENGTH: 29
<212> TYPE: DNA
<213> ORGANISM: Artificial Sequence
<220> FEATURE:
<223> OTHER INFORMATION: CRISPR Recognition sequence 71
<220> FEATURE:
<221> NAME/KEY: misc_feature
<222> LOCATION: (1)..(29)

<400> SEQUENCE: 91
gagggagatg gtgcaagccg atgtggagc                              29

<210> SEQ ID NO 92
<211> LENGTH: 29
<212> TYPE: DNA
<213> ORGANISM: Artificial Sequence
<220> FEATURE:
<223> OTHER INFORMATION: CRISPR Recognition sequence 72
<220> FEATURE:
<221> NAME/KEY: misc_feature
```

<222> LOCATION: (1)..(29)

<400> SEQUENCE: 92
taagagctgg gccacaggtt tgtgggcac                                    29

<210> SEQ ID NO 93
<211> LENGTH: 29
<212> TYPE: DNA
<213> ORGANISM: Artificial Sequence
<220> FEATURE:
<223> OTHER INFORMATION: CRISPR Recognition sequence 73
<220> FEATURE:
<221> NAME/KEY: misc_feature
<222> LOCATION: (1)..(29)

<400> SEQUENCE: 93
tgggccacag gtttgtgggc accaggacg                                    29

<210> SEQ ID NO 94
<211> LENGTH: 26
<212> TYPE: DNA
<213> ORGANISM: Artificial Sequence
<220> FEATURE:
<223> OTHER INFORMATION: FORWARD PRIMER
<220> FEATURE:
<221> NAME/KEY: misc_feature
<222> LOCATION: (1)..(26)

<400> SEQUENCE: 94
aagaaataag ctgaatcagc tctgac                                       26

<210> SEQ ID NO 95
<211> LENGTH: 23
<212> TYPE: DNA
<213> ORGANISM: Artificial Sequence
<220> FEATURE:
<223> OTHER INFORMATION: REVERSE PRIMER
<220> FEATURE:
<221> NAME/KEY: misc_feature
<222> LOCATION: (1)..(23)

<400> SEQUENCE: 95
gtgctaatct gacctaacca gag                                          23

<210> SEQ ID NO 96
<211> LENGTH: 22
<212> TYPE: DNA
<213> ORGANISM: Artificial Sequence
<220> FEATURE:
<223> OTHER INFORMATION: FORWARD PRIMER
<220> FEATURE:
<221> NAME/KEY: misc_feature
<222> LOCATION: (1)..(22)

<400> SEQUENCE: 96
gatccttcag tgttccaagt ac                                           22

<210> SEQ ID NO 97
<211> LENGTH: 21
<212> TYPE: DNA
<213> ORGANISM: Artificial Sequence
<220> FEATURE:
<223> OTHER INFORMATION: REVERSE PRIMER
<220> FEATURE:
<221> NAME/KEY: misc_feature
<222> LOCATION: (1)..(21)

<400> SEQUENCE: 97
ctgttgagta acagaaacct c                                              21

<210> SEQ ID NO 98
<211> LENGTH: 20
<212> TYPE: DNA
<213> ORGANISM: Artificial Sequence
<220> FEATURE:
<223> OTHER INFORMATION: FORWARD PRIMER
<220> FEATURE:
<221> NAME/KEY: misc_feature
<222> LOCATION: (1)..(20)

<400> SEQUENCE: 98
gacgtagtct tcagctattc                                                20

<210> SEQ ID NO 99
<211> LENGTH: 21
<212> TYPE: DNA
<213> ORGANISM: Artificial Sequence
<220> FEATURE:
<223> OTHER INFORMATION: REVERSE PRIMER
<220> FEATURE:
<221> NAME/KEY: misc_feature
<222> LOCATION: (1)..(21)

<400> SEQUENCE: 99
gtgcagaaag aaagcagaaa c                                              21

<210> SEQ ID NO 100
<211> LENGTH: 499
<212> TYPE: DNA
<213> ORGANISM: Artificial Sequence
<220> FEATURE:
<223> OTHER INFORMATION: gRNA + scaffold for Fut8 Exon 7
<220> FEATURE:
<221> NAME/KEY: misc_feature
<222> LOCATION: (1)..(499)

<400> SEQUENCE: 100
attccaagat gagtgttcgc gttttagagc tagaaatagc aagttaaaat aaggctagtc     60
cgttatcaac ttgaaaaagt ggcaccgagt cggtgctttt ttgctccgcg gcacgagaac   120
tcaaagcccc ggggcctggg tcccacgcgg ggtcccttac ccagggtgcc ccgggcgctc   180
atttgcatgt cccacccaac aggtaaacct gacaggtcat cgcggccagg tacgacctgg   240
cggtcagagc accaaacata cgagccttgt gatgagttcc gttgcatgaa attctcccaa   300
aggctccaag atggacagga aagggcgcgg ttcggtcacc gtaagtagaa taggtgaaag   360
actcccgtgc cttataaggc ctgtgggtga cttcttctca ccgaattggc gctatgctac   420
tgggttttag agctagaaat agcaagttaa aataaggcta gtccgttatc aacttgaaaa   480
agtggcaccg agtcggtgc                                                499

<210> SEQ ID NO 101
<211> LENGTH: 499
<212> TYPE: DNA
<213> ORGANISM: Artificial Sequence
<220> FEATURE:
<223> OTHER INFORMATION: gRNA + scaffold for GMD exon 3
<220> FEATURE:
<221> NAME/KEY: misc_feature
<222> LOCATION: (1)..(499)

<400> SEQUENCE: 101
actaggcagg tgctgtcggt gttttagagc tagaaatagc aagttaaaat aaggctagtc     60
cgttatcaac ttgaaaaagt ggcaccgagt cggtgctttt ttgctccgcg gcacgagaac   120

```
tcaaagcccc ggggcctggg tcccacgcgg ggtcccttac ccagggtgcc ccgggcgctc    180
atttgcatgt cccacccaac aggtaaacct gacaggtcat cgcggccagg tacgacctgg    240
cggtcagagc accaaacata cgagccttgt gatgagttcc gttgcatgaa attctcccaa    300
aggctccaag atggacagga aagggcgcgg ttcggtcacc gtaagtagaa taggtgaaag    360
actcccgtgc cttataaggc ctgtgggtga cttcttctca ccgcatcaat gaagtcaaac    420
ctagttttag agctagaaat agcaagttaa ataaggcta gtccgttatc aacttgaaaa    480
agtggcaccg agtcggtgc                                                 499
```

```
<210> SEQ ID NO 102
<211> LENGTH: 96
<212> TYPE: DNA
<213> ORGANISM: Artificial Sequence
<220> FEATURE:
<223> OTHER INFORMATION: gRNA+ scaffold for GMD Exon 4
<220> FEATURE:
<221> NAME/KEY: misc_feature
<222> LOCATION: (1)..(96)

<400> SEQUENCE: 102
agttggcacc ttgcggcttc gttttagagc tagaaatagc aagttaaaat aaggctagtc    60
cgttatcaac ttgaaaaagt ggcaccgagt cggtgc                              96
```

```
<210> SEQ ID NO 103
<211> LENGTH: 236
<212> TYPE: DNA
<213> ORGANISM: Artificial Sequence
<220> FEATURE:
<223> OTHER INFORMATION: mutated sequence

<400> SEQUENCE: 103
aatcccaagg actgcagcaa agccagaaag ctggtatgta atatcaacaa aggctgtggc    60
tatggatgtc aactccatca tgtggtttac tgcttcatga ttgcttatgg cacccagcgc   120
actcatcttg gaatctcaga attggcgcta tgctactgga ggatgggaga ctgtgtttag   180
acctgtaagt gagacatgca cagacaggtc tggcctctcc actggacact ggtcag       236
```

```
<210> SEQ ID NO 104
<211> LENGTH: 218
<212> TYPE: DNA
<213> ORGANISM: Artificial Sequence
<220> FEATURE:
<223> OTHER INFORMATION: mutated sequence

<400> SEQUENCE: 104
aatcccaagg actgcagcaa agccagaaag ctggtatgta atatcaacaa aggctgtggc    60
tatggatgtc aactccatca tgtggtttac tgcttcatga ttgctcatct tggaatctca   120
gaattggcgc tatgctactg gaggatggga ctgtgttt agacctgtaa gtgagacatg    180
cacagacagg tctggcctct ccactggaca ctggtcag                           218
```

```
<210> SEQ ID NO 105
<211> LENGTH: 214
<212> TYPE: DNA
<213> ORGANISM: Artificial Sequence
<220> FEATURE:
<223> OTHER INFORMATION: mutated sequence

<400> SEQUENCE: 105
aatcccaagg actgcagcaa agccagaaag ctggtatgta atatcaacaa aggctgtggc    60
```

```
tatggatgtc aactccatca tgtggtttac tgcttcatga ttgcttatgg cacccagaat    120
tggcgctatg ctactggagg atgggagact gtgtttagac ctgtaagtga gacatgcaca    180
gacaggtctg gcctctccac tggacactgg tcag                                214
```

<210> SEQ ID NO 106
<211> LENGTH: 213
<212> TYPE: DNA
<213> ORGANISM: Artificial Sequence
<220> FEATURE:
<223> OTHER INFORMATION: mutated sequence

<400> SEQUENCE: 106

```
aatcccaagg actgcagcaa agccagaaag ctggtatgta atatcaacaa aggctgtggc     60
tatggatgtc aactccatca tgtggtttac tgcttcatga ttgcttatgg cacccaaatt    120
ggcgctatgc tactggagga tgggagactg tgtttagacc tgtaagtgag acatgcacag    180
acaggtctgg cctctccact ggacactggt cag                                 213
```

<210> SEQ ID NO 107
<211> LENGTH: 211
<212> TYPE: DNA
<213> ORGANISM: Artificial Sequence
<220> FEATURE:
<223> OTHER INFORMATION: mutated sequence

<400> SEQUENCE: 107

```
aatcccaagg actgcagcaa agccagaaag ctggtatgta atatcaacaa aggctgtggc     60
tatggatgtc aactccatca tgtggtctac tgcttcatga ttgcttatgg cacccagcga    120
acactcatct ctggaggatg ggagactgtg tttagacctg taagtgagac atgcacagac    180
aggtctggcc tctccactgg acactggtca g                                   211
```

<210> SEQ ID NO 108
<211> LENGTH: 202
<212> TYPE: DNA
<213> ORGANISM: Artificial Sequence
<220> FEATURE:
<223> OTHER INFORMATION: mutated sequence

<400> SEQUENCE: 108

```
aatcccaagg actgcagcaa agccagaaag ctggtatgta atatcaacaa aggctgtggc     60
tatggatgtc aactccatca tgtggtttac tgcttcatga ttgcttatgg cacccagcga    120
acactcatct tggaatctgt gtttagacct gtaagtgaga catgcacaga caggtctggc    180
ctctccactg gacactggtc ag                                             202
```

<210> SEQ ID NO 109
<211> LENGTH: 226
<212> TYPE: DNA
<213> ORGANISM: Artificial Sequence
<220> FEATURE:
<223> OTHER INFORMATION: mutated sequence

<400> SEQUENCE: 109

```
aatcccaagg actgcagcaa agccagaaag ctggtatgta atatcaacaa aggctgtggc     60
tatggatgtc aactccatca tgtggtttac tgcttcatga ttgcttatgg cacccagcga    120
acattggata ttgggaagaa ttagagttga ggatgggaga ctgtgtttag acctgtaagt    180
gagacatgca cagacaggtc tggcctctcc actggacact ggtcag                   226
```

<210> SEQ ID NO 110
<211> LENGTH: 315
<212> TYPE: DNA
<213> ORGANISM: Artificial Sequence
<220> FEATURE:
<223> OTHER INFORMATION: mutated sequence

<400> SEQUENCE: 110

```
aatcccaagg actgcagcaa agccagaaag ctggtatgta atatcaacaa aggctgtggc      60
tatggatgtc aactccatca tgtggtttac tgcttcatga ttgcttatgg cacccagcga     120
acactcatct tggaatctca gaattggcac acagatcctg gactcccgga tgaacactaa     180
gtacgacgag aatgacaagc tgatccggga agtgaaagtg atcaccctat gctactggag     240
gatgggagac tgtgtttaga cctgtaagtg agacatgcac agacaggtct ggcctctcca     300
ctggacactg gtcag                                                      315
```

<210> SEQ ID NO 111
<211> LENGTH: 285
<212> TYPE: DNA
<213> ORGANISM: Artificial Sequence
<220> FEATURE:
<223> OTHER INFORMATION: mutated sequence

<400> SEQUENCE: 111

```
aatcccaagg actgcagcaa agccagaaag ctggtatgta atatcaacaa aggctgtggc      60
tatggatgtc aactccatca tgtggtttac tgcttcatga ttgcttatgg cacccagcga     120
acactcacac tcatcttgga atctcagaat tggaatctca tcttggaatc tcagaattgg     180
aatctcagaa ttggcgctat gctactggag gatgggagac tgtgtttaga cctgtaagtg     240
agacatgcac agacaggtct ggcctctcca ctggacactg gtcag                     285
```

<210> SEQ ID NO 112
<211> LENGTH: 242
<212> TYPE: DNA
<213> ORGANISM: Artificial Sequence
<220> FEATURE:
<223> OTHER INFORMATION: mutated sequence

<400> SEQUENCE: 112

```
aatcccaagg actgcagcaa agccagaaag ctggtatgta atatcaacaa aggctgtggc      60
tatggatgtc aactccatca tgtggtttac tgcttcatga ttgcttatgg cacactcatt     120
atcctcgggg gagcagccac tcaaattttg gcgctatgct actggaggat gggagactgt     180
gtttagacct gtaagtgaga catgcacaga caggtctggc ctctccactg gacactggtc     240
ag                                                                    242
```

<210> SEQ ID NO 113
<211> LENGTH: 242
<212> TYPE: DNA
<213> ORGANISM: Artificial Sequence
<220> FEATURE:
<223> OTHER INFORMATION: consensus sequence
<220> FEATURE:
<221> NAME/KEY: misc_feature
<222> LOCATION: (114)..(114)
<223> OTHER INFORMATION: n is a, c, g, or t
<220> FEATURE:
<221> NAME/KEY: misc_feature
<222> LOCATION: (116)..(120)
<223> OTHER INFORMATION: n is a, c, g, or t
<220> FEATURE:
<221> NAME/KEY: misc_feature
<222> LOCATION: (122)..(123)
<223> OTHER INFORMATION: n is a, c, g, or t
<220> FEATURE:
<221> NAME/KEY: misc_feature
<222> LOCATION: (127)..(132)
<223> OTHER INFORMATION: n is a, c, g, or t
<220> FEATURE:
<221> NAME/KEY: misc_feature
<222> LOCATION: (134)..(134)
<223> OTHER INFORMATION: n is a, c, g, or t
<220> FEATURE:
<221> NAME/KEY: misc_feature
<222> LOCATION: (136)..(136)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t

<400> SEQUENCE: 113
aatcccaagg actgcagcaa agccagaaag ctggtatgta atatcaacaa aggctgtggc       60
tatggatgtc aactccatca tgtggtttac tgcttcatga ttgcttatgg cacncnnnnn      120
annctcnnnn nngnanccac tcananttg gcgctatgct actggaggat gggagactgt      180
gtttagacct gtaagtgaga catgcacaga caggtctggc ctctccactg gacactggtc      240
ag                                                                    242

<210> SEQ ID NO 114
<211> LENGTH: 245
<212> TYPE: DNA
<213> ORGANISM: Artificial Sequence
<220> FEATURE:
<223> OTHER INFORMATION: mutated sequence

<400> SEQUENCE: 114
aatcccaagg actgcagcaa agccagaaag ctggtatgta atatcaacaa aggctgtggc       60
tatggatgtc aactccatca tgtggtttac tgcttcatga ttgcttatgg cacccagcga      120
acactcatct tgcgaacact catcttggaa tctcagaatt gtactggagg atgggagact      180
gtgtttagac ctgtaagtga gacatgcaca gacaggtctg gcctctccac tggacactgg      240
tcagg                                                                 245

<210> SEQ ID NO 115
<211> LENGTH: 255
<212> TYPE: DNA
<213> ORGANISM: Artificial Sequence
<220> FEATURE:
<223> OTHER INFORMATION: mutated sequence

<400> SEQUENCE: 115
aatcccaagg actgcagcaa agccagaaag ctggtatgta atatcaacaa aggctgtggc       60
tatggatgtc aactccatca tgtggtttac tgcttcatga ttgcttatgg cacccagcga      120
acactcatct tggaatctca gaattggcgc tttggaatct cagaattggc gctactggag      180
gatgggagac tgtgtttaga cctgtaagtg agacatgcac agacaggtct ggcctctcca      240
ctggacactg gtcag                                                      255

<210> SEQ ID NO 116
<211> LENGTH: 97
<212> TYPE: DNA

```
<213> ORGANISM: Artificial Sequence
<220> FEATURE:
<223> OTHER INFORMATION: mutated sequence

<400> SEQUENCE: 116
acatgaagtt gcactatggt gacctcaccg acagcacctg cctagtgaag tcaaacctac    60
agagatctac aatcttggtg cccagagcca tgtcaag                             97

<210> SEQ ID NO 117
<211> LENGTH: 95
<212> TYPE: DNA
<213> ORGANISM: Artificial Sequence
<220> FEATURE:
<223> OTHER INFORMATION: mutated sequence

<400> SEQUENCE: 117
tggtgacctc accgacagca cctgcctagt aaaaaatcat caatgaagtc aaacctacag    60
agatctacaa tcttggtgcc cagagccatg tcaag                               95

<210> SEQ ID NO 118
<211> LENGTH: 83
<212> TYPE: DNA
<213> ORGANISM: Artificial Sequence
<220> FEATURE:
<223> OTHER INFORMATION: mutated sequence

<400> SEQUENCE: 118
acatgaagtt gcactatggt gacctcaccg atgaagtcaa acctacagag atctacaatc    60
ttggtgccca gagccatgtc aag                                            83

<210> SEQ ID NO 119
<211> LENGTH: 66
<212> TYPE: DNA
<213> ORGANISM: Artificial Sequence
<220> FEATURE:
<223> OTHER INFORMATION: mutated sequence

<400> SEQUENCE: 119
tagatctctg taggtttgac ttcattgatg aagatctaca atcttggtgc ccagagccat    60
gtcaag                                                               66

<210> SEQ ID NO 120
<211> LENGTH: 300
<212> TYPE: DNA
<213> ORGANISM: Artificial Sequence
<220> FEATURE:
<223> OTHER INFORMATION: mutated sequence

<400> SEQUENCE: 120
acatgaagtt gcactatggt gacctcaccg acagcacctg tgttttggca ccaaaatcaa    60
cgggactttc caaatgtcg cgcaaatgga gaatcgcgca ggggaatggc ctgccgcact   120
ttctggcggg cagaaacagc gagtggcgct ggcaagagcg attgttgcgt gatgaaccgc   180
tcggggcgct ggacgcctta acgcgactcg agatgcagga tttgattgtg tctagtaaaa   240
atcatcaatg aagtcaaacc tacagagatc tacaatcttg gtgcccagag ccatgtcaag   300

<210> SEQ ID NO 121
<211> LENGTH: 134
<212> TYPE: DNA
<213> ORGANISM: Artificial Sequence
<220> FEATURE:
<223> OTHER INFORMATION: mutated sequence
```

<400> SEQUENCE: 121

```
acatgaagtt gcactatggt gacctcaccg acagcacctg cctagtaaaa atcatctgac      60
cgccaggtcg taaaatcatc aatgaagtca aacctacaga gatctacaat cttggtgccc     120
agagccatgt caag                                                        134
```

<210> SEQ ID NO 122
<211> LENGTH: 180
<212> TYPE: DNA
<213> ORGANISM: Cricetulus griseus

<400> SEQUENCE: 122

```
atttcctttg acttagcaga gtacactgca gatgttgatg gagttggcac cttgcggctt      60
ctggatgcaa ttaagacttg tggccttata aattctgtga agttctacca ggcctcaact     120
agtgaactgt atggaaaagt gcaagaaata ccccagaaag agaccacccc tttctatcca     180
```

<210> SEQ ID NO 123
<211> LENGTH: 172
<212> TYPE: DNA
<213> ORGANISM: Artificial Sequence
<220> FEATURE:
<223> OTHER INFORMATION: mutated sequence

<400> SEQUENCE: 123

```
atttcctttg acttagcaga gtacactgca gatgttgatg gagttggcac ttctggatgc      60
aattaagact tgtggcctta taaattctgt gaagttctac caggcctcaa ctagtgaact     120
gtatggaaaa gtgcaagaaa tacccccagaa agagaccacc cctttctatc ca             172
```

<210> SEQ ID NO 124
<211> LENGTH: 144
<212> TYPE: DNA
<213> ORGANISM: Artificial Sequence
<220> FEATURE:
<223> OTHER INFORMATION: mutated sequence

<400> SEQUENCE: 124

```
atttcctttg acttagcaga gtacactgca gatgttgaga cttgtggcct tataaattct      60
gtgaagttct accaggcctc aactagtgaa ctgtatggaa aagtgcaaga aatacccccag    120 aaagagacca cccctttcta tcca                                             144
```

<210> SEQ ID NO 125
<211> LENGTH: 71
<212> TYPE: PRT
<213> ORGANISM: Artificial Sequence
<220> FEATURE:
<223> OTHER INFORMATION: mutated sequence

<400> SEQUENCE: 125

```
Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Asn Trp Arg Tyr Ala Thr Gly Gly Trp
        35                  40                  45

Glu Thr Val Phe Arg Pro Val Ser Glu Thr Cys Thr Asp Arg Ser Gly
    50                  55                  60

Leu Ser Thr Gly His Trp Ser
65                  70
```

```
<210> SEQ ID NO 126
<211> LENGTH: 70
<212> TYPE: PRT
<213> ORGANISM: Artificial Sequence
<220> FEATURE:
<223> OTHER INFORMATION: mutated sequence

<400> SEQUENCE: 126
```

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Arg Thr Leu Ile Ser Gly Gly Trp Glu
        35                  40                  45

Thr Val Phe Arg Pro Val Ser Glu Thr Cys Thr Asp Arg Ser Gly Leu
    50                  55                  60

Ser Thr Gly His Trp Ser
65                  70

```
<210> SEQ ID NO 127
<211> LENGTH: 67
<212> TYPE: PRT
<213> ORGANISM: Artificial Sequence
<220> FEATURE:
<223> OTHER INFORMATION: mutated sequence

<400> SEQUENCE: 127
```

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Arg Thr Leu Ile Leu Glu Ser Val Phe
        35                  40                  45

Arg Pro Val Ser Glu Thr Cys Thr Asp Arg Ser Gly Leu Ser Thr Gly
    50                  55                  60

His Trp Ser
65

```
<210> SEQ ID NO 128
<211> LENGTH: 59
<212> TYPE: PRT
<213> ORGANISM: Artificial Sequence
<220> FEATURE:
<223> OTHER INFORMATION: mutated sequence

<400> SEQUENCE: 128
```

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Arg Thr His Leu Gly Ile Ser Glu Leu
        35                  40                  45

Ala Leu Cys Tyr Trp Arg Met Gly Asp Cys Val
    50                  55

```
<210> SEQ ID NO 129
<211> LENGTH: 53
<212> TYPE: PRT
<213> ORGANISM: Artificial Sequence
<220> FEATURE:
```

<223> OTHER INFORMATION: mutated sequence

<400> SEQUENCE: 129

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala His Leu Gly Ile Ser Glu Leu Ala Leu Cys Tyr Trp Arg
        35                  40                  45

Met Gly Asp Cys Val
    50

<210> SEQ ID NO 130
<211> LENGTH: 54
<212> TYPE: PRT
<213> ORGANISM: Artificial Sequence
<220> FEATURE:
<223> OTHER INFORMATION: mutated sequence

<400> SEQUENCE: 130

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Ile Gly Ala Met Leu Leu Glu Asp Gly
        35                  40                  45

Arg Leu Cys Leu Asp Leu
    50

<210> SEQ ID NO 131
<211> LENGTH: 81
<212> TYPE: PRT
<213> ORGANISM: Artificial Sequence
<220> FEATURE:
<223> OTHER INFORMATION: mutated sequence

<400> SEQUENCE: 131

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Gln Thr Leu Ile Leu Arg Thr Leu Ile
        35                  40                  45

Leu Glu Ser Gln Asn Cys Thr Gly Gly Trp Glu Thr Val Phe Arg Pro
    50                  55                  60

Val Ser Glu Thr Cys Thr Asp Arg Ser Gly Leu Ser Thr Gly His Trp
65                  70                  75                  80

Ser

<210> SEQ ID NO 132
<211> LENGTH: 59
<212> TYPE: PRT
<213> ORGANISM: Artificial Sequence
<220> FEATURE:
<223> OTHER INFORMATION: mutated sequence

<400> SEQUENCE: 132

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe

```
                20                  25                  30

Met Ile Ala Tyr Gly Thr Gln Arg Thr Leu Ile Leu Glu Ser Gln Asn
        35                  40                  45

Trp His Thr Asp Pro Gly Leu Pro Asp Glu His
    50                  55
```

<210> SEQ ID NO 133
<211> LENGTH: 78
<212> TYPE: PRT
<213> ORGANISM: Artificial Sequence
<220> FEATURE:
<223> OTHER INFORMATION: mutated sequence

<400> SEQUENCE: 133

```
Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
                20                  25                  30

Met Ile Ala Tyr Gly Thr Gln Arg Thr Leu Thr Leu Ile Leu Glu Ser
        35                  40                  45

Gln Asn Trp Asn Leu Ile Leu Glu Ser Gln Asn Trp Asn Leu Arg Ile
    50                  55                  60

Gly Ala Met Leu Leu Glu Asp Gly Arg Leu Cys Leu Asp Leu
65                  70                  75
```

<210> SEQ ID NO 134
<211> LENGTH: 68
<212> TYPE: PRT
<213> ORGANISM: Artificial Sequence
<220> FEATURE:
<223> OTHER INFORMATION: mutated sequence

<400> SEQUENCE: 134

```
Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
                20                  25                  30

Met Ile Ala Tyr Gly Thr Gln Arg Thr Leu Ile Leu Glu Ser Gln Asn
        35                  40                  45

Trp Arg Phe Gly Ile Ser Glu Leu Ala Leu Leu Glu Asp Gly Arg Leu
    50                  55                  60

Cys Leu Asp Leu
65
```

<210> SEQ ID NO 135
<211> LENGTH: 47
<212> TYPE: PRT
<213> ORGANISM: Artificial Sequence
<220> FEATURE:
<223> OTHER INFORMATION: mutated sequence

<400> SEQUENCE: 135

```
Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
                20                  25                  30

Met Ile Ala Tyr Gly Thr Gln Arg Thr Leu Asp Ile Gly Lys Asn
        35                  40                  45
```

<210> SEQ ID NO 136

```
<211> LENGTH: 61
<212> TYPE: PRT
<213> ORGANISM: Artificial Sequence
<220> FEATURE:
<223> OTHER INFORMATION: mutated sequence

<400> SEQUENCE: 136

Asn Pro Lys Asp Cys Ser Lys Ala Arg Lys Leu Val Cys Asn Ile Asn
1               5                   10                  15

Lys Gly Cys Gly Tyr Gly Cys Gln Leu His His Val Val Tyr Cys Phe
            20                  25                  30

Met Ile Ala Tyr Gly Thr Leu Ile Ile Leu Gly Gly Ala Ala Thr Gln
        35                  40                  45

Ile Leu Ala Leu Cys Tyr Trp Arg Met Gly Asp Cys Val
    50                  55                  60

<210> SEQ ID NO 137
<211> LENGTH: 36
<212> TYPE: PRT
<213> ORGANISM: Cricetulus griseus

<400> SEQUENCE: 137

Met Lys Leu His Tyr Gly Asp Leu Thr Asp Ser Thr Cys Leu Val Lys
1               5                   10                  15

Ile Ile Asn Glu Val Lys Pro Thr Glu Ile Tyr Asn Leu Gly Ala Gln
            20                  25                  30

Ser His Val Lys
        35

<210> SEQ ID NO 138
<211> LENGTH: 27
<212> TYPE: PRT
<213> ORGANISM: Artificial Sequence
<220> FEATURE:
<223> OTHER INFORMATION: mutated sequence

<400> SEQUENCE: 138

Met Lys Leu His Tyr Gly Asp Leu Thr Asp Glu Val Lys Pro Thr Glu
1               5                   10                  15

Ile Tyr Asn Leu Gly Ala Gln Ser His Val Lys
            20                  25

<210> SEQ ID NO 139
<211> LENGTH: 29
<212> TYPE: PRT
<213> ORGANISM: Artificial Sequence
<220> FEATURE:
<223> OTHER INFORMATION: mutated sequence

<400> SEQUENCE: 139

Val Thr Ser Pro Thr Ala Pro Ala Lys Ile Ile Asn Glu Val Lys Pro
1               5                   10                  15

Thr Glu Ile Tyr Asn Leu Gly Ala Gln Ser His Val Lys
            20                  25

<210> SEQ ID NO 140
<211> LENGTH: 31
<212> TYPE: PRT
<213> ORGANISM: Artificial Sequence
<220> FEATURE:
<223> OTHER INFORMATION: mutated sequence

<400> SEQUENCE: 140
```

-continued

Met Lys Leu His Tyr Gly Asp Leu Thr Asp Ser Thr Cys Leu Val Lys
1               5                   10                  15

Ser Asn Leu Gln Arg Ser Thr Ile Leu Val Pro Arg Ala Met Ser
            20                  25                  30

<210> SEQ ID NO 141
<211> LENGTH: 21
<212> TYPE: PRT
<213> ORGANISM: Artificial Sequence
<220> FEATURE:
<223> OTHER INFORMATION: mutated sequence

<400> SEQUENCE: 141

Ile Ser Val Gly Leu Thr Ser Leu Met Lys Ile Tyr Asn Leu Gly Ala
1               5                   10                  15

Gln Ser His Lys Val
            20

<210> SEQ ID NO 142
<211> LENGTH: 106
<212> TYPE: PRT
<213> ORGANISM: Artificial Sequence
<220> FEATURE:
<223> OTHER INFORMATION: mutated sequence

<400> SEQUENCE: 142

Met Leu Lys His Tyr Gly Asp Leu Thr Asp Ser Thr Cys Val Leu Ala
1               5                   10                  15

Pro Lys Ser Thr Gly Leu Ser Lys Met Ser Pro Arg Pro Val Asp Ala
            20                  25                  30

Asn Gly Glu Ser Arg Arg Gly Met Ala Cys Arg Thr Phe Trp Arg Ala
        35                  40                  45

Glu Thr Ala Ser Gly Ala Gly Lys Ser Val Asp Ser Ser Thr Gly Ile
    50                  55                  60

Ile Val Ala Thr Ala Arg Gly Ala Gly Arg Leu Asn Ala Thr Arg Asp
65                  70                  75                  80

Ala Gly Phe Asp Cys Val Lys Ser Ser Met Lys Ser Asn Leu Gln Arg
                85                  90                  95

Ser Thr Ile Leu Val Pro Arg Ala Met Ser
            100                 105

<210> SEQ ID NO 143
<211> LENGTH: 43
<212> TYPE: PRT
<213> ORGANISM: Artificial Sequence
<220> FEATURE:
<223> OTHER INFORMATION: mutated sequence

<400> SEQUENCE: 143

Met Lys Leu His Tyr Gly Asp Leu Thr Asp Ser Thr Cys Leu Val Lys
1               5                   10                  15

Ile Ile Pro Pro Gly Arg Lys Ile Asn Glu Val Lys Pro Thr Glu
            20                  25                  30

Ile Tyr Asn Leu Gly Ala Gln Ser His Val Lys
        35                  40

<210> SEQ ID NO 144
<211> LENGTH: 64
<212> TYPE: PRT
<213> ORGANISM: Cricetulus griseus

<400> SEQUENCE: 144

```
Ile Ser Phe Asp Leu Ala Glu Tyr Thr Ala Asp Val Asp Gly Val Gly
1               5                   10                  15

Thr Leu Arg Leu Leu Asp Ala Ile Lys Thr Cys Gly Leu Ile Asn Ser
            20                  25                  30

Val Lys Phe Tyr Gln Ala Ser Thr Ser Glu Leu Tyr Gly Lys Val Gln
        35                  40                  45

Glu Ile Pro Gln Lys Glu Thr Thr Pro Phe Tyr Pro Arg Ser Pro Tyr
    50                  55                  60
```

<210> SEQ ID NO 145
<211> LENGTH: 58
<212> TYPE: PRT
<213> ORGANISM: Artificial Sequence
<220> FEATURE:
<223> OTHER INFORMATION: mutated sequence

<400> SEQUENCE: 145

```
Ile Ser Phe Asp Leu Ala Glu Tyr Thr Ala Asp Val Asp Gly Val Gly
1               5                   10                  15

Thr Ser Gly Cys Asn Asp Leu Trp Pro Tyr Lys Phe Cys Glu Val Leu
            20                  25                  30

Pro Gly Leu Asn Thr Val Trp Lys Ser Ala Arg Asn Thr Pro Lys Arg
        35                  40                  45

Asp His Pro Phe Leu Ser Lys Val Ala Leu
    50                  55
```

<210> SEQ ID NO 146
<211> LENGTH: 49
<212> TYPE: PRT
<213> ORGANISM: Artificial Sequence
<220> FEATURE:
<223> OTHER INFORMATION: mutated sequence

<400> SEQUENCE: 146

```
Ile Ser Asp Ala Tyr Thr Ala Asp Val Glu Thr Cys Gly Leu Ile Asn
1               5                   10                  15

Ser Val Lys Phe Tyr Gln Ala Ser Thr Ser Glu Leu Tyr Gly Lys Val
            20                  25                  30

Gln Glu Ile Pro Gln Lys Glu Thr Thr Pro Phe Tyr Pro Arg Ser Pro
        35                  40                  45

Tyr
```

<210> SEQ ID NO 147
<211> LENGTH: 575
<212> TYPE: PRT
<213> ORGANISM: Rattus norvegicus

<400> SEQUENCE: 147

```
Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80
```

```
Gly Arg Val Arg Val Leu Glu Glu Gln Leu Val Lys Ala Lys Glu Gln
                85                  90                  95

Ile Glu Asn Tyr Lys Lys Gln Ala Arg Asn Gly Leu Gly Lys Asp His
           100                 105                 110

Glu Ile Leu Arg Arg Ile Glu Asn Gly Ala Lys Glu Leu Trp Phe
           115                 120                 125

Phe Leu Gln Ser Glu Leu Lys Lys Leu Lys His Leu Glu Gly Asn Glu
    130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
            195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Asn Asp Lys Asn Ile Gln Val
            275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Glu Ala Thr Lys Lys
            340                 345                 350

Leu Gly Phe Lys His Pro Val Ile Gly Val His Val Arg Arg Thr Asp
    355                 360                 365

Lys Val Gly Thr Glu Ala Ala Phe His Pro Ile Glu Glu Tyr Met Val
    370                 375                 380

His Val Glu Glu His Phe Gln Leu Leu Ala Arg Arg Met Gln Val Asp
385                 390                 395                 400

Lys Lys Arg Val Tyr Leu Ala Thr Asp Pro Ala Leu Leu Lys Glu
            405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
            435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Val Tyr Pro
```

```
                500                 505                 510
His Lys Pro Arg Thr Asp Glu Glu Ile Pro Met Glu Pro Gly Asp Ile
            515                 520                 525

Ile Gly Val Ala Gly Asn His Trp Asp Gly Tyr Ser Lys Gly Val Asn
            530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 148
<211> LENGTH: 575
<212> TYPE: PRT
<213> ORGANISM: Mus musculus

<400> SEQUENCE: 148

Met Arg Ala Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Gly Leu Gly Lys Asp His
            100                 105                 110

Glu Ile Leu Arg Arg Ile Glu Asn Gly Ala Lys Glu Leu Trp Phe
        115                 120                 125

Phe Leu Gln Ser Glu Leu Lys Lys Leu Lys His Leu Glu Gly Asn Glu
    130                 135                 140

Leu Gln Arg His Ala Asp Glu Ile Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
        195                 200                 205

Lys Leu Val Cys Asn Ile Asn Lys Gly Cys Gly Tyr Gly Cys Gln Leu
    210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Asn Asp Lys Asn Ile Gln Val
        275                 280                 285

Val Glu Leu Pro Ile Val Asp Ser Leu His Pro Arg Pro Pro Tyr Leu
    290                 295                 300
```

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
            325                 330                 335

Arg Pro Gln Pro Trp Leu Glu Lys Glu Ile Glu Glu Ala Thr Lys Lys
        340                 345                 350

Leu Gly Phe Lys His Pro Val Ile Gly Val His Val Arg Arg Thr Asp
    355                 360                 365

Lys Val Gly Thr Glu Ala Ala Phe His Pro Ile Glu Glu Tyr Met Val
370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Thr Leu Leu Lys Glu
                405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
            500                 505                 510

His Lys Pro Arg Thr Glu Glu Ile Pro Met Glu Pro Gly Asp Ile
        515                 520                 525

Ile Gly Val Ala Gly Asn His Trp Asp Gly Tyr Ser Lys Gly Ile Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 149
<211> LENGTH: 575
<212> TYPE: PRT
<213> ORGANISM: Cricetulus griseus

<400> SEQUENCE: 149

Met Arg Ala Trp Thr Gly Ser Trp Arg Trp Ile Met Leu Ile Leu Phe
1                   5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
    50                  55                  60

Glu Ser Leu Arg Ile Pro Glu Gly Pro Ile Asp Gln Gly Thr Ala Thr
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Ala Arg Asn Asp Leu Gly Lys Asp His
            100                 105                 110

```
Glu Ile Leu Arg Arg Ile Glu Asn Gly Ala Lys Glu Leu Trp Phe
            115                 120                 125

Phe Leu Gln Ser Glu Leu Lys Lys Leu Lys Lys Leu Glu Gly Asn Glu
        130                 135                 140

Leu Gln Arg His Ala Asp Glu Ile Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Glu Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Arg
                195                 200                 205

Lys Leu Val Cys Asn Ile Asn Lys Gly Cys Gly Tyr Gly Cys Gln Leu
        210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Leu
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Pro Tyr Leu
    290                 295                 300

Pro Leu Ala Val Pro Glu Asp Leu Ala Asp Arg Leu Leu Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Arg Glu Ile Glu Glu Thr Thr Lys Lys
            340                 345                 350

Leu Gly Phe Lys His Pro Val Ile Gly Val His Val Arg Arg Thr Asp
        355                 360                 365

Lys Val Gly Thr Glu Ala Ala Phe His Pro Ile Glu Gly Tyr Met Val
    370                 375                 380

His Val Glu Glu His Phe Gln Leu Leu Glu Arg Arg Met Lys Val Asp
385                 390                 395                 400

Lys Lys Arg Val Tyr Leu Ala Thr Asp Asp Pro Ser Leu Leu Lys Glu
                405                 410                 415

Ala Lys Thr Lys Tyr Ser Asn Tyr Glu Phe Ile Ser Asp Asn Ser Ile
            420                 425                 430

Ser Trp Ser Ala Gly Leu His Asn Arg Tyr Thr Glu Asn Ser Leu Arg
        435                 440                 445

Gly Val Ile Leu Asp Ile His Phe Leu Ser Gln Ala Asp Phe Leu Val
    450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Val Tyr Pro
        500                 505                 510

His Gln Pro Arg Thr Lys Glu Glu Ile Pro Met Glu Pro Gly Asp Ile
    515                 520                 525
```

```
Ile Gly Val Ala Gly Asn His Trp Asn Gly Tyr Ser Lys Gly Val Asn
    530                 535                 540

Arg Lys Leu Gly Lys Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575

<210> SEQ ID NO 150
<211> LENGTH: 575
<212> TYPE: PRT
<213> ORGANISM: Homo sapiens

<400> SEQUENCE: 150

Met Arg Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Asp
            20                  25                  30

Asn Asp His Pro Asp His Ser Ser Arg Glu Leu Ser Lys Ile Leu Ala
        35                  40                  45

Lys Leu Glu Arg Leu Lys Gln Gln Asn Glu Asp Leu Arg Arg Met Ala
50                  55                  60

Glu Ser Leu Arg Ile Pro Glu Gly Pro Ile Asp Gln Gly Pro Ala Ile
65                  70                  75                  80

Gly Arg Val Arg Val Leu Glu Glu Gln Leu Val Lys Ala Lys Glu Gln
                85                  90                  95

Ile Glu Asn Tyr Lys Lys Gln Thr Arg Asn Gly Leu Gly Lys Asp His
            100                 105                 110

Glu Ile Leu Arg Arg Arg Ile Glu Asn Gly Ala Lys Glu Leu Trp Phe
        115                 120                 125

Phe Leu Gln Ser Glu Leu Lys Lys Leu Lys Asn Leu Glu Gly Asn Glu
130                 135                 140

Leu Gln Arg His Ala Asp Glu Phe Leu Leu Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
            180                 185                 190

Arg Arg Ile Thr Tyr Leu Gln Asn Pro Lys Asp Cys Ser Lys Ala Lys
        195                 200                 205

Lys Leu Val Cys Asn Ile Asn Lys Gly Cys Gly Tyr Gly Cys Gln Leu
210                 215                 220

His His Val Val Tyr Cys Phe Met Ile Ala Tyr Gly Thr Gln Arg Thr
225                 230                 235                 240

Leu Ile Leu Glu Ser Gln Asn Trp Arg Tyr Ala Thr Gly Gly Trp Glu
                245                 250                 255

Thr Val Phe Arg Pro Val Ser Glu Thr Cys Thr Asp Arg Ser Gly Ile
            260                 265                 270

Ser Thr Gly His Trp Ser Gly Glu Val Lys Asp Lys Asn Val Gln Val
        275                 280                 285

Val Glu Leu Pro Ile Val Asp Ser Leu His Pro Arg Pro Pro Tyr Leu
290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
                325                 330                 335
```

```
Arg Pro Gln Pro Trp Leu Glu Lys Glu Ile Glu Ala Thr Lys Lys
            340                 345                 350

Leu Gly Phe Lys His Pro Val Ile Gly Val His Val Arg Thr Asp
            355                 360                 365

Lys Val Gly Thr Glu Ala Ala Phe His Pro Ile Glu Glu Tyr Met Val
370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Ser Leu Leu Lys Glu
            405                 410                 415

Ala Lys Thr Lys Tyr Pro Asn Tyr Glu Phe Ile Ser Asp Asn Ser Ile
            420                 425                 430

Ser Trp Ser Ala Gly Leu His Asn Arg Tyr Thr Glu Asn Ser Leu Arg
            435                 440                 445

Gly Val Ile Leu Asp Ile His Phe Leu Ser Gln Ala Asp Phe Leu Val
            450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
            485                 490                 495

Tyr Tyr Phe Gly Gly Gln Asn Ala His Asn Gln Ile Ala Ile Tyr Ala
            500                 505                 510

His Gln Pro Arg Thr Ala Asp Glu Ile Pro Met Glu Pro Gly Asp Ile
            515                 520                 525

Ile Gly Val Ala Gly Asn His Trp Asp Gly Tyr Ser Lys Gly Val Asn
            530                 535                 540

Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
            565                 570                 575

<210> SEQ ID NO 151
<211> LENGTH: 575
<212> TYPE: PRT
<213> ORGANISM: Bos taurus

<400> SEQUENCE: 151

Met Arg Pro Trp Thr Gly Ser Trp Arg Trp Ile Met Leu Ile Leu Phe
1               5                   10                  15

Ala Trp Gly Thr Leu Leu Phe Tyr Ile Gly Gly His Leu Val Arg Gly
            20                  25                  30

Asn Asp His Pro Asp His Ser Ser Arg Glu Leu Ser Lys Ile Leu Ala
            35                  40                  45

Lys Leu Glu Arg Leu Lys Gln Gln Asn Glu Asp Leu Arg Arg Met Ala
50                  55                  60

Glu Ser Leu Arg Ile Pro Glu Gly Pro Ile Asp Gln Gly Pro Ala Ser
65                  70                  75                  80

Gly Arg Ile Arg Ala Leu Glu Glu Gln Leu Val Lys Ala Lys Glu Gln
            85                  90                  95

Ile Glu Asn Tyr Lys Lys Gln Thr Arg Asn Gly Leu Gly Lys Asp His
            100                 105                 110

Glu Ile Leu Arg Arg Arg Ile Glu Asn Gly Ala Lys Glu Leu Trp Phe
            115                 120                 125

Phe Leu Gln Ser Glu Leu Lys Lys Leu Lys Asn Leu Glu Gly Asn Glu
```

```
                130               135                 140
Leu Gln Arg His Ala Asp Glu Phe Leu Ser Asp Leu Gly His His Glu
145                 150                 155                 160

Arg Ser Ile Met Thr Asp Leu Tyr Tyr Leu Ser Gln Thr Asp Gly Ala
                165                 170                 175

Gly Asp Trp Arg Glu Lys Glu Ala Lys Asp Leu Thr Glu Leu Val Gln
                180                 185                 190

Arg Arg Ile Thr Tyr Leu Gln Asn Pro Lys Asp Cys Ser Lys Ala Lys
                195                 200                 205

Lys Leu Val Cys Asn Ile Asn Lys Gly Cys Gly Tyr Gly Cys Gln Leu
                210                 215                 220

His His Val Val Tyr Cys Phe Met Ile Ala Tyr Gly Thr Gln Arg Thr
225                 230                 235                 240

Leu Ile Leu Glu Ser His Asn Trp Arg Tyr Ala Thr Gly Gly Trp Glu
                245                 250                 255

Thr Val Phe Arg Pro Val Ser Glu Thr Cys Thr Asp Arg Ser Gly Val
                260                 265                 270

Ser Thr Gly His Trp Ser Gly Glu Ile Lys Asp Lys Asn Val Gln Val
                275                 280                 285

Val Glu Leu Pro Ile Val Asp Ser Leu His Pro Arg Pro Pro Tyr Leu
                290                 295                 300

Pro Leu Ala Val Pro Glu Asp Leu Ala Asp Arg Leu Val Arg Val His
305                 310                 315                 320

Gly Asp Pro Ala Val Trp Trp Val Ser Gln Phe Val Lys Tyr Leu Ile
                325                 330                 335

Arg Pro Gln Pro Trp Leu Glu Lys Glu Ile Glu Ala Thr Lys Lys
                340                 345                 350

Leu Gly Phe Lys His Pro Val Ile Gly Val His Val Arg Arg Thr Asp
                355                 360                 365

Lys Val Gly Thr Glu Ala Ala Phe His Pro Ile Glu Glu Tyr Met Val
                370                 375                 380

His Val Glu Glu His Phe Gln Leu Leu Ala Arg Arg Met Gln Val Asp
385                 390                 395                 400

Lys Lys Arg Val Tyr Leu Ala Thr Asp Asp Pro Ser Leu Leu Lys Glu
                405                 410                 415

Ala Lys Thr Lys Tyr Pro His Tyr Glu Phe Ile Ser Asp Asn Ser Ile
                420                 425                 430

Ser Trp Ser Ala Gly Leu His Asn Arg Tyr Thr Glu Asn Ser Leu Arg
                435                 440                 445

Gly Val Ile Leu Asp Ile His Phe Leu Ser Gln Ala Asp Phe Leu Val
                450                 455                 460

Cys Thr Phe Ser Ser Gln Val Cys Arg Val Ala Tyr Glu Ile Met Gln
465                 470                 475                 480

Thr Leu His Pro Asp Ala Ser Ala Asn Phe His Ser Leu Asp Asp Ile
                485                 490                 495

Tyr Tyr Phe Gly Gly Gln Asn Ala His Asn Gln Ile Ala Ile Tyr Pro
                500                 505                 510

His Glu Pro Arg Thr Ala Asp Glu Ile Pro Met Glu Pro Gly Asp Ile
                515                 520                 525

Ile Gly Val Ala Gly Asn His Trp Asp Gly Tyr Ser Lys Gly Val Asn
                530                 535                 540
```

-continued

```
Arg Lys Leu Gly Arg Thr Gly Leu Tyr Pro Ser Tyr Lys Val Arg Glu
545                 550                 555                 560

Lys Ile Glu Thr Val Lys Tyr Pro Thr Tyr Pro Glu Ala Glu Lys
                565                 570                 575
```

DNA-BINDING DOMAIN OF CRISPR SYSTEM, NON-FUCOSYLATED AND PARTIALLY FUCOSYLATED PROTEINS, AND METHODS THEREOF

CROSS-REFERENCE TO RELATED APPLICATIONS

This application is a divisional of U.S. application Ser. No. 15/526,971, filed May 15, 2017, which is a National Stage application under 35 U.S.C. § 371 of International Application No. PCT/IB2015/058777, having an International Filing Date of Nov. 13, 2015, which claims the benefit of priority of Indian Patent Application No. 5767/CHE/2014, having a filing date of Nov. 15, 2014.

SEQUENCE LISTING

This application contains a Sequence Listing that has been submitted electronically as an ASCII text file named Sequence_Listing.txt. The ASCII text file, created on Jul. 6, 2020, is 116,254 bytes in size. The material in the ASCII text file is hereby incorporated by reference in its entirety.

TECHNICAL FIELD

The present disclosure pertains to the field of biotechnology, genetic engineering and immunology. Particularly, the present disclosure relates to developing cell lines where specific biological pathways are modified. Such modifications are in the enzymes of the cell, particularly in enzymes involved in glycosylation of proteins. The present disclosure develops protein expression systems wherein specific modification of glycan chain of the protein is achieved. The specific modification of the glycan chain produces partially fucosylated and non-fucosylated proteins, including antibodies. Such products are used in developing therapeutics and biomarkers, and in diagnosis and prognosis of diseases. The present disclosure employs the Clustered Regularly Interspaced Short Palindromic Repeats (CRISPR) technology.

BACKGROUND AND PRIOR ART OF THE DISCLOSURE

Glycosylation in eukaryotes has been studied intensively for decades as the most common covalent post translational protein modification mechanism. About 1-2% of the human transcriptome (about 250-500 glycogenes) is predicted to translate proteins which are responsible for glycosylation (Campbell and Yarema 2005). Glycosylation of cellular proteins plays many key biological functions such as protein folding, stability, intracellular and inter-cellular trafficking, cell-cell and cell matrix Interaction.

There are four distinct groups of Glycoproteins: N-linked, O-linked, glycosaminoglycans, and glycosylphosphatidylinositol-anchored proteins. N-linked glycosylation occurs through the side chain amide nitrogen of asparagine residues, while O-linked glycosylation uses the oxygen atom in the side chain of serine or threonine residues. N-linked glycosylation takes place in the amino acid sequence of Asn-X-Ser/Thr, where X can be any amino acid except proline and aspartic acid (Helenius and Aebi 2004).

Fucose (6-deoxy-L-galactose) is a monosaccharide that is present in many glycoproteins and glycolipids present in vertebrates, invertebrates, plants, and bacteria. Fucosylation is the process of transferring a fucose residue to various proteins and oligosaccharides. Fucosylation is regulated by several molecules, including fucosyltransferases, guanosine diphosphate (GDP)-fucose synthetic enzymes, and GDP-fucose transporter(s). A large number of fucosylated glycoproteins are secretary proteins or membrane proteins on the cell surface.

There are 14.1 million new cancer cases, 8.2 million cancer deaths and 32.6 million people living with cancer (within 5 years of diagnosis) in 2014 worldwide. The high mortality rate of cancer serves as a reminder of the need for more effective therapies. The most prominent change in oncology drug development in the last 20 years has been the shift from classic cytotoxics to drugs that affect signaling pathways implicated in cancer, known as "Monoclonal Antibodies" or mAbs. A decade ago, there are only two mAbs on the market and currently there are around 30 FDA approved mAbs of diverse therapeutic modalities, like Adalimumab, Infliximab, Rituximab etc. mAbs are the fastest growing segment in pharmaceutical industry and this rapid expansion is set to continue. There are more than 100 monoclonal antibody-based biologic drugs in clinical trials. Many of these are in phase II and phase III trials and will be coming before the Regulatory agencies for approval. Improvement of monoclonal antibody therapeutics through technologies described here will pave the way for better clinical outcome for patients.

Human IgG1 antibody is a highly fucosylated glycoprotein. Two N-linked biantennary oligosaccharides consisting of core hepta-saccharide with variable addition of fucose, galactose, bisecting N-acetylglucosamine and sialic acid are present at Asn-297 of IgG1. Antibody glycosylation leads to unique biological functions known as "effector functions"—Antibody Dependent Cellular Cytotoxicity (ADCC) and Complement Dependent Cytotoxicity (CDC). ADCC is a cell mediated immune system where immune cells (like natural killer cells) lyse the target cells identified through antibodies against cell surface antigens.

The effector function of IgG molecule is defined by the interaction of antibody Fc region with leukocyte receptors, known as FcγRs, or interactions with complement components. The composition of the oligosaccharide structure is critically important for effector function through FcγR binding (Shields et al. 2002; Shinkawa et al. 2003; Niwa et al. 2004; Niwa, Shoji-Hosaka, et al. 2004; Yamane-Ohnuki et al. 2004). Crystal structure analysis of human IgG1 has revealed intricate interaction of the oligosaccharide chains with the CH2 domain (Harris et al. 1998; Radaev et al. 2001).

The efficiency of the ADCC mechanism is considerably dependent on the level of antibody fucosylation. The lower the fucosylation, the higher is the rate of ADCC. Therefore, loss of fucosylation has significant biological consequences. The loss could be due to non-functional fucosyltransferase enzymes, resulting in non-fucosylation of cellular proteins. The absence of fucose from the primary N-acetylglucosamine results in the IgG1 antibody having increased binding affinity for the FcγRIIIa receptor, with consequent increase of 50-100 times higher efficacy of ADCC. Improvement of ADCC with non-fucosylated IgG is directly proportional to the increased affinity for FcγRIIIα which allows the non-fucosylated IgG Fc to overcome the competition from high concentrations of fucosylated IgG in normal serum. Plausible rationale for the increased affinity of non-fucosylated IgG Fc for FcγRIIIa may be the reduction or absence of steric inhibition at the receptor-ligand interface (Harris, 1998; Radaev, 2001).

In mammalian expression system, the enzyme α1,6-fucosyltransferase encoded by the Fut8 gene is responsible for transferring fucose moiety from GDP-fucose to N-acetylglucosamine of N-glycan chain in proteins (Miyoshi, 1999). Disruption of this gene function through various means leads to production of non-fucosylated proteins, including antibodies (Naoko Yamane-Ohnuki, 2004).

GDP-D-mannose 4,6-dehydratase (GMD) is a member of the sugar nucleotide-modifying subfamily of the short-chain dehydrogenase/reductase (SDR) family (Webb, Mulichak et al. 2004).

In mammalian expression systems, GDP-fucose, an essential substrate of fucosylation, is synthesized in the cytoplasm through de novo and salvage pathways. In the de novo pathway of fucosylation, GDP-fucose is synthesized through conversion of GDP-mannose to GDP-4-keto-6-deoxy-mannose, catalyzed by the enzyme GDP-mannose 4,6-dehydratase (GMD). This GDP-Fucose is then transported inside the golgi and used as a substrate for protein fucosylation by the enzyme α1-6 fucosyltransferase (FUT8). The enzyme transfers the fucose moiety from GDP-fucose to N-acetylglucosamine of the N-glycan chain (Miyoshi, 1999). These critical enzymes, GDP-mannose 4,6-dehydratase and α,1-6 fucosyltransferase are encoded by GMD and FUT8 genes respectively.

Non-fucosylated forms of therapeutic antibodies developed in mammalian platforms, where fucose biosynthesis is impaired, may have clinical advantage over the fucosylated forms due to the enhanced efficiency of ADCC towards target tumor cells.

Historically, gene knock out systems completely depended on Homologous recombination (HR) mediated targeted mutation, deletion and/or insertion. The HR system, although very specific, is highly inefficient, as thousands of clones need to be screened to find one mutated clone. Moreover, deleting allelic variations would take even further time and much larger screening. Multiple technologies have evolved in the last decade to achieve targeted gene modification using a combination of a DNA sequence recognition domain and a nuclease domain. These systems are highly efficient at identifying specific sites of interest and then introducing DNA strand breaks. DNA double-strand break (DSB) at genomic target locus activates DNA repair, which is utilized for modifying genes. The DNA damage response is highly conserved in eukaryotic cells. The concept of DSB-based genome engineering is easily transferrable between highly diverse organisms. Creating double strand break increases the frequency of gene knock out at targeted loci by thousand folds through homologous recombination and non-homologous end joining mechanisms.

Zinc Finger Nuclease (ZFN) is one of the most frequently used techniques for gene disruption. It requires three bases at the DNA level for each zinc finger tandem array. Moreover, target site overlap and cross-talk between individual fingers in a zinc-finger array considerably complicate the production of sequence-specific ZFNs. Additionally, major drawback of ZFNs includes elaborate and time-consuming experimental selection process to identify the ZFN motifs for specific DNA sequence recognition.

There are methods in the prior art for disruption of Fut8 and GMD genomic loci. However, none of the methods target the specific location on the FUT8 and GMD genomic loci by the CRISPR technology.

The present disclosure overcomes the disadvantages or limitations associated with methods of the prior art by using the CRISPR technology to target a specific location on the FUT8 genomic loci or the GMD genomic loci, which results in complete disruption of the gene and related function, providing a cell that produces non-fucosylated proteins.

STATEMENT OF THE DISCLOSURE

Accordingly, the present disclosure relates to a DNA-binding domain of CRISPR system, wherein the DNA-binding domain comprises sequence selected from the group consisting of SEQ ID No.13, SEQ ID No. 15, SEQ ID No.17 to SEQ ID No. 37, SEQ ID No. 39, SEQ ID No. 41, SEQ ID No. 43, SEQ ID No.45, SEQ ID No. 47 to SEQ ID No. 93 and combinations thereof; a CRISPR-nuclease complex comprising the DNA-binding domain as mentioned above and nuclease; a vector comprising a DNA binding domain as mentioned above; a cell comprising a vector as mentioned above; a method of obtaining a fucose knockout cell, said method comprising steps of—a) Obtaining a CRISPR-nuclease construct, and b) Transfecting a cell with the construct of step (a) to obtain a fucose knockout cell; a method of obtaining protein with fucosylation ranging from 0% to 100%, said method comprising steps of—a) Obtaining a CRISPR-nuclease construct, b) Transfecting a cell with the construct of step (a) to obtain a cell with fucosylation activity ranging from 0% to 100%, and c) Obtaining the protein expressed by the cell of step (b); a protein with 0% to 100% fucosylation, obtained by the method as mentioned above; and a composition comprising the protein as mentioned above, optionally along with pharmaceutically acceptable excipient.

BRIEF DESCRIPTION OF THE ACCOMPANYING FIGURES

FIG. 2A depicts the CHOK1 Fut8 amino-acid sequence encoded by the sequence set forth in SEQ ID No. 1.

FIG. 3B depicts the target sequence of Fut8 exon 7, part of the complete Fut8 Exon 7 sequence set forth in SEQ ID No. 7.

FIG. 4C depicts the target sequence of GMD exon 3, part of the complete GMD Exon 3 sequence set forth as SEQ ID No. 9.

FIG. 4D depicts the target sequence of GMD exon 4, part of the complete GMD Exon 4 sequence set forth as SEQ ID No. 10.

FIG. 8A depicts fluorescence profile in LCA-FITC flow cytometry assay of clonal CHOK1 cells transfected with pD1401 (gRNA 514-553) CRISPR/Cas construct targeting FUT8 exon 7.

FIG. 8B depicts fluorescence profile in LCA-FITC flow cytometry assay of Clonal CHOK1 cells transfected with pD1401 (gRNA 167-207) or pD1301 (gRNA 404) or pD1401 (gRNA 167-207)+pD1301 (gRNA 404) CRISPR/Cas construct targeting GMD exon 3 and/or exon 4.

FIG. 8C depicts fluorescence profile in LCA-FITC flow cytometry assay of Clonal CHOK1 cells transfected with pD1401 (gRNA 167-207) CRISPR/Cas construct targeting GMD exon 3.

FIG. 9A depicts Fut 8 exon7 genomic locus, respective amino acid sequence, and important enzyme motifs like beta 2 strand and 3H2 helix and CRISPR recognition sequence; the nucleotide sequence of the complete Fut 8 exon 7 is set forth as SEQ ID No. 7 and the corresponding amino acid sequence is set forth as SEQ ID No. 8.

Figure 9A:
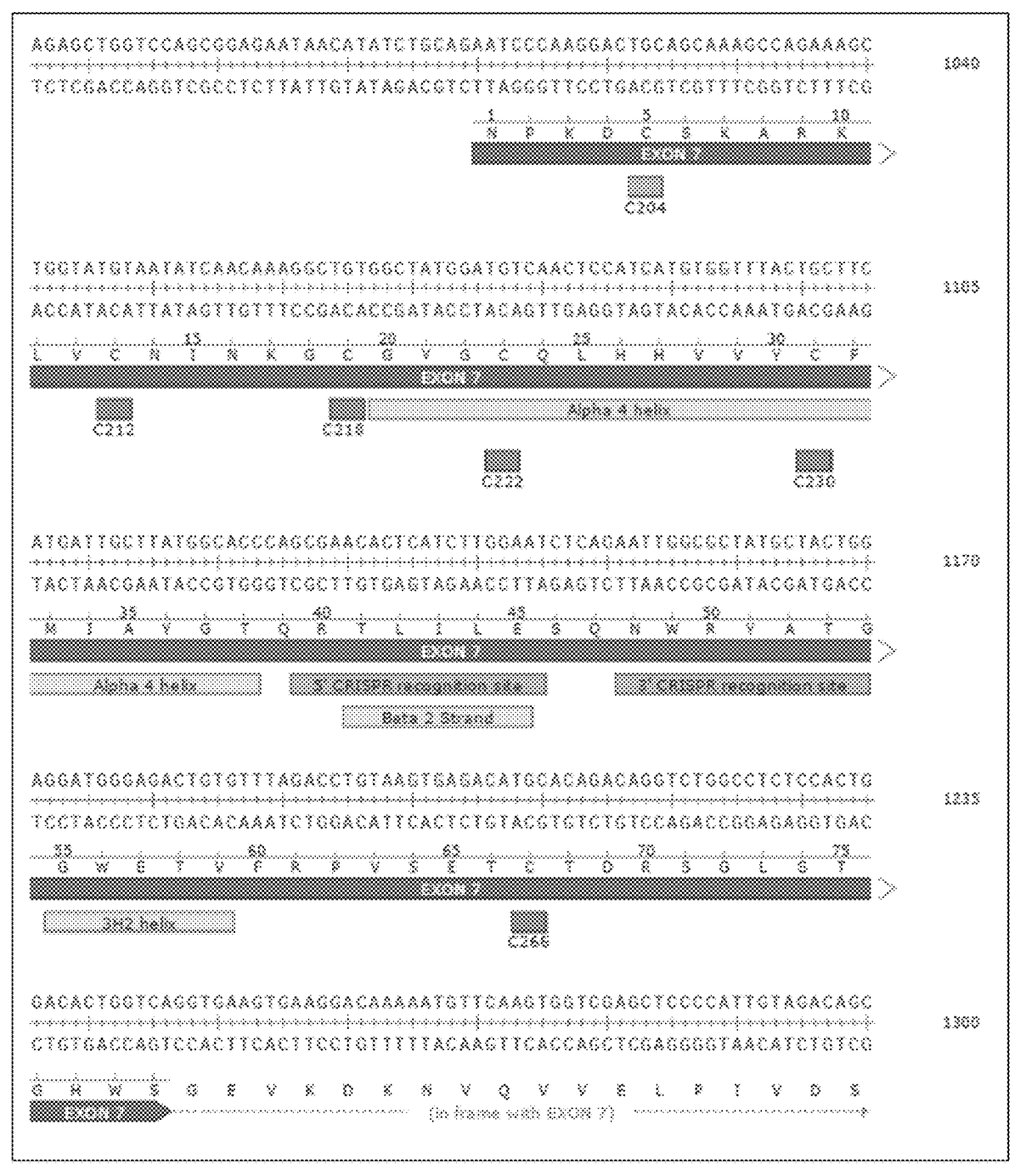
Figure 9B:
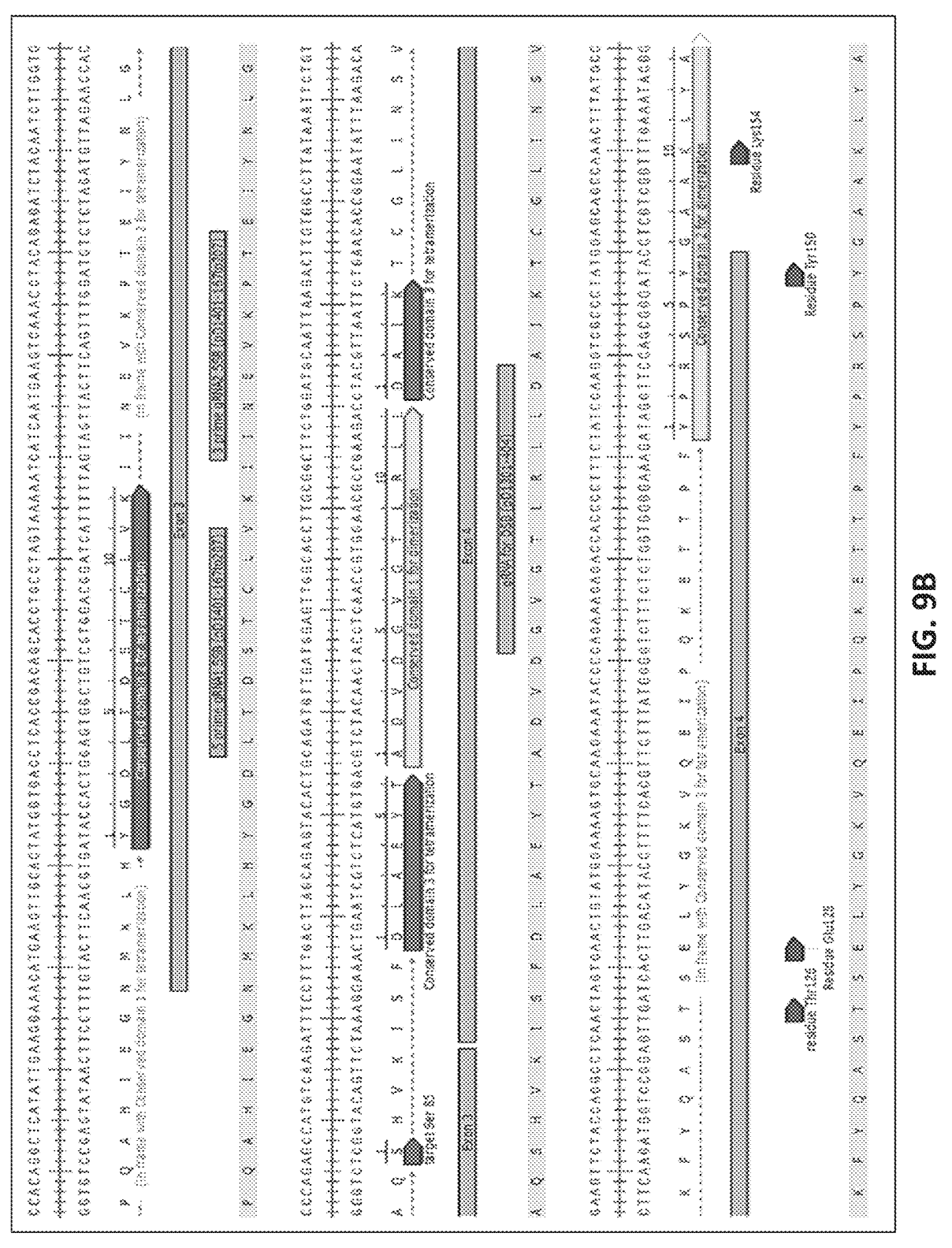

FIG. 9B depicts GMD exon 3 and exon 4 genomic locus, corresponding amino acid sequence and CRISPR recognition sequences; the sequences of the complete GMD exons 3 and 4 are set forth as SEQ ID Nos. 9 and 10, respectively, and the corresponding amino acid sequences are set forth as SEQ ID Nos. 11 and 12, respectively.

Figure 10:
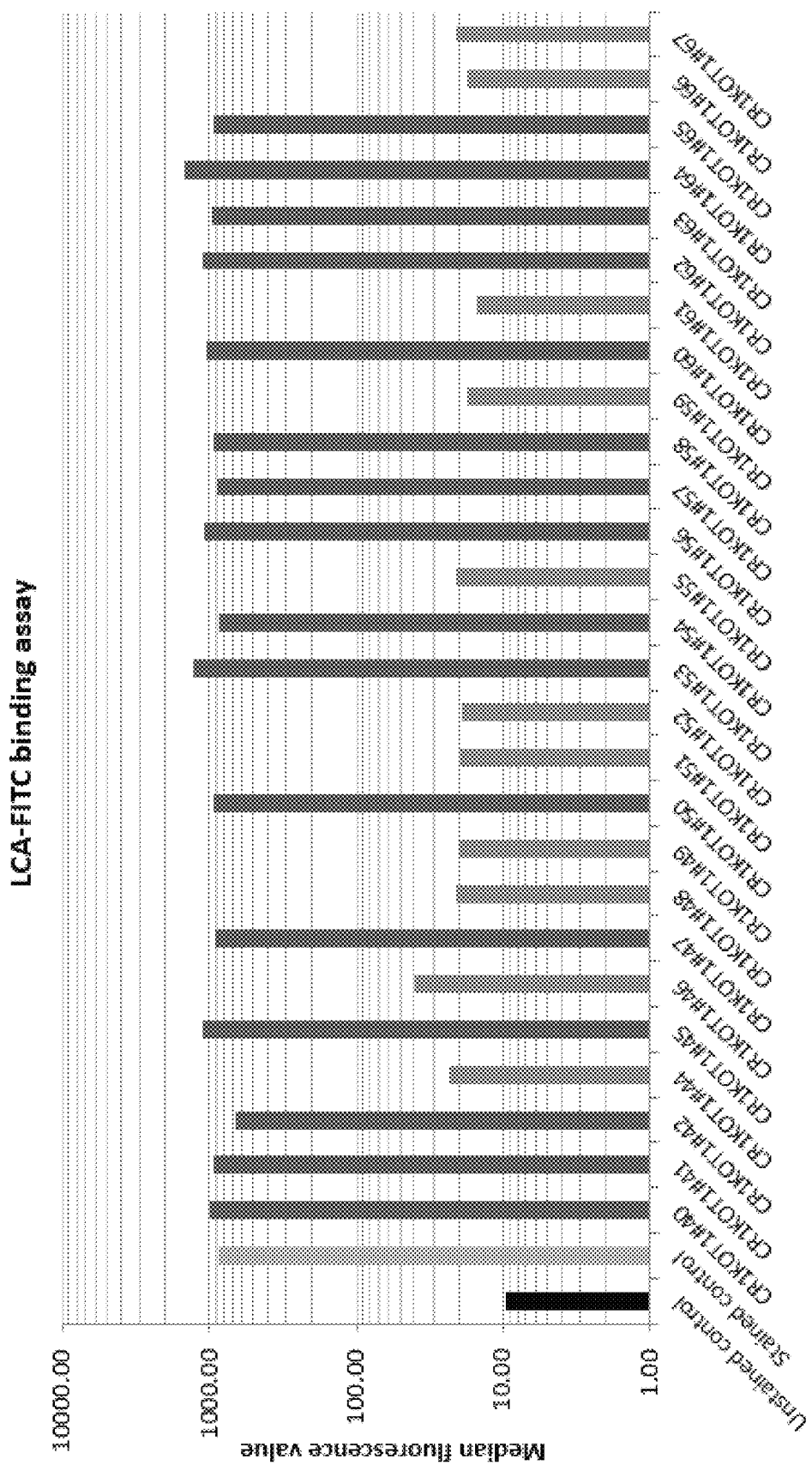

FIG. 10 depicts LCA-FITC flow cytometry assay for clonal CHOK1 cells transfected with pD1401 (gRNA 514-553) CRISPR/Cas construct targeting FUT8 exon 7.

Figure 11:
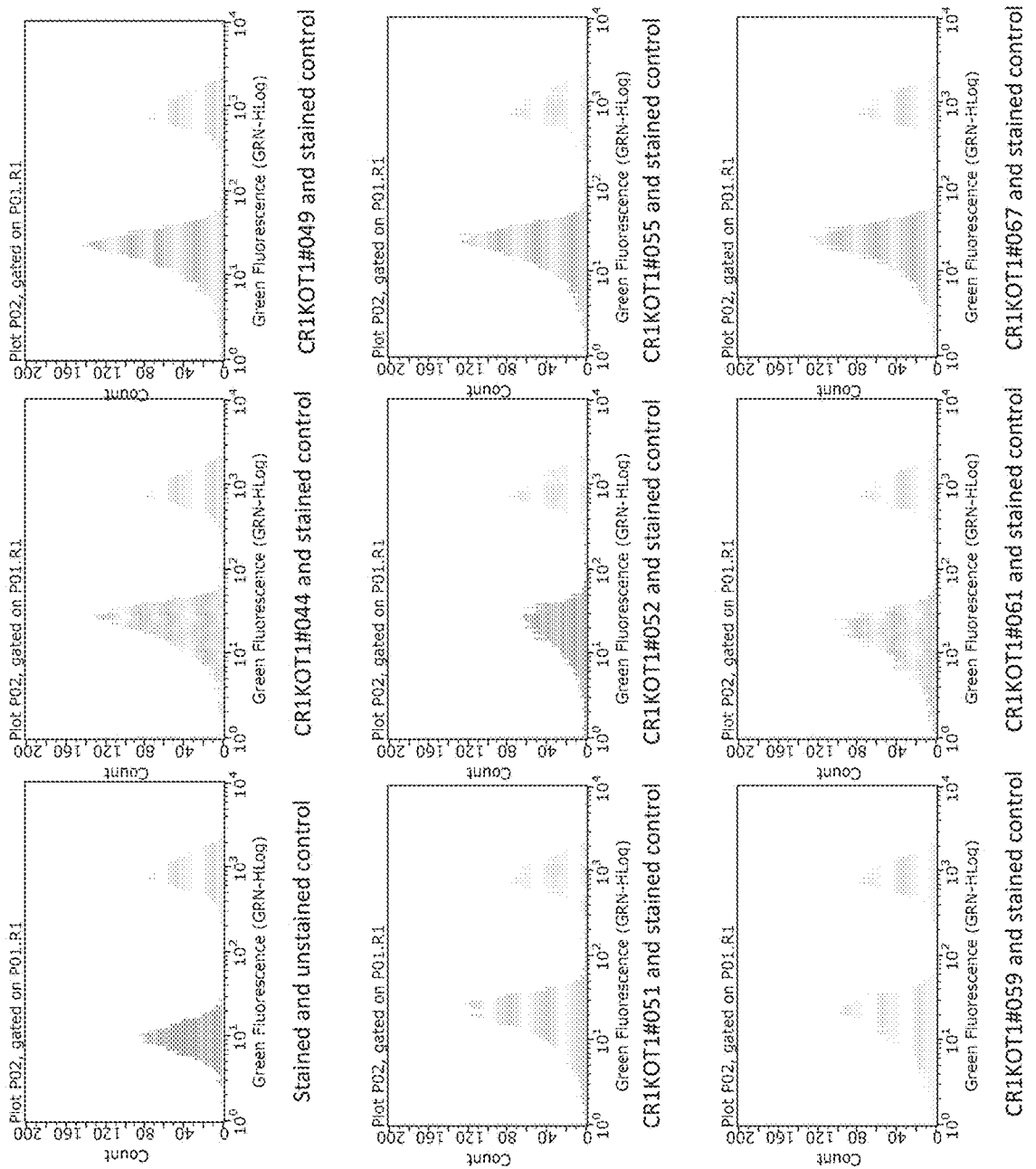

FIG. 11 depicts fluorescence profile in LCA-FITC flow cytometry assay for clonal CHOK1 cells transfected with pD1401 (gRNA 514-553) CRISPR/Cas construct targeting FUT8 exon 7.

Figure 12:
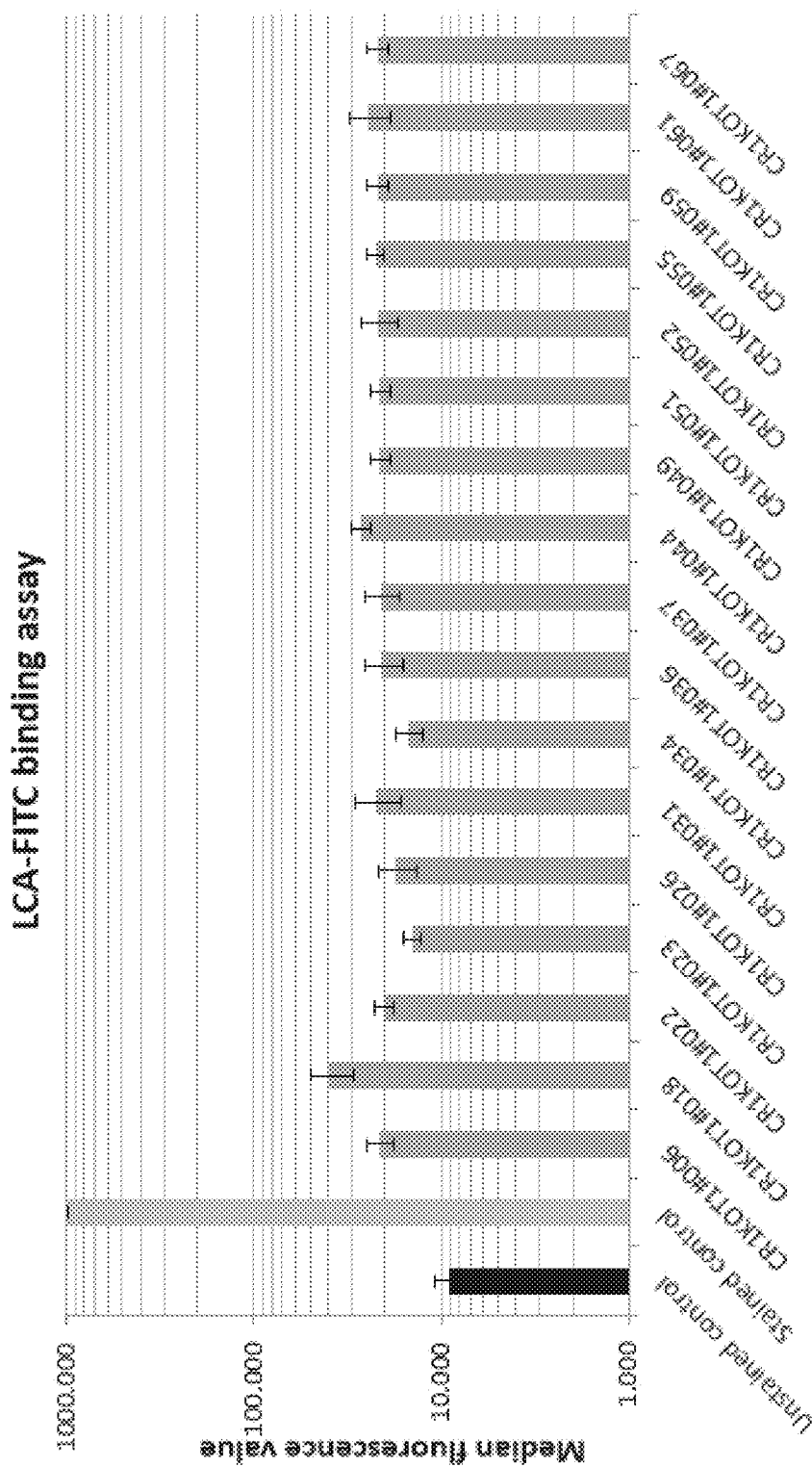

FIG. 12 depicts LCA-FITC flow cytometry assay of clonal CHOK1 cells transfected with pD1401 (gRNA 514-553) CRISPR/Cas construct targeting FUT8 exon 7.

Figure 13A:
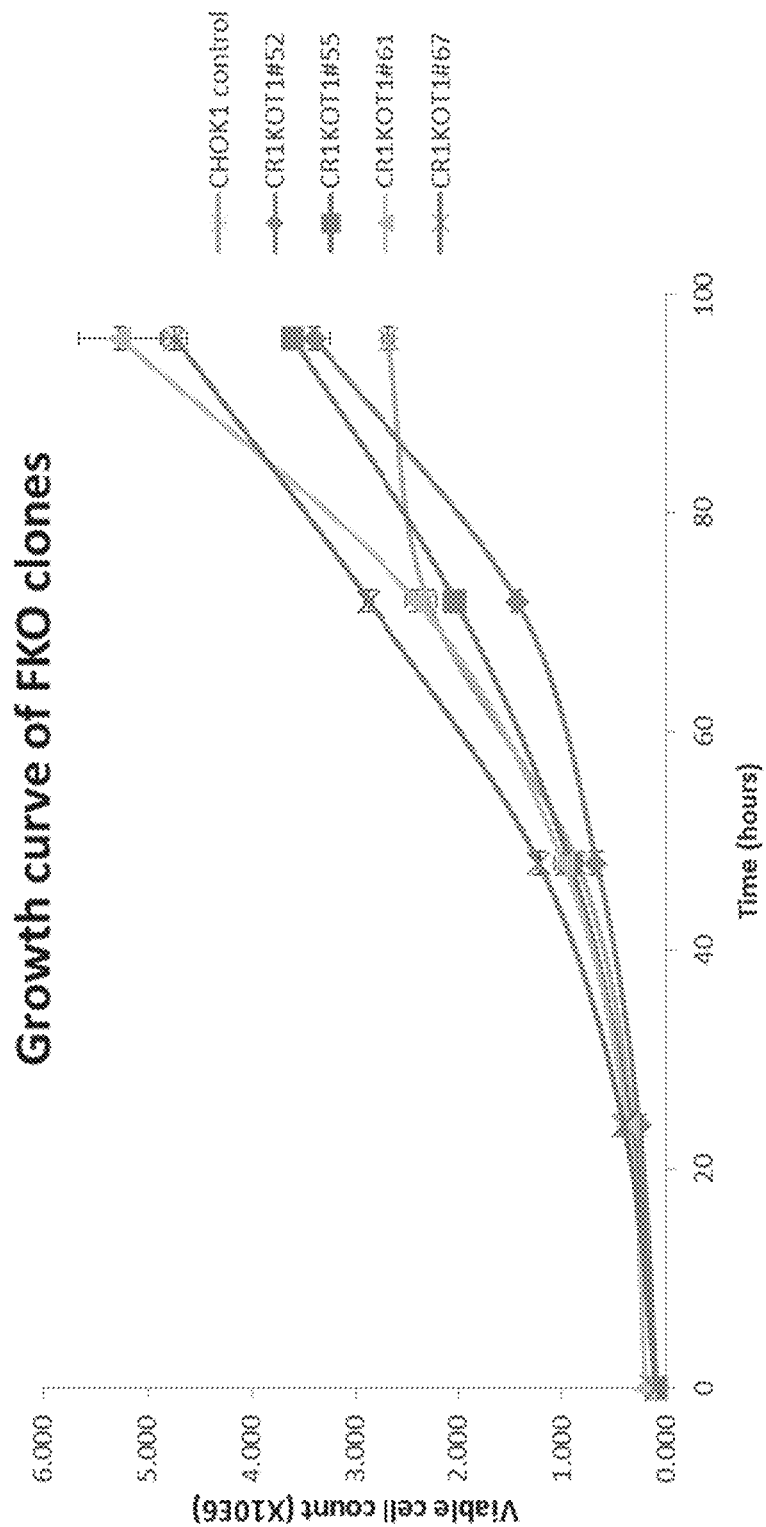
Figure 13B:
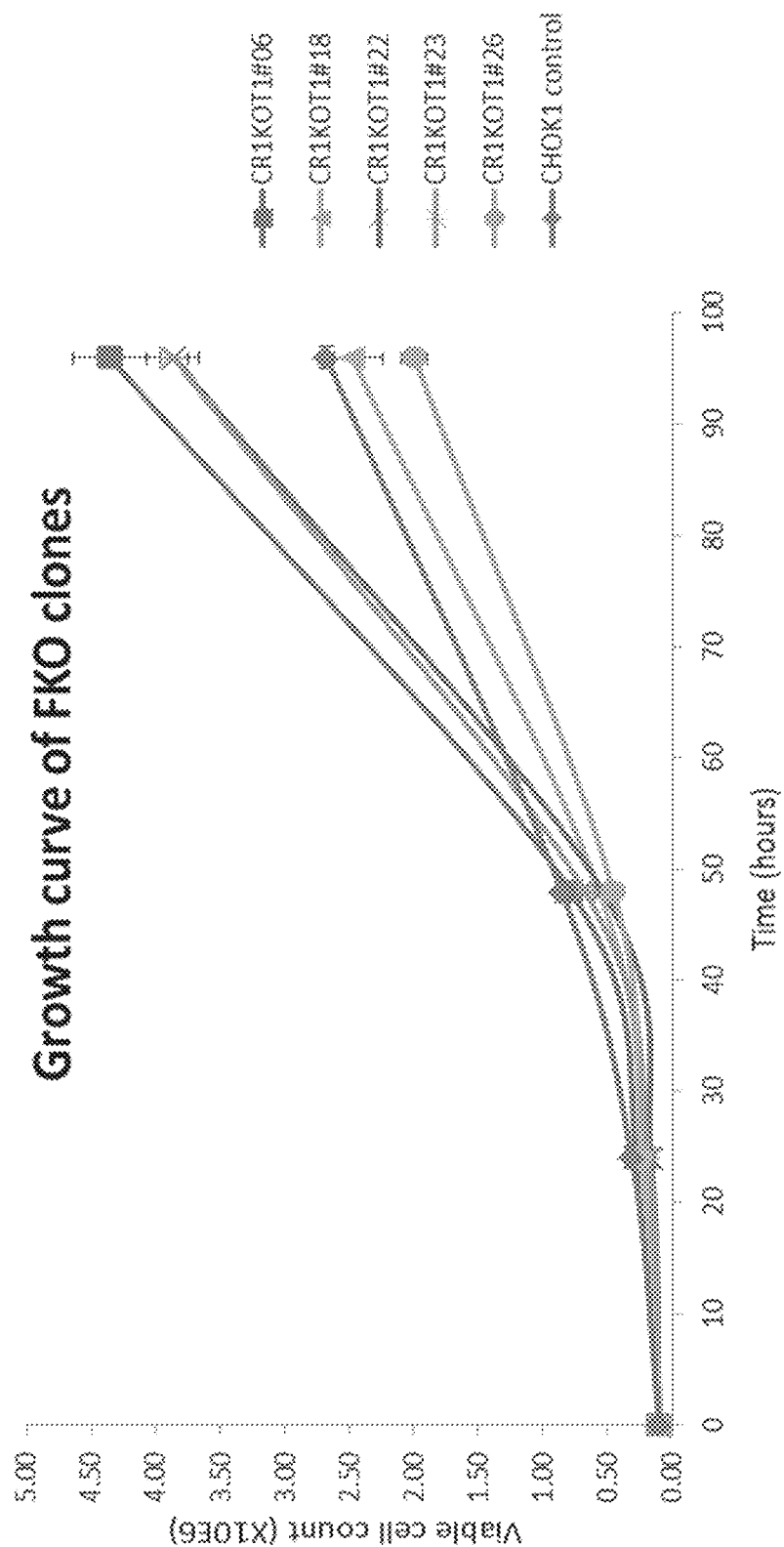
Figure 13C:
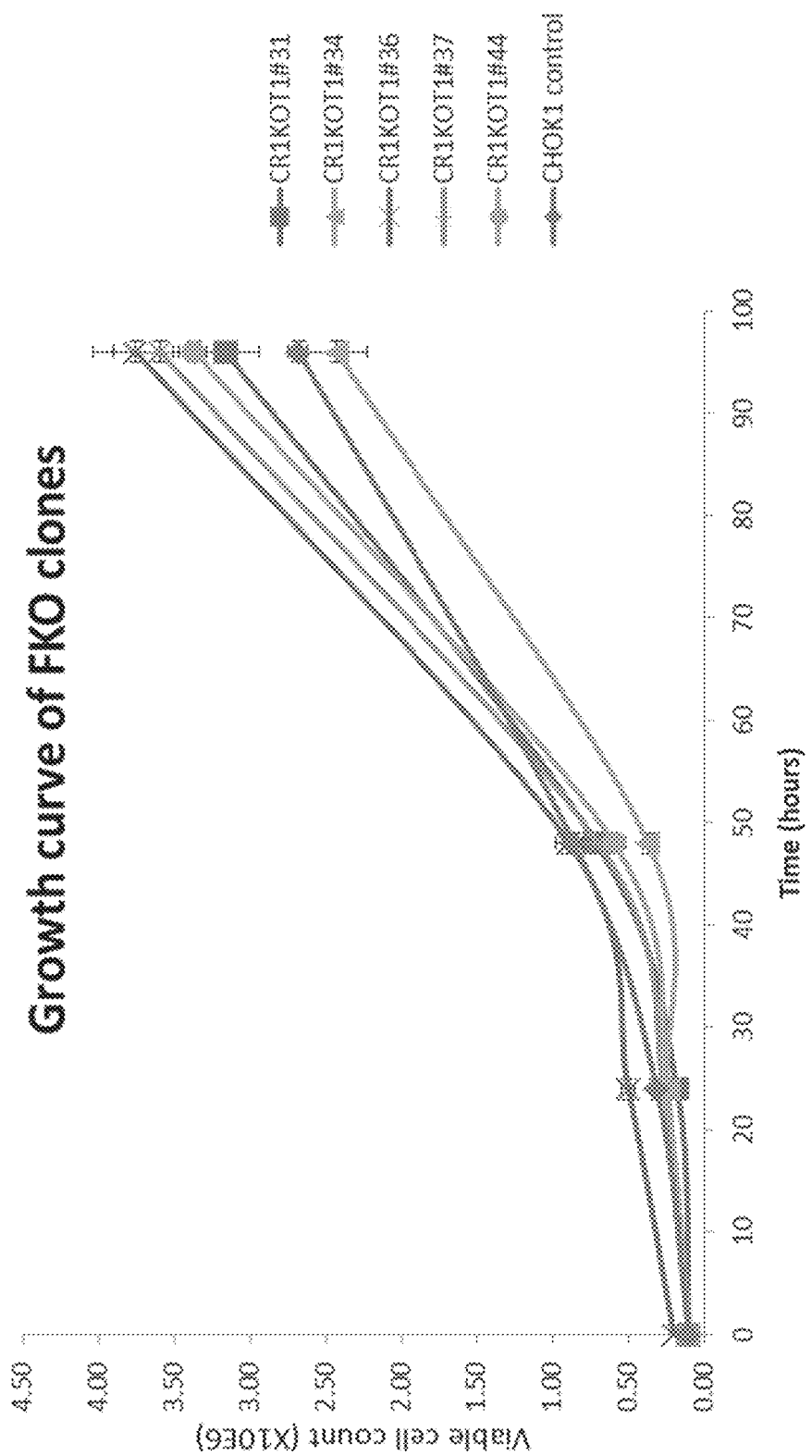

FIGS. 13A to 13C depict growth curve of clonal CHOK1 cells transfected with pD1401 (gRNA 514-553) CRISPR/Cas construct targeting FUT8 exon 7.

Figure 14:
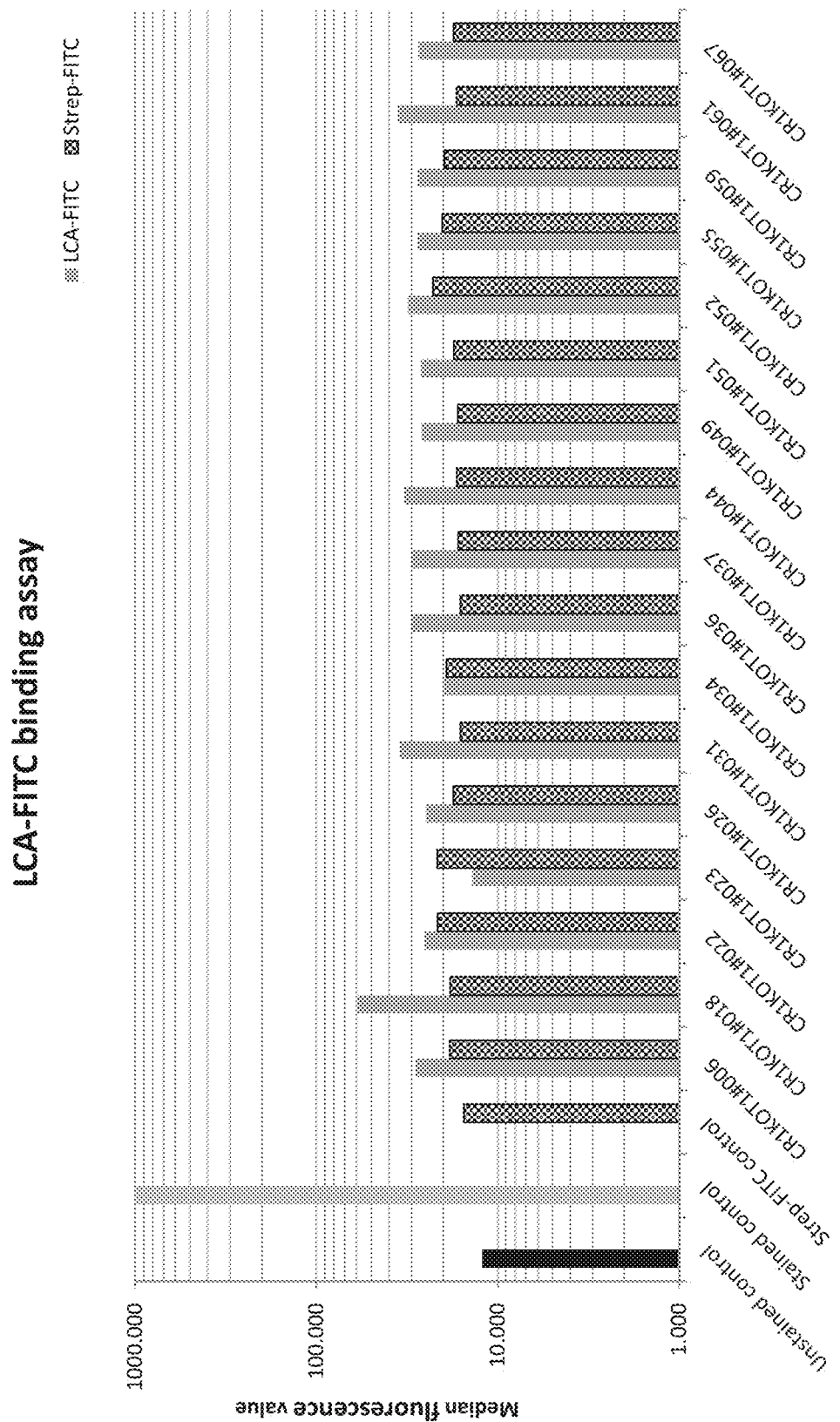

FIG. 14 depicts comparison of clonal CHOK1 cells transfected with pD1401 (gRNA 514-553) CRISPR/Cas construct targeting FUT8 exon 7 with LCA-FITC flow cytometry and Strep-FITC assay.

Figure 15A:
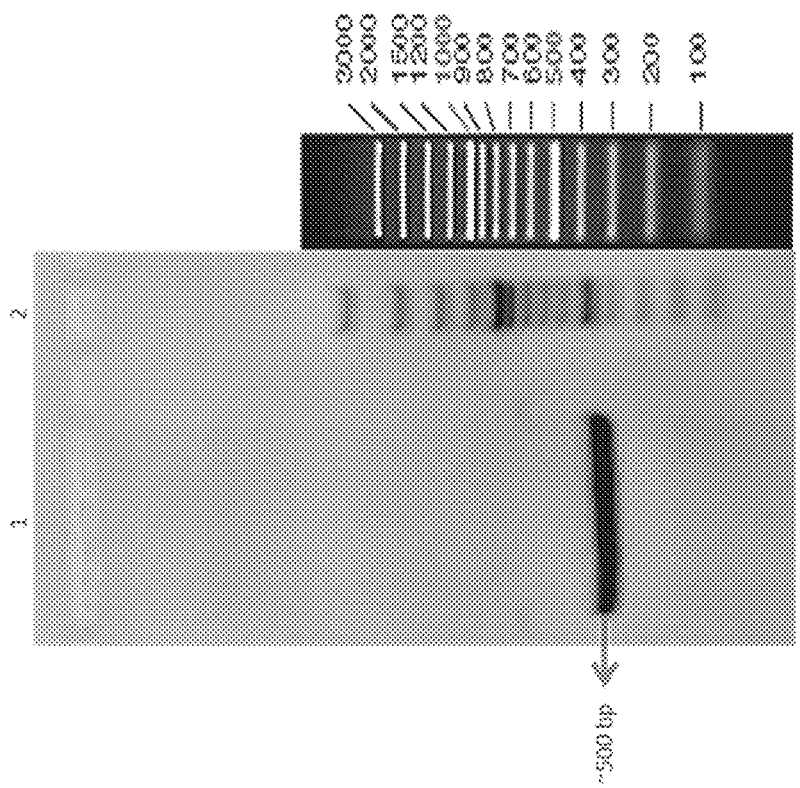

FIG. 15A depicts representative figure of the PCR amplified product of representative CRISPR/Cas Fut8 clone (CR1-KO-T1#022) when run on 1% agarose gel.

Figure 15B:
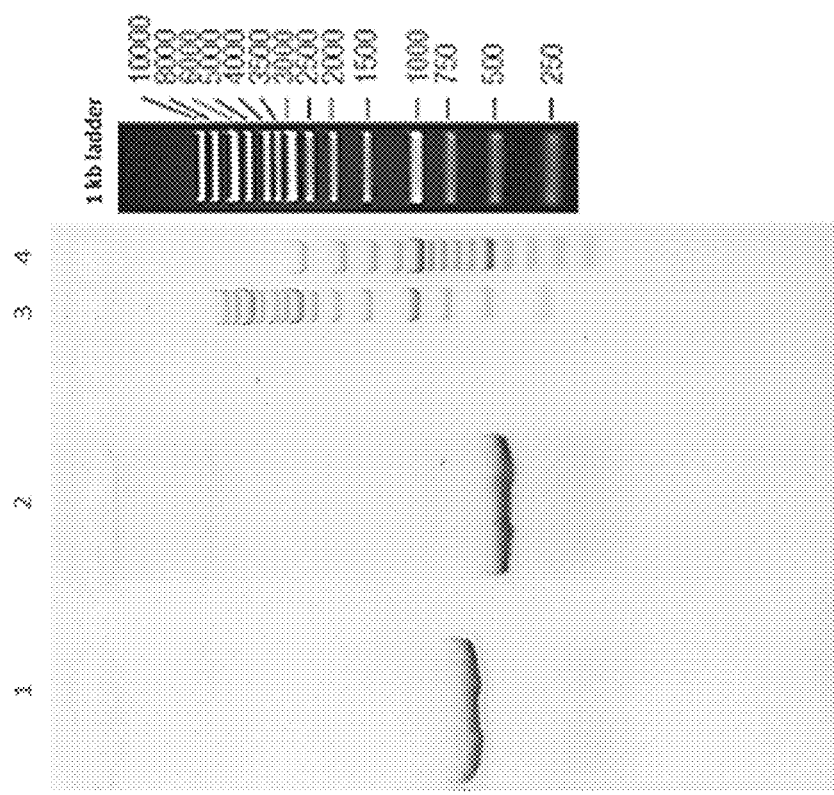

FIG. 15B depicts representative figure of the PCR amplified product of representative CRISPR/Cas GMD clones (GMD_1.12 and GMD_1.27) when run on 1% agarose gel.

Figure 15C:
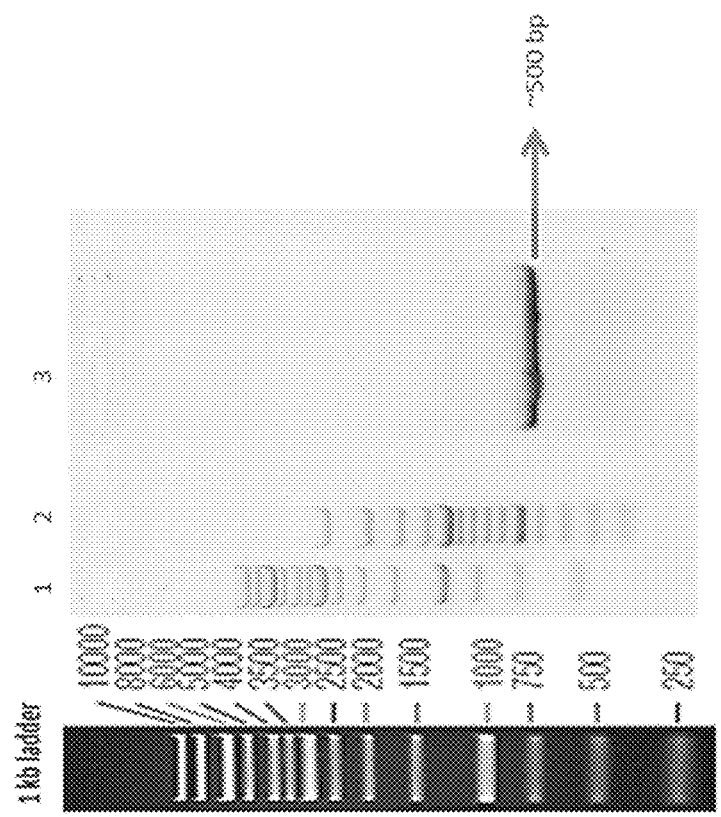

FIG. 15C depicts representative 1% agarose gel run with PCR amplification of genomic DNA of GMD 2.30 clonal cell line with primers specific for GMD Exon 4 locus.

Figure 16A:
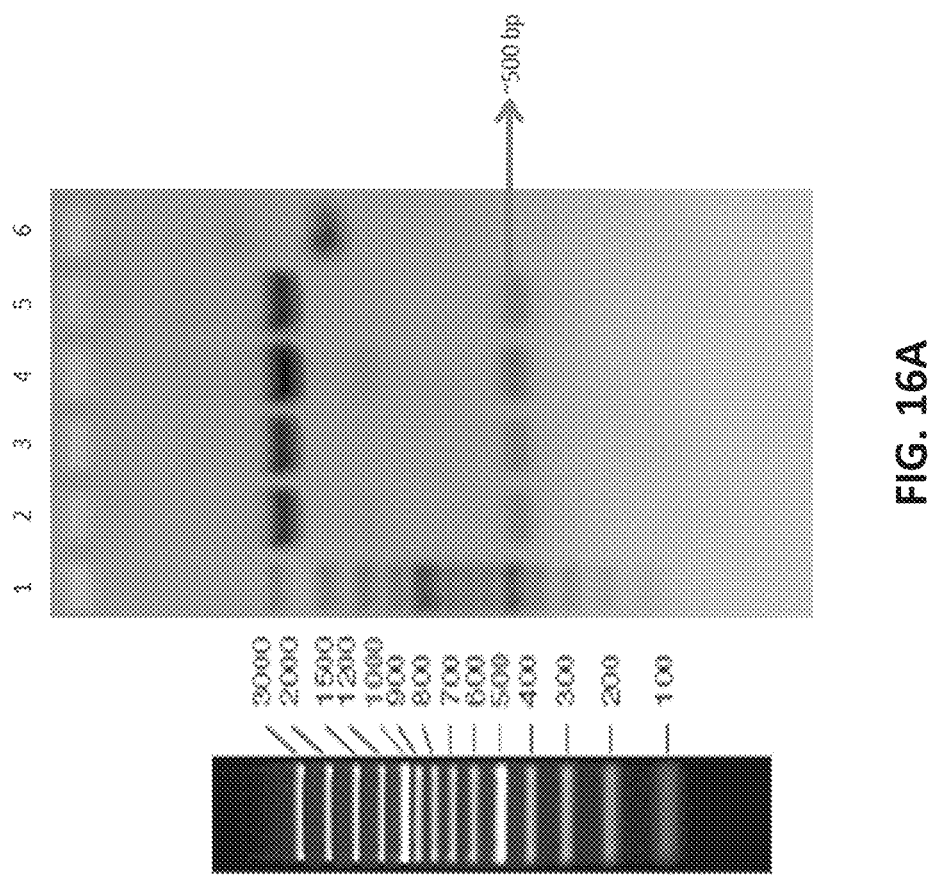
Figure 16B:
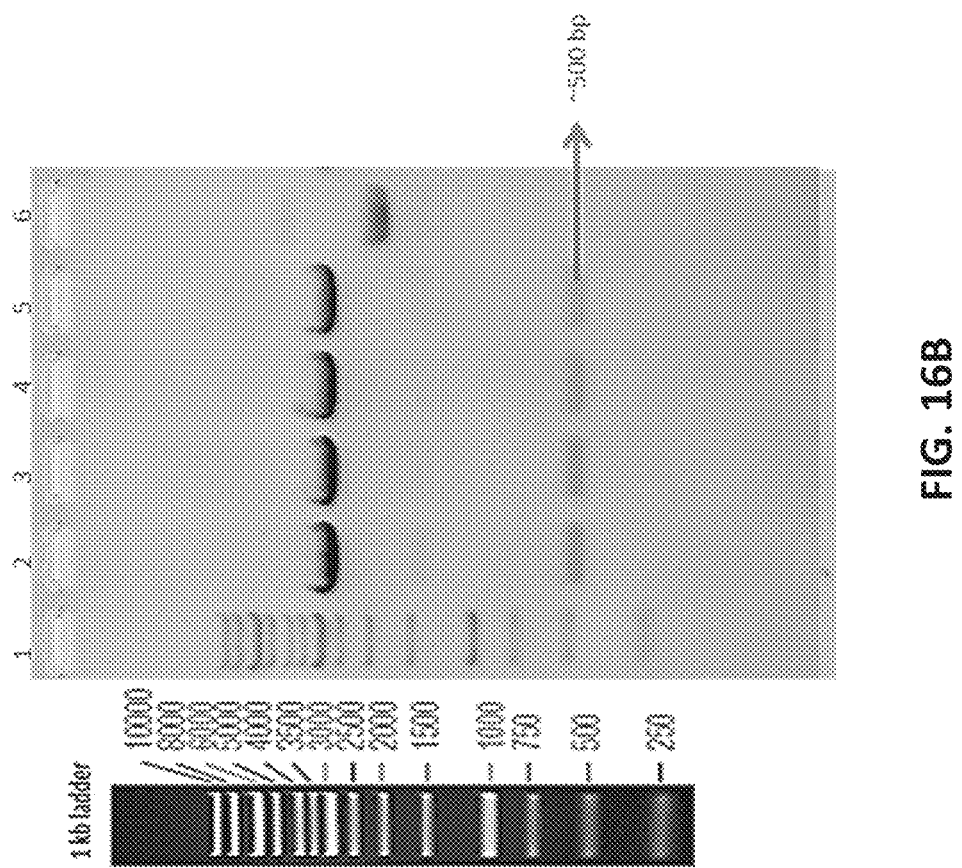
Figure 16C:
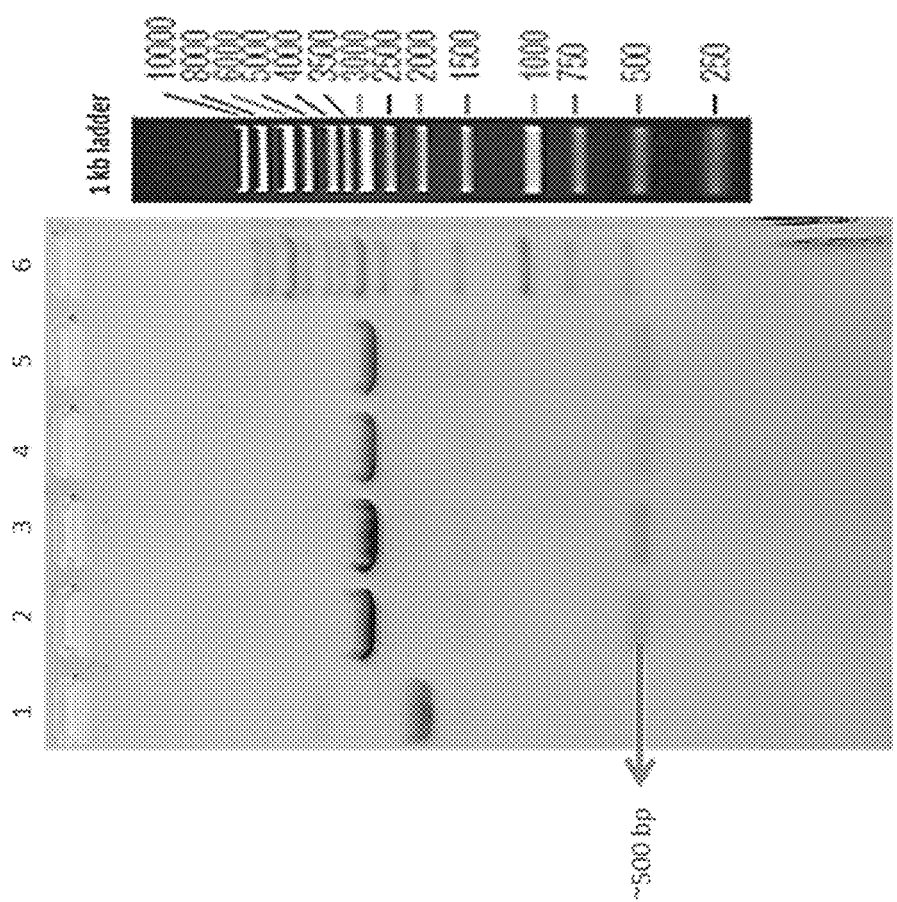

FIGS. 16A to 16C depicts the representative restriction enzyme digestion of PCR amplified product in pTZ57R/T vector to confirm presence of inserts from different knock out cell lines.

FIGS. 17A to 17G depict representative genomic DNA sequence alignment in FUT8 knock out cell line clones showing deletion in FUT8 gene sequence at Exon 7. CHOK1 control, SEQ ID No. 7; CR1KOT1#055, SEQ ID No. 103; CR1KOT1#067, SEQ ID No. 104; CR1KOT1#018, SEQ ID No. 105; CR1KOT1#051, SEQ ID No. 106; CR1KOT1#044, SEQ ID No. 107; CR1KOT1#061, SEQ ID No. 108; CR1KOT1#023, SEQ ID No. 109; CR1KOT1#022, SEQ ID No. 110; CR1KOT1#036, SEQ ID No. 111; CR1KOT1#037, SEQ ID No. 112; Consensus, SEQ ID NO: 113; CR1KOT1#052, SEQ ID No. 114; CR1KOT1#059, SEQ ID No. 115.

FIGS. 17H to 17L depict the nucleotide sequence alignments with GMD knock out clonal cell lines. GMD Exon 3 control, SEQ ID No. 9; GMD 1.27, SEQ ID No. 116; GMD 1.43, SEQ ID No. 117; GMD 1.44, SEQ ID No. 118; GMD 1.41, SEQ ID No. 119; GMD 1.12, SEQ ID No. 120; GMD 1.37, SEQ ID No. 121; GMD Exon 4 control, SEQ ID No. 122; GMD 2.30, SEQ ID No. 123; GMD 3.51 Exon 4, SEQ ID No. 124.

FIGS. 18A and 18B depict FUT8 CRISPR/Cas construct, pD1401 (gRNA 514-553), resulted in Deletion, premature stop codons at the target locus of FUT8 Exon 7. CHOK1 control, SEQ ID No. 8; CR1KOT1#018, SEQ ID No. 125; CR1KOT1#044, SEQ ID No. 126; CR1KOT1#061, SEQ ID No. 127; CR1KOT1#055, SEQ ID No. 128; CR1KOT1#067, SEQ ID No. 129; CR1KOT1#051, SEQ ID No. 130; CR1KOT1#052, SEQ ID No. 131; CR1KOT1#022, SEQ ID No. 132; CR1KOT1#036, SEQ ID No. 133; CR1KOT1#059, SEQ ID No. 134; CR1KOT1#023, SEQ ID No. 135; CR1KOT1#037, SEQ ID No. 136.

FIG. 18C depicts GMD CRISPR/Cas construct, pD1401 (gRNA 167-207) resulted in Deletion, premature stop codons and frame shift mutations at the target locus of GMD Exon 3. GMD Exon 3 control, SEQ ID No. 137; GMD 1.44, SEQ ID No. 138; GMD 1.43, SEQ ID No. 139; GMD 1.27, SEQ ID No. 140; GMD 1.41, SEQ ID No. 141.

FIG. 18D depicts GMD CRISPR/Cas construct, pD1401 (gRNA 167-207) resulted in insertion, premature stop codons and frame shift mutations at the target locus of GMD Exon 3. GMD Exon 3 control, SEQ ID No. 137; GMD 1.12, SEQ ID No. 142.

FIG. 18E depicts GMD CRISPR/Cas construct, pD1401 (gRNA 167-207) resulted in insertion, premature stop codons at the target locus of GMD Exon 3.

FIG. 18F depicts GMD CRISPR/Cas construct, pD1301 (gRNA 404) resulted in insertion, premature stop codons and frameshift mutations at the target locus of GMD Exon 4. GMD Exon 4 control, SEQ ID No. 144; GMD 2.30, SEQ ID No. 145.

FIG. 18G depicts that cell line transfected with both GMD CRISPR/Cas constructs, pD1301 (gRNA 404) and pD1401 (gRNA 167-207) reveal deletion of amino acids at the Exon 4 locus and Exon 3 locus remained unchanged. GMD Exon 4 control, SEQ ID No. 144; GMD 3.51 Exon 4, SEQ ID No. 146.

Figure 19:
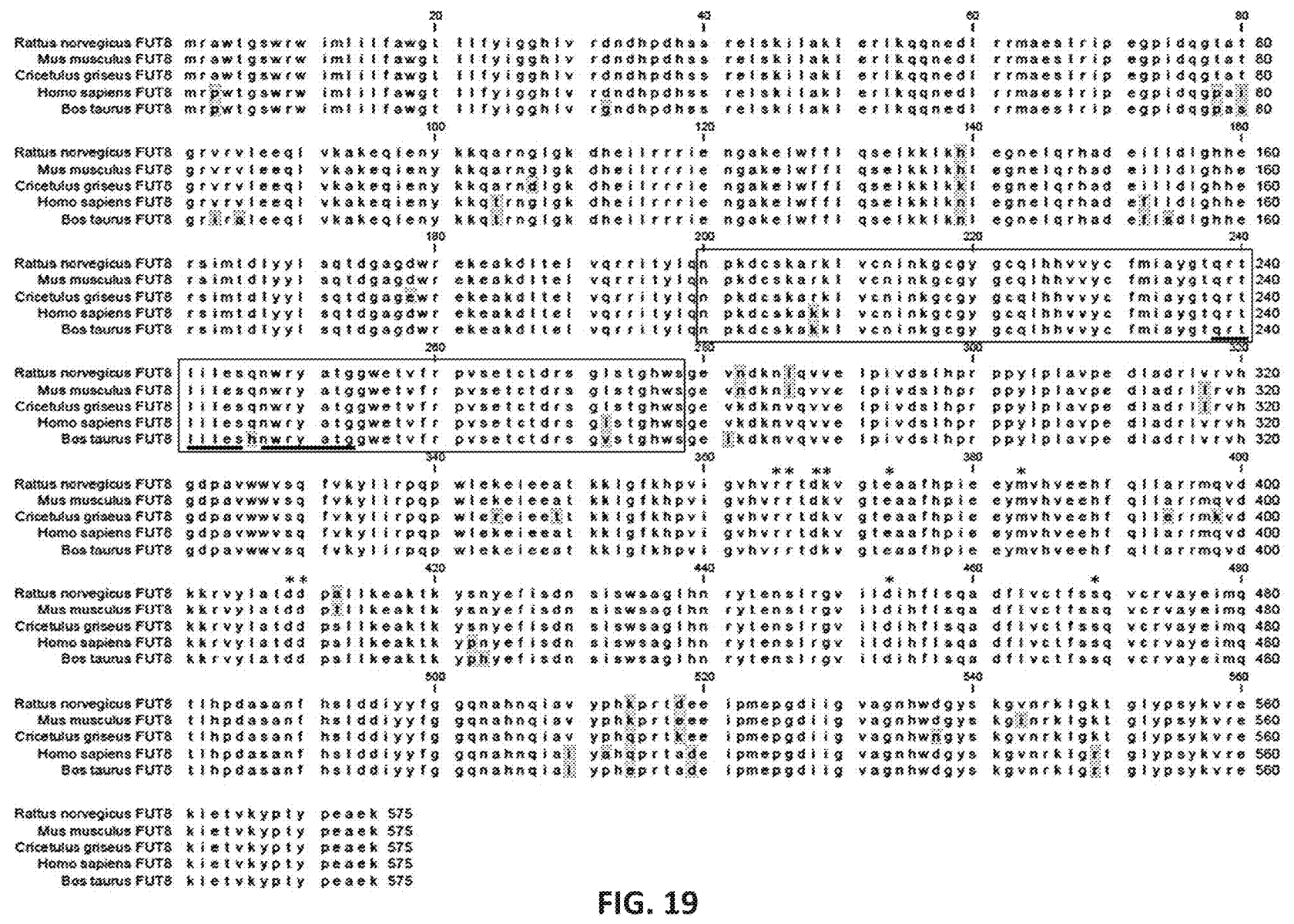

FIG. 19 depicts FUT8 amino acid sequence comparison in several eukaryotes. *Rattus norvegicus* FUT8, SEQ ID NO:147; *Mus musculus* FUT8, SEQ ID NO:148; *Cricetulus griseus* FUT8, SEQ ID NO:149; *Homo sapiens* FUT8, SEQ ID NO:150; *Bos taurus* FUT8, SEQ ID NO:151.

FIG. 20 depicts transfection efficiency of CHOK1 cell line using different protocols.

DETAILED DESCRIPTION OF THE DISCLOSURE

The present disclosure relates to a DNA-binding domain of CRISPR system, wherein the DNA-binding domain comprises sequence selected from the group consisting of SEQ ID No.13, SEQ ID No. 15, SEQ ID No.17 to SEQ ID No. 37, SEQ ID No. 39, SEQ ID No. 41, SEQ ID No. 43, SEQ ID No.45, SEQ ID No. 47 to SEQ ID No. 93 and combinations thereof.

In an embodiment of the present disclosure, SEQ ID No. 13, SEQ ID No.15, SEQ ID No. 39 and SEQ ID No. 17 to SEQ ID No. 37 bind to Fut8 gene sequence; and SEQ ID No. 41, SEQ ID No. 43, SEQ ID No. 45 and SEQ ID No. 47 to SEQ ID No.93 bind to GMD gene sequence.

In another embodiment of the present disclosure SEQ ID No. 13 transcribes to SEQ ID No. 14; SEQ ID No.15 transcribes to SEQ ID No. 16; SEQ ID No. 37 transcribes to SEQ ID No.38; SEQ ID No. 39 transcribes to SEQ ID No.40; SEQ ID No. 41 transcribes to SEQ ID No. 42; SEQ ID No. 43 transcribes to SEQ ID No.44 and SEQ ID No. 45 transcribes to SEQ ID No. 46.

The present disclosure also relates to a CRISPR-nuclease complex comprising the DNA-binding domain as mentioned above and nuclease.

In an embodiment of the present disclosure, the nuclease is Cas9 endonuclease.

In another embodiment of the present disclosure, the nuclease is Cas9n endonuclease.

The present disclosure also relates to a vector comprising a DNA binding domain as mentioned above.

In an embodiment of the present disclosure, the vector further comprises nuclease.

The present disclosure also relates to a cell comprising a vector as mentioned above.

In an embodiment of the present disclosure, the cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

The present disclosure also relates to a method of obtaining a fucose knockout cell, said method comprising steps of:
  a) Obtaining a CRISPR-nuclease construct; and
  b) Transfecting a cell with the construct of step (a) to obtain a fucose knockout cell.

The present disclosure also relates to a method of obtaining protein with fucosylation ranging from 0% to 100%, said method comprising steps of:
  a) Obtaining a CRISPR-nuclease construct;
  b) Transfecting a cell with the construct of step (a) to obtain a cell with fucosylation activity ranging from 0% to 100%; and
  c) Obtaining the protein expressed by the cell of step (b).

In an embodiment of the present disclosure, the CRISPR-nuclease construct provides the complex as mentioned above; and the complex cleaves gene sequence in cell, said gene selected from group the group consisting of Fut8, GMD and combination thereof.

In another embodiment of the present disclosure, the Fut8 gene sequence coding for α-1,6 Fucosyltransferase enzyme is cleaved at Exon 7.

In yet another embodiment of the present disclosure, the GMD gene sequence coding for a GDP-D-mannose 4,6-dehydratase enzyme is cleaved at Exon selected from the group consisting of Exon 3, Exon 4 and combination thereof.

In still another embodiment of the present disclosure, the cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

In still another embodiment of the present disclosure, the protein is 0% fucosylated, and the protein is obtained by disruption of Fut8 gene in the cell.

In still another embodiment of the present disclosure, the protein has 0% to 100% fucosylation, and the protein is obtained by disruption of GMD gene in the cell; and the method further comprises addition of L-Fucose in growth medium.

In still another embodiment of the present disclosure, the protein is an antibody.

In still another embodiment of the present disclosure the antibody is a monoclonal antibody.

In still another embodiment of the present disclosure the cell produces an endogenous protein.

In still another embodiment of the present disclosure, the method further comprises a step of introducing a protein encoding gene into the cell and obtaining the protein.

The present disclosure also relates to a protein with 0% to 100% fucosylation, obtained by the method as mentioned above.

In an embodiment of the present disclosure, the protein is an antibody.

The present disclosure also relates to a composition comprising the protein as mentioned above, optionally along with pharmaceutically acceptable excipient.

In an embodiment of the present disclosure, the protein is an antibody.

The present disclosure relates to production of non-fucosylated proteins, including non-fucosylated antibodies, from cell.

The present disclosure relates to production of partially fucosylated proteins, including partially fucosylated antibodies, from cell.

The present disclosure also relates to targeting and disrupting of genes upstream and downstream of the key biochemical steps involving GDP-Fucose.

The present disclosure employs the CRISPR technology to produce non-fucosylated proteins.

In the present disclosure, a cell without fucosylation activity is also referred to as "Fucose Knockout" of "FKO" cell.

The CRISPR (Clustered, Regularly Interspaced, Short Palindromic Repeat) system is an adaptable, naturally occurring immune mechanism, used by many bacteria to protect themselves from foreign nucleic acids, such as viruses or plasmids. CRISPRs are segments of prokaryotic DNA containing short repetitions of base sequences, followed by short segments of "spacer DNA". This Spacer DNA is foreign DNA obtained from previous exposures to a bacterial virus or plasmid. A set of enzymes called Cas (CRISPR-associated proteins) enzymes are found in association with these CRISPR sequences, and Cas are nucleases which can precisely snip DNA.

The bacterium copies the genetic material in each spacer DNA into an RNA molecule. Cas enzymes then take up one of the RNA molecules, which are referred to as the guide RNAs (gRNA). Together they form the CRISPR-Cas system. When the system encounters DNA from a virus that matches the CRISPR RNA, the RNA hybridises to the DNA sequence and the Cas enzyme then cleaves the DNA in two, preventing the virus from replicating.

There are various Cas enzymes that work in conjunction with CRISPR, but the most well-known and frequently employed in genetic engineering is Cas9 nuclease, which is derived from *Streptococcus pyogenes*. Together, they form the CRISPR/Cas9 system, called the type II CRISPR system.

Cas9 has been shown to be a key player in certain CRISPR mechanisms, specifically type II CRISPR systems where only one Cas protein is required. In this system, the endonuclease Cas9 participates in the processing of crRNAs which results in destruction of the target DNA. The Cas9 function is dependent on presence of two nuclease domains, a RuvC-like nuclease domain located at the amino terminus and a HNH-like nuclease domain that resides in the mid-region of the protein.

For site specific DNA recognition and cleavage, the nuclease Cas9 must complex with two RNA sequences, a crRNA (CRISPR RNA) and a separate trans-activating crRNA (tracrRNA or trRNA), that is partially complementary to the crRNA. The tracrRNA is required for crRNA maturation from a primary transcript encoding multiple pre-crRNAs. This occurs in the presence of RNase III and Cas9. During the cleavage of target DNA, the HNH and RuvC-like nuclease domains of the Cas9 nuclease cut both DNA strands, generating double-stranded breaks (DSBs). The recognition sites are defined by 20-nucleotide target sequence within an associated crRNA transcript. The HNH domain cleaves the complementary strand, while the RuvC domain cleaves the non-complementary strand. The double-stranded endonuclease activity of Cas9 also requires that a short conserved sequence, (2-5 nts) known as Protospacer-Associated Motif (PAM), follows immediately 3'- of the crRNA complementary sequence in the target DNA. The requirement of PAM sequence is obligatory for CRISPR/Cas function.

In general, a two vector system is used for CRISPR mediated gene editing, 1) a Cas9 endonuclease and 2) a complex of crRNA (CRISPR RNA) and tracrRNA (trans-activating crRNA). When these two constructs are co-expressed in mammalian cells, they form a complex and are recruited to target DNA sequence. The crRNA and tracrRNA are combined to form a chimeric guide RNA (gRNA) with the same function—to guide Cas9 to target gene sequences.

Homologous recombination mediated gene editing technologies are the first of its kind to be used for gene editing. However, frequency of successful events are very rare using HR, 1 in every $3 \times 10^4$ cells.

In recent days, Zink finger nuclease is becoming popular as they allow higher specificity of targeting with higher frequency of successful mutant events. It uses DNA binding proteins with nuclease activity that bind to DNA and create site-specific DSBs. While effective, these methods require extensive protein engineering tools to be successful and thereby limit flexibility in targeting complex genome sequences. The adaptation of CRISPR for mammalian cells has revolutionized genome editing with higher accuracy and ease of designing. Unlike ZFN, CRISPR/Cas does not require protein engineering for every gene being targeted.

The CRISPR system only requires a few simple DNA constructs to encode the gRNA and Cas9. In addition, multiple genes are targeted simultaneously. In this embodiment, CRISPR/Cas system is applied to target two separate genes, FUT8 and GMD, in fucose biosynthetic pathway.

Although information is produced for knock out CHOK cell line development with individual CRISPR/Cas complex for FUT8 and GMD gene, it is clear that the complex could be used together to simultaneously knock out both genes in CHOK cell lines and other relevant cell lines.

Although it is rare for a 20 bp gRNA sequence to have 100% homology at multiple sites throughout the genome, sgRNA-Cas9 complexes are tolerant of several mismatches in their targets. Cas9 has been reported to bind multiple locations in genome nonspecifically, however it creates DNA double strand break only at a handful of those sites. Experimental data also suggest certain levels of mismatch at the DNA target site allows DNA double strand break. Therefore, strategies for increasing CRISPR/Cas specificity are pursued.

One such observation is a point mutation of Aspartate to Alanine (D10A) mutation at the RuvC catalytic domain resulted in single strand breaks (nicks) instead of double strand breaks. The mutant Cas9 is known as Cas9n. Using Cas9n at two neighbouring DNA target site allows DNA nicks at close proximity, and if the target sites are appropriately spaced, it creates a double strand break.

Therefore, the specificity of DSB creation is higher, which is eventually repaired by NHEJ mechanism. Nonspecifically bound Cas9n creates only nicks which is generally repaired through HR mediated repair and rarely causes mutation or off target effects. In this disclosure, Cas9n and CRISPR are used to knockout both Fut8 and GMD genes. In one of the GMD target locus, wild type Cas9 endonuclease is also used.

In the present disclosure, CRISPR-Cas construct upon expression in a cell provides CRISPR-Cas complex.

In the present disclosure, the terms CRISPR-Cas complex and CRISPR-Cas system and are used interchangeably.

The present disclosure relates to a method for obtaining non-fucosylated protein, by disruption or inactivation of the fucosylating machinery in a cell.

The present disclosure relates to a method for obtaining partially fucosylated protein, by disruption or inactivation of the fucosylating machinery in a cell.

In an embodiment, the protein is an antibody.

In a preferred but non-limiting embodiment, the antibody is a monoclonal antibody.

In the present disclosure, the terms "non-fucosylated antibody", "afucosylated antibody", "0% fucosylated antibody" and "100% non-fucosylated antibody" are used interchangeably and have the same meaning and scope.

The present disclosure particularly relates to disruption or inactivation of the FUT8 gene or GMD gene in a cell. It is understood for anyone skilled in the art that both FUT8 and GMD genes could be disrupted together in the same cell line to achieve fucose knock out cell line using the CRISPR/Cas constructs described in this disclosure.

The FUT8 gene encodes the enzyme α-1,6 fucosyltransferase. The GMD gene encodes GDP-D-mannose 4,6-dehydratase.

In an embodiment of the present disclosure, the cell is a cell that naturally produces a protein.

In an embodiment of the present disclosure, the cell is a cell that naturally produces an antibody.

In an embodiment of the present disclosure, the cell is a cell that does not naturally produce a given protein, and a gene encoding the protein is introduced into the cell.

In an embodiment of the present disclosure, the cell is a cell that does not naturally produce an antibody, and a gene encoding an antibody is introduced into the cell.

In an embodiment of the present disclosure, the cell is a cell that naturally produces an antibody, and a gene encoding an antibody is introduced into the cell.

In an embodiment, the cell is a eukaryotic cell.

In an embodiment, the cell is mammalian cell.

In a non-limiting embodiment, the cell is Chinese Hamster Ovary cell.

In a non-limiting embodiment, the cell is Chinese Hamster Ovary K1 (CHOK1) cell.

In an embodiment, the CHOK1 cell is an antibody producing cell.

In an embodiment, the antibody produced by the method of the present disclosure is a therapeutic antibody.

In another embodiment, the CHOK1 cell is not an antibody producing cell, and a gene encoding an antibody is introduced into the cell.

In embodiments of the present disclosure, the cell line is selected from the group consisting of COS, CHO-S, CHO-K1, CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G11.16Ag.20, perC6, Hybridoma cell which produces antibody, embryonic stem cell, Namalwa cell, insect cell line from *Spodoptera fugiperda* (Sf), *Pichia*, *Saccharomyces* and *Schizosaccharomyces*.

In a non-limiting embodiment of the present disclosure, the cell is a cell with Glutamine synthetase knockout (GS-/-), preferably a CHOK1 cell with Glutamine synthetase knockout (GS-/-).

In an embodiment, the cell is referred to as a "Fucose Knockout" cell or "FKO" cell or "Fucose Knockout" platform or "FKO" platform.

In an embodiment, the cell is referred to as a Recombinant cell.

In an embodiment, CRISPR (Clustered Regularly Interspaced Short Palindromic Repeats)—Cas complex is used to disrupt or inactivate the Fucosylation pathway of a cell.

In an embodiment, CRISPR (Clustered Regularly Interspaced Short Palindromic Repeats)—Cas complex is used to disrupt or inactivate one or more genes of the Fucosylation pathway of a cell.

In an embodiment, CRISPR (Clustered Regularly Interspaced Short Palindromic Repeats)—Cas complex is used to disrupt or inactivate or mutate gene selected from the group comprising a 1,6 Fucosyl transferase (Fut8 gene), GDP mannose 4, 6 dehydratase (GMD gene), GDP-keto-6 deoxymannose 3,5 epimerase 4-reductase (FX gene), GDP-beta-L-fucose pyrophosphorylase (GEPP gene), and Fucose kinase gene.

In an embodiment, the present disclosure relates to disruption of a combination of Fut8 gene and GMD gene in a cell by CRISPR/Cas complex of the present disclosure.

In the de novo pathway of fucosylation, GDP-fucose is synthesized through conversion of GDP-mannose to GDP-4-keto-6-deoxy-mannose, catalyzed by the enzyme GDP-mannose 4, 6-dehydratase (GMD). This GDP-Fucose is then transported inside the golgi and used as a substrate for protein fucosylation by the enzyme α-(1-6) fucosyltransferase. The enzyme transfers the fucose moiety from GDP-fucose to N-acetyl glucosamine of the N-glycan chain.

In an embodiment, CRISPR (Clustered Regularly Interspaced Short Palindromic Repeats)—Cas complex) is used to disrupt the Fut8 gene encoding the α-1,6 fucosyltransferase enzyme.

In an embodiment, CRISPR (Clustered Regularly Interspaced Short Palindromic Repeats)—Cas complex is used to disrupt the GMD gene encoding the GDP-mannose 4, 6-dehydratase enzyme. In an embodiment of the present disclosure, the N-terminal catalytic region of fucosyl transferase enzyme is targeted by CRISPR/Cas complex In an embodiment of the present disclosure, the active site of the GDP-mannose 4, 6-dehydratase enzyme is targeted by CRISPR/Cas complex.

In a particular embodiment, Exon 7 of the gene sequence of Fut8 is targeted by CRISPR (Clustered Regularly Interspaced Short Palindromic Repeats) Cas complex.

In an embodiment of the present disclosure, the Fucosyltransferase enzyme is mutated at an amino acid position selected from the amino acid sequences at the beta 2 strand and the 3H2 helix region coded by exon 7 coding sequence. The resulting clones may result in premature translation stop therefore absence of downstream sequences such as Arg-365, Arg-366, Asp-368, Lys-369, Glu-373, Tyr-382, Asp-409, Asp-410, Asp-453, Ser-469 and combinations thereof.

In a particular embodiment, Exon 3 or Exon 4 of the gene sequence of GMD is targeted by CRISPR/Cas (Clustered Regularly Interspaced Short Palindromic Repeats) constructs.

The CRISPR/Cas constructs are designed as a two vector system, in general. One construct codes for the Cas9 endonuclease expression and the second vector expresses the gRNA—which is made up of the crRNA and tracrRNA. The crRNA is usually designed as 20 nucleotide long fragment that recognizes the target sequence depending on proper positioning of tracrRNA, PAM sequence and the functional complex of crRNA-Cas9-tracrRNA. In certain cases, one single vector expresses both gRNA and the Cas9 protein for higher activity and ease of use. Target recognition specificity comes from the crRNA design.

In embodiments of the present disclosure, the DNA binding domain is also referred to as the DNA recognition domain.

In an embodiment of the present disclosure, polynucleotides encoding said CRISPR/Cas complex are also provided, as are cells comprising said polynucleotides.

In a particular embodiment, nucleotides encoding for the DNA binding domain of CRISPR Cas9 complex are provided. In another embodiment, nucleotides encoding for the nuclease domain of CRISPR Cas9 complex are provided.

In an embodiment, the nuclease is Cas9.

In another embodiment, the nuclease is Cas9n (nickase) D10A mutant.

In an embodiment of the present disclosure, the CRISPR/Cas complex recognizes target site in FUT8 gene or GMD gene. In an embodiment of the present disclosure, the nuclease is a homing endonuclease. In another embodiment, the nuclease is a meganuclease. It is also known that the specificity of homing endonucleases and meganucleases can be engineered to bind non-natural target sites. Further, in exemplary embodiments, homing endonucleases include I-Scel, I-Ceul, PI-PspI, PI-Sce, I-ScelY, I-CsmI, I-PanI, I-SceII, I-PpoI, I-SceIII, I-CreI, I-TevI, I-TevII and I-TevIII. Their recognition sequences are known.

In an embodiment, a combination of one or more of the above-mentioned nucleases is used with the DNA binding domain of the CRISPR-Cas protein complex.

In an embodiment, transfection is used to introduce a CRISPR/Cas complex into a cell. Though a lipofection protocol is provided as an exemplary embodiment, any method of transfection known to one skilled in the art is equally applicable to the methods of the present disclosure.

In another embodiment, the present disclosure provides methodologies for producing recombinant proteins in any host cell where the host cell has endogenous FUT8 gene or GMD expression which is targeted through CRISPR/Cas technology to disrupt endogenous FUT8 or GMD gene as described herein. The resulting cell line is null for FUT8 gene or GMD gene expression and is further used for expression of gene of interest.

In the present disclosure, seventeen FUT8 knock out clonal cell lines are created from a screen of less than 60 clonal cell lines generated after transfection with pD1401 (gRNA 514-553) CRISPR/Cas complex. In comparison, only three FUT8 −/− cell lines could be selected from approximately 120,000 clonal cell lines as reported in the prior art.

In the present disclosure, thirty GMD knock out clonal cell lines are created from a screen of less than 200 clonal cell lines after transfection with pD1401 (gRNA 167-207) and pD1301 (gRNA 404) CRISPR/Cas complex.

The specificity, safety and simplicity of the protocol are some of the advantages offered by CRISPR/Cas complex and the method of the present disclosure over the prior art methods. CRISPR mediated gene disruption provides a unique advantage of specificity of target locus that allows customized CRISPR/Cas complex to recognize user defined target sequence of any complexity. CRISPR/Cas complex are more effective than ZFN in terms of genome editing efficiency and significantly less toxic, thereby allowing higher efficiency in generating mutant clones against a particular locus. In the present disclosure, FUT8 genomic loci and GMD genomic loci are targeted for sequence specific modification through CRISPR gRNAs.

The methodology described herein has achieved an efficiency of more than 28% success rate of generating CHOK1 FUT8 knock out cell lines (17 CHOK1 knock out cell lines from a screen of less than 60 clonal cell populations) and more than 15% success rate of generating CHOK1 GMD knock out cell lines (30 CHOK1 GMD knock out cell line out of 200 clonal cell population). This unanticipated achievement following the methodology and the specific CRISPR constructs of the present disclosure has vastly improved the FUT8 and GMD knock out cell line development.

Also, the present disclosure has used only one set of CRISPR constructs targeting a very specific genomic location in the CHOK1 FUT8 DNA sequence and two separate sites at the CHOK1 GMD genomic loci. Surprisingly, the CRISPR/Cas complex results in not only disrupting the targeted amino acids but also produced long deletions which introduced frame shift mutations and premature stop codon. Thereby, the present disclosure has achieved many CHOK1 FUT8 knock out cell lines and multiple GMD knock out cell lines with very minimal DNA modifications at the target locus as well as large genome level modifications at the targeted FUT8 and GMD loci. Generation of such a large number of CHOK1 FUT8 and GMD knock out cell lines is unexpected, considering the small number of clonal populations screened for fucose knock out phenotype. This surprising achievement provides for screening multiple CHOK1 FUT8 knock out cell lines and GMD knock out cell lines to establish best performing clonal lines for over expression of monoclonal antibody.

In an embodiment, the gene of interest is introduced in the resulting cell line through an expression vector comprising DNA sequences encoding the protein of interest, thereby producing recombinant protein.

In another embodiment, the expressed protein of interest includes antibodies, including monoclonal antibodies.

In embodiments, inactivating a FUT8 gene results in a cell line which produces recombinant proteins at higher levels.

In embodiments, inactivating a GMD gene results in a cell line which produces recombinant proteins at higher levels.

In certain embodiments, inactivating a FUT8 gene provides a cell line in which one or more activities (functions) of a protein is increased, as compared to proteins produced in cells where the FUT8 gene is not inactivated.

In certain embodiments, inactivating a GMD gene provides a cell line in which one or more activities (functions) of a protein is increased, as compared to proteins produced in cells where the GMD gene is not inactivated.

In an embodiment, the non-fucosylated protein produced by the cell is a non-fucosylated antibody. In a non-limiting embodiment, the non-fucosylated protein is a non-fucosylated IgG1 antibody, and preferably a non-fucosylated IgG1 monoclonal antibody.

In an embodiment, the non-fucosylated antibody exhibits greater effector function than a corresponding fucosylated antibody.

In an embodiment, the non-fucosylated antibody exhibits more efficacious therapeutic properties than a corresponding fucosylated antibody.

In an embodiment, the non-fucosylated antibody exhibits higher Antibody dependent Cellular Toxicity (ADCC) than a corresponding fucosylated antibody.

In the present disclosure, the methods, preparation and use of the proteins disclosed employ, unless otherwise indicated, conventional techniques in molecular biology, biochemistry, computational chemistry, cell culture, recombinant DNA technology, Polymerase Chain Reaction (PCR) and related fields. These techniques, their principles, and requirements are explained in the literature and known to a person skilled in the art. The techniques for determining nucleic acid and amino acid sequence identity are known to one skilled in the art.

The cell with the disrupted fucosylation machinery is a cell that naturally produces antibodies, or a cell in which a gene encoding an antibody is introduced before or after disruption of fucosylation.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid.

The term "antibody" used here includes both polyclonal and monoclonal antibody preparations and also includes the following: Chimeric antibody molecules, F(ab')2 and F(ab) fragments, Fv molecules, single chain Fv molecules (ScFv), dimeric and trimeric antibody fragments, minibodies, humanized monoclonal antibody molecules, human antibodies, fusion proteins comprising Fc region of antibody and any functional fragments arising out of these molecules, where derivative molecules retain immunological functionality of the parent antibody molecule.

The term "monoclonal antibody" in the present disclosure, refers to an antibody composition having a homogeneous antibody population. The antibody is not limited to the species or source of the antibody or by the manner in which it is made. The term encompasses whole immunoglobulins as well as fragments such as Fab, F(ab')2, Fv, and other fragments, as well as chimeric and humanized homogeneous antibody populations that exhibit immunological binding properties of the parent monoclonal antibody molecule.

It is to be noted that clones/cells of the present disclosure are referred to by terms such as CR1KOT1#06, CR1KOT1#23 etc., which are internal denominations and do not represent any particular feature of the cell. These cell lines are developed using pD1401 (gRNA 514-553) CRISPR/Cas complex.

It is to be noted that clones/cells of the present disclosure are referred to by terms such as C1GMD1.12, C1GMD1.27 etc., which are internal denominations and do not represent any particular feature of the cell. These cell lines are developed using pD1401 (gRNA 167-207) CRISPR/Cas complex.

It is to be noted that clones/cells of the present disclosure are referred to by terms such as CIGMD2.30, CIGMD2.34 etc., which are internal denominations and do not represent any particular feature of the cell. These cell lines are developed using pD1301 (gRNA 404) CRISPR/Cas complex.

It is to be noted that clones/cells of the present disclosure are referred to by terms such as CIGMD3.36, CIGMD3.43 etc., which are internal denominations and do not represent any particular feature of the cell. These cell lines are developed using a combination of pD1401 (gRNA 167-207) and pD1301 (gRNA 404) CRISPR/Cas complex.

In an embodiment, a composition comprising the non-fucosylated antibody, optionally along with a pharmaceutically acceptable carrier or additive or excipient is provided. Pharmaceutically acceptable carrier or additive or excipient is determined by the composition being administered, as well as by the particular method used to administer the composition and is known to a person skilled in the art.

All sequences provided in the present disclosure are read in the 5' to 3' direction, unless stated otherwise.

Excipients are important for achieving protein stabilization and improving other qualities of biologics. A variety of excipients are added to compositions to stabilize proteins, act as antimicrobials, aid in the manufacture of the dosage form, control or target drug delivery, and minimize pain upon injection.

Excipients can be broadly divided into five categories based on their modes of action:
1. Protein stabilizers: These excipients stabilize the protein native conformation. Examples include polyols, sugars, amino acids, amines, and salting out salts. Sucrose and trehalose are the most frequently used sugars and large polyols are better stabilizers than smaller polyols.
2. Polymers and proteins: Hydrophilic polymers, such as Polyethylene Glycols (PEGs), polysaccharides, and inert proteins, are used non-specifically to stabilize proteins and enhance protein assembly. Examples include Dextran, Hydroxyl Ethyl Starch (HETA), PEG-4000, and gelatin.
3. Surfactants: Non-ionic surfactants are widely used to stabilize proteins, suppress aggregation, and assist in protein refolding. Polysorbate 80 and Polysorbate 20, also known as Tween 80 and Tween 20, respectively, are generally used in mAb therapeutics. Other examples include Brij 35, Triton X-10, Pluronic F127, and Sodium Doceyl Sulfate (SDS).
4. Amino acids: These excipients stabilize proteins by a variety of mechanisms. Examples include Histidine, Arginine, and Glycine. Other amino acids used as formulation excipients include Methionine, Proline, Lysine, Glutamic acid, and Arginine mixtures.
5. Preservatives: These compounds are included in formulations to prevent microbial growth. Examples include Benzyl alcohol, m-Cresol, and Phenol.

The biological material used in the present disclosure is obtained from outside India.

Rationale for Targeting Specific Genomic Sequence in FUT 8 Locus

FUT8 is comprised of three domains, an N-terminal coiled-coil domain, a catalytic domain, and a C-terminal SH3 domain.

Fut8 protein structure is studied extensively to understand the functional domain of the enzyme amino acid sequence. Three dimensional crystal structure of FUT8 enzyme revealed 15 strands and 16 helices. There are at least three regions, N terminus (residues 68-107), C-terminus (573-575) and residues 368-372 which are disordered.

The putative catalytic domain of the FUT8 enzyme is consisted of two domains, an open sheet alpha/beta domain and the Rossmann fold widely known for nucleotide binding region. The alpha/beta domain consisted of five helices and three beta strands, which are alpha 4, 3H1, 3H2, 3H3, beta 1, beta 2 and beta3 strands. The domain is located in the N terminus of the protein sequence. There is no clear evidence how the N terminus catalytic domain is responsible for enzyme functionality.

The Rossmann fold is located downstream at residue 359-492 and contains several alpha helix and beta strands. A series of residues Arg 365, Arg 366, Asp-368, Lys-369, Glu-373, Tyr-382, Asp-409, Asp-410, Asp-453, and Ser-469 play an important role in catalytic domain of FUT8 enzyme.

Ten amino acid residues, Arg 365, Arg 366, Asp-368, Lys-369, Glu-373, Tyr-382, Asp-409, Asp-410, Asp-453, and Ser-469 of human FUT8 enzyme protein are conserved among various species, including vertebrates, insect, nematode, and ascidian as observed in FIG. 19 of the present disclosure.

To understand the contribution of specific amino acid sequence in FUT8 gene in α 1,6 fucosyltransferase activity, regions of FUT8 amino acid sequence are compared among multiple species. The alignment shows that the enzyme sequences constitute highly conserved amino acid residues at the beta 2 strand and the 3H2 helix region. Thus, these amino acid positions are the target of CRISPR/Cas complex in the method of the present disclosure.

Rationale for Targeting GMD and FUT8 Genes in CHOK1 Cell Line

Fucose knock out platform is useful to achieve non fucosylated monoclonal antibody molecule development. In many instances, developing completely non fucosylated antibody is a preferred outcome and therefore strategies are made in this disclosure to create complete knock out of Fucose biosynthetic pathway genes. In certain cases, the monoclonal antibody therapeutic drug product may require partial fucosylation which is not available naturally. To create designed versions of fucosylated monoclonal antibodies for therapeutic purposes, the GMD knock out CHOK1 cell line is very useful.

GMD gene is involved in the fucosylation pathway, upstream of FUT8 gene and responsible for GDP-fucose synthesis through conversion of GDP-mannose to GDP-4-keto-6-deoxy-mannose. This step is one of the critical steps of de novo fucose biosynthetic pathway. GDP fucose is also produced in cells through salvage pathway and is used for fucosylation of cellular proteins. In salvage pathway, cells uptake fucose from growth media. The de novo pathway for fucose biosynthesis is completely stopped if the GMD gene is knocked out and completely non-functional. The GDP-Fucose biosynthesis still remains active through salvage pathway if the growth media is supplemented with Fucose. Therefore, fucose biosynthetic pathway and cellular protein fucosylation still remains active.

The GMD knock out CHOK1 cell lines provide a unique advantage wherein if the monoclonal antibody need to be 100% defucosylated, GMD double knock out cellular platform is used. In cases, where the monoclonal antibodies require specific level of fucosylation, the salvage pathway to generate GDP-Fucose is utilized through supplementation of growth media with L-Fucose. Essentially, the level of monoclonal antibody fucosylation is achieved through titrating levels of L-Fucose in growth medium. Therefore, GMD KO strategy provides 100% non fucosylated product to variable levels of fucosylation by simple titration of L-Fucose in CHOK1 culture media. This is a unique strategy to control fucosylation of monoclonal antibody production in CHOK1 cells.

On the other hand, Fut8 enzyme functions downstream of GDP-Fucose biosynthesis step and is the last enzymatic step for fucosylation of cellular proteins in golgi. Fucosylation precursors from both de novo and salvage pathway use FUT8 enzyme for final fucose moiety transfer. Therefore, knocking out Fut8 gene essentially stops both de novo and salvage pathway of cellular protein fucosylation. This approach results in 100% defucosylation of monoclonal antibodies produced in the Fut8 knock out CHOK1 cell line.

Targeting Active Site of GMD:

The enzyme GDP-D-mannose 4,6-dehydratase (GMD) catalyzes the conversion of GDP-D-mannose to the intermediate GDP-4-keto-6-deoxy-D-mannose. This serves as a branching point to several different deoxyhexoses, including GDP-D-rhamnose, GDP-L-fucose, GDP-6-deoxy-D-talose, and the GDPdideoxy amino sugar GDP-D-perosamine. Among these GDP-L-fucose is an important intermediary in fucose biosynthetic pathway. GMD is a member of the NDP-sugar modifying subfamily of the short-chain dehydrogenases/reductases (SDR).

As a member of this subfamily, GMD binds its cofactor NADP(H) in the N-terminal portion of the molecule in which a common glycine-rich region is present. The catalytic triad has been identified as Tyr-XXX-Lys and Ser/Thr, which are all important for catalysis. Although there is significant amino acid sequence variability in members of this group of enzyme, three dimensional structural similarities exist.

Structure analysis of GMD from *E. coli* suggests that the active molecule is in dimeric configuration. Whereas homolog from *Arabidopsis thaliana* is tetrameric, and that the NADP(H) binding site is intimately involved in creating the tetramer interface. It is most probable that the functional form of GMD enzyme in eukaryotes consists of tetrameric configuration. GMD crystalizes with four monomeric units and the monomers interact with each other to form the catalytic domain. Opposing monomers interact through hydrogen bonding between Asn 163, Arg 147, Glu166, Tyr145, and Arg147. Tetramerization of GMD results in suitable cofactor binding sites (NADPH) at the interface. Ser85 plays a crucial role in hydrogen bonding to the pyrophosphate at the active site. In addition, the nicotinamide ribose hydroxyls are within hydrogen bonding distance to the catalytic residues Tyr150 and Lys154, interactions that are highly conserved in SDR enzymes.

The RR loop, a segment of nine residues (Arg35-Arg43), stretches into the neighboring monomer making protein-protein interactions and contacts to the neighboring cofactor. Protein-protein interactions include Arg35 hydrogen bonding to Ser85 and Glu188. For substrate binding, it has been reported that GDP-D-mannose interaction could depend on the ability to make potential hydrogen bonds to Thr126, Ser127, and Glu128. Also, both catalytic residues Thr126 and Tyr150 as well as Ser85 could hydrogen bond to the hexose 04 hydroxyl. The catalytic mechanism proposed for GMD involves few key residues like Thr126, Ser127, Glu128, Tyr150 among others.

Considering the importance of these residues, multiple CRISPR/Cas complex are targeted which potentially disturb the tetrameric configuration of the active enzyme as well as affect the cofactor binding region and substrate interaction motifs. One CRISPR construct is designed in proposed dimeric interface of amino acid sequence ADVDGVGTLRLL. This region is part of Exon4 of the GMD gene. The CRISPR construct targets Cas9 endonuclease to create double stand DNA break in exon 4. The break site is positioned before key amino acid residues in the motif ADVDGVGTLRLL with the assumption that any modification in these amino acids directly affects catalytic mechanism of the GMD enzyme.

A second set of CRISPR/Cas complex is designed in exon 3 of the GMD gene. This CRISPR design is unique for high specificity, where a mutant Cas9, known as D10A Cas9 nickase mutant (Cas9n) is chosen, causing DNA single strand break. The two CRISPR/Cas complexes designed for two single strand DNA break allow high level of specificity. The constructs are designed at proposed tertrameric interface amino acid sequence motif YGDLTDSTCLVK. The two single stand breaks allow DNA repair by the NHEJ mechanism and it introduces mutations in this region. These mutations affect the important Ser85 residue involved in maintaining the interactions of monomers in the tetrameric configuration.

Position of important structural motifs in GMD gene exon 3 and exon 4 and CRISPR target locations are depicted in FIG. 9B.

Both CRISPR/Cas designs are unique and achieve higher potential in generating fucose knock out CHOK1 cell line.

Targeting Active Site of Fut8:

One of the most important aspects of the present disclosure is the targeting of the catalytic site of the enzyme α 1,6-fucosyltransferase, encoded by the Fut8 gene. Fut8 protein structure is studied extensively to understand the functional domain of the enzyme amino acid sequence. Three dimensional crystal structure of FUT8 enzyme revealed 15 strands and 16 helices. There are at least three regions, N terminus (residues 68-107), C-terminus (573-575) and residues 368-372 are disordered.

The putative catalytic domain of the FUT8 enzyme consists of two domains, an open sheet alpha/beta domain and the Rossmann fold widely known for nucleotide binding region. The alpha/beta domain consists of five helices and three beta strands, which are alpha 4, 3H1, 3H2, 3H3, beta 1, beta 2 and beta 3 strands. The domain is located in the N terminus of the protein sequence. There is no clear evidence how the N terminus catalytic domain is responsible for enzyme functionality. The CRISPR/Cas target sequences are targeted in this region. Fut 8 exon7 genomic locus, respective amino acid sequence and position of important structural motifs and CRISPR target locations are depicted in FIG. 9A.

This targeting is not a random selection, but has been arrived at, in the present disclosure, by experimentation to determine the highly specific location on the gene or enzyme, the disruption of which ensures that partial fucosylation that is caused by truncated or partially functional enzyme is avoided.

The Rossmann fold on the other hand, is located downstream at residue 359-492 and contains several alpha helix and beta strands. A series of residues Arg 365, Arg 366, Asp-368, Lys-369, Glu-373, Tyr-382, Asp-409, Asp-410, Asp-453 and Ser-469 play an important role in catalytic domain of FUT8 enzyme.

Thus, targeting the region equivalent to the active site of the enzyme ensures complete disruption of the Fut8 gene and provides efficacious results in comparison to either a technique that is unable to target a precise location on the Fut8 gene or a technique that targets another location on the Fut8 gene, which might result in partial disruption of Fut8 gene and enzyme activity. A cell with partially functional fucosylated machinery produces partially fucosylated proteins, which exhibits lower therapeutic functions as compared to non-fucosylated proteins. The cells produced by the method of the present disclosure produce completely or 100% non-fucosylated proteins, including 100% non-fucosylated antibodies.

The present disclosure introduces mutations at critical amino acid positions at the catalytic site of the FUT8 codon sequence through CRISPR/Cas complex. The CRISPR design is aimed to primarily target the N-terminal catalytic domain, specifically the beta 2 strand and the 3H2 helix region by incorporating single stranded breaks. The cellular DNA repair system introduces nucleotide changes while carrying out the single stand break repair and creates non-functional FUT8 enzyme.

The CRISPR system is well known for deletion and insertion in a localized manner and therefore creates frameshift mutation at the targeted exon7 and inserts stop codons. Introduction of stop codons ensures premature translation termination and the downstream Rossmann fold is excluded from enzyme structure, resulting in non-functional FUT8 enzyme.

In an embodiment of the present disclosure, the subsequent genomic DNA analysis of the modified CHOK1 cell lines reveals deletion, insertion, stop codon as well as frame shift mutations. Thus, the present disclosure envisages disruption of Fut8 gene and Fucosyltransferase enzyme by targeting amino acid positions in the beta 2 strand and the 3H2 helix through deletions, insertions and/or frame shift mutations.

The resulting clones may result in premature translation stop therefore causing extensive changes in critical downstream sequences such as Arg-365, Arg-366, Asp-368, Lys-369, Glu-373, Tyr-382, Asp-409, Asp-410, Asp-453, Ser-469 and combinations thereof.

FIG. 19 of the present disclosure depicts alignment of FUT8 amino acid sequence of rat, human, mouse, cattle and Chinese hamster. Amino acids in the Rossmann fold 365, 366, 368, 369 and 373 are marked with asterisks. Amino acids in shaded box indicate residues not aligned with consensus sequence. Amino acids in the exon 7 region are also marked. CRISPR recognition sequences are marked by thick lines.

In the present disclosure, the FUT8 amino acid sequence from CHOK1 genomic database is analyzed and it is confirmed that these critical amino acids are conserved in the FUT8 gene derived from CHOK1 cell line as well. Sequence specific CRISPR/Cas complex is designed, targeting gene sequences upstream of these amino acid motifs to introduce genomic modifications. It is analysed how altering amino acid sequences upstream of the critical FUT8 enzyme catalytic domain disrupts the enzyme function.

It is stated that mutation of these critical amino acids provides complete disruption of FUT8 gene functionality. Gene targeting using CRISPR/Cas technology is a novel approach to create a Fucose knock out cell line platform. CRISPR/Cas transfected cells are screened through FUT8 gene functionality assays. Selected clones are confirmed through sequencing of genomic FUT8 loci for mutations. The mutant fucose knock out CHOK1 cell line is then used for expressing non-fucosylated therapeutic proteins, including non-fucosylated therapeutic monoclonal antibodies or part of antibody.

CRISPR/Cas constructs specifically targeting the amino acid codon sequences in genomic locations are designed, and cloned in expression vectors, for e.g. pD1401 or pD1301 depending on the type of Cas9 gene. The CRISPR/Cas complex is transiently transfected in CHOK1 cells; the cells are plated in 96 well plates for single colony generation. Each clone is then screened for fucosylation of cellular proteins using fluorescence based *Lens Culinaris* Agglutinin assay (LCA). Clones positive for FUT8 or GMD gene disruption are further tested through enzymatic assays and kinetic analysis of mutant alleles of FUT8 gene or GMD gene. Finally, the genomic sequence at the FUT8 and GMD loci is analyzed for any mutation carried out through CRISPR/Cas. These mutations involve deletions or insertions, thereby introducing frame shift mutations of the FUT8 and GMD codon sequence, and rendering the sequence disrupted and the enzymes non-functional.

The fucose knock out CHOK1 cell line derived from above mentioned process is used as a cell line platform for expressing proteins, monoclonal antibodies, peptides, fusion proteins of therapeutic purposes, biomarker development, diagnostic and prognosis uses.

The present disclosure is further described with reference to the following examples, which are only illustrative in nature and should not be construed to limit the scope of the present disclosure in any manner.

Reagent Preparation

Advanced DMEM complete growth medium—500 ml
1. 50 ml FBS (final concentration 10%) is added to the upper chamber of the 500 ml filter unit.
2. 10 ml of 200 mM glutamine (final concentration 4 mM) is added.
3. 5 ml of 100× Pen-strep solution (final concentration 1×) is added.
4. The volume is adjusted up to 500 ml with advanced DMEM media.
5. The complete media is filtered through 0.22 µm filter.
6. The upper chamber is dismantled and the reservoir or media bottle is closed.
7. The media can be used within 30 days of preparation.
8. The media is stored at 2° C. to 8° C. and away from continuous exposure to light.
9. In cases where LCA selection media is prepared, 10 ml of 10 mg/ml stock LCA reagent is mixed with 500 ml of prepared DMEM media to achieve final 200 µg/ml LCA concentration in DMEM media.

Materials & Equipment
1. Bio safety cabinet
2. Sorvall ST 16R centrifuge
3. Water bath
4. Inverted phase contrast microscope
5. $CO_2$ incubator
6. Millipore GUAVA 8HT easyCyte benchtop flow cytometer
7. Vi-cell XR cell viability analyser
8. Hemocytometer
9. Refrigerator
10. Eppendorf minispin centrifuge
11. Micropipettes
12. Micro tips
13. 96 well tissue culture plates 14. 12 well tissue culture plates
15. 6 well tissue culture plates
16. Serological pipettes (10 ml, 25 ml and 50 ml)
17. 1000 ml filtration unit-0.22 μm pore size
18. 70% ethanol
19. Advanced DMEM
20. Dulbecco's Phosphate Buffered Saline (DPBS)
21. Fetal Bovine Serum (FBS)
22. Penicillin Streptomycin (Penstrep)
23. Glutamine
24. 0.05% Trypsin EDTA
25. 0.4% Trypan blue
26. Microfuge tubes (1.5 ml and 2 ml)
27. Falcon tubes (15 ml and 50 ml)
28. Bovine serum albumin fraction V
29. Fluorescein Lens Culinaris Agglutinin (LCA-FITC)
30. Fluorescein Streptavidin (Strep-FITC)

TABLE 1

Reagents used in this diclosure

| S. No. | Reagent | Composition |
|---|---|---|
| 1 | Agarose | Agarose (SIGMA, Cat- A9539) |
| 2 | 1 kb DNA ladder | 1 kb ladder (Thermoscientific Cat-SM0311) |
| 3 | 100 bp DNA ladder | 100 bp ladder (Thermoscientific, Cat-SM0322) |
| 4 | QIAGEN genomic DNA isolation kit | DNeasy Blood & Tissue Kit (QIAGEN, Cat-69504) |
| 5 | Taq DNA polymerase | Taq DNA polymerase with thermopol (NEB, Cat-M0267 & M0273L) |
| 6 | Phusion high-fidelity DNA polymerase | Phusion high-fidelity DNA polymerase (Thermo Scientific, Cat-F530L) |
| 7 | InsTAclone PCR cloning | TA cloning vector pTZ57R/T (Thermo Scientific, Cat- K1214) |
| 8 | Competent cells DH10B cells | Max Efficiency DH10B competent cells (Invitrogen, Cat- 18297-010) |
| 9 | Competent cells DH5alpha cells | NEB 5-alpha competent cells (NEB, Cat-C2987P) |
| 10 | Ethanol absolute (99.9%) | Sdfine chem, Cat- 58051 L05 |
| 11 | Plasmid DNA isolation | QiaPrep spin miniprep Kit (QIAGEN, Cat-27104) |
| 12 | DNA elution kit | QIAGEN Gel Extraction kit (Cat-20021 and 20051) |
| 13 | Restriction enzymes | EcoRI-HF (NEB, Cat-R3101) Hind III-HF (NEB, Cat- R3104) |
| 14 | T4 ligase | T4 DNA Ligase (NEB, Cat-M0202) |

TABLE 2

Media and buffers used in this disclosure

| S. No. | Media/Buffers | Composition |
|---|---|---|
| 1 | 6X loading DNA dye | Sucrose-4 g, Bromophenol blue-0.025 g, made up to 10 mL using purified water. |
| 3 | 50X TAE buffer | Tris base-121 g, Glacial acetic acid-28.6 mL, EDTA (0.5M) pH-8- 50 mL, made up to a volume of 500 mL with purified water. |

Example 1: Designing of CRISPR/Cas Constructs

The objective of this example is to design CRISPR/Cas complex for specific inactivation of FUT8 and the GMD alleles.

1.1—CRISPR Constructs

CRISPR is based on a class of RNA-guided endonucleases known as Cas9 from the microbial adaptive immune system found in Streptococcus pyogenes. Cas9 nuclease is directed to specific sites on the genome by guide RNAs (gRNAs). The Cas9/gRNA complex binds to a 20 bp target sequence that is followed by a 3 bp protospacer activation motif (PAM) NGG or NAG on the specific gene that needs to be edited (Jinek, 2012; Mali, 2013). Thus, the binding of this whole complex creates double stranded breaks (DSBs).

A crucial step in targeted genome editing at genomic loci that need to be modified, is the introduction of these DSBs. Once, DSBs are introduced, they are repaired either by non-homologous end joining (NHEJ) or homology directed repair (HDR).

NHEJ is known for the efficient introduction of insertion/deletion mutations (indels) that in turn cause disruption of the translational reading frame of the target coding sequence or at binding sites of trans-acting factors in promoters or enhancers. On the other hand, HDR mediated repair can insert specific point mutations or sequences at the target locus. Thus, co-transfection of cell types with vectors that express the Cas9 nuclease and the gRNAs targeted to a specific gene locus can efficiently knock down the expression of target genes. The expected frequency of mutations at these specific sites ranges from >1% to 50% (Sander 2014).

Selection of mutants is performed by simple screening using sequencing, without the use of drug resistance marker selection. In order to increase the specificity of gene disruption, the present disclosure uses mutant Cas9 (D10A) that is guided by two guide RNAs for a single gene locus and that introduces two single stranded breaks or nicks. This also reduces the chances of non-specific binding at other random sites. A vector encoding Cas9-D10A and the 2 gRNAs are used to cause efficient gene knock-out.

The GMD and Fut8 genomic loci are targeted for sequence specific deletions through CRISPR/CAS9 technology and generate defucosylated mammalian expression systems.

1.2—the Complete Process of Obtaining CRISPR Construct is Composed of the Following Steps:
1. CRISPR Designing.
2. Primer Designing.
3. Synthesis of Oligonucleotides.
4. Transformation of CRISPR constructs pD1401 (gRNA 514-553), pD1401 (gRNA 167-207) and pD1301 (gRNA 404) on LB (Luria Broth)+ampicillin plate.
5. inoculation of transformed cells (CRISPR constructs) into LB with Ampicillin broth.
6. Isolation of Plasmid pD1401 (gRNA 514-553), pD1401 (gRNA 167-207) and pD1301 (gRNA 404) from DH10B or DH5alpha cells.
7. Transfection into CHOK1 cells; screening and selection by LCA assay.
8. Genomic DNA isolation of selected clones using QIAGEN DNeasy Blood & Tissue Kit.
59. Quantification by Spectrophotometry.
10. Optimization of PCR Condition.
11. Cross checking the Genomic DNA sample by PCR,
12. Electrophoresis on agarose gel.
13. PCR amplification using Phusion polymerase and tailing using Taq polymerase.
14. PCR product gel elution using QIAGEN kit.
15. TA cloning using pTZ57R/T vector.
16. Transformation of ligated sample pTZ57R/T+ CRISPR (PCR) in DH10B or DH5alpha cells.
17. Inoculation of transformed cells (pTZ57R/T+ CRISPR (PCR)) into LB with Ampicillin broth.
18. Isolation of plasmid DNA (pTZ57R/T+ CRISPR(PCR) from DH5alpha and DH10B cells using QIAGEN plasmid DNA isolation kit.

19. Cross checking for the presence of insert by restriction digestion (Sites).
20. Sequencing primers; and
21. Confirmation of the INDELs by sequencing.

Figure 1A:
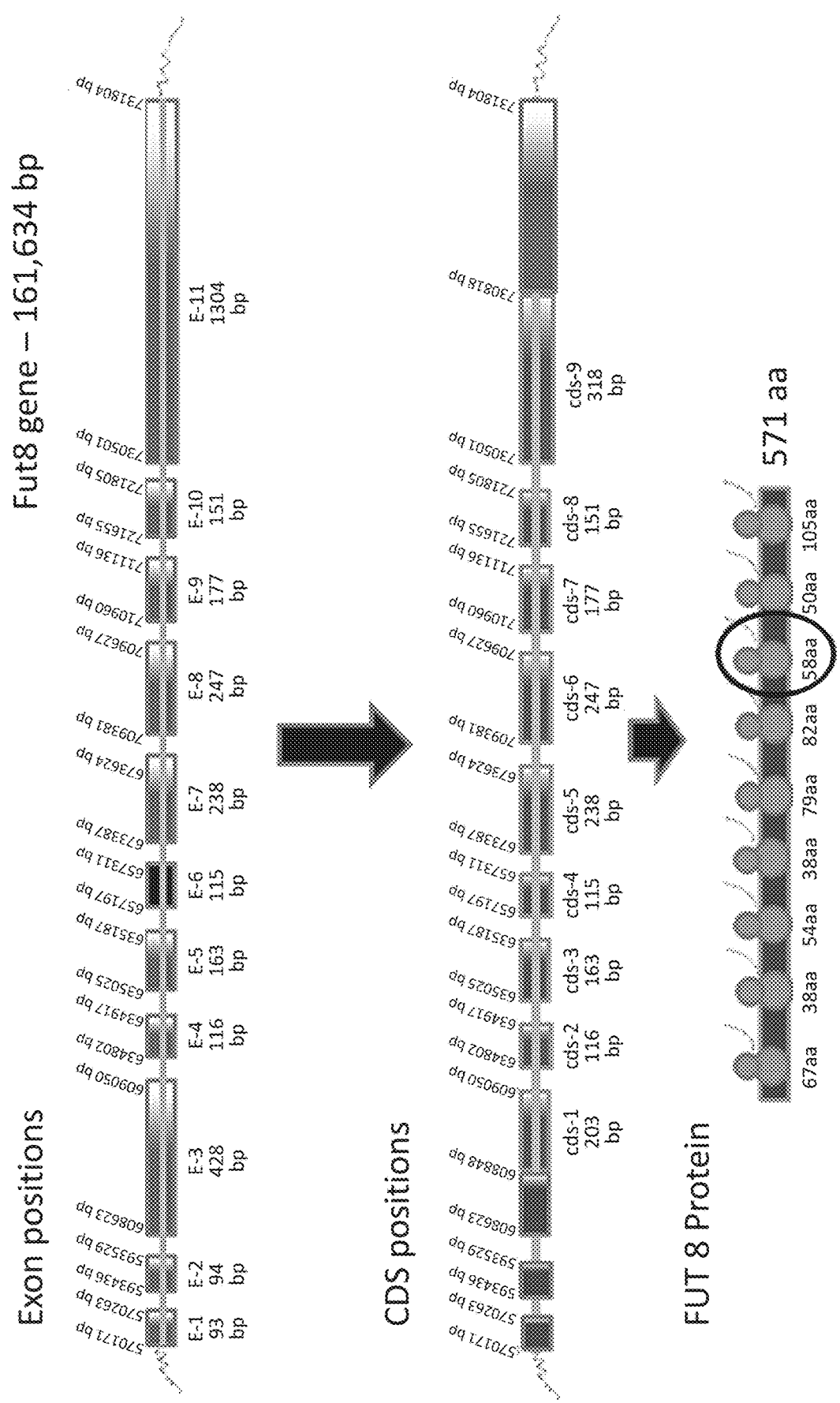
FIG. 1A depicts the Fut8 gene coding sequence and protein sequence.

FIG. 1A of the present disclosure depicts the Fut8 coding sequence and protein sequence. FUT8 genomic sequence is analyzed from database sequence, sequence ID NW_003613860. FUT8 genomic sequence spans from 570171-731804 bases and contains eleven exons depicted as E1 to E11 in the figure. Base pairs locations for each exon are also indicated. E1, E2 and part of E3 constitute un-translated region in the upstream sequence, and part of E11 is also part of un-translated region. Translated regions are described as CDS 1 to CDS 9. Length of each CDS is indicated below the CDS number. CDS1 to CDS9 code for amino acid sequences varying from 38 amino acids to 105 amino acids.

*Cricetulus griseus* or Chinese Hamster fucosyltransferase 8 (Fut8) mRNA (3126 bp) is derived from NCBI Reference Sequence: XM_003501735.1, also represented by SEQ ID No.1 of the present disclosure.

Alternative exons are represented in upper and lower case letters.

Fut8 protein structure is studied extensively to understand the functional domain of the enzyme. Three dimensional crystal structure of FUT8 enzyme revealed 15 strands and 16 helices.

Amino acid sequence of FUT8 gene is provided in FIG. 2A.

The CRISPR/Cas binding regions are designed in such a way that the specificity of site recognition is high and at the same time the CRISPR/Cas complex carries out the intended DNA single strand break.

In an embodiment, Cas9n (D10A mutant of Cas9 endonuclease) is used for the CRISPR/Cas complex. The Cas9n endonuclease causes single strand DNA break. The two CRISPR recognition sites (5' recognition site and 3' recognition site are spaced at 5 base pair distance, allowing two single stand breaks at close proximity. The resulting breaks allow the NHEJ process of DNA break repair and that introduces mutations in this region.

The CRISPR construct has two unique 20 basepair CRISPR recognition sequences flanked by gRNA scaffolds in tandem with U6 promoter elements for efficient expression of the gRNA sequences. The unique design allows one single vector to express two separate gRNA scaffolds and two unique CRISPR recognition sequences on the genomic DNA.

The nucleotide and amino acid sequence of wild type Cas9 gene is provided in Seq ID Nos. 3 and 4 respectively.

The nucleotide and amino acid sequence of the Cas9n endonuclease is provided in Seq ID Nos. 5 and 6 respectively.

The CRISPR/Cas design is uniquely positioned to target beta 2 strand and the 3H2 helix region by incorporating single stranded breaks. The design is compatible with two single strand breaks at close proximity, thereby imparting higher specificity of target recognition as NHEJ repair mechanism occurs only at these targeted genomic locations. Nonspecific single stand breaks, if created are usually repaired by homologous recombination which is accurate and rarely creates any mutation.

The primary target of the present disclosure is to create mutations at the N-terminal catalytic domain, the beta 2 strand and 3H2 helix. Insertion and deletions through CRISPR/Cas at this location makes the FUT8 enzyme non-functional. In addition, frame shift mutations also cause premature translation stop codons, the Rossmann fold which is downstream of this region does not express then. Amino acid residues in Rossmann fold such as Arg 365, Arg 366, Asp-368, Lys-369, Glu-373, Tyr-382, Asp-409, Asp-410, Asp-453, and Ser-469 are very important for FUT8 functionality. The truncated enzyme will be non-functional and leads to Fucose knock out cell line.

FIG. 2A of the present disclosure depicts the CHOK1 Fut8 amino-acid sequence. Complete amino acid sequence of FUT8 gene is provided. Amino acid sequence from each CDS is indicated with large arrowheads. Small arrows indicate critical amino acids present in Exon 7 (CDS5) which are targeted in the Fut8 gene by CRISPR constructs.

The CHO whole cell genome shotgun sequencing data with accession number NW_003613860 for the Fut8 gene corresponds to a total of 161634 bp. The Pubmed accession number for the coding region or mRNA of the Fut8 gene is XM_003501735.1. The mRNA sequence, as shown in FIG. 1A, encompasses the complete coding sequence for expression of the FUT8 gene product, which is α-1,6 fucosyltransferase.

The Spidey alignment tool (http://www.ncbi.nlm.nih.gov/spidey/spideyweb.cgi) is used to identify the exons in the genomic DNA by aligning the mRNA sequence with the genomic DNA sequence. A total of 11 exons with the boundaries as shown in Table 3 are identified.

TABLE 3

Characterization of Fut8 mRNA

| EXON | Genomic coordinates | mRNA coordinates | Length (nucleotides) |
| --- | --- | --- | --- |
| Exon 1 | 570171-570263 | 1-93 | 93 |
| Exon 2 | 593436-593529 | 94-187 | 94 |
| Exon 3 | 608623-609050 | 188-615 | 428 |
| Exon 4 | 634802-634917 | 616-731 | 116 |
| Exon 5 | 635025-635187 | 732-894 | 163 |
| Exon 6 | 657197-657311 | 895-1009 | 115 |
| Exon 7 | 673387-673624 | 1010-1247 | 238 |
| Exon 8 | 709381-709627 | 1248-1494 | 247 |
| Exon 9 | 710960-711136 | 1495-1671 | 177 |
| Exon 10 | 721655-721805 | 1672-1822 | 151 |
| Exon 11 | 730501-731804 | 1823-3126 | 1304 |

FUT8 enzyme functionalities through site directed mutagenesis studies of critically important amino acid residues in the catalytic domain has been confirmed.

A 100% identity between the genomic DNA and mRNA sequence is observed. Organization of the Fut8 gene showing all the 11 exons and position of the gRNAs targeting exon7 is shown in FIG. 1A of the present disclosure. The construct with mutant Cas9 nuclease (Cas9n) is designed, which creates single strand break (nick) at the target site. Two separate gRNAs are designed at close proximity in exon7 to create two nicks for eventual DNA repair.

In the present disclosure, CRISPR/Cas9 technology target sites are localized to the first few exons of the Fut8 gene. This is done to avoid partial fucosylation that can be caused by truncated or partially functional enzyme.

Exon-7 (CDS-5) nucleotide sequence of Fut8 is represented by SEQ ID No. 7 of the present disclosure.

AATCCCAAGGACTGCAGCAAAGCCAGAAAGCTGGTATGTAATATCAACAA

AGGCTGTGGCTATGGATGTCAACTCCATCATGTGGTTTACTGCTTCATGA

TTGCTTATGGCACCCAGCGAACACTCATCTTGGAATCTCAGAATTGGCGC

```
TATGCTACTGGAGGATGGGAGACTGTGTTTAGACCTGTAAGTGAGACATG

CACAGACAGGTCTGGCCTCTCCACTGGACACTGGTCAG
```

Exon-7 (CDS-5) amino acid sequence of Fut8 of CHO cell is represented by SEQ ID No. 8 of the present disclosure. The targeted amino acid positions in the protein/peptide sequence are underlined.

```
NPKDCSKARKLVCNINKGCGYGCQLHHVVYCFMIAYGTQRTLILESQNWR

YATGGWETVFRPVSETCTDRSGLSTGHWS
```

Similar to the strategy outlined above for the Fut8 gene, the Spidey alignment tool (http://www.ncbi.nlm.nih.gov/spidey/spideyweb.cgi) is used to identify the GMD gene exons in the genomic DNA by aligning the GMD mRNA sequence with the genomic DNA sequence. A total of 10 exons with a 5' untranslated region and a poly A tail are identified and tabulated in Table 4.

Organization of the GMD gene showing all the 10 exons are provided in Table 4 of the present disclosure. The other CRISPR/Cas targets on the GMD gene, that are considered for targeting are also provided in Table 6.

TABLE 4

Characterization of GMD mRNA

| EXON | Genomic coordinates | mRNA coordinates | Length (nucleotides) |
|---|---|---|---|
| Exon 1 | 1-31 | 228-258 | 31 |
| Exon 2 | 7779-7884 | 259-364 | 106 |
| Exon 3 | 9961-10070 | 365-474 | 110 |
| Exon 4 | 123180-123357 | 475-652 | 178 |
| Exon 5 | 125698-125801 | 653-756 | 104 |
| Exon 6 | 147875-148025 | 757-907 | 151 |
| Exon 7 | 324508-324615 | 908-1015 | 108 |
| Exon 8 | 346684-346784 | 1016-1116 | 101 |
| Exon 9 | 441581-441654 | 1117-1190 | 74 |
| Exon 10 | 441819-442215 | 1191-1587 | 397 |

GMD Exon-3 nucleotide sequence is represented by SEQ ID No. 9 of the present disclosure.

```
ACATGAAGTTGCACTATGGTGACCTCACCGACAGCACCTGCCTAGTAAAA

ATCATCAATGAAGTCAAACCTACAGAGATCTACAATCTTGGTGCCCAGAG

CCATGTCAAG
```

GMD Exon-4 nucleotide sequence is represented by SEQ ID No. 10 of the present disclosure.

```
ATTTCCTTTGACTTAGCAGAGTACACTGCAGATGTTGATGGAGTTGGCAC

CTTGCGGCTTCTGGATGCAATTAAGACTTGTGGCCTTATAAATTCTGTGA

AGTTCTACCAGGCCTCAACTAGTGAACTGTATGGAAAAGTGCAAGAAATA

CCCCAGAAAGAGACCACCCCTTTCTATCCAAGGTCGCCCTATG
```

Figure 2B:
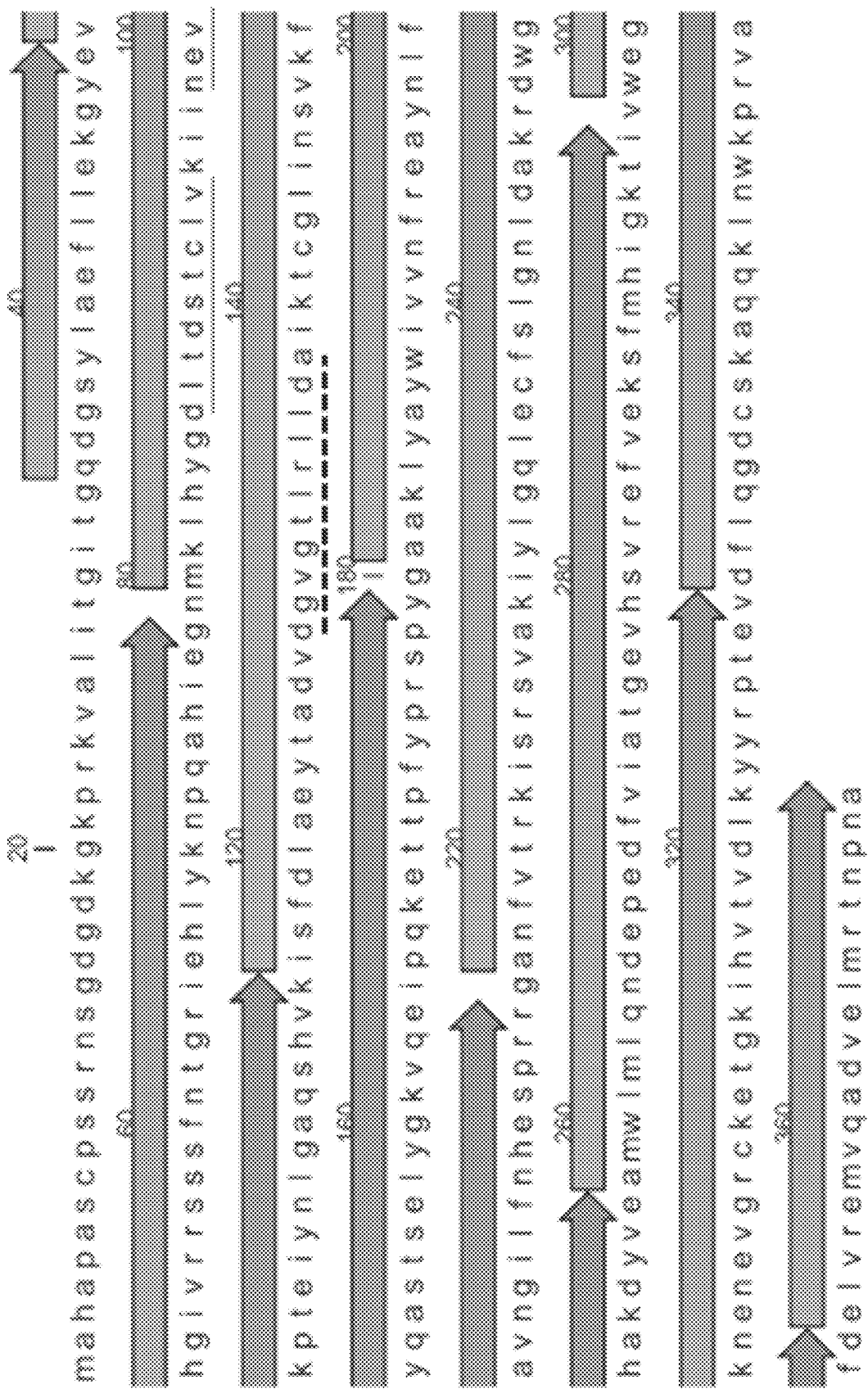
FIG. 2B depicts the complete amino acid sequence of GMD encoded by the sequence set forth in SEQ ID No. 2.

The targeted amino acid positions in the protein/peptide sequence are in bold letters (FIG. 2B). GMD Exon-3 amino acid sequence is represented by SEQ ID No. 11 of the present disclosure.

```
MKLHYGDLTDSTCLVKIINEVKPTEIYNLGAQSHVK
```

GMD Exon-4 amino acid sequence is represented by SEQ ID No. 12 of the present disclosure.

```
ISFDLAEYTADVDGVGTLRLLDAIKTCGLINSVKFYQASTSELYGKVQEIP

QKETTPFYPRSPY
```

1.3—Sequence of Interest in Fut8 Gene to be Targeted Using CRISPR

In Exon 7 of the Fut8 gene, the sequences provided below are used to bind to the target DNA.

CRISPR recognition sequence 1 is represented by SEQ ID No. 13.

```
AATTGGCGCTATGCTACTGGAGG
``` gRNA1—is represented by SEQ ID No. 14.

```
AAUUGGCGCUAUGCUACUGGAGG
```

CRISPR recognition sequence 2 is represented by SEQ ID No. 15.

```
CCAGCGAACACTCATCTTGGAAT
``` gRNA2—is represented by SEQ ID No. 16.

```
CCAGCGAACACUCAUCUUGGAAU
```

Multiple CRISPR/Cas potential sites all throughout FUT8 and GMD genomic sequences are designed. The following table indicates important sites at FUT8 genomic sequences.

TABLE 5

CRISPR recognition sequences (gRNA) designed for FUT8 gene sequence

| Exon location | SEQ ID Nos. | Locus name | CRISPR/Cas recognition DNA sequence (5' to 3') |
|---|---|---|---|
| Exon 3 | SEQ ID No. 17 | gRNA 520-558 | TGACCACCCTGACCATTCTAGCAGAGAACTCTCCAAGATTC TTGCAAAGCTGGAGC |
| Exon 3 | SEQ ID No. 18 | gRNA 549-590 | TCTCCAAGATTCTTGCAAAGCTGGAGCGCTTAAAACAACA AAATGAAGACTTGAGGAGA |
| Exon 4 | SEQ ID No. 19 | gRNA 687-731 | AGGCCAAAGAACAGATTGAAAATTACAAGAAACAAGCTAG GAATG |

TABLE 5-continued

CRISPR recognition sequences (gRNA) designed for FUT8 gene sequence

| Exon location | SEQ ID Nos. | Locus name | CRISPR/Cas recognition DNA sequence (5' to 3') |
|---|---|---|---|
| Exon 7 | SEQ ID No. 20 | gRNA 1019-1057 | AATCCCAAGGACTGCAGCAAAGCCAGAAAGCTGGTATGTA ATATCAACAAAGGCTG |
| Exon 7 | SEQ ID No. 21 | gRNA 1128-1168 | GCACCCAGCGAACACTCATCTTGGAATCTCAGAATTGGCGC TATGCTACTGGAGGATG |
| Exon 7 | SEQ ID No. 22 | gRNA 1199-1238 | AGACCTGTAAGTGAGACATGCACAGACAGGTCTGGCCTCT CCACTGGACACTGGTCA |
| Exon 7 | SEQ ID No. 23 | gRNA 1120-1176 | CACCCAGCGAACACTCATCTTGGAATCTCAGAATTGGCGCT ATGCTACTGGAGGATG |
| Exon 8 | SEQ ID No. 24 | gRNA 1331-1369 | TTACCCTTGGCTGTACCAGAAGACCTTGCAGATCGACTCCT GAGAGTCCATGGTGA |
| Exon 8 | SEQ ID No. 25 | gRNA 1343-1385 | GTACCAGAAGACCTTGCAGATCGACTCCTGAGAGTCCATG GTGATCCTGCAGTGTGG |
| Exon 8 | SEQ ID No. 26 | gRNA 1351-1389 | AGACCTTGCAGATCGACTCCTGAGAGTCCATGGTGATCCTG CAGTGTGGTGGGTAT |
| Exon 8 | SEQ ID No. 27 | gRNA 1426-1468 | GATCCGTCCACAACCTTGGCTGGAAAGGGAAATAGAAGAA ACCACCAAGAAGCTTGGCTT |
| Exon 8 | SEQ ID No. 28 | gRNA 1430-1468 | CGTCCACAACCTTGGCTGGAAAGGGAAATAGAAGAAACCA CCAAGAAGCTTGGCTT |
| Exon 11 | SEQ ID No. 29 | gRNA 1868-1909 | CATCCTGATGCCTCTGCAAACTTCCATTCTTTAGATGACAT CTACTATTTTGGAGGCCA |
| Exon 11 | SEQ ID No. 30 | gRNA 1868-1906 | CATCCTGATGCCTCTGCAAACTTCCATTCTTTAGATGACAT CTACTATTTTGGAGG |
| Exon 11 | SEQ ID No. 31 | gRNA 1977-1936 | CAACCAGATTGCAGTTTATCCTCACCAACCTCGAACTAAAG AGGAAATCCCCATGGAAC |
| Exon 11 | SEQ ID No. 32 | gRNA 1991-2032 | GAACCTGGAGATATCATTGGTGTGGCTGGAAACCATTGGA ATGGTTACTCTAAAGGTGT |
| Exon 11 | SEQ ID No. 33 | gRNA 2020-2059 | AAACCATTGGAATGGTTACTCTAAAGGTGTCAACAGAAAA CTAGGAAAAACAGGCCT |
| Exon 11 | SEQ ID No. 34 | gRNA 1961-2001 | CAACCTCGAACTAAAGAGGAAATCCCCATGGAACCTGGAG ATATCATTGGTGTGGCTG |
| Exon 11 | SEQ ID No. 35 | gRNA 1957-1996 | TCACCAACCTCGAACTAAAGAGGAAATCCCCATGGAACCT GGAGATATCATTGGTGT |
| Exon 11 | SEQ ID No. 36 | gRNA 1982-2020 | ATCCCCATGGAACCTGGAGATATCATTGGTGTGGCTGGAA ACCATTGGAATGGTTA |

All of these sites are unique and are used for creating potential gene knock out strategy in CHO and other cell lines. All sequences in the table above are represented in 5' to 3' direction. The corresponding 20 base pair target specific crRNA sequence will be derived from the CRISPR recognition sequence provided in each design mentioned in above table 5.

Table 5 of the present disclosure lists different Fut8 target sequences that are considered for CRISPR knock out targeting. A total of twenty different sequences are considered initially. It is made sure that none of the gRNAs span onto an exon-intron boundary as this may render the gRNAs inactive. Based on this approach, a 57 bp stretch on exon 7 is chosen as the target for CRISPR/Cas mediated knock out target. This includes two gRNAs, one on each strand that causes two single stranded breaks.

The target sequence in Fut8 gene that is used in an embodiment of the present method is shown in below FIG. 3B of the present disclosure as gRNA 1120-1176. The sites of cleavage are indicated with an arrow. The distance between the two gRNAs is 5 bases. The gRNA 1120-1176 recognition sequence is underlined in FIG. 3B. The corresponding synthesized fragment is incorporated into the pD1401 vector and named as pD1401 gRNA 514-553, the features of which are described subsequently in the disclosure.

This method of the present disclosure uses Cas9n (nickase mutant) in targeting Fut8 genomic sequence, exon 7 with CRISPR/Cas system. The Cas9n endonuclease makes single stand break (SSB) in opposite strand of DNA. The CRISPR/Cas recognition sequences in the upper and lower strands are underlined. Corresponding single strand break sites are indicated as black arrow heads. The three nucleotide PAM sequences are indicated in bold letters.

In this embodiment, one of the designs is used for targeting at exon 7 gRNA 1120-1176. The CRISPR/Cas vector construct for this design is termed as pD1401 gRNA (514-553).

The 5' and 3' CRISPR recognition sequence is indicated in small and italicized, two separate sites complementary to this recognition sequence are recognized at the FUT8 genomic sequence. The sequence represented with bold letters indicate gRNA scaffold sequence for CRISPR/Cas complex to get engaged.

```
gRNA + scaffold for Fut8 Exon 7
                                        SEQ ID No. 100
attccaagatgagtgttcgcGTTTTAGAGCTAGAAATAGCAAGTTAAAATA
AGGCTAGTCCGTTATCAACTTGAAAAAGTGGCACCGAGTCGGTGCTTTTTT
GCTCCGCGGCACGAGAACTCAAAGCCCCGGGGCCTGGGTCCCACGCGGGGT
CCCTTACCCAGGGTGCCCCGGGCGCTCATTTGCATGTCCCACCCAACAGGT
AAACCTGACAGGTCATCGCGGCCAGGTACGACCTGGCGGTCAGAGCACCAA
ACATACGAGCCTTGTGATGAGTTCCGTTGCATGAAATTCTCCCAAAGGCTC
CAAGATGGACAGGAAAGGGCGCGGTTCGGTCACCGTAAGTAGAATAGGTGA
AAGACTCCCGTGCCTTATAAGGCCTGTGGGTGACTTCTTCTCACCgaattg
gcgctatgctactggGTTTTAGAGCTAGAAATAGCAAGTTAAAATAAGGCT
AGTCCGTTATCAACTTGAAAAAGTGGCACCGAGTCGGTGC 5' CRISPR recognition sequence in the synthesized
DNA from DNA2.0-
                                        SEQ ID No. 37
ATTCCAAGATGAGTGTTTCGC Target specific crRNA sequence (5' to 3'
direction):
                                        Seq ID No. 38
AUUCCAAGAUGAGUGUUCGC 3' CRISPR recognition sequence in the synthesized
DNA from DNA2.0-
                                        SEQ ID No. 39
AATTGGCGCTATGCTACTGG Target specific crRNA sequence (5' to 3'
direction):
                                        Seq ID No. 40
AAUUGGCGCUAUGCUACUGG gRNA scaffold from DNA2.0-
GTTTTAGAGCTAGAAATAGCAAGTTAAAATAAGGCTAGTCCGTTATCAACT
TGAAAAAGTGGCACCGAGTCGGTGC
```

Figure 3A:
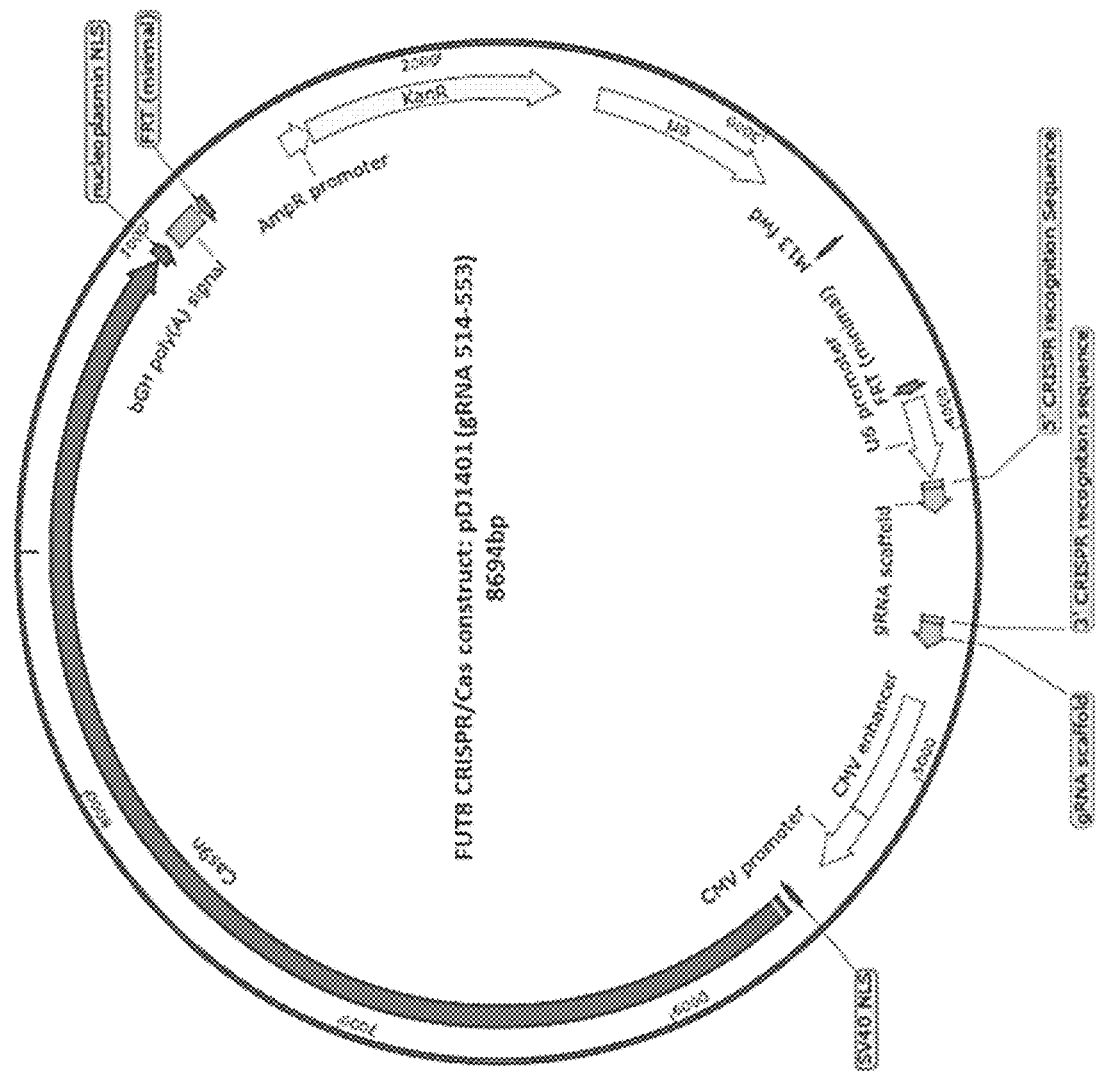
FIG. 3A depicts the construct map for CRISPR/Cas vector construct pD1401 gRNA.

The construct map is provided in FIG. 3A and important sequence regions are marked.

1.4—Design of the GMD Crispr Construct

FIG. 9B of the present disclosure provides GMD genomic locus and CRISPR recognition sequences.

The CHO whole cell genome shotgun sequencing data with accession number NW_003613635.1 for the GMD gene locus consisting of 442215 bp is obtained from Pubmed. The Pubmed accession number for the coding region or mRNA of the GMD gene is NM_001246696.1.

GMD is a member of the NDP-sugar modifying subfamily of the short-chain dehydrogenases/reductases (SDR). As a member of this subfamily, GMD binds its cofactor NADP (H) in the N-terminal portion of the molecule in which a common glycine-rich region is present. The catalytic triad has been identified as Tyr-XXX-Lys and Ser/Thr, which are all important for catalysis. Structure analysis of GMD from E. coli suggests the active molecule is in dimeric configuration. Whereas homolog from Arabidopsis thaliana is tetrameric, and that the NADP (H) binding site is intimately involved in creating the tetramer interface. It is most probable that the functional form of GMD enzyme in eukaryotes consists of tetrameric configuration.

The CRISPR/Cas binding regions are designed in such a way that the specificity of site recognition is high and at the same time the CRISPR/Cas complex carries out the intended DNA single strand break.

In an embodiment, Cas9n (D10A mutant of Cas9 endonuclease) is used for the CRISPR/Cas complex. The Cas9n endonuclease causes single strand DNA break. The two CRISPR recognition sites (5' recognition site and 3' recognition site are spaced at 5 base pair distance, allowing two single stand breaks at close proximity. The resulting breaks allow the NHEJ process of DNA break repair and that introduces mutations in this region.

The CRISPR construct has two unique 20 base pair CRISPR recognition sequences flanked by gRNA scaffolds in tandem with U6 promoter elements for efficient expression of the gRNA sequences. The unique design allows one single vector to express two separate gRNA scaffolds and two unique CRISPR recognition sequences on the genomic DNA.

The CRISPR/Cas design is uniquely positioned to target the YGDLTDSTCLVK motif and DLAEYT motif responsible for tetrameric interface of the GMD multimeric functional protein structure. Two single strand breaks induced by the Cas9n endonuclease at this region allow NHEJ mediated DNA repair. Mutations incorporated during DNA repair result in frame shift mutation, deletion, insertion as well as premature stop codons. Such mutation not only alters the critical motif for tertramerization but also creates mutations in the downstream Ser85 residue, which is involved in involved in maintaining the interactions of monomers in the tetrameric configuration. The design is compatible with two single strand breaks at close proximity, thereby imparting higher specificity of target recognition as NHEJ repair mechanism occurs only at these targeted genomic locations. Nonspecific single stand breaks, if created are usually repaired by homologous recombination which is accurate and rarely creates any mutation.

Figure 1B:
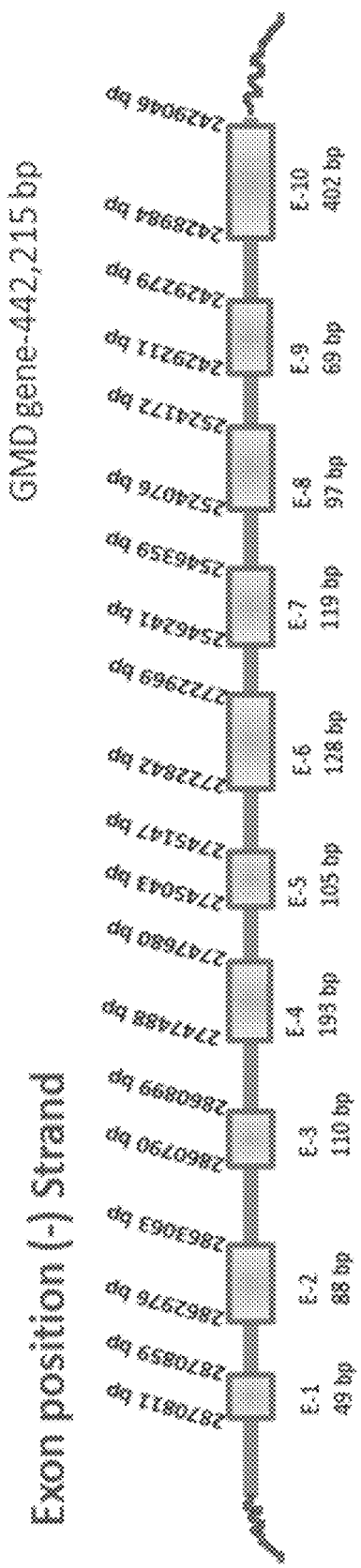
FIG. 1B depicts the GMD gene organization.

FIG. 1B of the present disclosure depicts the CHOK1 GMD genome organization.

Complete amino acid sequence of GMD gene is provided in FIG. 2B. Amino acid sequence from each CDS is indicated with large arrowheads. The two CRISPR target regions are underlined in Exon 3 and Exon 4 which are targeted in the GMD gene. Each exon is represented with arrow marks. Thin underlines indicate the CRISPR recognition sites for single strand break location and the thick broken line indicates CRISPR recognition site for double strand break location.

Two different strategies for gene knock out are used, one is the use of the mutant Cas9 (Cas9n) that generates single stranded breaks (SSBs) and the second is to use wild type Cas9 generating double stranded breaks (DSBs).

Figure 4A:
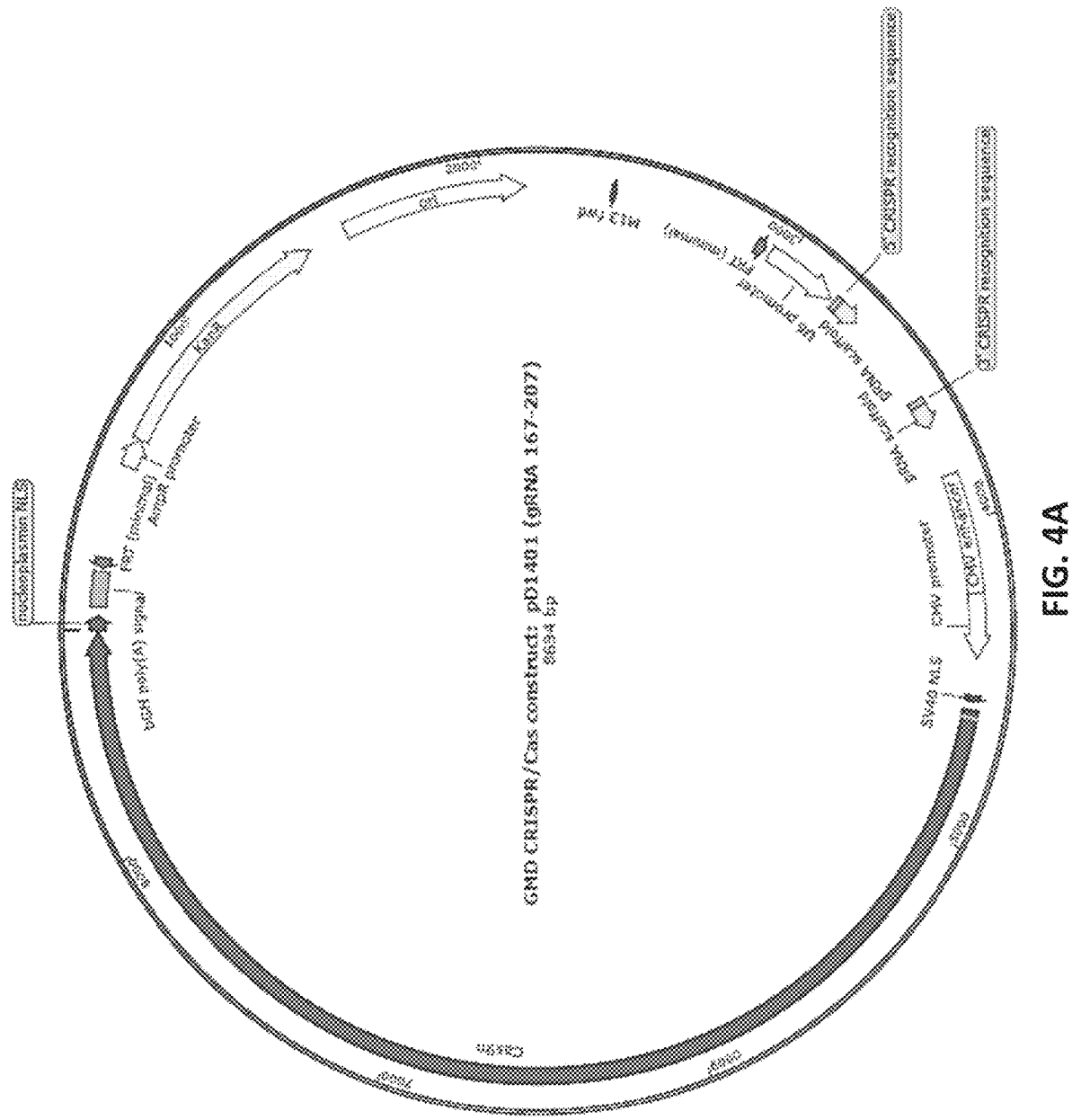
FIG. 4A depicts the GMD CRISPR/Cas construct pD1401 (gRNA 167-207) targeting Exon3 of GMD gene.

At the GMD Exon 3 Locus,

The method of the present disclosure uses Cas9n (nickase mutant) in targeting GMD genomic sequence, exon 3 with CRISPR/Cas system. The Cas9n endonuclease makes single stand break (SSB) in opposite strand of DNA. The construct is named as pD1401 (gRNA 167-207) and is represented by FIG. 4A of the present disclosure.

The 5' and 3' CRISPR recognition sequence is indicated in small and italicized, two separate sites complementary to this sequence are recognized at the GMD genomic sequence. The sequence represented with bold letters indicates gRNA scaffold sequence for CRISPR/Cas complex to get engaged.

SEQ ID No. 101
actaggcaggtgctgtcggtGTTTTAGAGCTAGAAATAGCAAGTTAAAATA

GGCTAGTCCGTTATCAACTTGAAAAAGTGGCACCGAGTCGGTGCTTTTTG

CTCCGCGGCACGAGAACTCAAAGCCCCGGGGCCTGGGTCCCACGCGGGGTC

CCTTACCCAGGGTGCCCCGGGCGCTCATTTGCATGTCCCACCCAACAGGTA

AACCTGACAGGTCATCGCGGCCAGGTACGACCTGGCGGTCAGAGCACCAAA

CATACGAGCCTTGTGATGAGTTCCGTTGCATGAAATTCTCCCAAAGGCTCC

AAGATGGACAGGAAAGGCGCGGTTCGGTCACCGTAAGTAGAATAGGTGAA

AGACTCCCGTGCCTTATAAGGCCTGTGGGTGACTTCTTCTCACCGcatcaa tgaagtcaaacctaGTTTTAGAGCTAGAAATAGCAAGTTAAAATAAGGCTA

GTCCGTTATCAACTTGAAAAAGTGGCACCGAGTCGGTGC

Figure 4B:
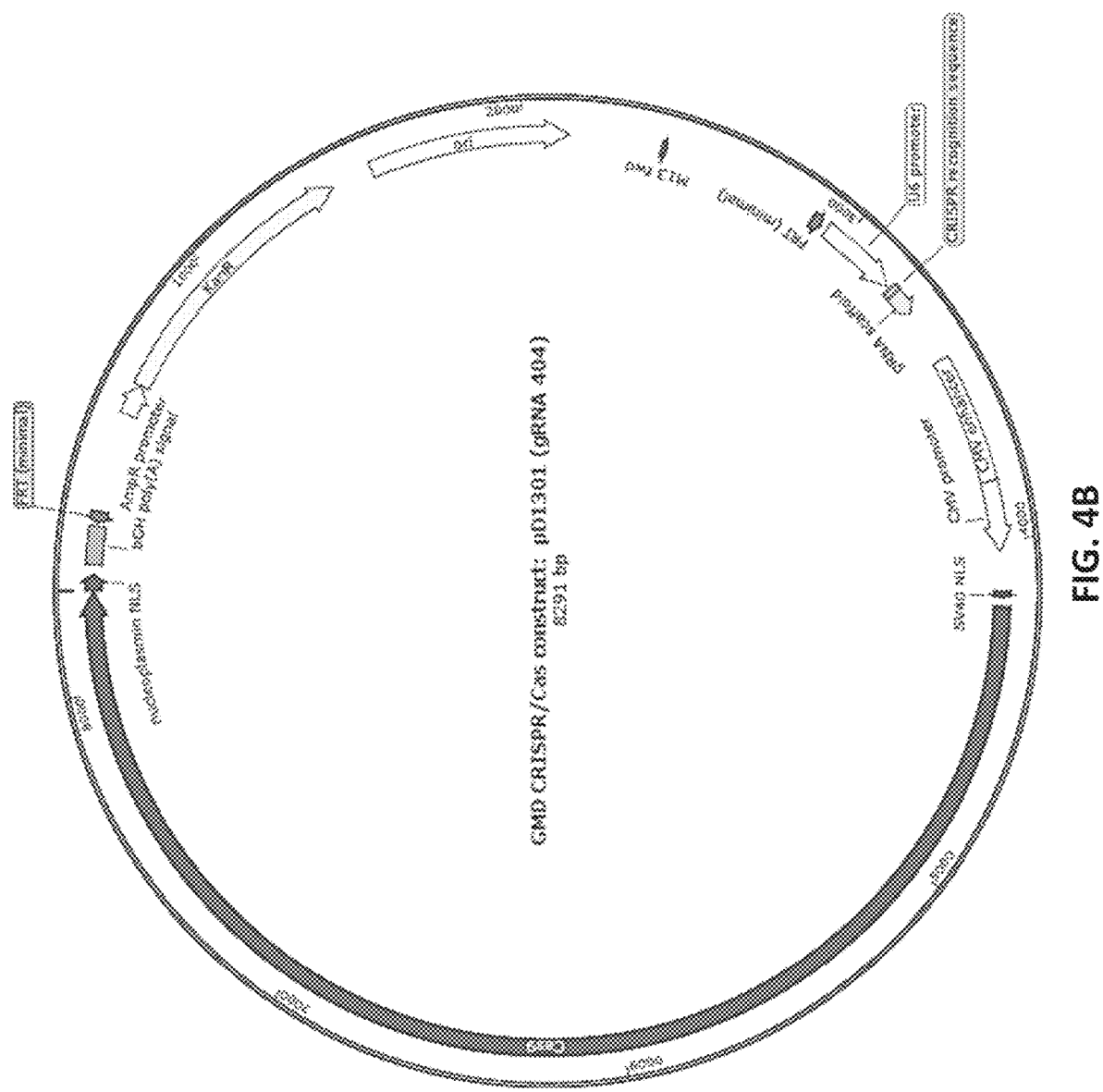
FIG. 4B depicts the GMD CRISPR/Cas construct pD1301 (gRNA 404) targeting Exon4 of GMD gene.

5' CRISPR recognition sequence in the synthesized DNA from DNA2.0 =
SEQ ID No. 41
ACTAGGCAGGTGCTGTCGGT Target specific crRNA sequence (5' to 3' direction):
Seq ID No. 42
ACUAGGCAGGUGCUGUCGGU 3' CRISPR recognition sequence in the synthesized DNA from DNA2.0-
SEQ ID No. 43
CATCAATGAAGTCAAACCTA Target specific crRNA sequence (5' to 3' direction):
SEQ ID No. 44
CAUCAAUGAAGUCAAACCUA At the GMD Exon 4 Locus, Exon 4 of GMD gene is targeted with wild type Cas9 endonuclease. This wild type Cas9 makes double strand break (DSB) at the target site. The construct is named as pD1301 (gRNA 404) and is represented by FIG. 4B of the present disclosure.

The CRISPR recognition sequence is indicated in small and italicized. The double stranded genomic DNA sequence is recognized based on this sequence by CRISPR/Cas system. The sequence represented with bold letters indicates gRNA scaffold sequence for CRISPR/Cas complex to get engaged.

SEQ ID No. 102
agttggcaccttgcggcttcGTTTTAGAGCTAGAAATAGCAAGTTAAAATA

AGGCTAGTCCGTTATCAACTTGAAAAAGTGGCACCGAGTCGGTGC

CRISPR recognition sequence in the synthesized DNA from DNA2.0-
SEQ ID No. 45
AGTTGGCACCTTGCGGCTTC Target specific crRNA sequence (5' to 3' direction):
SEQ ID No.46
AGUUGGCACCUUGCGGCUUC CRISPR Recognition Sequences for GMD Gene The following table represents CRISPR/Cas recognition sequences throughout GMD coding sequences for potential single strand break sites. Any of these recognition sequences is used for Cas9n endonuclease mediated single strand break and repair strategy of CRISPR/Cas system to knock out GMD gene.

Table 6 Provides all CRISPR Sequences for GMD

| Exon location | SEQ ID Nos. | Locus name | CRISPR/Cas recognition DNA sequence 5' to 3') |
|---|---|---|---|
| Exon 3 | SEQ ID No. 47 | gRNA 394-434 | GACCTCACCGACAGCACCTGCCTAGTAAAAATCATCAATG AAGTCAAACCTACAGAGA |
| Exon 3 | SEQ ID No. 48 | gRNA 394-436 | GACCTCACCGACAGCACCTGCCTAGTAAAAATCATCAATG AAGTCAAACCTACAGAGATC |
| Exon 3 | SEQ ID No 49 | gRNA 384-422 | GCACTATGGTGACCTCACCGACAGCACCTGCCTAGTAAAA ATCATCAATGAAGTCA |
| Exon 4 | SEQ ID No. 50 | gRNA 541-580 | CTTCTGGATGCAATTAAGACTTGTGGCCTTATAAATTCTGT GAAGTTCTACCAGGCC |
| Exon 4 | SEQ ID No. 51 | gRNA 541-581 | CTTCTGGATGCAATTAAGACTTGTGGCCTTATAAATTCTGT GAAGTTCTACCAGGCCT |
| Exon 4 | SEQ ID No. 52 | gRNA 531-571 | CACCTTGCGGCTTCTGGATGCAATTAAGACTTGTGGCCTTA TAAATTCTGTGAAGTTC |
| Exon 4 | SEQ ID No. 53 | gRNA 565-603 | GGCCTTATAAATTCTGTGAAGTTCTACCAGGCCTCAACTAG TGAACTGTATGGAAA |
| Exon 5 | SEQ ID No. 54 | gRNA 693-735 | TGCCTATTGGATTGTAGTGAACTTTCGAGAGGCTTATAATC TCTTTGCGGTGAACGGCAT |
| Exon 6 | SEQ ID No. 55 | gRNA 828-866 | TTACCTTGGACAACTGGAATGTTTCAGTTTGGAAATCTGG ACGCCAAACGAGACT |
| Exon 6 | SEQ ID No. 56 | gRNA 829-871 | TACCTTGGACAACTGGAATGTTTCAGTTTGGGAAATCTGGA CGCCCAAACGAGACTGGGGC |

-continued

| Exon location | SEQ ID Nos. | Locus name | CRISPR/Cas recognition DNA sequence 5' to 3') |
|---|---|---|---|
| Exon 7 | SEQ ID No. 57 | gRNA 916-956 | TGGCTGATGTTACAAAATGATGAACCAGAGGACTTTGTCAT AGCTACTGGGGAAGTTC |
| Exon 10 | SEQ ID No 58 | gRNA 1345-1387 | AACCCTCGACTGCCTGTGTCGTCCCCACAGCTAAGAGCTGG GCCAC |
| Exon 10 | SEQ ID No. 59 | gRNA 1345-1386 | AACCCTCGACTGCCTGTGTCGTCCCCACAGCTAAGAGCTGG GCCA |
| Exon 10 | SEQ ID No. 60 | gRNA 1393-1155 | TGCCTGTGTCGTCCCCACAGCTAAGAGCTGGGCCACAGGTT TGTGGGCACCAGGAC |
| Exon 10 | SEQ ID No. 61 | gRNA 1243-1285 | AACCCCAACGCCTGAGCACCTCTACAAAAAATTCGCGAGA CATGGACTATGGTGCAGAGC |
| Exon 10 | SEQ ID No. 62 | gRNA 1244-1285 | ACCCCAACGCCTGAGCACCTCTACAAAAAATTCGCGAGAC ATGGACTATGGTGCAGAGC |
| Exon 10 | SEQ ID No. 63 | gRNA 1267-1228 | GAGCTCATGAGAACCAACCCCAACGCCTGAGCACCTCTAC AAAAAATTCGCGAGACA |
| Exon 10 | SEQ ID No 64 | gRNA 1242-1280 | CAACCCCAACGCCTGAGCACCTCTACAAAAAATTCGCGAG ACATGGACTATGGTGC |
| Exon 10 | SEQ ID No. 65 | gRNA 1330-1371 | AGACCATCGACCATAAACCCTCGACTGCCTGTGTCGTCCCC ACAGCTAAGAGCTGGGCC |
| Exon 10 | SEQ ID No. 66 | gRNA 1280-1238 | GAACCAACCCCAACGCCTGAGCACCTCTACAAAAAATTCG CGAGACATGGACTATGGTGC |
| Exon 10 | SEQ ID No. 67 | gRNA 1330-1372 | AGACCATCGACCATAAACCCTCGACTGCCTGTGTCGTCCCC ACAGCTAAGAGCTGGGCCA |
| Exon 10 | SEQ ID No. 68 | gRNA 1415-1457 | ACACTCCAGAGCTAAGGCCACTTCGCTTTTGTCAAAGGCTC CTCTGAA |
| Exon 10 | SEQ ID No. 69 | gRNA 1542-1580 | AGTCTTGAGATTGTTTTTCTCTTTTCTTATTAAATGATCTTT CTATGAACCAGC |
| Exon 10 | SEQ ID No. 70 | gRNA 1320-1361 | CCACTCCTGAGACCATCGACCATAAACCCTCGACTGCCTGT GTCGTCCCCACAGCTA |

In this case, a total of nineteen target sequences in GMD gene sequence are designed for CRISPR recognition sites. All sequences are represented in 5' to 3' direction; the corresponding 20 base pair target specific crRNA sequence will be derived from CRISPR recognition sequence provided in each design mentioned in above table 6.

One of these above mentioned designs, gRNA 394-434 is used to create CRISPR/Cas complex pD1401 (gRNA 167-207) for transfection of CHOK1 cells. The CRISPR/Cas complex creates two single stranded DNA breaks at the complementary strand of the recognized coding sequence of GMD gene. Successful DNA repair at the target site creates non-functional GMD gene and thereby fucose knock out CHOK1 cell lines are developed. The features of pD1401 (gRNA 167-207) are described subsequently in the disclosure.

Although this embodiment uses one of the designs, any one of the above mentioned CRISPR recognition site creates a non-functional GMD gene. Therefore, any of these potential sites alone or in combination is used for fucose knock out CHOK1 cell line development.

The target sequence in GMD exon 3 that is used in an embodiment of the present method is mentioned in the table 6 as gRNA 394-434. FIG. 4C describes the CRISPR recognition sequence.

The sites of cleavage are indicated with an arrow. The distance between the two gRNAs is 6 bases. The gRNA 394-434 sequence is underlined in FIG. 4C. The corresponding synthesized fragment is incorporated into the pD1401 vector and named as pD1401 gRNA 167-207, the features of which are described subsequently in the disclosure. This method of the present disclosure uses Cas9n (nickase mutant) in targeting GMD genomic sequence, exon 3 with CRISPR/Cas system. The Cas9n endonuclease makes single stand break (SSB) in opposite strand of DNA.

The following table represents CRISPR/Cas recognition sequences throughout GMD coding sequences for potential double strand break sites. Any of these recognition sequences are used for wild type Cas9 endonuclease mediated double strand break and repair strategy of CRISPR/Cas system to knock out GMD gene.

TABLE 7

CRISPR/Cas recognition sequences throughout GMD
coding sequences for potential double strand break sites

| Exon location | SEQ ID Nos. | Locus name | CRISPR/Cas recognition DNA sequence (5' to 3') |
|---|---|---|---|
| Exon 3 | SEQ ID No. 71 | gRNA 166 | TGACCTCACCGACAGCACCTGCCTAGTAA |
| Exon 4 | SEQ ID No. 72 | gRNA 299 | ATGTTGATGGAGTTGGCACCTTGCGGCTT |
| Exon 4 | SEQ ID No. 73 | gRNA 406 | ACCCCAGAAAGAGACCACCCCTTTCTATC |
| Exon 4 | SEQ ID No. 74 | gRNA 366 | AGGCCTCAACTAGTGAACTGTATGGAAAA |
| Exon 4 | SEQ ID No. 75 | gRNA 306 | TGGAGTTGGCACCTTGCGGCTTCTGGATG |
| Exon 5 | SEQ ID No. 76 | gRNA 483 | TTGGATTGTAGTGAACTTTCGAGAGGCTT |
| Exon 5 | SEQ ID No. 77 | gRNA 508 | GCTTATAATCTCTTTGCGGTGAACGGCAT |
| Exon 6 | SEQ ID No. 78 | gRNA 642 | ACGCCAAACGAGACTGGGGCCATGCCAAG |
| Exon 9 | SEQ ID No. 79 | gRNA 918 | GCTCCAAGGCGCAGCAGAAACTGAACTGG |
| Exon 10 | SEQ ID No. 80 | gRNA 1016 | AACCCCAACGCCTGAGCACCTCTACAAAA |
| Exon 10 | SEQ ID No. 81 | gRNA 1096 | ACTCCTGAGACCATCGACCATAAACCCTC |
| Exon 10 | SEQ ID No. 82 | gRNA 1017 | ACCCCAACGCCTGAGCACCTCTACAAAAA |
| Exon 10 | SEQ ID No. 83 | gRNA 1015 | CAACCCCAACGCCTGAGCACCTCTACAAA |
| Exon 10 | SEQ ID No. 84 | gRNA 1103 | AGACCATCGACCATAAACCCTCGACTGCC |
| Exon 10 | SEQ ID No. 85 | gRNA 1046 | CTCTACAAAAAATTCGCGAGACATGGACT |
| Exon 10 | SEQ ID No. 86 | gRNA 1174 | GCACCAGGACGGGGACACTCCAGAGCTAA |
| Exon 10 | SEQ ID No. 87 | gRNA 1211 | TAAGGCCACTTCGCTTTTGTCAAAGGCTC |
| Exon 10 | SEQ ID No. 88 | gRNA 1110 | CGACCATAAACCCTCGACTGCCTGTGTCG |
| Exon 10 | SEQ ID No. 89 | gRNA 1011 | GAACCAACCCCAACGCCTGAGCACCTCTA |
| Exon 10 | SEQ ID No. 90 | gRNA 1118 | AACCCTCGACTGCCTGTGTCGTCCCCACA |
| Exon 10 | SEQ ID No. 91 | gRNA 987 | GAGGGAGATGGTGCAAGCCGATGTGGAGC |
| Exon 10 | SEQ ID No. 92 | gRNA 1160 | TAAGAGCTGGGCCACAGGTTTGTGGGCAC |
| Exon 10 | SEQ ID No. 93 | gRNA 1167 | TGGGCCACAGGTTTGTGGGCACCAGGACG |

Twenty three unique CRISPR recognition sequences (gRNA) are designed throughout the GMD gene sequence. All sequences are represented in 5' to 3' direction; the corresponding 20 base pair target specific crRNA sequence will be derived from CRISPR recognition sequence provided in each design mentioned in above table 7.

One of these above mentioned designs, gRNA 306 is used to create CRISPR/Cas complex pD1301 (gRNA 404) for transfection of CHOK1 cells. The CRISPR/Cas complex creates one double stranded DNA break at the recognized coding sequence of GMD gene. Successful DNA repair at the target site creates non-functional GMD gene and thereby fucose knock out CHOK1 cell lines are developed.

Although one of the designs is used in this embodiment, any one of the above mentioned CRISPR recognition site creates a non-functional GMD gene. Therefore, any of these potential sites alone or in combination are used for fucose knock out CHOK1 cell line development.

The target sequence in GMD exon 4 that is used in an embodiment of the present method is shown in the above table 7 as gRNA 306. FIG. 4D describes the CRISPR recognition sequence. The sites of cleavage are indicated with an arrow. The corresponding synthesized fragment is incorporated into the pD1301 vector and named as pD1301 gRNA 404, the features of which are described subsequently in the disclosure. This method of the present disclosure uses wild type Cas9 endonuclease in targeting GMD genomic sequence, exon 4 with CRISPR/Cas system. The wild type Cas9 endonuclease makes Double stand break (DSB) in both strands of DNA.

1.5—CRISPR/Cas Complex Synthesis

CRISPR technology is based on a class of RNA-guided endonucleases known as Cas9 from the microbial adaptive immune system found in *Streptococcus pyogenes*. Cas9 nuclease is directed to specific sites on the genome by guide RNAs (gRNAs). Two components must be introduced and/or expressed in cells or an organism to perform CRISPR based genome editing: the Cas9 nuclease; and a 'guide RNA' (gRNA).

Twenty nucleotides recognition sequence at the 5' end of the gRNA direct Cas9 to a specific target DNA site using standard RNA-DNA complementarity base pairing rules. These target sites must lie immediately 5' of a PAM sequence that matches the canonical form 5-NGG.

The present disclosure uses two different kinds of Cas9 endonuclease in this disclosure as described below. In both cases a single transfection vector encoding gRNA and nuclease is used, thereby increasing the transfection efficiency of the CHOK1 cells.

a) The CAs9 wild type nuclease is used for GMD gene targeting at Exon4. The construct allows double stand break (DSB) at the targeted site.

b) A mutant Cas9 nuclease (D10A), known as Cas9n is used to target GMD exon 3 locus and Fut8 Exon 7 locus, the constructs create single strand breaks instead of a double strand DNA break. This design is aimed to improve specificity of CRISPR/Cas constructs.

In case of single strand breaks, two DNA target sites are targeted at close proximity where single stand break or nicks happen in opposite DNA stands. Thereby, it recruits DNA repair machinery (NHEJ) to repair the DNA damage. Recruiting two gRNA/Cas9n complex at a specific interval to initiate DNA repair improves the specificity to the targeted site. Nonspecific binding of only one of the gRNA/Cas9n complex to unrelated sites causes nicks which are usually repaired through homologous recombination based repair with very low rate of mutation. Therefore, this approach increases the specificity of targeting the Fut8 and GMD gene Unique regions of both genes are targeted based on the enzyme structure information in a way to abolish enzyme catalytic function or by disrupting higher order structure.

The important features of the vectors are, a) Cas9—a nuclease that is first discovered as a component of the CRISPR system in *Streptococcus pyogenes* and has been adapted for utility in mammalian cells. RNA-guided Cas9 is able to efficiently introduce precise double-stranded breaks at endogenous genomic loci in mammalian cells with high efficiencies.

Cas9-D10A—A D10A mutant of Cas9 nuclease (Cas9n) nicks single strands and combined with a pair of offset guide RNAs complementary to opposite strands of target genomic loci. This helps reduce off-target activity seen with wild type Cas9.

b) chimeric gRNA scaffold—The chimeric guide RNA (gRNA) scaffold consists of a 20-nucleotide target specific complementary region, a 42-nucleotide Cas9-binding RNA structure and a 40-nucleotide transcription terminator derived from *S. pyogenes* that directs Cas9 nuclease to the target site for genome modification. In this case there are two gRNA scaffolds, one for each gRNA.

c) Kanamycin-r—An effective bacteriocidal agent that inhibits ribosomal translocation thereby causing miscoding. The gene coding for kanamycin resistance is Neomycin phosphotransferase II (NPT II/Neo). *E. coli* transformed with plasmid containing the kanamycin resistance gene can grow on media containing 25 μg/ml kanamycin.

d) P_CMV—The CMV promoter is a constitutive mammalian promoter and mediates strong expression in various cellular systems.

e) P_hU6.1—human A type 3 core promoter for RNA expression.

1.6—the Complete Process of Obtaining CRISPR Construct is Composed of the Following Steps:

22. CRISPR target designing.
23. Vector constructions with two separate vector backbones, namely pD1401 and pD1301 vectors with gRNA insert.
24. Transformation of CRISPR constructs pD1401 (gRNA 514-553), pD1401 (gRNA 167-207) and pD1301 (gRNA 404) into *E coli* competent cells (DH10B or DH5alpha) and plating on LB (Luria Bertani)-Agar supplemented with kanamycin.
25. Inoculation of transformed cells (CRISPR constructs) into LB broth with Kanamycin.
26. Isolation of Plasmid DNA pD1401 (gRNA 514-553), pD1401 (gRNA 167-207) and pD1301 (gRNA for 404) from DH1 OB or DH5alpha cells.
27. Transfection of CHOK1 cells: screening and selection by LCA assay.
28. Genomic DNA isolation of selected clones using QIAGEN DNeasy Blood & Tissue Kit.
29. Quantification by Spectrophotometry.
30. Optimization of PCR Condition.
31. Cross checking the Genomic DNA sample by PCR.
32. Electrophoresis on agarose gel.
33. PCR amplification using Phusion polymerase and tailing using Tag polymerase.
34. PCR product gel elution using QIAGEN kit.
35. TA cloning using pTZ57R/T vector.
36. Transformation of ligated sample pTZ57R/T+ CRISPR (PCR) in DH10B or DH5alpha cells.
37. Inoculation of transformed cells (pTZ57R/T+ CRISPR (PCR)) into LB with Ampicillin broth.
38. Isolation of plasmid DNA (pTZ57R/T+ CRISPR (PCR) from DH5alpha and DH10B cells using QIAGEN plasmid DNA isolation kit.
39. Cross checking for the presence of insert by restriction digestion.
40. Sequencing primers; and
41. Confirmation of the INDELs by sequencing.

Example 2: Transfection of Cells with Talen Constructs

This example contains procedure for CHOK1 cell transfection with CRISPR constructs. It also provides for selection and confirmation of single cell stable cell lines for developing FUT8 knock out CHOK1 cell line using CRISPR technology, and selection of positive clones by flow-cytometry based functional assay.

Transfection Protocol

Transfection isoptimized using CHOK1 cells of both adherent and suspension type. Liposome and modified liposome mediated transfection reagents are tested for e.g., Lipofectamine 2000, Lipofectamine 3000, Lipofectamine LTX with Plus™ reagent, MIRUS TransIT X2, MIRUS TransIT 2020, MIRUS TransIT 293, MIRUS TransIT CHO transfection kit. DNA concentration ranging from 0.5 μg to 5 μg are tested for various incubation times for e.g., 4 hrs, 24 hrs and 48 hrs. Multiple DNA to transfection reagent ratios (μg:μl) are also tested. The optimum transfection efficiency is achieved using 1:3 DNA to transfection reagent ratio, 24 hrs incubation and Lipofectamine LTX with Plus™ reagent. Optimization experiments performed with GFP expressing plasmid DNA.

FIG. 20 depicts transfection efficiency of CHOK1 cell line using the protocol described in the disclosure. Transfection efficiency is determined using a Green Fluorescent Protein expressing plasmid construct. Number of green cells observed after transfection compared to the total number of viable cells determines transfection efficiency of the protocol established. Panel A represents the bright field image and panel B represents the same microscopic field for red channel fluorescence.

Transfection efficiency is calculated by the following formula:

Transfection efficiency=(Number of GFP expressing cells/Total number of cells)*100

Optimized transient transfection efficiency is 40-50% in CHOK1 cells.

Transfection:

CHOK1 cells are seeded at more than 90% viability and at a density of $0.25 \times 10^6$ cells/well in a 6 well tissue culture plate and allowed to adhere for 24 hrs. CRISPR constructs pD1401 (gRNA 514-553), pD1401 (gRNA 167-207), pD1301 (gRNA 404), combination of pD1401 (gRNA 167-207)+pD1301 (gRNA 404) are used for transfection using Lipofectamine LTX with Plus™ reagent. 2.5 µg of construct is used with 1:3 DNA to transfection reagent ratio. The cells are incubated for 20-24 hrs after transfection. Prior to transfection, DNA quantity and quality is estimated by UV spectrophotometry. A 260/280 value DNA represents quality and protein contamination. The ratio of absorbance at 260 nm and 280 nm is used to assess the purity of DNA. $A_{260/280} > 1.8$ is generally accepted as "pure" or good quality DNA. 3-4 µl of DNA sample is placed on the micro cuvette and DNA concentration is estimated using Eppendorf Biophotometer D30 against suitable blank.

TABLE 8

| CRISPR DNA dilution: | |
| --- | --- |
| For n wells | |
| pD1401 (gRNA 514-553) or pD1401 (gRNA 167-207) or pD1301 (gRNA 404) or pD1401 (gRNA 167-207) + pD1301 (gRNA 404) | 2.5 µg * n |
| Plus TM reagent | 1.33*2 µl |
| Media without serum | Up to 1 ml*n |
| Lipofectamine LTX dilution: | |
| Lipofectamine LTX | 15 µl*n |
| Media without serum | Up to 0.5 ml*n |

Media change is provided to the cells with serum free media, 1 hour prior to transfection. CRISPR constructs and Lipofectamine LTX solution are diluted, mixed gently and incubated for 5-10 minutes at 20-25° C. DNA and transfection reagent dilutions (3 ml) are mixed and incubated for 20-30 minutes at Room Temperature for complex formation. The media is aspirated from the wells. 1.5 ml of DNA and transfection reagent complex is added drop wise to the plated cells.

The cells are incubated for 4 hours at 37° C. in a 5% $CO_2$ Incubator. The complete media is added at 1.5 ml/well and incubated for 20-24 hours at 37° C. in a 5% $CO_2$ Incubator. After 20-24 hours of transfection, cells are trypsinized and to single cell dilution is prepared.

Single cell dilution is obtained by serial dilution of the cells to a concentration of 0.5 cell/100 µl. Cell count is taken using hemocytometer. The cells are allowed to grow for few days at 37° C. in a 5% $CO_2$ Incubator. Plate scanning is done to identify single cell colonies under the inverted phase contrast microscope. Cells growing into distinctly small single colonies are marked for further amplification. After 2-3 weeks, single cell clones are amplified from one well of 96 well plate to one well of 6 well plate by trypsinization. Cells are allowed to grow for 2-3 days at 37° C. at 5% $CO_2$ in a $CO_2$ incubator. Cells are further amplified from one well to two wells in a 24 well plate (replica plating) for further screening.

LCA-FITC (Lens Culinaris Agglutin-Fluorescein Isothiocyanate) Binding Assay

Fluorescein isothiocyanate (FITC) is a fluorochrome conjugated to LCA. Therefore, presence of fucosylated proteins on cell membrane of control CHOK1 cells is recognized by fluorescein conjugated LCA. These cells fluoresce brighter in specific flow cytometer channel. The fluorescence observed is represented as fluorescence unit. The cells where fucose pathway is disrupted, the knockout lines are not able to produce fucosylated cellular proteins and hence the cell membrane proteins are non fucosylated. Testing these cells with Fluorescein-LCA conjugate results in fluorescence comparable to background. Therefore, the Fucose knock out cells fluoresce at a much lower level (less than 100RFU) compared to control CHOK1 cell line.

Cells are trypsinized, transferred to a microfuge tube and spun at 1500 rpm (revolution per minute) for 5 minutes using Eppendorf minispin centrifuge. The media is removed and fresh media is added in the tubes. Both transfected and untransfected CHOK1 cells are processed simultaneously. The cells are tested for LCA-FITC flow cytometry based analysis using "Millipore GUAVA 8 easyCyte HT" benchtop flow cytometer.

54 clones from transfection with pD1401 (gRNA 514-553) are screened for fucose knockout profile. Similarly, 200 clones from transfection with pD1401 (gRNA 167-207) or pD1301 (gRNA 404) or a combination of pD1401 (gRNA 167-207)+pD1301 (gRNA 404) are screened for fucose knock out profile.

Fluorescein Lens Culinaris Agglutinin (LCA-FITC) stock 5 mg/ml is diluted to get 2 µg/ml final concentration in assay buffer (DPBS containing 2% BSA). Cells are spun at 1500 rpm for 5 minutes using Eppendorf minispin centrifuge. The media is aspirated and the pellet is re-suspended in 0.25-1 ml of assay buffer containing 2 µg/ml LCA-FITC. CHOK1 control cells are re-suspended in 0.25-1 ml of assay buffer alone (unstained control) and 0.25-1 ml of assay buffer containing 2 µg/ml LCA-FITC (stained control). All samples are diluted to get $0.1-0.2 \times 10^6$ cells/ml in final assay buffer. The samples are then incubated in dark on ice for 30 minutes. Then 200 µl of each sample is aliquoted in a 96 well plate. The plate is then loaded in the Millipore GUAVA easyCyte 8HT benchtop flow cytometer for data acquisition and analysis. Data analysis is done using Incyte software. In some experiments Accuri C6 flow cytometer is used for data acquisition and analysis.

Fluorescein-streptavidin (Strep-FITC) negative staining is also performed. Fluorescein lens culinaris agglutinin (LCA-FITC) stock 5 mg/ml is diluted to get 2 µg/ml final concentration in assay buffer (DPBS containing 2% BSA). Fluorescein streptavidin (Strep-FITC) stock 1 mg/ml is diluted to get 2 µg/ml final concentration in assay buffer (DPBS containing 2% BSA). Cell suspensions are taken in duplicates and are spun at 1500 rpm for 5 minutes using Eppendorf minispin centrifuge. Media is aspirated and in one tube the pellet is resuspended in assay buffer containing 2 µg/ml LCA-FITC and the duplicate sample in assay buffer containing 2 µg/ml Strep-FITC. CHOK1 control cells are re-suspended in assay buffer alone (unstained control), assay buffer containing 2 µg/ml LCA-FITC (stained control) and assay buffer containing 2 µg/ml Strep-FITC.

All the samples are diluted to get $0.1-0.2 \times 10^6$ cells/ml in 0.25-1 ml assay buffer. The samples are then incubated in dark on ice for 30 minutes. Then 200 µl of each sample is aliquoted in a 96 well plate. The plate is loaded in the Millipore GUAVA easyCyte 8HT benchtop flowcytometer for data acquisition and analysis. Data analysis is done using Incyte software. In some experiments Accuri C6 flow cytometer is used for data acquisition and analysis.

CHOK1 cells are transfected with pD1401 (gRNA 514-553) construct targeting Fut8 locus and the results are provided below.

TABLE 9

| Sl. No. | Sample ID | Median RFU |
|---|---|---|
| 1 | Unstained control | 6.668 |
| 2 | Stained control | 968.184 |
| 3 | CR1KOT1#3 | 684.544 |
| 4 | CR1KOT1#4 | 680.126 |
| 5 | CR1KOT1#6 | 16.211 |
| 6 | CR1KOT1#7 | 134.668 |
| 7 | CR1KOT1#13 | 594.511 |
| 8 | CR1KOT1#15 | 635.291 |
| 9 | CR1KOT1#18 | 26.249 |
| 10 | CR1KOT1#19 | 430.674 |
| 11 | CR1KOT1#21 | 244.798 |
| 12 | CR1KOT1#22 | 18.021 |
| 13 | CR1KOT1#23 | 11.880 |
| 14 | CR1KOT1#24 | 341.785 |
| 15 | CR1KOT1#25 | 523.925 |
| 16 | CR1KOT1#26 | 10.434 |
| 17 | CR1KOT1#27 | 539.167 |
| 18 | CR1KOT1#28 | 515.236 |
| 19 | CR1KOT1#29 | 589.063 |
| 20 | CR1KOT1#30 | 682.042 |
| 21 | CR1KOT1#31 | 13.682 |
| 22 | CR1KOT1#32 | 711.406 |
| 23 | CR1KOT1#33 | 935.327 |
| 24 | CR1KOT1#34 | 14.318 |
| 25 | CR1KOT1#35 | 641.110 |
| 26 | CR1KOT1#36 | 13.161 |
| 27 | CR1KOT1#37 | 16.703 |
| 28 | CR1KOT1#38 | 583.947 |

Median RFU refers to median value of relative fluorescence unit.

Results—

Figure 7A:
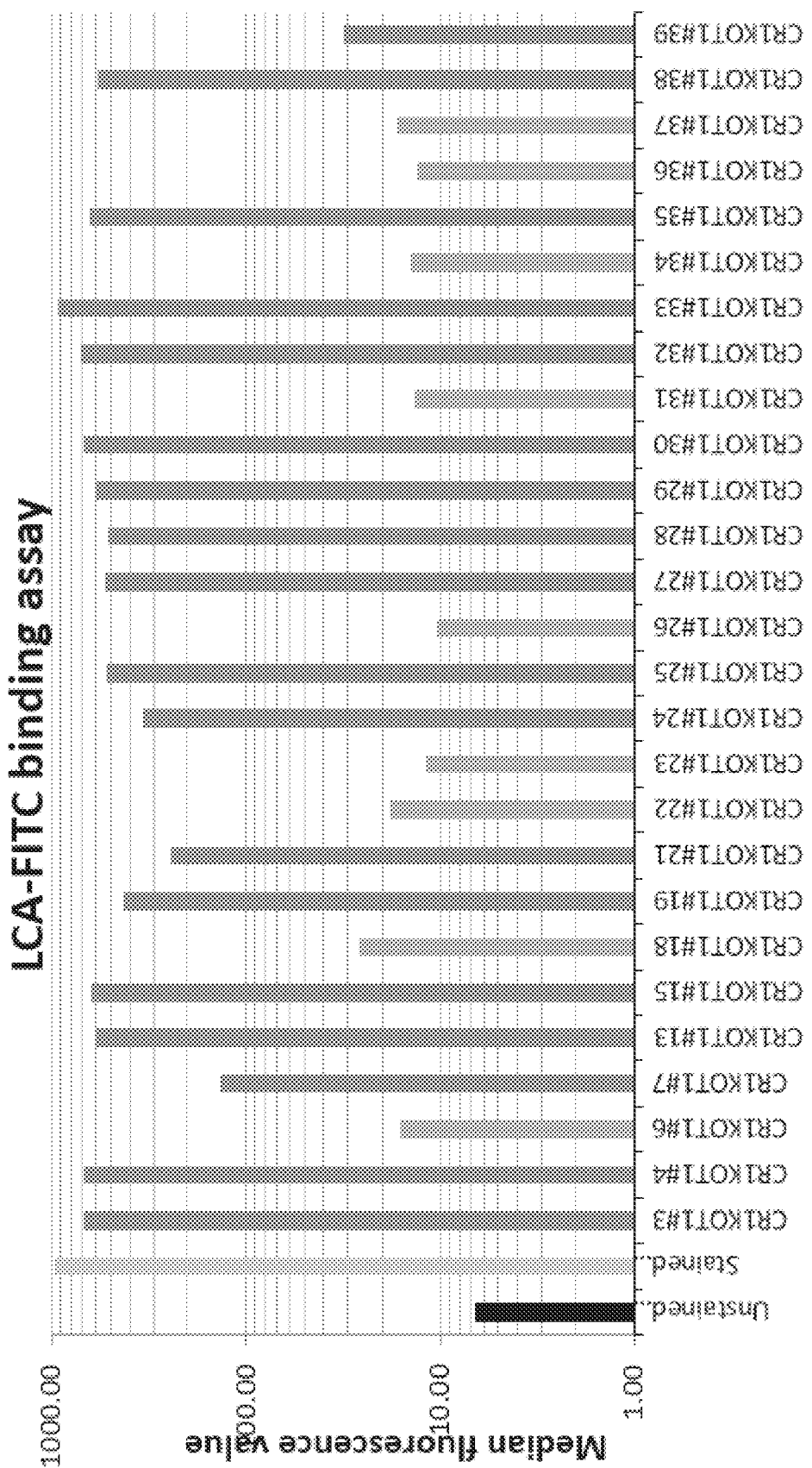
FIG. 7A depicts LCA-FITC flow cytometry assay of clonal CHOK1 cells transfected with pD1401 (gRNA 514-553) CRISPR/Cas construct targeting FUT8 exon 7.

The graphical results and fluorescence profile provided in the table above are also depicted in FIG. 7A and FIG. 8A of the present disclosure. The figures depict the graphical result and fluorescence profile observed for the CHOK1 cell lines CR1KOT1#6, CR1KOT1#18, CR1KOT1#22, CR1KOT1#23, CR1KOT1#26, CR1KOT1#31, CR1KOT1#34, CR1KOT1#37, in Flow cytometry based LCA-FITC Binding Assay. This flow cytometry assay detects fucosylated proteins present on cell surface. Thus CHOK1 control cells fluoresce highly as many fucosylated proteins are present in Control CHOK1 cell line. In cases where the CRISPR/Cas complex is able to disrupt the FUT8 gene in transfected cell lines, the LCA FITC fluorescence is minimized as there is no fucosylated protein on surface of these cell lines. The figure reveals significant fluorescence loss when CR1KOT1#6, CR1KOT1#18, CR1KOT1#22, CR1KOT1#23, CR1KOT1#26, CR1KOT1#31, CR1KOT1#34 and CR1KOT1#37, are tested in this assay, indicating these cell lines are CHOK1 FUT8 knock out cell lines.

CHOK1 cells are transfected with pD1401 (gRNA 167-207), pD1301 (gRNA 404), pD1401 (gRNA 167-207)+pD1301 (gRNA 404) constructs targeting GMD locus, and the results are provided in the table below.

TABLE 10

| | | Median RFU | |
|---|---|---|---|
| Sample ID | CRISPR construct used | LCA-FITC | Strep-FITC |
| CHOK1 | — | 405,109.00 | 8,024.50 |
| C1GMD1.12 | pD1401 (gRNA 167-207) | 20,447.50 | 3,806.00 |
| C1GMD1.27 | pD1401 (gRNA 167-207) | 18,749.00 | 3,672.00 |
| C1GMD2.30 | pD1301 (gRNA 404) | 18,124.00 | 4,065.50 |
| C1GMD2.34 | pD1301 (gRNA 404) | 349,435.00 | 4,071.00 |
| C1GMD3.4 | pD1401 (gRNA 167-207) + pD1301 (gRNA 404) | 23,583.00 | 5,833.00 |
| C1GMD3.36 | pD1401 (gRNA 167-207) + pD1301 (gRNA 404) | 78,197.00 | 3,643.00 |
| C1GMD3.43 | pD1401 (gRNA 167-207) + pD1301 (gRNA 404) | 37,593.00 | 8,240.00 |
| C1GMD3.49 | pD1401 (gRNA 167-207) + pD1301 (gRNA 404) | 20,797.50 | 4,525.50 |
| C1GMD3.51 | pD1401 (gRNA 167-207) + pD1301 (gRNA 404) | 23,722.00 | 4,945.00 |

Figure 7B:
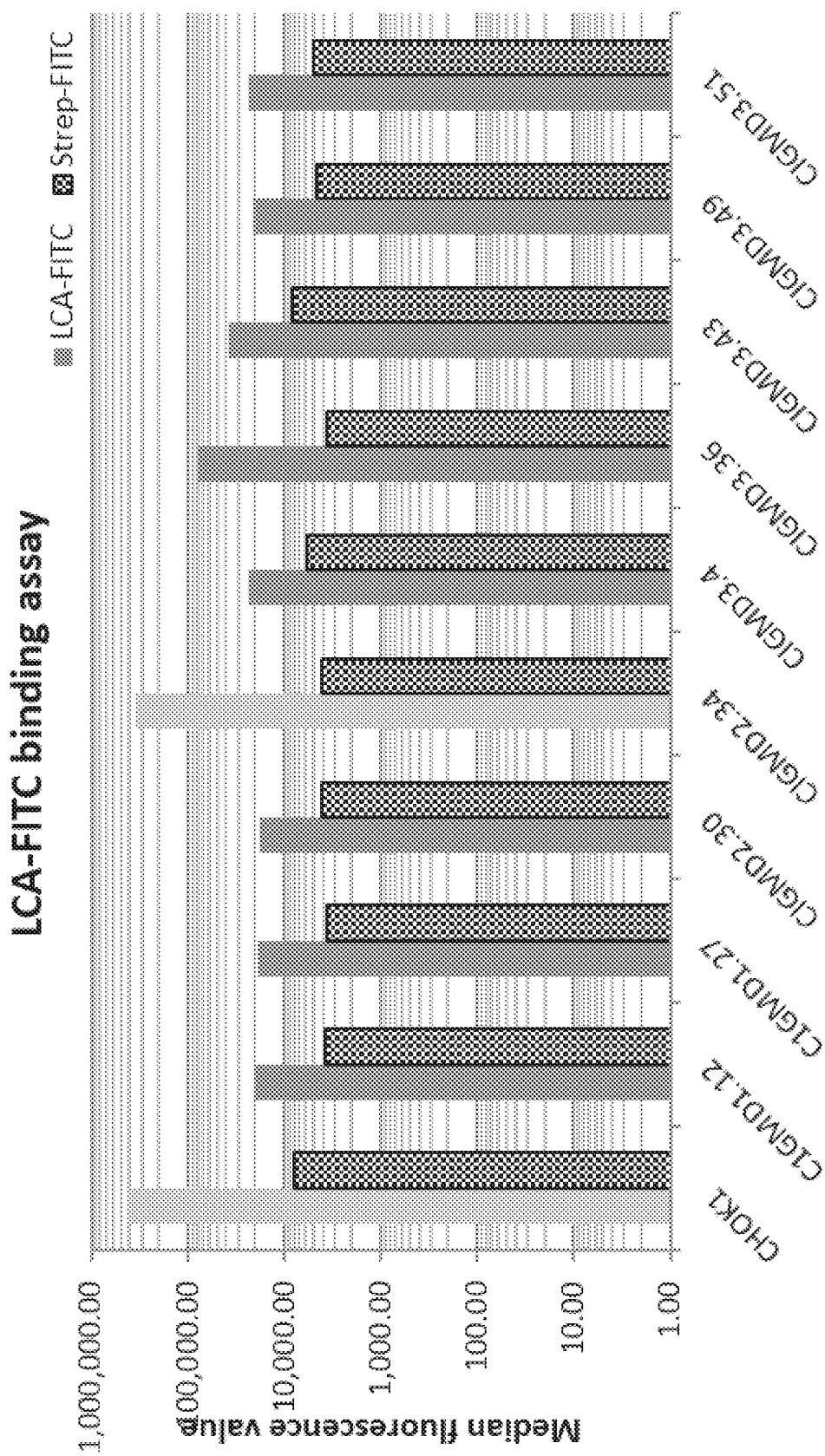
FIG. 7B depicts LCA-FITC flow cytometry assay of clonal CHOK1 cells transfected with pD1401 (gRNA 167-207) or pD1301 (gRNA 404) or pD1401 (gRNA 167-207)+pD1301 (gRNA 404) CRISPR/Cas constructs targeting GMD exon 3 and/or exon 4.

The graphical results and fluorescence profile provided in the table above are also depicted in FIGS. 7B and 8B of the present disclosure. The figures depict the graphical result and fluorescence profile observed for the CHOK1, C1GMD1.12, C1GMD1.27, C1GMD2.30, C1GMD2.34, C1GMD3.4, C1GMD3.36, C1GMD3.43, C1GMD3.49, C1GMD3.51 in Flow cytometry based LCA-FITC Binding Assay. This flow cytometry assay detects fucosylated proteins present on cell surface. Thus CHOK1 control cells fluoresce highly as many fucosylated proteins are present in Control CHOK1 cell line. In cases where the CRISPR/Cas complex is able to disrupt the GMD gene in transfected cell lines, the LCA FITC fluorescence is minimized as there is no fucosylated protein on surface of these cell lines. The figure reveals significant fluorescence loss when C1GMD1.12, C1GMD1.27, C1GMD2.30, C1GMD3.4, C1GMD3.36, C1GMD3.43, C1GMD3.49, C1GMD3.51 are tested in this assay indicating these cell lines are potential CHOK1 GMD knock out cell lines.

Another set of transfection is also tested with LCA FITC fluorescence assay. Flow cytometry data is provided in the table below.

TABLE 11

| | | Median RFU | |
|---|---|---|---|
| Sample ID | CRISPR Construct used | LCA-FITC | Strep-FITC |
| CHOK1 | — | 313,999.50 | 4,952.50 |
| CR1KOT1 | pD1401 (gRNA 167-207) | 17,976.00 | 5,169.00 |
| C1GMD1.37 | pD1401 (gRNA 167-207) | 21,508.00 | 4,331.00 |
| C1GMD1.4 | pD1401 (gRNA 167-207) | 22,506.00 | 5,019.00 |
| C1GMD1.41 | pD1401 (gRNA 167-207) | 23,326.50 | 4,961.00 |
| C1GMD1.43 | pD1401 (gRNA 167-207) | 22,446.50 | 4,695.00 |
| C1GMD1.44 | pD1401 (gRNA 167-207) | 24,080.50 | 5,506.00 |

Figure 7C:
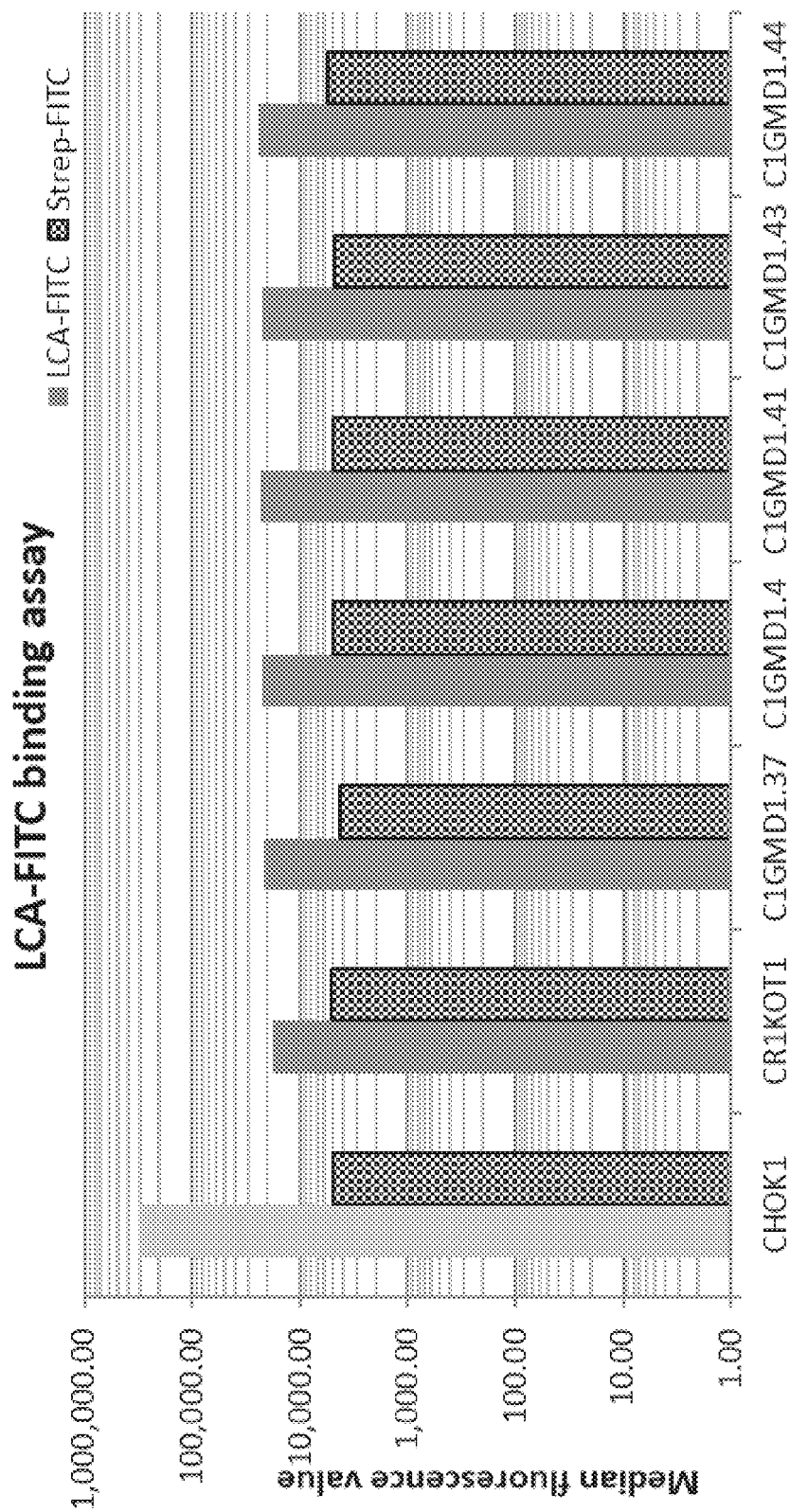
FIG. 7C depicts LCA-FITC flow cytometry assay of clonal CHOK1 cells transfected with pD1401 (gRNA 167-207) CRISPR/Cas construct targeting GMD exon 3.

The graphical results and fluorescence profile provided in the table above are also depicted in FIGS. 7C and 8C of the present disclosure. The figures depict the graphical result and fluorescence profile observed for the CHOK1, C1GMD1.37, C1GMD1.4, C1GMD1.41, C1GMD1.43 and C1GMD1.44, in Flow cytometry based LCA-FITC Binding Assay. This flow cytometry assay detects fucosylated proteins present on cell surface. Thus CHOK1 control cells fluoresce highly as many fucosylated proteins are present in Control CHOK1 cell line. In cases where the CRISPR/Cas complex is able to disrupt the GMD gene in transfected cell lines, the LCA FITC fluorescence is minimized as there is no fucosylated protein on surface of these cell lines. The figure reveals significant fluorescence loss when C1GMD1.37, C1GMD1.4, C1GMD1.41, C1GMD1.43, C1GMD1.44 are tested in this assay indicating these cell lines are potential CHOK1 GMD knock out cell lines.

LCA (*Lens culinaris* Agglutinin) Selection Assay—

Figure 5:
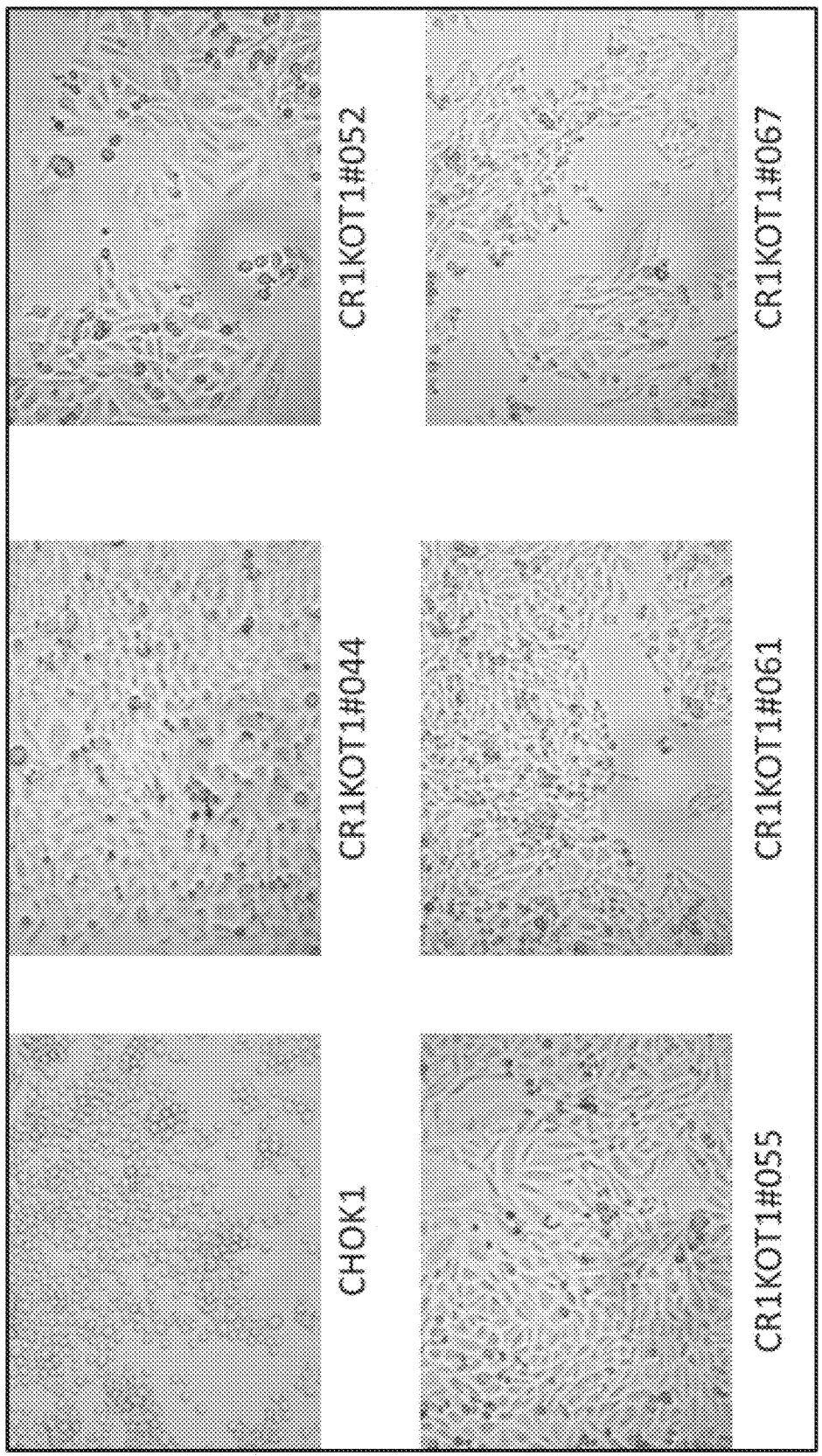
FIG. 5 depicts the CHOK1 control cells and CHOK1 clonal cell lines transfected with CRISPR/Cas construct pD1401 (gRNA 514-553) targeting Fut8 gene, observed at Day 1.
Figure 6A:
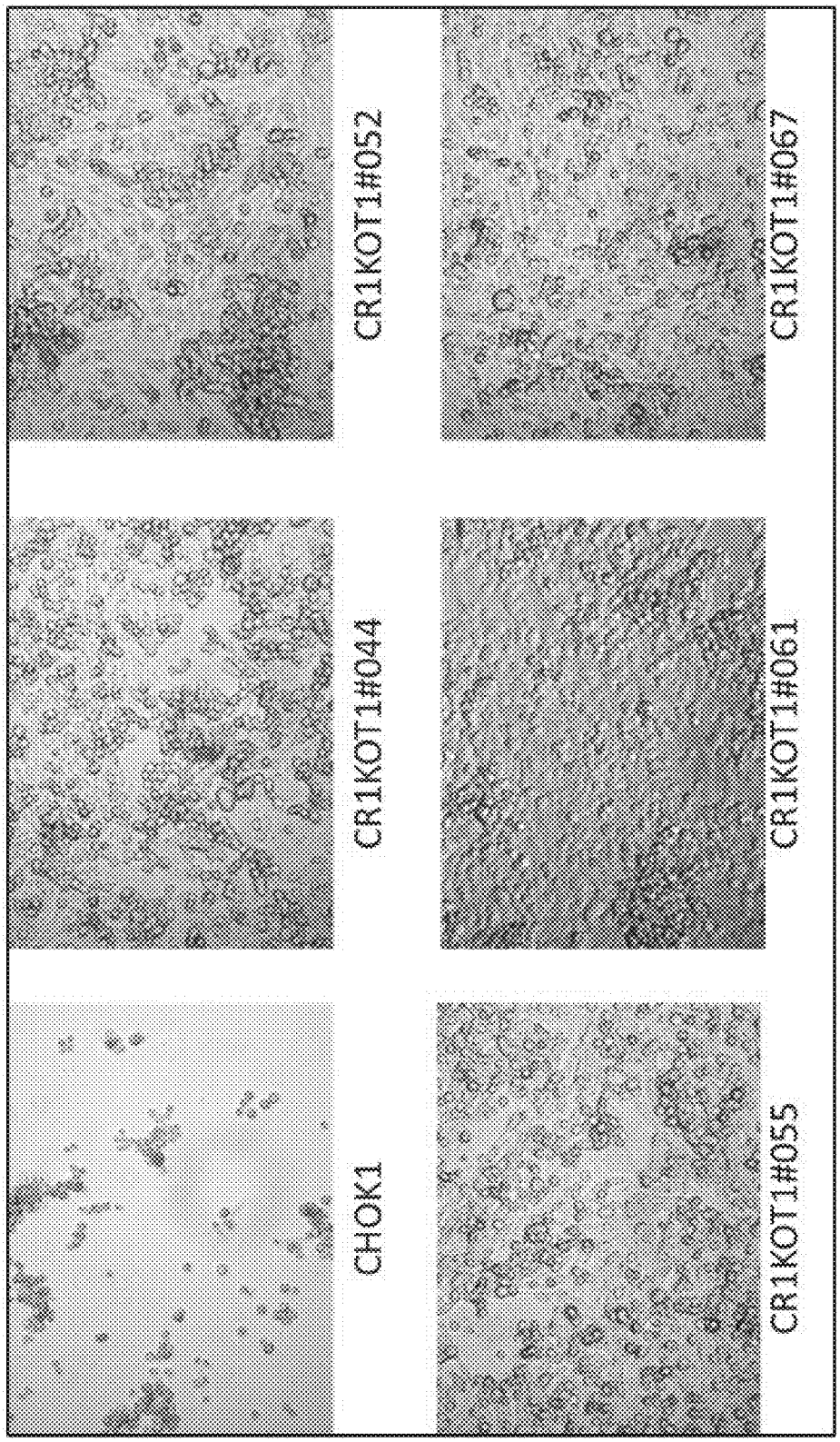
FIG. 6A depicts CHOK1 control cells and CHOK1 cell lines transfected with CRISPR/Cas construct pD1401 (gRNA 514-553) targeting Fut8 gene, observed at Day 4.

Multiple single cell clonal cell line populations are separated in replica plates after transfection with CRISPR/Cas complex. These cell lines are then tested with 200m LCA reagent in the culture medium. The cells are observed every day to confirm cell health and morphology and photographs are taken at appropriate time points. FIG. 5 indicates photographs taken after one day of culture after LCA selection start point and FIG. 6A indicates photographs taken after 4 days of culture. The cell lines indicated here show resistance against LCA depicted by resistant cells on day one which has multiplied and grown into large colonies of cells after Day 4 of culture in presence of LCA reagent. Cell morphology is observed with microscope and observations are recorded on days 1, and 4.

Cells are regularly observed under the inverted phase contrast microscope and monitored for colony morphology. The photographs taken at different time points of LCA selection assay with 200 µg/ml LCA clearly show that CHOK1 control cells are completely dead at Day 4 of culture, whereas the selected clones show continuous cell growth and healthy cell morphology even after 4 days of culture.

It is observed from these figures that the following clones—CR1KOT1#44, CR1KOT1#52, CR1KOT1#55, CR1KOT1#61 and CR1KOT1#67, maintain colony morphology even after treatment with 200 µg/ml LCA. Therefore these clones are considered to be potential FUT 8 knockout phenotype.

Figure 6B:
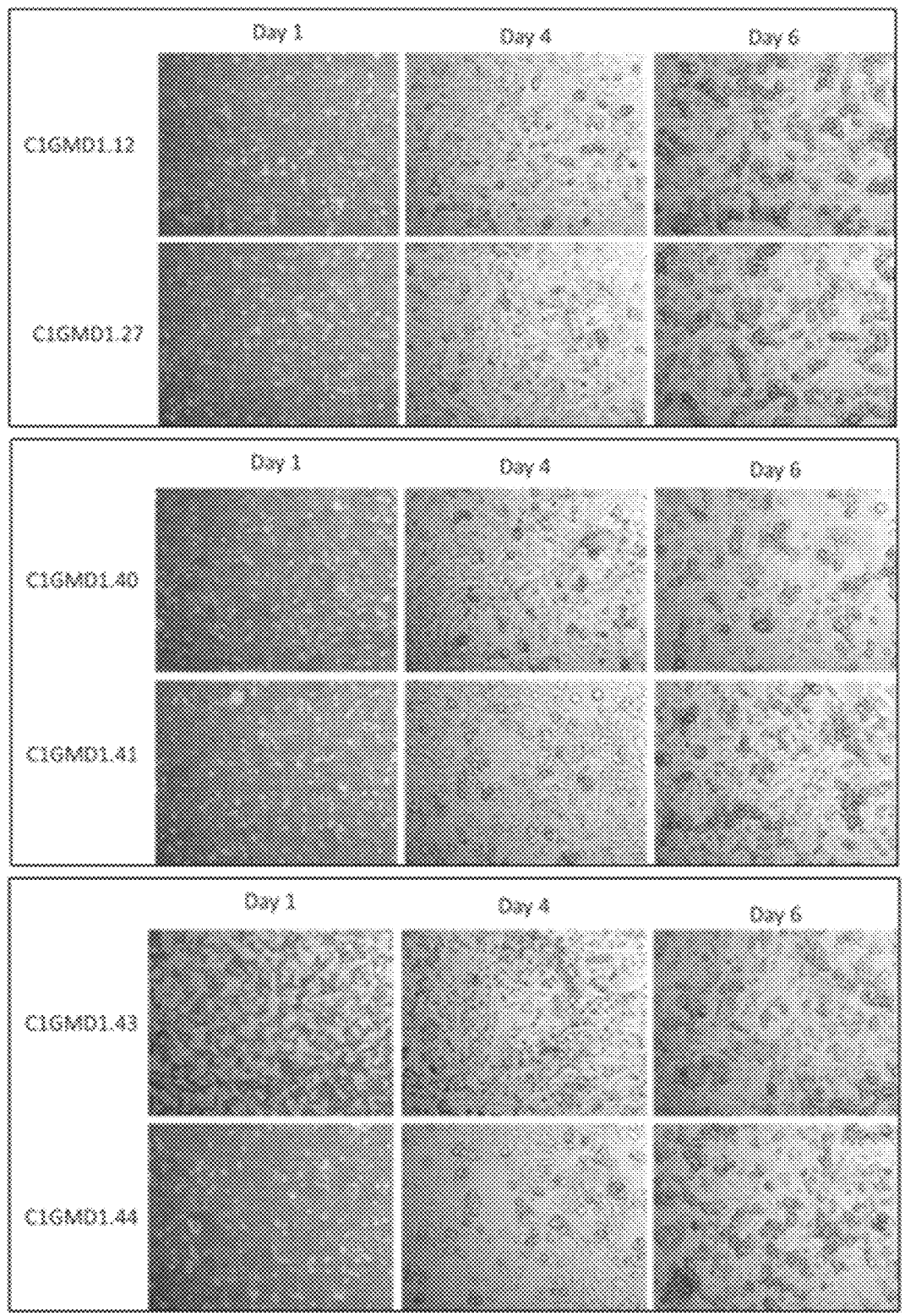
FIG. 6B depicts CHOK1 cell lines transfected with CRISPR/Cas constructs pD1401 (gRNA 167-207) targeting GMD gene exon3.

During LCA selection of pD1401 (gRNA 167-207) transfected clones, viability of the clones on Day 1, Day 4 and Day 6 are compared, in FIG. 6B of the present disclosure. It is observed from these figures that the following clones C1GMD1.12, C1GMD1.27, C1GMD1.40, C1GMD1.41, C1GMD1.43 and C1GMD1.44 maintain colony morphology even after treatment with 200 µg/ml LCA. Therefore these clones are considered to be potential FUT 8 knockout phenotype.

The cell lines indicated here show resistance against LCA by day one which has multiplied and grown into large colonies of cells after Day 4 and Day 6 of culture in presence of LCA reagent. Cell morphology is observed with microscope and observations are recorded on days 1, 4 and 6. Cells are regularly observed under the inverted phase contrast microscope and monitored for colony morphology. The photographs taken at different time points of LCA selection assay with 200 µg/ml LCA clearly show that CHOK1 control cells are completely dead at Day 4 of culture, whereas the selected clones show continuous cell growth and healthy cell morphology even after 4 days of culture.

LCA-FITC Binding Assay:

For second set of LCA-FITC binding assay, following clones have shown fucose knock out flow cytometry profile CR1KOT1#44, CR1KOT1#46, CR1KOT1#48, CR1KOT1#49, CR1KOT1#51, CR1KOT1#52, CR1KOT1#55, CR1KOT1#59, CR1KOT1#61, CR1KOT1#66, CR1KOT1#67 (FIG. 10). Fluorescein *Lens Culinaris* Agglutinin (LCA-FITC) stock of 5 mg/ml is diluted to get 2 µg/ml final concentration in assay buffer (DPBS containing 2% BSA). Cells are spun at 1500 rpm for 5 minutes using Eppendorf minispin centrifuge. The media is aspirated and the pellet re-suspended in 0.25-1 ml of assay buffer containing 2 µg/ml LCA-FITC.

CHOK1 control cells are re-suspended in 0.25-1 ml of assay buffer alone (unstained control) and 0.25-1 ml of assay buffer containing 2 µg/ml LCA-FITC (stained control). All samples are diluted to get 0.1-0.2×10$^6$ cells/ml in final assay buffer. The samples are then incubated in dark on ice for 30 minutes. Then 200 µl of each sample is aliquoted in a 96 well plate. The plate is then loaded in the Millipore GUAVA easyCyte 8HT benchtop flow cytometer for data acquisition and analysis. Data analysis is done using Incyte software.

TABLE 12

| Sl. No. | Sample ID | Median RFJ |
|---|---|---|
| 1 | Unstained control | 9.604 |
| 2 | Stained control | 869.216 |
| 3 | CR1KOT1#40 | 1003.328 |
| 4 | CR1KOT1#41 | 937.068 |
| 5 | CR1KOT1#42 | 662.994 |
| 6 | CR1KOT1#44 | 23.044 |
| 7 | CR1KOT1#45 | 1111.122 |
| 8 | CR1KOT1#46 | 39.878 |
| 9 | CR1KOT1#47 | 920.470 |
| 10 | CR1KOT1#48 | 20.646 |
| 11 | CR1KOT1#49 | 20.338 |
| 12 | CR1KOT1#50 | 947.668 |
| 13 | CR1KOT1#51 | 19.404 |
| 14 | CR1KOT1#52 | 19.210 |
| 15 | CR1KOT1#53 | 1287.536 |
| 16 | CR1KOT1#54 | 858.085 |
| 17 | CR1KOT1#55 | 20.608 |
| 18 | CR1KOT1#56 | 1083.210 |
| 19 | CR1KOT1#57 | 887.343 |
| 20 | CR1KOT1#58 | 944.689 |
| 21 | CR1KOT1#59 | 17.307 |
| 22 | CR1KOT1#60 | 1057.409 |
| 23 | CR1KOT1#61 | 14.960 |
| 24 | CR1KOT1#62 | 1102.714 |
| 25 | CR1KOT1#63 | 974.268 |
| 26 | CR1KOT1#64 | 1464.378 |
| 27 | CR1KOT1#65 | 924.585 |
| 28 | CR1KOT1#66 | 17.355 |
| 29 | CR1KOT1#67 | 20.936 |

The results provided in the table above are also depicted in graphical representation in FIG. 10 and fluorescence profile in FIG. 11 of the present disclosure.

FIG. 10 depict the graphical result observed for the CHOK1 cell lines CR1KOT1#44, CR1KOT1#46, CR1KOT1#48, CR1KOT1#49, CR1KOT1#51, CR1KOT1#52, CR1KOT1#55, CR1KOT1#59, CR1KOT1#61, CR1KOT1#66, CR1KOT1#67 in Flow cytometry based LCA-FITC Binding Assay. FIG. 11 depicts representative fluorescence profiles observed in cell lines CR1KOT1#44, CR1KOT1#49, CR1KOT1#51, CR1KOT1#52, CR1KOT1#55, CR1KOT1#59, CR1KOT1#61, CR1KOT1#67. All clones are passaged for additional days before being analyzed in this experiment. This flow cytometry assay detects fucosylated proteins present on cell surface. Thus CHOK1 control cells fluoresce highly as many fucosylated proteins are present in Control CHOK1 cell line. In cases where the CRISPR/Cas is able to disrupt the FUT8 gene in transfected cell lines, the LCA FITC fluorescence is minimized as there is no fucosylated protein on surface of these cell lines. The figure reveals significant fluorescence loss when CR1KOT1#44, CR1KOT1#46, CR1KOT1#48, CR1KOT1#49, CR1KOT1#51, CR1KOT1#52, CR1KOT1#55, CR1KOT1#59, CR1KOT1#61, CR1KOT1#66, CR1KOT1#67 are tested in this assay indicating these cell lines are CHOK1 FUT8 knock out cell lines.

Conclusion—17 potential candidates for fut8 knockout CHOK1 cell line are identified.

Those 17 clones are as follows:
CR1KOT1#006, CR1KOT1#018, CR1KOT1#022, CR1KOT1#023, CR1KOT1#026, CR1KOT1#031, CR1KOT1#034, CR1KOT1#036, CR1KOT1#037, CR1KOT1#044, CR1KOT1#049, CR1KOT1#051, CR1KOT1#052, CR1KOT1#055, CR1KOT1#059, CR1KOT1#061 and CR1KOT1#067.

13 potential candidates for GMD knock out CHOK1 cell lines are identified. The clones are as follows:
C1GMD1.12, C1GMD1.27, C1GMD1.37, C1GMD1.4, C1GMD1.41, C1GMD1.43, C1GMD1.44, C1GMD2.30, C1GMD3.4, C1GMD3.36, C1GMD3.43, C1GMD3.49, C1GMD3.51

Example 3: LCA-FITC Binding Assay

Clonal fucose knock out CHOK1 cell lines are tested in independent repeat experiments using LCA-FITC binding assay:

Following clonal cell lines are tested for repeatability of LCA-FITC binding assay.
CR1KOT1#006, CR1KOT1#018, CR1KOT1#022, CR1KOT1#023, CR1KOT1#026, CR1KOT1#031, CR1KOT1#034, CR1KOT1#036, CR1KOT1#037, CR1KOT1#044, CR1KOT1#049, CR1KOT1#051, CR1KOT1#052, CR1KOT1#055, CR1KOT1#059, CR1KOT1#061 and CR1KOT1#067.

Fluorescein Lens Culinaris Agglutinin (LCA-FITC) stock of 5 mg/ml is diluted to get 2 µg/ml final concentration in assay buffer (DPBS containing 2% BSA). Cells are spun at 1500 rpm for 5 minutes using Eppendorf minispin centrifuge. The media is aspirated and the pellet re-suspended in 0.25-1 ml of assay buffer containing 2 µg/ml LCA-FITC. CHOK1 control cells are re-suspended in 0.25-1 ml of assay buffer alone (unstained control) and 0.25-1 ml of assay buffer containing 2 µg/ml LCA-FITC (stained control). All samples are diluted to get $0.1-0.2\times10^6$ cells/ml in final assay buffer. The samples are then incubated in dark on ice for 30 minutes. Then 200 µl of each sample is aliquoted in a 96 well plate. The plate is then loaded in the Millipore GUAVA easyCyte 8HT benchtop flow cytometer for data acquisition and analysis. Data analysis is done using Incyte software.

Results:

Following table describe the data repeatability of LCA-FITC binding assay for all selected clones.

TABLE 13

| Sl. No. | Sample ID | Trial 1 | Trial 2 | Trial 3 | Mean | SEM |
| --- | --- | --- | --- | --- | --- | --- |
| 1 | Unstained control | 6.668 | 8.771 | 12.189 | 9.209 | 1.61 |
| 2 | Stained control | 968.184 | 984.168 | 982.260 | 978.204 | 5.04 |
| 3 | CR1KOT1#006 | 16.211 | 19.475 | 28.399 | 21.362 | 3.64 |
| 4 | CR1KOT1#018 | 26.249 | 33.250 | 59.006 | 39.501 | 9.96 |
| 5 | CR1KOT1#022 | 18.021 | 17.410 | 25.411 | 20.281 | 2.57 |
| 6 | CR1KOT1#023 | 11.880 | 17.120 | 13.775 | 14.258 | 1.53 |
| 7 | CR1KOT1#026 | 10.434 | 17.491 | 24.953 | 17.626 | 4.19 |
| 8 | CR1KOT1#031 | 13.682 | 18.932 | 34.881 | 22.498 | 6.37 |
| 9 | CR1KOT1#034 | 14.318 | 10.896 | 19.826 | 15.013 | 2.60 |
| 10 | CR1KOT1#036 | 13.161 | 19.505 | 29.793 | 20.820 | 4.85 |
| 11 | CR1KOT1#037 | 16.703 | 16.601 | 29.906 | 21.070 | 4.42 |
| 12 | CR1KOT1#044 | 23.044 | 24.937 | 32.886 | 26.956 | 3.01 |
| 13 | CR1KOT1#049 | 20.338 | 17.215 | 26.426 | 21.327 | 2.70 |
| 14 | CR1KOT1#051 | 19.404 | 18.555 | 26.543 | 21.501 | 2.53 |
| 15 | CR1KOT1#052 | 19.210 | 15.024 | 31.349 | 21.861 | 4.90 |
| 16 | CR1KOT1#055 | 20.608 | 19.368 | 27.686 | 22.554 | 2.59 |
| 17 | CR1KOT1#059 | 17.307 | 21.119 | 27.764 | 22.063 | 3.06 |
| 18 | CR1KOT1#061 | 14.960 | 23.307 | 35.791 | 24.686 | 6.05 |
| 19 | CR1KOT1#067 | 20.936 | 18.053 | 27.323 | 22.104 | 2.74 |

Pictorial depiction of the LCA FITC binding assay is presented in FIG. 12. Data analysis suggests highly reproducible LCA FITC binding pattern for the clonal fucose knock out CHOK1 cell lines.

These fucose knock out CHOK1 cell lines are further tested for growth characteristics and compared to untransfected parental CHOK1 cell line.

Example 4: Streptavidin-FITC Assay

Clonal fucose knock out CHOK1 cell lines are tested with Streptavidin-FITC conjugate to ensure specific interaction of LCA-FITC binding:

Streptavidin conjugated FITC (Strep-FITC) staining of the clones is carried out to ensure that there is no non-specific binding of FITC dye. Cell membrane proteins do not bind to Streptavidin-FITC conjugate whereas fucosylated membrane proteins bind specifically to LCA-FITC conjugate. Control CHOK1 cells are stained with both LCA-FITC and Strep-FITC in separate reactions to confirm this specificity. All clones are similarly stained with Streptavidin-FITC and LCA-FITC conjugates to determine non-specific binding.

FIG. 14 of the present disclosure depicts the LCA Flow cytometry assay, and comparison of the clones through LCA-FITC and Strep-FITC assay respectively. For the following clones Fucose knockout phenotype is observed, CR1KOT1#006, CR1KOT1#018, CR1KOT1#022, CR1KOT1#023, CR1KOT1#026, CR1KOT1#031, CR1KOT1#034, CR1KOT1#036, CR1KOT1#037, CR1KOT1#044, CR1KOT1#049, CR1KOT1#051, CR1KOT1#052, CR1KOT1#055, CR1KOT1#059, CR1KOT1#061 and CR1KOT1#067. In all clones, a significant reduction of fluorescence compared to control is observed and thereby this proves absence of fucosylated protein on cell surface for the clones. This data provides functional proof that these cell lines lack fucosylated protein due to FUT8 gene disruption carried out using the complex in the method of the present disclosure.

Fluorescein streptavidin (Streptavidin-FITC) stock 1 mg/ml is diluted to get 2 µg/ml final concentration in assay buffer (DPBS containing 2% BSA). Cells are spun at 1500 rpm for 5 minutes using Eppendorf minispin centrifuge. The media is aspirated and the pellet re-suspended in 0.25-1 ml of assay buffer containing 2 µg/ml Streptavidin-FITC. CHOK1 control cells are re-suspended in 0.25-1 ml of assay buffer alone (unstained control) and 0.25-1 ml of assay buffer containing 2 µg/ml Streptavidin-FITC (stained control). All samples are diluted to get $0.1-0.2\times10^6$ cells/ml in final assay buffer. The samples are then incubated in dark on ice for 30 minutes.

Then 200 µl of each sample is aliquoted in a 96 well plate. The plate is then loaded in the Millipore GUAVA easyCyte 8HT benchtop flow cytometer for data acquisition and analysis. Data analysis is done using Incyte software.

Comparison with Streptavidin-FITC is carried out to ensure specific interaction of LCA-FITC conjugate. The data suggests only background fluorescence observed with Streptavidin-FITC conjugate when tested with CHOK1 control cell line and any of the CRISPR/Cas transfected cell lines.

FIG. 14 depicts the specificity of the LCA—FITC flow cytometry assay developed to screen the CHOK1 Fucose knock out cell lines. Flow cytometry experiments are carried out with Streptavidin-FITC conjugate. Streptavidin-FITC does not recognize cell surface proteins on CHOK1 control cell line indicating specific interaction of LCA-FITC conjugate. Additionally, the Streptavidin-FITC conjugate reveals similar levels of background fluorescence between positive and negative cell lines identified by LCA-FITC conjugate. FIG. 14 shows no non-specific interaction of LCA-FITC conjugate used in this study when compared to Streptavidin-FITC conjugate.

Growth Curve Determination for Fucose Knock Out CHOK1 Cell Lines:

Growth curve determination of selected clones are performed to ensure that growth profile is not altered significantly compared to wild type CHOK1 cells during the process of knockout cell line development. $0.1 \times 10^6$ CHOK1 cells are seeded in 6 well tissue culture plates. Seeding is done for 5 time points for each clone. For each time point, triplicate seeding is done (e.g., 15 wells for 5 time points). At each time, point cell counts are taken in triplicates. Viable cell count is performed using either hemocytometer or Vi-cell XR cell viability analyser. Respective growth curves are generated with SEM as error bar. Table 14 describes representative growth data from one of the FUT8 knock out cell lines.

CR1KOT1#018, CR1KOT1#026, CR1KOT1#034, CR1KOT1#052 and CR1KOT1#055 have shown slightly slower growth potential compared to other cell lines.

Example 5: Genomic Sequencing Assays

CRISPR transfected clones selected through functional assay, namely LCA-FITC flow cytometry assay are used for genomic sequence analysis. The FUT 8 genomic locus of Chinese Hamster is well reported in literature (NW_003613860) and is used as wild type sequence to understand type of gene modification in each cell line clone. Similarly, GMD genomic locus of Chinese Hamster is obtained from sequence database, NW_003613635.1, NP_001233625.1, NM_001246696.1 and is used as wild type sequence to understand the type gene modification in each cell line. The objective of this example is to analyse genomic DNA sequencing results obtained from CRISPR/Cas transfected CHOK1 FUT8 knock out cell lines and CHOK1 GMD knock out cell lines. All cell lines reported here are clonal cell lines and are selected from LCA media selection assay and LCA-FITC flow cytometry assay.

TABLE 14

| | Mean viable cell count (×10^6) | | | | |
|---|---|---|---|---|---|
| Time (hrs) | CHOK1 control | CR1KOT1#52 | CR1KOT1#55 | CR1KOT1#61 | CR1KOT1#67 |
| 0 | 0.100 | 0.100 | 0.100 | 0.200 | 0.100 |
| 24 | 0.313 | 0.261 | 0.344 | 0.370 | 0.411 |
| 48 | 0.858 | 0.671 | 0.925 | 0.992 | 1.226 |
| 72 | 2.295 | 1.439 | 2.031 | 2.411 | 2.875 |
| 96 | 2.680 | 3.398 | 3.603 | 5.272 | 4.738 |

| | Mean viable cell count (×10^6) | | | | |
|---|---|---|---|---|---|
| Time (hrs) | CHOK1 control | CR1KOT1#06 | CR1KOT1#18 | CR1KOT1#22 | CR1KOT1#23 | CR1KOT1#26 |
| 0 | 0.100 | 0.100 | 0.100 | 0.100 | 0.100 | 0.100 |
| 24 | 0.313 | 0.270 | 0.217 | 0.167 | 0.183 | 0.243 |
| 48 | 0.858 | 0.790 | 0.567 | 0.540 | 0.680 | 0.457 |
| 96 | 2.680 | 4.357 | 2.477 | 3.857 | 3.867 | 1.997 |

| | Mean viable cell count (×10^6) | | | | |
|---|---|---|---|---|---|
| Time (hrs) | CHOK1 control | CR1KOT1#31 | CR1KOT1#34 | CR1KOT1#36 | CR1KOT1#37 | CR1KOT1#44 |
| 0 | 0.100 | 0.100 | 0.100 | 0.200 | 0.100 | 0.100 |
| 24 | 0.313 | 0.180 | 0.240 | 0.500 | 0.267 | 0.253 |
| 48 | 0.858 | 0.713 | 0.370 | 0.890 | 0.700 | 0.597 |
| 96 | 2.680 | 3.160 | 2.427 | 3.753 | 3.593 | 3.367 |

Results: Viable cell count for each cell lines are tested and used for growth curve determination. Following clonal fucose knock out CHOK1 cell lines are used for growth curve development, CR1KOT1#006, CR1KOT1#018, CR1KOT1#022, CR1KOT1#023, CR1KOT1#026, CR1KOT1#031, CR1KOT1#034, CR1KOT1#036, CR1KOT1#037, CR1KOT1#044, CR1KOT1#049, CR1KOT1#051, CR1KOT1#052, CR1KOT1#055, CR1KOT1#061 and CR1KOT1#067.

The data is analyzed and plotted in growth curve. The growth curves of respective cell line are provided in FIGS. 13A, 13B and 13C of the present disclosure.

It is observed from the figures that the majority of the clonal cell lines have comparable growth potential with respect to CHOK1 parental cell line. These clonal cell lines are used for over-expression of therapeutic proteins and/or monoclonal antibodies. Viable cell count is taken every day for 5 days in optimal growth conditions, using Vi-Cell counter. Few clonal fucose knock out CHOK1 cell lines Briefly, the selected clonal cell lines are grown in appropriate growth conditions for genomic DNA isolation, purified genomic DNA is used for PCR amplification using primers flanking the FUT8 and GMD target loci, the PCR amplified product is then purified and cloned in a suitable vector using *E. coli* competent cells, resulting ampicillin resistant *E. coli* colonies are selected and cultured, plasmid DNA are isolated from each bacterial clone, approximately 5-10 individual bacterial colonies are tested per clonal cell lines through automated sequencing to understand the type of modification at the FUT8 target genomic locus.

Following reagents and solutions are used to carry out genome sequencing of the selected clones The entire genome sequencing protocol is divided in following four processes A. Genomic DNA isolation from selected clones
B. PCR strategy to amplify specific genomic locus for each cell line.
C. Cloning of PCR products in sequencing vectors D. Sequence data analysis and identification of INDELs Genomic DNA Isolation from Selected Clones Clonal CHOK1 cell lines are grown in Advanced DMEM media with 10% Fetal bovine serum, 4 mM glutamine, 100 units/ml Penicillin and 100 µg/ml Streptomycin in T175 flasks at 37° C. in presence of 5% $CO_2$ and 75% relative humidity in controlled condition incubators. The cell growth is observed every day and viability is monitored. Cells are harvested at 80% confluency and greater than 95% viability with trypsinization. On the day of isolation, culture media is removed and adherent cells are first washed with 10 ml of DPBS followed by addition of 4 ml of 0.05% trypsin EDTA solution for trypsinization. The cells are incubated at 37° C. for 2-3 minutes and harvested. Cells are then mixed with 10 ml of DPBS and centrifuged at 1500 rpm for 5 min. The spent media is removed and cell pellet is resuspended in 10 ml DPBS. Cells are washed again using centrifugation at 1500 rpm for 5 min. DPBS is removed completely by aspiration. The final cell pellet is used for genomic DNA isolation.

Genomic DNA is isolated from CHOK1 control cells and CHOK1 CRSPR/Cas transfected clonal cell lines showing LCA resistance and selected through LCA flow cytometry assay. Commercially available QIAGEN gDNA extraction kit is used for isolating genomic DNA following manufacturers protocol.

PCR Strategy Design

Genomic DNA sequence of Chinese Hamster is analysed from publicly available database sequence NW_003613860. FUT8 Exon 7 DNA sequences and partial intron sequence is used for designing PCR strategy to amplify the FUT8 target locus.

GMD exon and intron sequences are obtained from NW_003613635.1 and NM_001246696.1 and sequence analysis are carried out for Exon 3 and Exon 4.

Primers are designed based on primer length, PCR product length, GC content, melting temperature and potential homoduplex and heteroduplex formation. Primers are designed flanking the FUT8 target locus as provided below. The amplified PCR product is intended for mutation analysis due to CRISPR mediated SSB and subsequent DNA repair. Following nucleotide sequence represents the region of interest with primer sequences in bold letters.

Fut8 Exon 7 and associated intron sequences used for PCR primer design:

aagaaataagctgaatcagctctgacttattgtgtgattttcaatacctgt gaccaaaatgagaagttaactccttatatcttatcttatttgtttctctgg aagAATCCCAAGGACTGCAGCAAAGCCAGAAAGCTGGTATGTAATATCAAC

AAAGGCTGTGGCTATGGATGTCAACTCCATCATGTGGTTTACTGCTTCATG

ATTGCTTATGGCACCCAGCGAACACTCATCTTGGAATCTCAGAATTGGCGC

TATGCTACTGGAGGATGGGAGACTGTGTTTAGACCTGTAAGTGAGACATGC

ACAGACAGGTCTGGCCTCTCCACTGGACACTGGTCAGgtaaggagcatgtg caccatgaaagatctctggttaggtcagattagcac Introns are represented from base 21 to base 106 and from base 345 to base 371 in lower case letters. Exon 7 is represented from base 107 to base 344 in upper case letters. The primer binding sites of Left and Right are underlined.

GMD Exon 3 and Exon 4 and associated intron sequences used for PCR primer design:

Following sequences are used.

GMD Exon 3 and Surrounding Introns gatccttcagtgttccaagtactgggtttgcaggggtgggcagtcacacct gggaacaccagtttgaccttcattttcatatgtgaataatacatatttcag ttttgatattgaaatgtttctcttgttatctcatatcttgatgatcttttt ataaatcttaaagACATGAAGTTGCACTATGGTGACCTCACCGACAGCACC

TGCCTAGTAAAAATCATCAATGAAGTCAAACCTACAGAGATCTACAATCTT

GGTGCCCAGAGCCAGAGCCATGTCAAGgtaagctcttctcattgccatggc ttctttggctgtgcctttgtagtgttctctattcactcacatttgttgttt ctcaatacaatagcaaccactagttcttatcaagtttagtcttcagtatta gtttgggaattcatcctaataaaaatactcataaattttaaggtgaggtt tctgttactcaacag Introns are represented from base 23 to base 166 and from base 277 to base 447 in lower case letters. Exon 3 is represented from base 167 to base 276 in upper case letters. The primer binding sites of Left and Right are underlined.

GMD Exon 4 and Surrounding Introns gacgtagtcttcagctattctatactggaagtagatgatattctcattgga aattctgttaggaagtaacccttcttgtcttcttacctgcatagaatccca ggatataaaacttgtgcttgtcgcccttgccattgtctctcactggtggcc tttattgcatctcatatctgccttctcttccagATTTCCTTTGACTTAGC

AGAGTACACTGCAGATGTTGATGGAGTTGGCACCTTGCGGCTTCTGGATGC

AATTAAGACTTGTGGCCTTATAAATTCTGTGAAGTTCTACCAGGCCTCAAC

TAGTGAACTGTATGGAAAAGTGCAAGAAATACCCCAGAAAGAGACCACCCC

TTTCTATCCAAGGTCGCCCTATGgtaagaattcctgtgcccagctgtatgt gaggctctctgcaggtgtggggatgtttctgctttctttctgcac Introns are represented from base 21 to base 187 and from base 381 to base 432 in lower case letters. Exon 4 is represented from base 188 to base 380 in upper case letters. The primer binding sites of Left and Right are underlined.

Primer Design for Identifying the INDEL by PCR

Genomic PCR is performed using QIAGEN gDNA extraction kit using the following primers mentioned in table 15.

TABLE 15

| PCR Sets | Primer Name | Primer sequence (5' to 3') | PCR product size | Base | $T_m$ | % GC |
|---|---|---|---|---|---|---|
| CRISPR primers at FUT8 Exon 7 | CRP_P1_FW | AAGAAATAAGCTGAATCAGCTCTGAC-SEQ ID No. 94 | 394 bp | 26 | 55.2 | 38 |

TABLE 15-continued

| PCR Sets | Primer Name | Primer sequence (5' to 3') | PCR product size | Base | $T_m$ | % GC |
|---|---|---|---|---|---|---|
| | CRP_P1_Rv | GTGCTAATCTGACCTAACCAGAG-SEQ ID No. 95 | | 23 | 54.7 | 47.8 |
| CRISPR primers at GMD Exon 3 | GMD_P01_Fw | GATCCTTCAGTGTTCCAAGTAC-SEQ ID No. 96 | 468 bp | 22 | 53 | 45.5 |
| | GMD_P01_Rv | CTGTTGAGTAACAGAAACCTC-SEQ ID No. 97 | | 21 | 50.8 | 42.9 |
| CRISPR primers at GMD Exon 4 | GMD_P03_Fw | GACGTAGTCTTCAGCTATTC-SEQ ID No. 98 | 453 bp | 20 | 49.9 | 45 |
| | GMD_P03_Rv | GTGCAGAAAGAAAGCAGAAAC-SEQ ID No. 99 | | 21 | 52.6 | 42.9 |

The following section provides experimental details for PCR product generation from CHOK1 genomic DNA from control cell lines and LCA selected clonal cell lines, cloning of PCR products in E coli competent cells and sequencing of cloned PCR products.

Optimization of PCR Condition—

The experiments are designed to standardize PCR conditions. The parameters tested include, genomic DNA concentration (from 100 ng to 1000 ng), primer concentrations (2 nmole to 20 nmole), PCR annealing temperature (from 55.8° C. to 62.9° C.) and time (20 secs to 50 secs), PCR product extention time (30 secs to 60 secs) and PCR cycle number is set at 30 cycles. Arrived optimized condition is described in following section.

PCR reactions are carried out using proof reading polymerase Phusion polymerase to ensure that PCR mediated mutations are limited. Following PCR amplification cycles, Taq polymerase enzyme is added in the mix for tailing. The tailing step is important as the extra base added to the PCR products allows direct cloning in sequencing vector described in the next section. In order to add dATP overhangs to PCR product for cloning in TA cloning vector, the Phusion polymerase amplified product is incubated with Taq DNA polymerase for 20 minutes at 72° C.

Cross Checking the Genomic DNA Sample by PCR—

Genomic DNA PCR products are analysed in agarose gel electrophoresis and the product length is confirmed using a molecular weight standard. PCR samples with clear amplification profile are used in the next processing step.

PCR Product Gel Elution Using QIAGEN Kit—

The amplified PCR products are loaded in freshly prepared 1% agarose gel and electrophoresed at 100V for one hour to separate amplified PCR products from unused primers and any other dimers produced during the amplification process. The amplified products are excised from gel and eluted using commercially available Qiagen gel elution kit. DNA is eluted with highly pure molecular biology grade water.

Cloning of PCR Products in Sequencing Vectors—

Agarose gel purified PCR amplified products are then used for cloning in commercially available pTZ57R/T vector through DNA ligation process. Conditions for DNA ligation have been standardized previously.

Transformation of ligated sample pTZ57R/T+ CRISPR (PCR) in DH5alpha E. coli competent cells—Ligated DNA is transformed in E. coli DH5alpha competent cells, available commercially. Transformation protocol as described by manufacturer is followed to achieve high level transformation efficiency. After transformation, the E. coli cells are grown in presence of Ampicillin antibiotic for growth of transformed colonies.

Inoculation of transformed cells (pTZ57R/T+ CRISPR (PCR)) into LB media with Ampicillin—Each separate colony is inoculated in LB+Ampicillin broth in 5 ml culture volume and grown overnight for plasmid DNA isolation.

Isolation of plasmid DNA (pTZ57R/T+ CRISPR(PCR) from DH5alpha transformed cells—4.5 ml of overnight grown cultures are used for plasmid DNA isolation using commercially available QIAGEN plasmid DNA isolation kit following manufacturers protocol. The plasmid DNA is eluted with highly pure molecular biology grade water.

4.3.5 Cross checking of plasmids for the presence of insert—Each plasmid preparation is tested for presence of insert using suitable restriction enzyme digestion followed by agarose gel electrophoresis. The size of insert is compared with suitable molecular weight standards.

Sequence Data Analysis and Identification of INDELs

Sequencing—The confirmed plasmids are then sequenced with specific sequencing primers present in the pTZ57R/T vector backbone. Sequence data is generated in automated DNA sequencing instruments following appropriate protocols. Sequencing is carried out with both forward and reverse sequencing primers to ensure proper sequence information.

DNA sequence analysis—DNA sequencing data from all plasmids are analyzed. DNA sequence from plasmid DNA derived from CHOK1 control cell line and various CRISPR mediated FUT8 knock out CHOK1 clonal cell lines and GMD knock out CHOK1 cell lines are compared and differences in DNA sequences are identified. From each CHOK1 cell line clone, PCR products are generated and cloned in E. coli. Multiple E. coli clones are sequenced to confirm nucleotide sequence modification at the target genomic locus.

Composite analysis of the sequence data is used to identify potential FUT8 and GMD knock out CHOK1 cell lines where FUT8 and GMD genomic target loci are modified through deletion and/or insertions (INDELs). The DNA sequences are then aligned to show distinct differences. FIG. 17A to 17G provides the alignment of nucleotide sequences of CHOK1 control cell line and FUT8 and FIG. 17H to 17L) provides the nucleotide sequence alignments with GMD knock out clonal cell lines and CHOK1 control cell line. The DNA sequence information is used to assign amino acid sequence of the FUT8 gene (exon 7). Using standard codon usage for GMD gene, exon 3 and exon 4 regions are analyzed. The amino acid sequences are then aligned to identify deletion, frame shift mutation, insertion of stop codons as well as amino acid substitutions at specific locations. FIG. 17A to 17G depicts the extent of nucleotide modification observed in the CHOK1 FUT8 knock out cell lines and FIG. 17H to 17L in CHOK1 GMD knock out cell lines when compared to CHOK1 control cell line. The data provides a representation of FUT8 and GMD genomic DNA organization among multiple CHOK1 FUT8 and GMD knock out cell lines.

PCR Reaction

First, the double-stranded DNA template is denatured at a high temperature at 94° C. Sequence-specific primers mentioned in the Table 15 are then annealed (60.4° C.) to sites flanking the target sequence. A thermostable DNA polymerase (Phusion polymerase) extends (72° C.) the annealed primers, thereby doubling the amount of the original DNA sequence. This newly synthesized product then becomes an additional template for subsequent cycles of amplification. These three steps are repeated for 30 cycles, resulting in a $10^9$ fold increase in target DNA concentration. In order to add dATP overhangs to PCR product for cloning in TA cloning vector, the PCR Phusion polymerase amplified product is incubated with Taq polymerase for 20 minutes at 72° C.

TABLE 16

| Initial denaturation | 94° C. | 3 minutes | |
|---|---|---|---|
| Denaturation | 94° C. | 30 seconds | 30 Cycles |
| Annealing | 60.4° C. | 50 seconds | |
| Extension | 72° C. | 1 minute | |
| Final extension | 72° C. | 10 minutes | |
| Throughout the process | 4° C. | | |

TABLE 17

| PCR conditions | | |
|---|---|---|
| Reagents | Sample | Control |
| Template | Respectively | 0.0 µL |
| dNTPs | 1 µL | 1 µL |
| Fw primer | 1 µL | 1 µL |
| Rv primer | 1 µL | 1 µL |
| Phusion Polymerase | 1 µL | 1 µL |
| Phusion buffer HF (5X) | 10 µL | 10 µL |
| Purified water | Respectively | 36 µL |
| Total reaction mixture | 50 µL | 50 µL |

FIG. 15A of the present disclosure depicts representative figure of the PCR amplified product of representative CRISPR/Cas Fut8 clone (CR1-KO-T1#022) when run on 1% agarose gel. Genomic DNA is isolated and amplified with CRP_P1_Fw and CRP_P01_Rv primers at standardized PCR conditions. The amplified product is electrophoresed in 1% agarose gel. Lane 1 provides Genomic DNA of CR1-KO-T1#022 clone amplified with specific primers and Lane 2 provides DNA molecular weight standard.

The result reveals expected product size of amplified product. The PCR amplified product is gel purified and cloned in bacterial clones and sequenced to confirm the status of genomic FUT8.

FIG. 15B of the present disclosure depicts representative figure of the PCR amplified product of representative CRISPR/Cas GMD clones (GMD_1.12 and GMD_1.27) when run on 1 agarose gel. Genomic DNA is isolated and amplified with GMD_P01_Fw and GMD_P01_Rv primer set and GMD_P03_Fw and GMD_P03_Rv primer set, respectively at standardized PCR conditions. The amplified product is electrophoresed in 1% agarose gel. The result reveals expected product size of amplified product. The PCR amplified product is gel purified and cloned in bacterial clones and sequenced to confirm the status of genomic GMD Exon 3 and Exon 4 sequences.

In FIG. 15B, Lane 1 depicts genomic DNA of GMD_1.12 clone amplified with specific primers, Lane 2 depicts genomic DNA of GMD_1.27 clone amplified with specific primers, Lane 3 depicts DNA molecular weight standard 1 kb DNA Ladder and Lane 4 depicts DNA molecular weight standard 100 bp DNA Ladder.

This representative figure describes PCR amplification of target FUT8 and GMD genomic loci using the primer sequences in Table 15 and Phusion polymerase. The PCR product is further modified with Taq DNA polymerase for tailing. Final PCR product is then electrophoresed in agarose gel for elution of amplified fragment.

FIG. 15C depicts representative 1% agarose gel run with PCR amplification of genomic DNA of GMD 2.30 clonal cell line with primers specific for GMD Exon 4 locus. Lane 1 depicts DNA molecular weight standard 1 kb DNA Ladder, Lane 2 depicts DNA molecular weight standard 100 bp DNA Ladder and Lane 3 depicts Genomic DNA of GMD 2.30 clone amplified with specific primers.

FIGS. 15A, 15B and 15C reveal amplified PCR products of appropriate size electrophorezed for gel elution. The same process is applied to amplify PCR amplified product from CHOK1 control and FUT8 knock out and GMD knock out CHOK1 clonal cell lines, which are gel extracted using QIAEX II Gel extraction kit.

Ligation

PCR amplified and gel eluted products are ligated in commercially available pTZ57R/T vector. Ligation protocol is described as follows

TABLE 18

| Ligation mix | |
|---|---|
| DNA (pTZ57R/T) | 1 µL |
| DNA (CRISPR(PCR product)) | 4 µL |
| T4 DNA ligase | 1 µL |
| T4 DNA ligase buffer(10X) | 1 µL |
| Purified water | to 10 µL |
| Total | 10 µL |

The above ligation mix is incubated at 4° C. overnight and 50% of ligated mix is transformed into DH5alpha *E. coli* competent cells by heat shock method.

Transformation of Ligated Sample into Bacterial Cell by Heat Shock Method

The purpose to transform bacterial cells is to clone and propagate the plasmid DNA. 20 µL aliquot of competent *E. coli* cells (DH5alpha) are taken from −80° C. freezer and thawed on ice for 5 minutes. 50% of ligated sample (pTZ57R/T+ CRISPR(PCR)) is added to the competent cells and gently mixed and incubated on ice for 20 minutes. The mix containing tube is placed on water bath/dry bath at 42° C. for 50 seconds. The tube is placed back on ice for 2 minutes. 0.950 ml of 37° C. warmed LB broth (without ampicillin antibiotic), is incubated at 37° C., 220 rpm for 1 hour, in shaker. 100 µL of the resulting culture is spread on warmed LB+ ampicillin culture plates. The plates are incubated overnight at 37° C. incubator.

Plasmid DNA Isolation from Bacterial Cells Using QIAPrep Spin Miniprep

The purpose of this procedure is to grow/culture bacteria that contain a specific DNA plasmid, which is used in following experiments. 5 mL of LB+ ampicillin broth is added into autoclaved tubes, isolated bacterial colonies are inoculated from the culture plates to the LB broth+Ampicillin culture tubes. Tubes are incubated at 220 rpm, at 37° C. overnight (approximately 16-18 hours depending on the growth of the bacterium). Overnight culture of 4.5 mL is centrifuged at 13 rpm for 1 minute. Plasmid DNA is isolated using commercially available QIAGEN plasmid isolation kit. Plasmid DNA is eluted with highly pure molecular biology grade water and stored at −20° C. freezer until further use.

Positive Clones Selected Using Restriction Digestion with EcoR I-HF and Hind III-HF Enzymes Plasmid DNA thus isolated is tested for presence of insert, in this case the PCR amplified fragment. The pTZ57R/T vector contains multiple restriction enzyme sites flanking the cloned PCR product. The restriction sites EcoRI and HindIII are selected for restriction digestion as described in below table. The reaction is carried out at 37° C. for 2 hours for complete digestion of the plasmid DNA. Following restriction digestion, the mixture is electrophoresed in 1% agarose gel for 1 hour. The PCR product insert, if present, separates from pTZ57R/T vector backbone and the confirmed bacterial clones are used for DNA sequencing.

TABLE 19

| Restriction enzyme digestion- reaction mix | |
|---|---|
| DNA (pTZ57R/T + CRISPR(PCR products)) | 2 µg |
| EcoRI-HF | 1 µL |
| Hind III-HF | 1 µL |
| Cut smart buffer(10X) from New England Biolabs | 2 µL |
| Purified water | to 20 µL |
| Total | 20 µL |

FIGS. 16A, 16B and 16C of the present disclosure depicts the representative restriction enzyme digestion of PCR amplified product in pTZ57R/T vector to confirm presence of inserts from different knock out cell lines. Plasmid DNA preparations from independent bacterial clones are digested with EcoRI and HindIII restriction enzymes flanking the PCR fragment cloned in the vector and the mixture is electrophoresed in 1% agarose gel. The size of resulting DNA fragments are estimated from the DNA molecular weight standards.

FIG. 16A depicts representative 1% agarose gel run of restriction digestion of pTZ57R/T plasmid with PCR product insert. Restriction digestion with EcoRI and HindIII results in 500 bp insert. The insert represents the PCR product obtained from amplification of CR1-KO-T1#022 cell line genomic DNA with primers specific for FUT8 exon 7 locus.

In the figure,
Lane-1 100 bp DNA Ladder
Lane-2 pTZ57R/T+ CR1-KO-T1#022 #a [EcoRI-HF & HindIII-HF]
Lane-3 pTZ57R/T+ CR1-KO-T1#022 #b [EcoRI-HF & HindIII-HF]
Lane-4 pTZ57R/T+ CR1-KO-T1#022 #c [EcoRI-HF & HindIII-HF]
Lane-5 pTZ57R/T+ CR1-KO-T1#022 #d [EcoRI-HF & HindIII-HF]
Lane-6 pTZ57R/T+ CR1-KO-T1#022 #d [Uncut]

FIG. 16B depicts representative 1% agarose gel run of restriction digestion of pTZ57R/T plasmid with PCR product insert. Restriction digestion with EcoRI and HindIII resulted in ~500 bp insert. The insert represents the PCR product obtained from amplification of GMD 1.27 cell line genomic DNA with primers specific for GMD exon 3 locus.

In the figure,
Lane-1 GeneRuler 1 kb DNA Ladder (Thermoscientific)
Lane-2 pTZ57R/T+(CHO_GMD_1.27) #a [BamHI-HF & XbaI]
Lane-3 pTZ57R/T+(CHO_GMD_1.27) #b [BamHI-HF & XbaI]
Lane-4 pTZ57R/T+(CHO_GMD_1.27) #c [BamHI-HF & XbaI]
Lane-5 pTZ57R/T+(CHO_GMD_1.27) #d [BamHI-HF & XbaI]
Lane-6 pTZ57R/T+(CHO_GMD_1.27) #d [Uncut]

FIG. 16C depicts representative 1% agarose gel run of restriction digestion of pTZ57R/T plasmid with PCR product insert. Restriction digestion with EcoRI and HindIII resulted in ~500 bp insert. The insert represents the PCR product obtained from amplification of GMD 2.30 cell line genomic DNA with primers specific for GMD exon 4 locus.

In the figure,
Lane-1 pTZ57R/T+(GMD_2.30) #a [Uncut]
Lane-2 pTZ57R/T+(GMD_2.30) #a [BamHI-HF & XbaI]
Lane-3 pTZ57R/T+(GMD_2.30) #b [BamHI-HF & XbaI]
Lane-4 pTZ57R/T+(GMD_2.30) #c [BamHI-HF & XbaI]
Lane-5 pTZ57R/T+(GMD_2.30) #d [BamHI-HF & XbaI]
Lane-6 1 kb DNA Ladder The results reveal that all tested clones harbor PCR product inserts of predicted length. The pTZ57R/T vector backbone is represented by the fragment observed at approximately 5.4 Kb band position. Based on this data, individual plasmid DNA samples are selected and used for DNA sequencing. The same process is applied to all PCR products cloned in pTZ57R/T vector and confirmed clones are selected for DNA sequencing. The result indicates presence of insert which is sequenced with sequencing primers present in the vector backbone.

Example 6: Confirmation of the Indels by Sequencing

DNA sequencing of the selected bacterial plasmid DNA is performed with upstream and downstream sequencing primers located in the pTZ57R/T vector backbone. Sequencing data is gathered using both primers and is analysed for proper DNA sequence information. Multiple bacterial plasmids are sequenced to generate composite DNA sequence information at the FUT8 and GMD target genomic loci for CHOK1 control cell line and clonal CHOK1 FUT8 and GMD knock out cell lines achieved through CRISPR/Cas complex.

Provided below are the genomic DNA sequences from CHOK1 control cell line and CHOK1 FUT8 and GMD knock out clonal cell lines, confirming the presence of insertion and/or deletion mutations in Fut8 gene and GMD gene, respectively by CRISPR constructs, as per the method of the present disclosure. Amplified targeted genomic locus from each cell line including the CHOK1control cell line is cloned as PCR products in multiple independent bacterial clones. Sequence verification is carried out with both forward and reverse sequencing primers from multiple independent bacterial clones (ranging from 5-15) to understand allelic variability of the FUT8 and GMD target loci. The DNA sequence data below is representative of genomic sequences at the targeted FUT8 locus from various FUT8 knock out cell lines.

DNA Sequence Analysis

CHOK1 control cell line (wild type)—sequence of Exon-7 of FUT8 gene is in upper case. Intron sequence is in lower case and underlined.

aagaaataagctgaatcagctctgacttattgtgtgatttcaatacct gtgaccaaaatgagaagttaactccttatatctttatcttatttgttt ctctggaagAATCCCAAGGACTGCAGCAAAGCCAGAAAGCTGGTATGT

AATATCAACAAAGGCTGTGGCTATGGATGTCAACTCCATCATGTGGTT

TACTGCTTCATGATTGCTTATGGCACCCAGCGAACACTCATCTTGGAA

TCTCAGAATTGGCGCTATGCTACTGGAGGATGGGAGACTGTGTTTAGA

CCTGTAAGTGAGACATGCACAGACAGGTCTGGCCTCTCCACTGGACAC

TGGTCAGgtaaggagcatgtgcaccatgaaagatctctggttaggtca gattagcac

CHOK1 FUT8 knockout clonal cell line sequences are provided below. It is observed that the Exon 7 sequence is mutated in the cell lines.

CR1KOT1#023
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGAACATTGGATATTGGGAAGAAT

TAGAGTTGAGTTGAGGATGGGAGACTGTGTTTAGACCTGTAAGTGAG

ACATGCACAGACAGGTCTGGCCTCTCCACTGGACACTGGTCAG

CR1KOT1#018
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGACCCAGAATTGGCGCTATGCTACTGGAGGAT

GGGAGACTGTGTTTAGACCTGTAAGTGAGACATGCACAGACAGGTCT

GGCCTCTCCACTGGACACTGGTCAG

CR1KOT1#055
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGCACTCATCTTGGAATCTCAGAA

TTGGCGCTATGCTACTGGAGGATGGGAGACTGTGTTTAGACCTGTAA

GTGAGACATGCACAGACAGGTCTGGCCTCTCCACTGGACACTGGTCAG

CR1KOT1#044
AATCCCAAGGACTGCAGCAAAGCCAGAAAGCTGGTATGTAATATCAA

CAAAGGCTGTGGCTATGGATGTCAACTCCATCATGTGGTCTACTGCT

TCATGATTGCTTATGGCACCCAGCGAACACTCATCTCTGGAGGATGG

GAGACTGTGTTTAGACCTGTAAGTGAGACATGCACAGACAGGTCTGG

CCTCTCCACTGGACACTGGTCAG

CR1KOT1#022
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGAACACTCATCTTGGAATCTCAG

AATTGGCACACAGATCCTGGACTCCCGGATGAACACTAAGTACGACG

AGAATGACAAGCTGATCCGGGAAGTGAAAGTGATCACCCTATGCTAC

TGGAGGATGGGAGACTGTGTTTAGACCTGTAAGTGAGACATGCACAG

ACAGGTCTGGCCTCTCCACTGGACACTGGTCAG

CR1KOT1#036
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGAACACTCACACTCATCTTGGAA

TCTCAGAATTGGAATCTCATCTTGGAATCTCAGAATTGGAATCTCAG

AATTGGCGCTATGCTACTGGAGGATGGGAGACTGTGTTTAGACCTGT

AAGTGAGACATGCACAGACAGGTCTGGCCTCTCCACTGGACACTGGT

CAG

CR1KOT1#037
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACACTCATTATCCTCGGGGGGAGCAGCCAC

TCAAATTTTGGCGCTATGCTACTGGAGGATGGGAGACTGTGTTTAGA

CCTGTAAGTGAGACATGCACAGACAGGTCTGGCCTCTCCACTGGACA

CTGGTCAG

CR1KOT1#051
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAAATTGGCGCTATGCTACTGGAGGAT

GGGAGACTGTGTTTAGACCTGTAAGTGAGACATGCACAGACAGGTCT

GGCCTCTCCACTGGACACTGGTCAG

CR1KOT1#052
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGAACACTCATCTTGCGAACACTC

ATCTTGGAATCTCAGAATTGTACTGGAGGATGGGAGACTGTGTTTAG

ACCTGTAAGTGAGACATGCACAGACAGGTCTGGCCTCTCCACTGGAC

ACTGGTCAGG

CRIKOT1#059
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGAACACTCATCTTGGAATCTCAG

AATTGGCGCTTTGGAATCTCAGAATTGGCGCTACTGGAGGATGGGAG

ACTGTGTTTAGACCTGTAAGTGAGACATGCACAGACAGGTCTGGCCT

CTCCACTGGACACTGGTCAG

CR1KOT1#061
AATCCCAAGGACTGCAGCAAAGCCAGAAAGCTGGTATGTAATATCAA

CAAAGGCTGTGGCTATGGATGTCAACTCCATCATGTGGTTTACTGCT

TCATGATTGCTTATGGCACCCAGCGAACACTCATCTTGGAATCTCGT

```
GTTTAGACTGTAAGTGAGACATGCACACGACAGGTCTGGCCTCTCCA
CTGGACACTGGTCAG

CR1KOT1#067
AATCCCAAGGACTGCACCGCAAAGCCAGAAAGCTGGTATGTAATATC
AACAAAGGCTGTGGCTATGGATGTCAACTCCATCATGTGGTTTACTG
CTTCATGATTGCTCATCTTGGAATCTCAGAATTGGCGCTATGCTACT
GGAGGATGGGAGACTGTGTTTTAGACCTGTAAGTGAGACATGCACAC
AGACAGGTCTGGCCTCTCCACTGGACACTGGTCAG
```

Figure 17A:
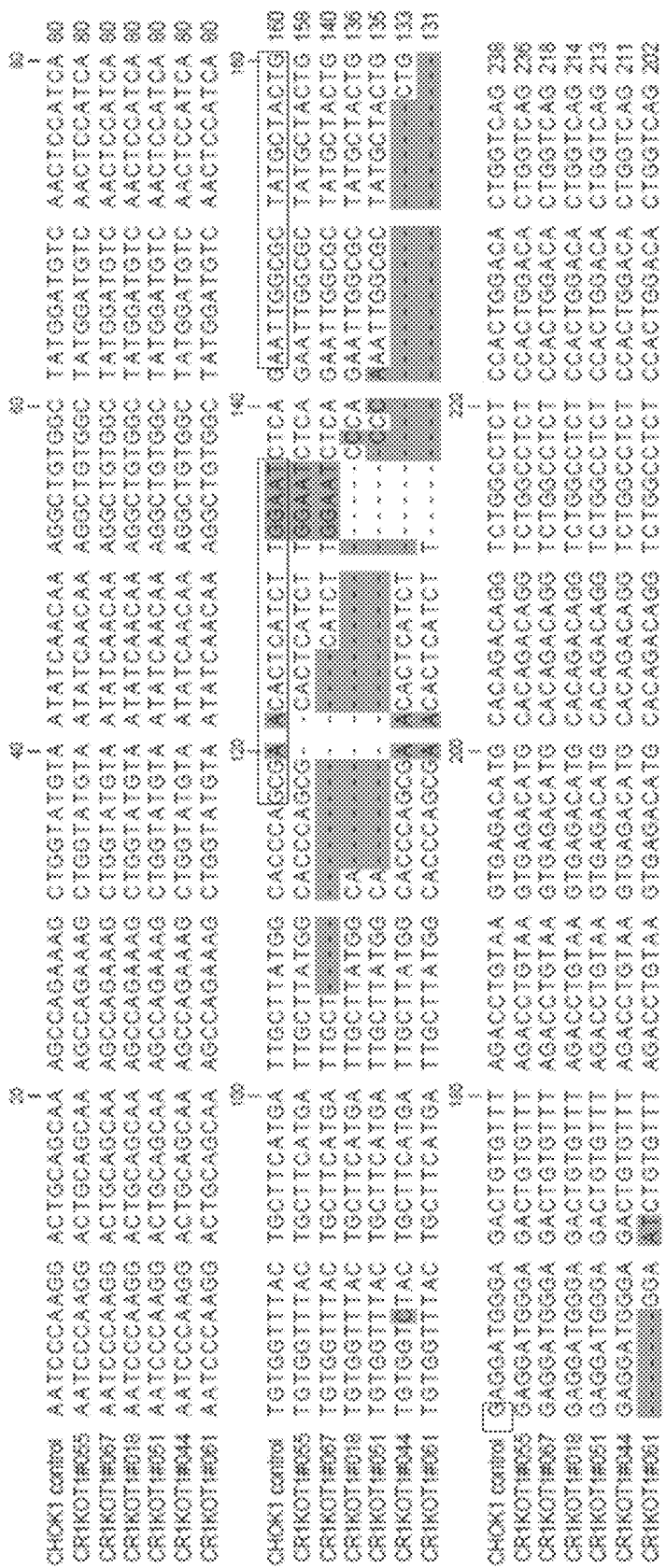

Representative genomic DNA sequence alignment in FUT8 knock out cell line clones showing deletion in FUT8 gene sequence is provided in FIG. 17 of the present disclosure. FIG. 17A to 17G depict nucleotide sequence analysis at the Fut8 exon 7 target locus. Genomic DNA of CRISPR/Cas transfected selected CHOK1 FUT8 knock out clones and CHOK1 control cell lines are used to PCR amplify targeted genomic FUT8 locus. Sequence data is collected from analysis of 5-15 independent bacterial clones sequenced with both forward and reverse sequencing primers. The sequencing data suggests deletions of variable lengths in multiple clones compared to CHOK1 control cell line. Largest deletion of bases is observed in clone CR1KOT1#061 and smallest deletion is just 2 bases in clone CR1KOT1#055. All deletions are located at the CRISPR/Cas target site.

Figures 17B, 17C:
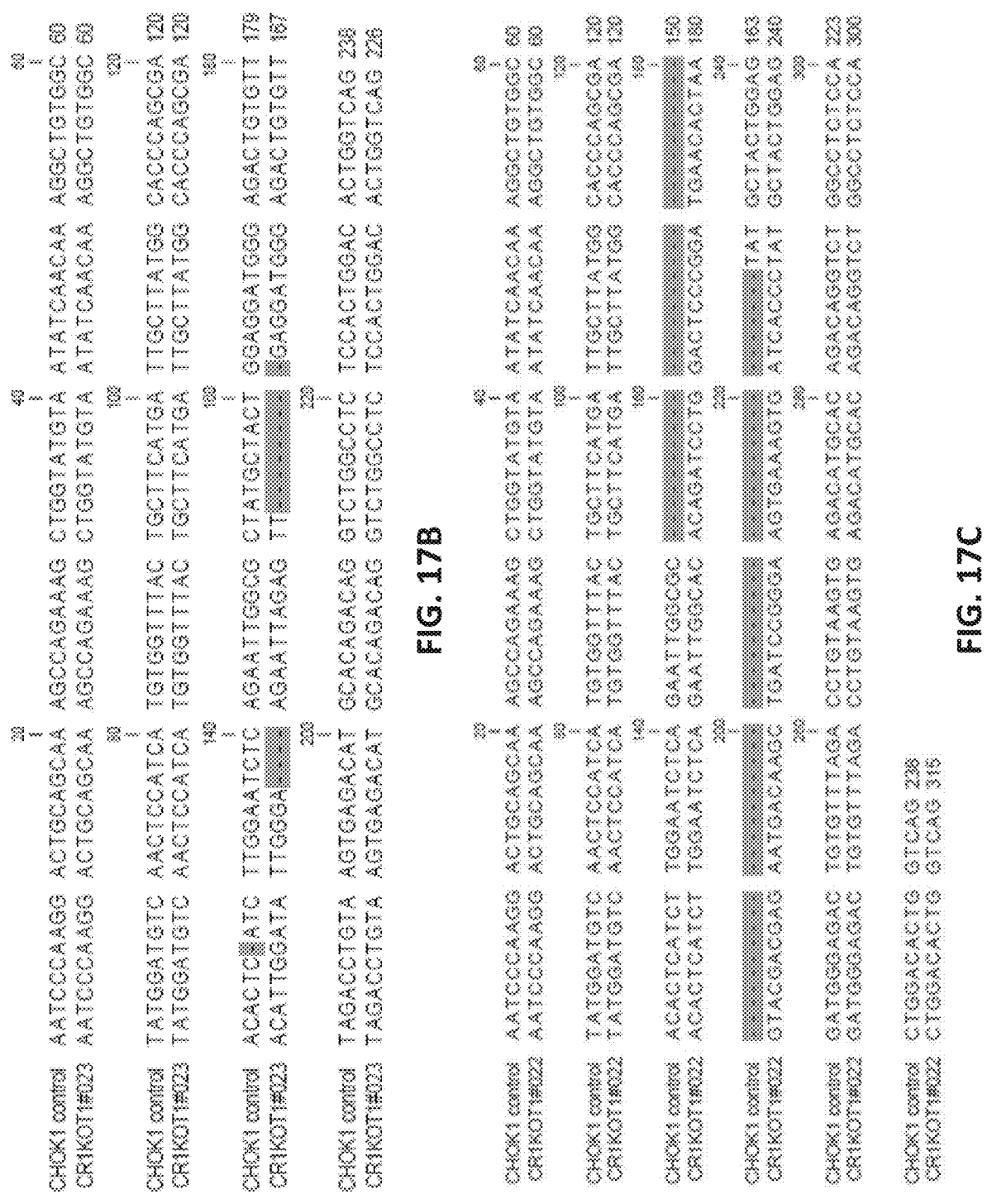
Figures 17D, 17E:
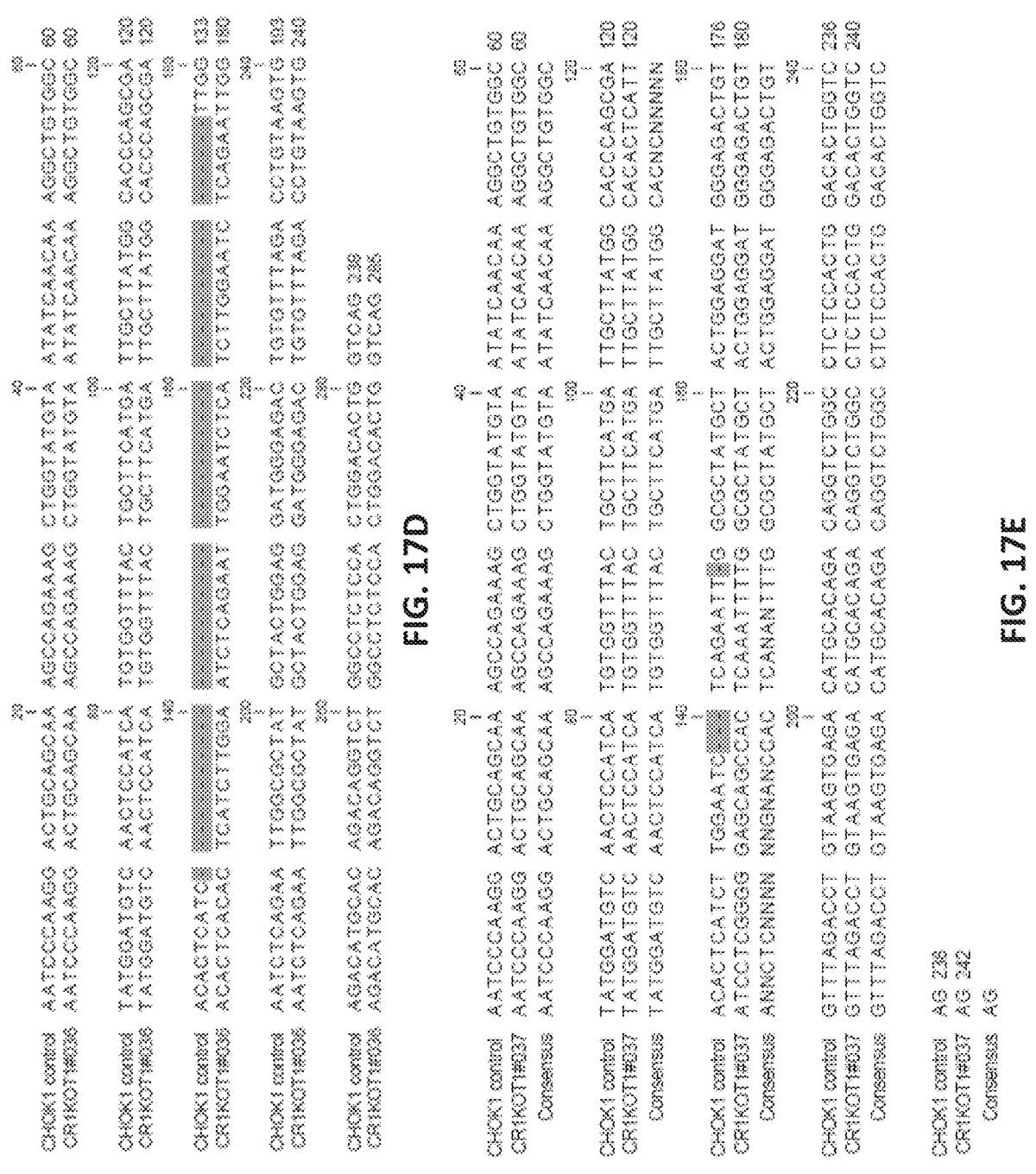
Figures 17F, 17G:
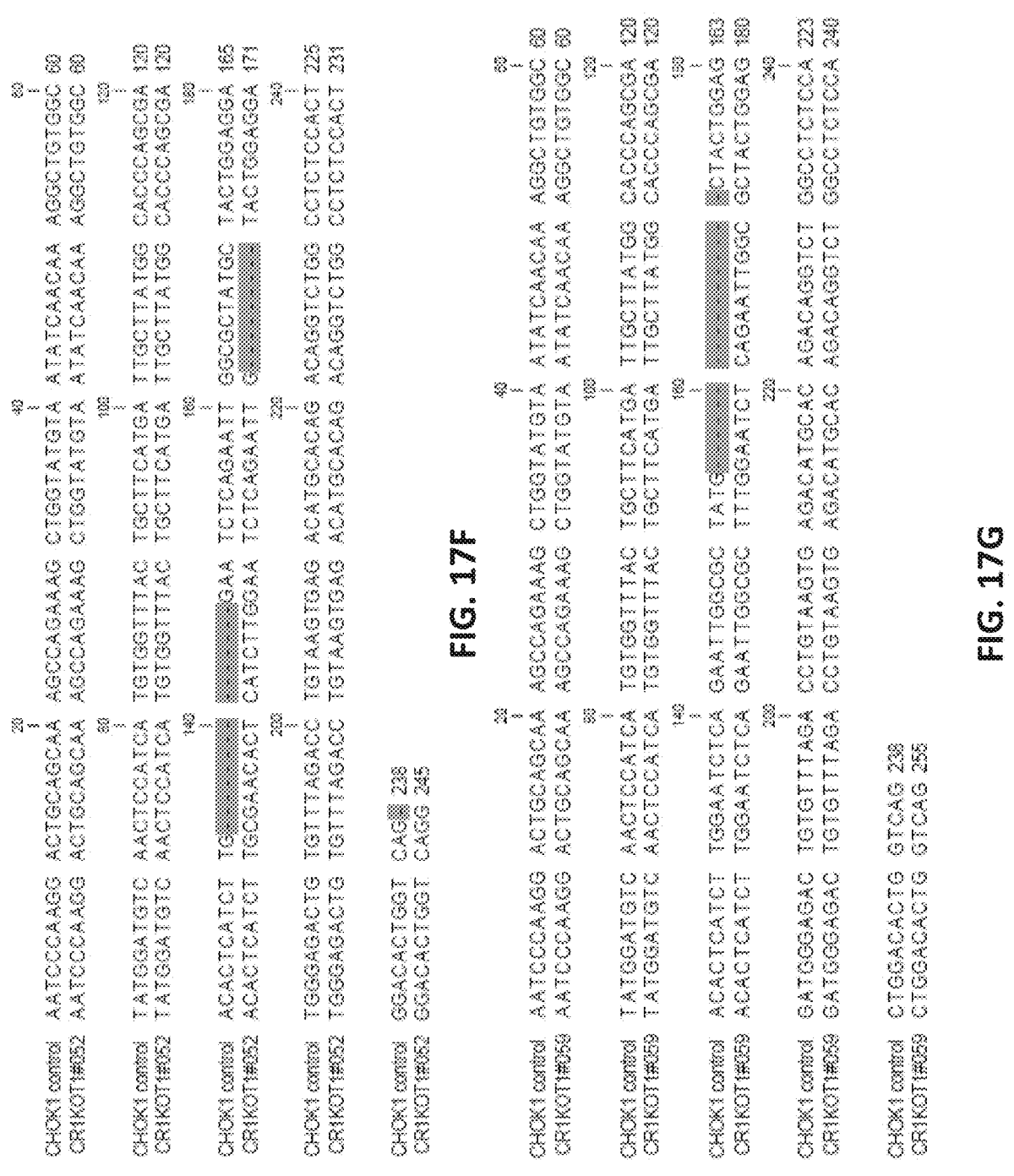

In FIG. 17A, the left and right CRISPR/Cas DNA binding sites are denoted by open boxes. FIG. 17B to 17G indicate multiple clones where the sequence data revealed insertion of new DNA sequence compared to CHOK1 control cell line. FIG. 17B, and FIG. 17F representing clone numbers CR1KOT1#023 and CR1KOT1#052 revealed both insertion and deletion of sequences compared to CHOK1 genomic sequence. Clone number CR1KOT1#037 (FIG. 17E) revealed unique insertion and extensive mismatch of bases compared to CHOK1 genomic sequence. Insertion of bases also varied in length as shown in FIGS. 17B to 17G.

The data suggests various INDELs present at the FUT8 genomic locus in CHOK1 FUT8 knock out cell lines. In many cases, it is observed that there are very specific modifications at the targeted bases, and in other cases the changes are broad and involve longer stretches of DNA. Such diversity of genomic modification through CRISPR/Cas complex is possible due to endogenous DNA single strand breaks at close proximity and repair through non homologous end joining. All of these cell lines are selected through functional screening assay, namely LCA-FITC flow cytometry assay.

The results also imply high efficiency of the functional assays to isolate and identify CHOK1 FUT8 knock out cell line.

It is also revealed that the design of the CRISPR/Cas complex depicted in this disclosure is unique as this one pair of CRISPR/Cas complex with the Cas9n endonuclease provides a highly sequence specific gene alteration at the targeted FUT8 locus in CHOK1 cell lines.

DNA Sequence Analysis of CHOK1 Cells Transfected with pD1401 (gRNA 167-207) CRISPR/Cas Complex to Target Exon 3 of GMD Gene CHOK1 control cell line (wild type)—sequence of Exon-3 of GMD gene is in upper case. Intron sequence is in lower case and underlined.

```
gatccttcagtgttccaagtactgggtttgcaggggtgggcagtca
cacctgggaacaccagtttgaccttcattttcatatgtgaataata
catatttcagttttgatattgaaatgtttctcttgttatctcatat
cttgatgatcttttataaatcttaaagACATGAAGTTGCACTATG
GTGACCTCACCGACAGCACCTGCCTAGTAAAAATCATCAATGAAGT
CAAACCTACAGAGATCTACAATCTTGGTGCCCAGAGCCATGTCAAG
gtaagctcttctcattgccatggcttctttggctgtgcctttgtag
tgttctattcactcacatttgttgtttctaatacaatagcaacca
ctagttcttatcaagtttagtcttcagtattagtttgggaattcat
cctaataaaaatactcataaattttaaggtgaggtttctgttact
caacag
```

CHOK1 GMD knockout clonal cell line sequences are provided below. It is observed that the Exon 3 sequence is mutated in the cell lines.

```
GMD_1.12
ACATGAAGTTGCACTATGGTGACCTCACCGACAGCACCTGTGTTT
TGGCACCAAAATCAACGGGACTTTCCAAAATGTCGTAATAACCCC
GCCCCGTTGACGCAAATGGAGAATCGCGCAGGGGAATGGCCTGCC
GCACTTTCTGGCGGGCAGAAACAGCGAGTGGCGCTGCCAAGAGCG
TTGATTCATCCACCGCGATTATTGTTGCGTGATGAACCGCTCCCG
GCQCTGGACGCCTTAACGCGACTCGAGATGCAGGATTTGATTGTG
TCTAGTAAAAATCATCAATGAAGTCAAACCACAGAGATCTACAAT
CTGGTGCCCAGACCCATGTCAAG

GMD_1.27
ACATGAAGITGCACIATGCTGACCTCACCGACAGCACCTCFCCIA
GIGAAGICAAACCTACAGAGATCTACAATCTTGCTGCCCAGAGCC
ATGTCAAG

GMD_1.37
ACATGAAGTTGCACTATGGTGACCTCACCGACAGCACCTGCCTA
GTAAAAATCATCTGACCGCCAGGTCGTAAAATCATCAATGAAGTC
AAACCTACAGAGATCTACAATCTTGGTGCCCAGAGCCATGTCAAG

GMD_1.41
TAGATCTCTGTAGGITTGACTTCATTGATGAAGATCTACAATCTT
GGTGCCCAGAGCCATGTCAAG

GMD_1.43
TGGTGACCTCACCGACAGCACCTGCCTAGTAAAAAATCATCAATG
AAGTCAAACCTACAGAGATCTACAATCTTGGTGCCCAGAGCCATG
TCAAG

GMD_1.44
ACATGAAGTTGCACTATGGTGACCTCACCGATGAAGTCAAACCTA
CAGAGATCTACAATCTTGGTGCCCAGAGCCATGTCAAG
```

DNA Sequence Analysis of CHOK1 Cells Transfected with pD1301 (gRNA 404) CRISPR/Cas Complex to Target Exon 4 of GMD Gene CHOK1 control cell line (wild type)—sequence of Exon-4 of GMD gene is in upper case. Intron sequence is in lower case and the primer locations are underlined.

gacgtagtcttcagctattctatactggaagtagatgatattctcat tggaaattctgttaggaagtaaccccttcttgtcttcttacctgcata gaatcccaggatataaaacttgtgcttgtcgcccttgccattgtctc tcactggtggcctttattgcatctcatatctgccttctctttccagA

TTTCCTTTGACTTAGCAGAGTACACTGCAGATGTTFGATGGAGTTGG

CACCTTGCGGCTTCTTGGATGCAATTAAGACTTGTGGCCTTATAAAT

TCTGTGAAGTTCTACCAGGCCTCAACTAGTGAACTGTATGGAAAAGT

GCAAGAAATACCCCAGAAAGAGACCACCCCTTTCTATCCAAGGTCGC

CCTATGgtaagaattcctgtgcccagctgtatgtgaggctctctgca ggtgtggggatgtttctgctttctttctgcac CHOK1 GMD knockout clonal cell line sequence is provided below. It is observed that the Exon 4 sequence is mutated in the clonal cell line.

GMD_2.30
ATTTCCTTTGACTTAGCAGAGTACACTGCAGATGTTGATGGAGTTGG

CACTTCTGGATGCAATTAAGACTTGTGGCCTTATAAATTCTGTGAAG

TTCTACCAGGCCTCAACTAGTGAACTGTATGGAAAAGTGCAAGAAAT

ACCCCAAAAGAGACCACCCCTTTCTATCCAAGGTCGCCCTATG

DNA Sequence Analysis of CHOK1 Cells Transfected with Both pD1401 (gRNA 167-207) and pD1301 (gRNA 404) CRISPR/Cas Complex to Target Exon 3 and Exon 4 of GMD Gene CHOK1 GMD knockout clonal cell line sequence is provided below. It is observed that the although both CRISPR/Cas complex were transfected, nucleotide mutations are observed in Exon 4 only. Analysis of Exon3 sequence revealed wild type Exon 3 in the clonal knock out cell line.

GMD_3.51
Exon 3 sequence-
ACATGAAGTTGCACTATGGTGACCTCACCGACAGCACCTGCCTAG

TAAAAATCATCAATGAAGTCAAACCTACAGAGATCTACAATCITG

GTGCCCAGAGCCATGTCAAG

Exon 4 sequence-
ATTTCCTTTGACTTAGCAGAGTACACTGCAGATGTTGAGACTTGT

GGCCTTATAAATTCTGTGAAGTTCTACCAGGCCTCAACTAGTGAA

CTGTATGGAAAAGTGCAAGAAATACCCCAGAAAGAGACCACCCCT

TTCTATCCAAGGTCGCCCTATG

Table showing list of sequences from clonal GMD knock out cell lines developed by transfection with pD1401 (gRNA 167-207) CRISPR/Cas complex.

TABLE 20

| Cell line information | Genetic makeup at GMD target genomic locus | DNA sequencing data |
|---|---|---|
| CHOK1 Control | Wild type | ACATGAAGTTGCACTATGGTGACCTCACC GACAGCACCTGCCTAGTAAAAATCATCAA TGAAGTCAAACCTACAGAGATCTACAATC TTGGTGCCCAGAGCCATGTCAAG |
| GMD_1.12 | Frame-shift & STOP codon | ACATGAAGTTGCACTATGGTGACCTCACC GACAGCACCTGTGTTTTGGCACCAAAATC AACGGGACTTTCCAAAATGTCGTAATAAC CCCGCCCCGTTGACGCAAATGGAGAATCG CGCAGGGGAATGGCCTGCCGCACTTTCTG GCGGGCAGAAACAGCGAGTGGCGCTGGCA AGAGCGTTGATTCATCGACCGGGATTATT GTTGCGTGATGAACCGCTCGGGGCGCTGG ACGCCTTAACGCGACTCGAGATGCAGGAT TTGATTGTGTCTAGTAAAAATCATCAATG AAGTCAAACCTACAGAGATCTACAATCTT GGTGCCCAGAGCCATGTCAAG |
| GMD 1.27 | Frame-shift | ACATGAAGTTGCACTATGGTGACCTCACC GACAGCACCTGCCTAGTGAAGTCAAACCT ACAGAGATCTACAATCTTGGTGCCCAGAG CCATGTCAAG |
| GMD 1.37 | Frame-shift & STOP codon | ACATGAAGTTGCACTATGGTGACCTCACC GACAGCACCTGCCTAGTAAAAATCATCTG ACCGCCAGGTCGTAAAATCATCAATGAAG TCAAACCTACAGAGATCTACAATCTTGGT GCCCAGAGCCATGTCAAG |
| GMD 1.41 | Stop codon & Deletion | TAGATCTCTGTAGGTTTGACTTCATTGAT GAAGATCTACAATCTTGGTGCCCAGAGCC ATGTCAAG |
| GMD 1.43 | Frame-shift & STOP codon | TGGTGACCTCACCGACAGCACCTGCCTAG TAAAAAATCATCAATGAAGTCAAACCTAC AGAGATCTACAATCTTGGTGCCCAGAGCC ATGTCAAG |
| GMD 1.44 | Deletion | ACATGAAGTTGCACTATGGTGACCTCACC GATGAAGTCAAACCTACAGAGATCTACAA TCTTGGTGCCCAGAGCCATGTCAAG |

Table showing list of sequences from clonal GMD knock out cell lines developed by transfection with pD1301 (gRNA 404) CRISPR/Cas complex.

TABLE 21

| Cell line information | Genetic makeup at GMD target genomic locus | DNA sequencing data |
|---|---|---|
| CHOK1 control | Wild type | ATTTCCTTTGACTTAGCAGAGTACACTGCA GATGTTGATGGAGTTGGCACCTTGCGGCTT CTGGATGCAATTAAGACTTGTGGCCTTATA AATTCTGTGAAGTTCTACCAGGCCTCAACT AGTGAACTGTATGGAAAAGTGCAAGAAATA CCCCAGAAAGAGACCACCCCTTTCTATCCA AGGTCGCCCTATG |
| GMD_2.30 | Frame-shift & STOP codon | ATTTCCTTTGACTTAGCAGAGTACACTGCA GATGTTGATGGAGTTGGCACTTCTGGATGC AATTAAGACTTGTGGCCTTATAAATTCTGT GAAGTTCTACCAGGCCTCAACTAGTGAACT GTATGGAAAAGTGCAAGAAATACCCCAAAA AGAGACCACCCCTTTCTATCCAAGGTCGCC CTATG |

Table showing list of sequences from clonal GMD knock out cell lines developed by transfection with both pD1401 (gRNA 167-207) and pD1301 (gRNA 404) CRISPR/Cas complex.

TABLE 22

| Cell line information | Genetic makeup at GMD target genomic locus | Exon number | DNA sequencing data |
|---|---|---|---|
| CHOK1 control | Wild type | Exon 3 | ACATGAAGTTGCACTATGGTGACCTC ACCGACAGCACCTGCCTAGTAAAAAT CATCAATGAAGTCAAACCTACAGAGA TCTACAATCTTGGTGCCCAGAGCCAT GTCAAG |
|  | Wild type | Exon 4 | ATTTCCTTTGACTTAGCAGAGTACAC TGCAGATGTTGATGGAGTTGGCACCT TGCGGCTTCTGGATGCAATTAAGACT TGTGGCCTTATAAATTCTGTGAAGTT CTACCAGGCCTCAACTAGTGAACTGT ATGGAAAAGTGCAAGAAATACCCCAG AAAGAGACCACCCCTTTCTATCCAAG GTCGCCCTATG |
| GMD_3.51 | Wild type | Exon 3 | ACATGAAGTTGCACTATGGTGACCTC ACCGACAGCACCTGCCTAGTAAAAAT CATCAATGAAGTCAAACCTACAGAGA TCTACAATCTTGGTGCCCAGAGCCAT GTCAAG |
|  | DELETION | Exon 4 | ATTTCCTTTGACTTAGCAGAGTACAC TGCAGATGTTGAGACTTGTGGCCTTA TAAATTCTGTGAAGTTCTACCAGGCC TCAACTAGTGAACTGTATGGAAAAGT GCAAGAAATACCCCAGAAAGAGACCA CCCCTTTCTATCCAAGGTCGCCCTAT G |

Representative genomic DNA sequence alignment in GMD CHOK1 knock out cell line clones showing deletion in GMD gene sequence is provided in FIGS. 17 H to 17L of the present disclosure. FIG. 17H to 17L depict nucleotide sequence analysis at the GMD target locus. Genomic DNA of CRISPR/Cas transfected selected CHOK1 GMD knock out clones and CHOK1 control cell lines are used to PCR amplify targeted genomic GMD loci, both exon 3 and exon 4 sequences. Sequence data is collected from analysis of 5-15 independent bacterial clones sequenced with both forward and reverse sequencing primers. The sequencing data suggests deletions of variable lengths in multiple clones compared to CHOK1 control cell line. Largest deletion of bases is observed in clone GMD 1.41 and smallest deletion of 8 bases in clone GMD 2.30. All deletions are located at the CRISPR/Cas target site.

In FIG. 17H, the left and right CRISPR/Cas DNA binding sites are denoted by open boxes. In FIG. 17K, the CRISPR/Cas binding site is denoted by open box. FIGS. 17I to 17J indicate clones where the sequence data revealed insertion of new DNA sequence compared to CHOK1 control cell line. FIG. 17K reveals small deletion at the GMD exon4 target site with pD1301 (gRNA 404) CRISPR/Cas insert which is the result of double strand DNA break. FIG. 17L represents the sequence data from GMD knock out CHOK1 cell line transfected with two CRISPR/Cas constructs, pD1401 (gRNA 167-207) and pD1301 (gRNA 404) where only GMD exon4 sequence is modified with 36 base pair deletion.

The data suggests various INDELs present at the GMD genomic locus in CHOK1 GMD knock out cell lines. In many cases, it is observed that there are very specific modifications at the targeted bases, and in other cases the changes are broad and involve longer stretches of DNA. Such diversity of genomic modification through CRISPR/Cas complex is possible due to endogenous DNA single strand breaks and DNA double strand break and subsequent DNA repair. All of these cell lines are selected through functional screening assay, namely LCA-FITC flow cytometry assay. The results also imply high efficiency of the functional assays to isolate and identify CHOK1 GMD knock out cell line.

It is also revealed that the design of the CRISPR/Cas complex depicted in this disclosure is unique as this one pair of CRISPR/Cas complex with the Cas9n endonuclease provides a highly sequence specific gene alteration at the targeted GMD locus in CHOK1 cell lines.

Amino Acid Sequence Analysis of the CHOK1 FUT8 Knock Out Cell Lines

FUT8 genomic DNA sequence CHOK1 control and CHOK1 FUT8 knock out cell lines are further analyzed to understand the impact of DNA sequence INDEL on FUT8 protein status. DNA sequences at the targeted FUT8 locus is translated into amino acid sequences using vertebrate codon bias. The amino acid sequence of exon7 region is studied closely and the results are summarized in table 23. When compared to CHOK1 control cell line, the FUT8 knock out cell lines revealed modifications involving deletions and insertion of amino acids as well as introduction of stop codons and frame shift mutations. It is observed that deletions of 10 amino acids or larger stretches of amino acid sequences compared to the CHOK1 FUT8 protein sequence is obtained.

In many instances, frame shift mutations are observed, which alter the C-terminal region of the FUT8 protein to make it non-functional enzyme. In addition, in several cases, stop codon is introduced as an effect of frame shift mutation and thereby the FUT8 protein is truncated and non-functional in these clones.

TABLE 23

| Cell line information | Genetic makeup at FUT8 target genomic locus | Amino acid sequence derived from DNA sequencing data |
|---|---|---|
| CHOK1 control cell line | Wild type FUT8 amino acid sequence | NPKDCSKARKLVCNINKGCGYGC QLHHVVYCFMIAYGTQRTLILES QNWRYATGGWETVFRPVSETCTD RSGLSTGHWS |
| CR1KOT# 018 | Deletion mutant | NPKDCSKARKLVCNINKGCGYGC QLHHVVYCFMIAYGTQNWRYATG GWETVFRPVSETCTDRSGLSTGH WS |
| CR1KOT1# 055 | Frame shift with STOP CODON | NPKDCSKARKLVCNINKGCGYGC QLHHVVYCFMIAYGTQRTHLGIS ELALCYWRMGDCV* |
| CR1KOT1# 044 | Deletion mutant | NPKDCSKARKLVCNINKGCGYGC QLHHVVYCFMIAYGTQRTLISGG WETVFRPVSETCTDRSGLSTGHW S |
| CR1KOT1# 022 | Frame shift with STOP CODON | NPKDCSKARKLVCNINKGCGYGC QLHHVVYCFMIAYGTQRTLILES QNWHTDPGLPDEH* |

TABLE 23-continued

| Cell line information | Genetic makeup at FUT8 target genomic locus | Amino acid sequence derived from DNA sequencing data |
|---|---|---|
| CR1KOT1# 036 | Frame shift with STOP CODON | NPKDCSKARKLVCNINKGCGYGC QLHHVVYCFMIAYGTQRTLTLIL ESQNWNLILESQNWNLRIGAMLL EDGRLCLDL* |
| CR1KOT1# 037 | Frame shift with STOP CODON | NPKDCSKARKLVCNINKGCGYGC QLHHVVYCFMIAYGTLIILGGAA TQILALCYWRMGDCV* |
| CR1KOT1# 051 | Frame shift with STOP CODON | NPKDCSKARKLVCNINKGCGYGC QLHHVVYCFMIAYGTQIGAMLLE DGRLCLDL* |
| CR1KOT1# 052 | INSERTION with frame | NPKDCSKARKLVCNINKGCGYGC QLHHVVYCFMIAYGTQRTLILRT LILESQNCTGGWETVFRPVSETC TDRSGLSTGHWS |
| CR1KOT1# 059 | Frame shift with STOP CODON | NPKDCSKARKLVCNINKGCGYGC QLHHVVYCFMIAYGTQRTLILES QNWRFGISELALLEDGRLCLDL* |
| CRIKOT1# 061 | DELETION | NPKDCSKARKLVCNINKGCGYGC QLHHVVYCFMIAYGTQRTLILES VFRPVSETCTDRSGLSTGHWS |
| CRIKOT1# 067 | Frame shift with STOP CODON | NPKDCSKARKLVCNINKGCGYGC QLHHVVYCFMIAHLGISELALCY WRMGDCV* |
| CRIKOT1# 023 | Frame shift with STOP CODON | NPKDCSKARKLVCNINKGCGYGC QLHHVVY CFMIAYGTQRTLDIGKN* |

Furthermore, it is observed that the selection of target amino acids in the FUT8 protein sequence is highly effective. Targeting conserved amino acids at positions of wild type FUT8 protein with only one pair of CRISPR/Cas complex has created mutations at the targeted locus in multiple knock out cell lines.

Representative amino acid sequence alignment in CHOK1 control and CHOK1 CRISPR/Cas transfected cell lines showing deletion in FUT8 gene sequence is provided in FIGS. 18A and 18B of the present disclosure. The translated amino acid sequence is predicted using standard codon usage. The data indicates various effects on FUT8 amino acid sequence due to the nucleotide deletion and/or insertion observed. Clones CR1KOT1#018, CR1KOT1#044, CR1KOT1#061, CR1KOT1#055, CR1KOT1#067 and CR1KOT1#051 revealed targeted deletion of specific amino acid positions. In clone numbers CR1KOT1#052, CR1KOT1#022, CR1KOT1#036, CR1KOT1#059, CR1KOT1#023, and CR1KOT1#037, addition of amino acids in the targeted region is seen (FIG. 18B). Some of the clones revealed deletion followed by frame shift mutations resulting in early stop codons. All these modifications indicate non-functional FUT8 protein in the CRISPR/Cas transfected CHOK1 FUT8 knock out cell lines.

In addition, the CRISPR/Cas complex creates frame shift mutations followed by stop codons which disrupted the c-terminal region of the FUT8 enzyme which contains important motif II and motif III in the Rossmann fold. The specific amino acids positions Tyr-382, Asp-4109, Asp-410, Asp-453, and Ser-469 which are involved in the catalytic domain of the FUT8 enzyme are therefore not expressed in these truncated versions of FUT8 gene. The end result of these critical mutations is non-functional α-1,6 fucosyltransferase enzyme, the protein product of FUT8 gene in the CHOK1 FUT8knock out cell lines.

Analysis of GMD Gene Exon 3 Locus in Clonal Cell Lines Transfected with pD1401 (gRNA 167-207) CRISPR/Cas Complex.

The clonal knock out lines reveal different kinds of mutations in the GMD gene protein sequence at the targeted region. Below table lists all mutations observed in the GMD knock out clonal cell lines.

TABLE 24

| Cell line information | Genetic makeup at GMD target genomic locus | Amino acid sequence derived from DNA sequencing data |
|---|---|---|
| CHOK1 control | Wild type | MKLHYGDLTDSTCLVKIINEVKPTEIYN LGAQSHVK |
| GMD_1.12 | Frame-shift STOP codon | MKLHYGDLTDSTCVLAPKSTGLSKMS PRPVDANGESRRGMACRTFWRAETASGA GKSVDSSTGIIVATARGAGRLNATRD AGFDCV**KSSMKSNLQRSTILVPRAMS |
| GMD_1.27 | Frame-shift | MKLHYGDLTDSTCLVKSNLQRSTILVPR AMS |
| GMD_1.37 | Frame-shift STOP codon | MKLHYGDLTDSTCLVKII*PPGRKIINE VKPTEIYNLGAQSHVK |
| GMD_1.41 | Stop & Deletion | *ISVGLTSLMKIYNLGAQSHVK |
| GMD_1.43 | Frame-shift & STOP codon | VTSPTAPA**KIINEVKPTEIYNLGAQS HVK |
| GMD_1.44_ | Deletion | MKLHYGDLTD_____EVKPTELYN LGAOSHVK |

Analysis of GMD Gene Exon 4 Locus in Clonal Cell Lines Transfected with pD1301 (gRNA 404) CRISPR/Cas Complex:

The clonal knock out cell line revealed mutations in the GMD gene protein sequence at the targeted region. Below table lists all mutations observed in the GMD knock out clonal cell line.

TABLE 25

| Cell line information | Genetic makeup at GMD target genomic locus | Amino acid sequence derived from DNA sequencing data |
|---|---|---|
| CHOK1 control | Wild type | ISFDLAEYTADVDGVGTLRLLDAIKT CGLINSVKFYQASTSELYGKVQEIPQ KETTPFYPRSPY |
| GMD_2.30 | Frame-shift & STOP codon | ISFDLAEYTADVDGVGTSGCN*DLWP YKFCEVLPGLN**TVWKSARNTPKRD HPFLSKVAL |

Analysis of GMD Gene Exon 3 and Exon 4 Loci in Clonal Cell Line Transfected with Both pD1401 (gRNA 167-207) and pD1301 (gRNA 404) CRISPR/Cas Complex:

The clonal knock out cell line revealed mutations only in the GMD gene exon 4 protein sequence among the targeted regions. Below table lists all mutations observed in the GMD knock out clonal cell line.

TABLE 26

| Cell line information | Genetic makeup at GAD target genomic locus | Exon number | Amino acid sequence derived from DNA sequencing data |
|---|---|---|---|
| CHOK1 control | Wild type | Exon 3 | MKLHYGDLTDSTCLVKIINE VKPTEIYNLGAQSHVK |
| | Wild type | Exon 4 | ISFDLAEYTADVDGVGTLRL LDAIKTCGLINSVKFYQAST SELYGKVQEIPQKETTPFYP RSPY |
| GMD_3.51 | Wild type | Exon 3 | MKLHYGDLTDSTCLVKIINE VKPTEIYNLGAQSHVKIS |
| | Deletion | Exon 4 | FDLAEYTADV‾‾‾‾‾‾‾‾‾‾ ETCGLINSVKFYQASTSELY GKVQEIPQKETTPFYPRSPY |

FIG. 18C represent amino acid analysis of GMD knock out CHOK1 clones generated by using pD1401 (gRNA 167-207). Multiple types of mutations at the target GMD exon3 locus are observed which include deletion of amino acid residues, substitution as well as premature stop codons. Such modifications render the GMD gene non-functional and thereby resulted in Fucose knock out cell lines. Clone number GMD 1.12 and GMD 1.37 reveal insertion of amino acid residues and frame shift mutations that introduced premature stop codons (FIGS. 18D and 18E). In case of clone GMD 2.30, where pD1301 (gRNA 404) is used for introducing DNA double stand break revealed insertion and frame shift mutations at the target GMD exon4 locus (FIG. 18F). Similarly, in clone GMD 3.51 (FIG. 18G) the data revealed deletion of amino acids at GMD exon4 only although the cell line is generated by transfecting with both pD1401 (gRNA 167-207) and pD1301 (gRNA 404) CRISPR/Cas constructs.

This data reveals the CRISPR/Cas design made to target two specific exon target site of GMD gene are very specific and both constructs are effective in specific targeting. The GMD CHOK1 knock out cell line thus developed is used for non fucosylated monoclonal antibody development.

Example 7—Use of Fucose Knockout Cell Line to Produce Partially Fucosylated and Non-Fucosylated Antibodies The fucose knock out CHOK1 cell expression platform is used for expression of non-fucosylated antibody, particularly non-fucosylated monoclonal antibody. Antibody genes encoding heavy chain and light chain of monoclonal antibody is cloned in suitable gene expression plasmids and is transfected in the fucose knock out CHOK1 cell platform described in the examples above. The monoclonal antibody produced using this platform/method is expressed as non-fucosylated antibody. The product is purified following established protocols and guidelines to develop biobetter monoclonal antibody product for therapeutic use. Nonfucosylated biobetter antibody produced using this platform results in higher level of ADCC and thereby better therapeutic outcome.

LCA-FITC flow cytometry data and further sequencing experiments of the present disclosure confirm that the FKO lines are unable to fucosylate membrane proteins. Thus, the cell obtained in the present disclosure produces non-fucosylated proteins, specifically non-fucosylated antibody. The characteristic features and therapeutic advantages of non-fucosylated antibodies, such as higher ADCC, are known to one of skill in the art.

The GMD knock out CHOK1 cell lines are useful in unique applications in non fucosylated monoclonal antibody development programs. GMD gene is upstream of the critical GDP-Fucose step in the fucose biosynthetic pathway. GDP fucose can be produced in CHOK1 cell either by de novo pathway which is completely depended on GMD gene function or through salvage pathway which is independent of GMD gene function but requires presence of L-Fucose in growth media. Therefore, it is possible to achieve a conditional regulation of fucosylation of monoclonal antibodies produced in the GMD knock out cell lines.

Scenario 1: Monoclonal antibody gene expression in GMD knock out CHOK1 cells without any L-Fucose in growth media. The monoclonal antibody produced is 100% afucosylated. In this case both de novo and salvage fucose biosynthetic pathways are non-functional.

Scenario 2: Monoclonal antibody gene expression in GMD knock out CHOK1 cells with optimal L-Fucose in growth media. The monoclonal antibody produced is 100% fucosylated. this case, the de novo pathway is completely blocked but the salvage pathway is functional. This allows complete fucosylation of the monoclonal antibody gene produced in the GMD knock out CHOK1 cell line Scenario 3: Monoclonal antibody gene expression in GMD knock out CHOK1 cells with various levels of L-Fucose in growth media. The monoclonal antibody produced in this condition is partially fucosylated. The dosage of L-Fucose in the growth medium determines the level of fucosylation of the monoclonal antibody. This dosage is titrated during culture condition to ensure level of monoclonal antibody fucosylation and thereafter titrated again to fine tune to achieve critical levels of fucosylation of target monoclonal antibody.

This is a unique advantage with GMD gene knock out CHOK1 cell line and this feature is uniquely described in this disclosure Although disclosure and exemplification has been provided by way of illustrations and examples for the purpose of clarity and understanding, it is apparent to a person skilled in the art that various changes and modifications can be practiced without departing from the spirit or scope of the disclosure. Accordingly, the foregoing descriptions and examples should not be construed as limiting the scope of the present disclosure.

It is intended that the scope of the disclosure be limited not by this detailed description, but rather by the claims appended hereto. It is also to be understood that the following claims are intended to cover all of the generic and specific features of the disclosure described herein.

Many modifications and variations are possible in light of the above teachings. It is therefore to be understood that the claimed subject matter may be practiced otherwise than as specifically described. Any reference to claim elements in the singular, for example, using the articles "a," "an," "the," or "said" is not to be construed as limiting the disclosure.

The description of the embodiments of the present disclosure reveals the general nature of the embodiments that are readily suitable for modification and/or adaptation for various applications by applying the current knowledge. Such specific embodiments of the disclosure, without departing from the generic concept, and, therefore, such adaptations and modifications should and are intended to be comprehended and considered within the meaning and range of equivalents of the disclosed embodiments.

It is also to be understood that the phrases or terms employed herein are for the purpose of description and not intended to be of any limitation. Throughout the present disclosure, the word "comprise", or variations such as "comprises" or "comprising" wherever used, are to be understood to imply the inclusion of a stated element, integer or step, or group of elements, integers or steps, but not the exclusion of any other element, integer or step, or group of elements, integers or steps.

Where a numerical limit or range is stated herein, the endpoints are included. Also, values and sub-ranges within a numerical limit or range are specifically included as if explicitly written out.

With respect to the use of any plural and/or singular terms in the present disclosure, those of skill in the art can translate from the plural to the singular and/or from the singular to the plural as is considered appropriate to the context and/or application. The various singular/plural permutations may be expressly set forth herein for the sake of clarity.

Any discussion of documents, acts, materials, devices, articles and the like that has been included in this specification is solely for the purpose of providing a context for the present disclosure. It is not to be taken as an admission that any or all of these matters form a part of the prior art base or are common general knowledge in the field relevant to the present disclosure, as it existed anywhere before the priority date of this application.

The contents of all references, patents, and published patent applications cited throughout this application are incorporated herein by reference for all purposes.

We claim:

1. A clustered regularly interspaced short palindromic repeats (CRISPR) RNA (crRNA) of a CRISPR system, wherein the crRNA is selected from the group consisting of SEQ ID No. 38 and SEQ ID No. 40.

2. The crRNA of claim 1, wherein SEQ ID No. 38 and SEQ ID No. 40 bind to Fut8 gene sequence; and wherein SEQ ID No. 38 is transcribed from SEQ ID No. 37, and SEQ ID No. 40 is transcribed from SEQ ID No. 39.

3. A CRISPR-nuclease complex comprising a nuclease and crRNA selected from the group consisting of SEQ ID No. 38 and SEQ ID No. 40.

4. The complex as claimed in claim 3, wherein the nuclease is Cas9 endonuclease or Cas9n endonuclease.

5. A vector comprising a nucleotide sequence encoding crRNA selected from the group consisting of SEQ ID No. 38 and SEQ ID No. 40, wherein the vector further comprises a nucleotide sequence encoding a Cas9 or Cas9n endonuclease.

6. An isolated cell comprising the vector of claim 5.

7. The isolated cell of claim 6, wherein the cell is selected from the group consisting of COS, CHO-S, CHO-K1, CHO-K1 GS(−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G1 1.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

8. A method of obtaining a fucose knockout cell, said method comprising steps of:
   (a) obtaining a CRISPR-nuclease construct comprising the crRNA of claim 1; and
   (b) transfecting a cell with the construct of step (a) to obtain a fucose knockout cell.

9. A method of obtaining protein with fucosylation ranging from 0% to 100%, said method comprising steps of:
   (a) culturing the isolated cell of claim 6 to express a protein, wherein the cell has fucosylation activity ranging from 0% to 100%; and
   (b) obtaining the expressed protein.

10. The method of claim 8, wherein the CRISPR-nuclease construct provides the CRISPR-nuclease complex of claim 3; wherein the complex cleaves FUT8 gene sequence in the cell, wherein the Fut8 gene sequence coding for α-1,6 Fucosyltransferase enzyme is cleaved at Exon 7, and wherein the cell is selected from the group consisting of COS, CHO-S, CHO-K1, CHO-K1 GS (−/−), CHO-DG44, CHO-DUXB11, CHO-DUKX, CHOK1SV, VERO, MDCK, W138, V79, B14AF28-G3, BHK, HaK, NS0, SP2/0-Ag14, HeLa, HEK293-F, HEK293-H, HEK293-T, YB23HL.P2.G1 1.16Ag.20, perC6, antibody producing Hybridoma cell, embryonic stem cell, Namalwa cell, insect cell line from *Spodoptera fugiperda* (Sf), *Pichia, Saccharomyces* and *Schizosaccharomyces*.

11. The method of claim 9, wherein the protein is 0% fucosylated, and wherein the protein is obtained by disruption of Fut8 gene in the cell.

12. The method of claim 9, wherein the protein is an antibody.

13. The method of claim 12, wherein the antibody is a monoclonal antibody.

14. The method of claim 9, wherein the cell produces an endogenous protein.

15. The method of claim 9, further comprising a step of introducing a protein encoding gene into the cell and obtaining the protein.

16. A CRISPR system comprising one or more CRISPR-nuclease complexes of claim 3.

17. The CRISPR system of claim 16, wherein the nuclease is a Cas9 endonuclease or Cas9n endonuclease.

18. The crRNA of claim 1, wherein SEQ ID No. 38 and SEQ ID No. 40 function as a pair.

* * * * *